(12) United States Patent
Henn et al.

(10) Patent No.: US 10,881,696 B2
(45) Date of Patent: *Jan. 5, 2021

(54) NETWORK-BASED MICROBIAL COMPOSITIONS AND METHODS

(71) Applicant: Seres Therapeutics, Inc., Cambridge, MA (US)

(72) Inventors: Matthew R. Henn, Somerville, MA (US); David N. Cook, Brooklyn, NY (US); Toshiro K. Ohsumi, Cambridge, MA (US); Mary-Jane Lombardo McKenzie, Arlington, MA (US); Kevin D. Litcofsky, Boston, MA (US); Han Zhang, Oakton, VA (US); John Grant Aunins, Doylestown, PA (US); David Arthur Berry, Brookline, MA (US)

(73) Assignee: Seres Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/990,539

(22) Filed: May 25, 2018

(65) Prior Publication Data

US 2018/0353554 A1 Dec. 13, 2018

Related U.S. Application Data

(62) Division of application No. 14/777,252, filed as application No. PCT/US2014/030817 on Mar. 17, 2014, now Pat. No. 10,076,546.

(60) Provisional application No. 61/798,666, filed on Mar. 15, 2013.

(51) Int. Cl.
| | | |
|---|---|---|
| *A61K 35/742* | (2015.01) | |
| *A61K 35/74* | (2015.01) | |
| *A61K 35/741* | (2015.01) | |
| *A61K 35/745* | (2015.01) | |

(52) U.S. Cl.
CPC ............ *A61K 35/742* (2013.01); *A61K 35/74* (2013.01); *A61K 35/741* (2013.01); *A61K 35/745* (2013.01)

(58) Field of Classification Search
None
See application file for complete search history.

(56) References Cited

U.S. PATENT DOCUMENTS

| | | |
|---|---|---|
| 3,009,861 A | 11/1961 | Alderton et al. |
| 3,009,864 A | 11/1961 | Gordon-Aldterton et al. |
| 3,228,838 A | 1/1966 | Rinfret |
| 3,608,030 A | 11/1971 | Grant |
| 4,077,227 A | 3/1978 | Larson |
| 4,205,132 A | 5/1980 | Sandine |
| 4,655,047 A | 4/1987 | Temple |
| 4,689,226 A | 8/1987 | Nurmi |
| 4,839,281 A | 6/1989 | Gorbach et al. |
| 5,196,205 A | 3/1993 | Borody |
| 5,425,951 A | 6/1995 | Goodrich |
| 5,436,002 A | 7/1995 | Payne |
| 5,443,826 A | 8/1995 | Borody |
| 5,599,795 A | 2/1997 | McCann |
| 5,648,206 A | 7/1997 | Goodrich |
| 5,951,977 A | 9/1999 | Nisbet et al. |
| 5,965,128 A | 10/1999 | Doyle et al. |
| 6,589,771 B1 | 7/2003 | Marshall |
| 6,645,530 B1 | 11/2003 | Borody |
| 7,326,551 B2 | 2/2008 | Maupin-Furlow et al. |
| 7,427,398 B2 | 9/2008 | Baillon et al. |
| 7,628,982 B2 | 12/2009 | Klaviniskis |
| 7,632,520 B2 | 12/2009 | Khandelwal |
| 7,708,988 B2 | 5/2010 | Farmer |
| 7,731,976 B2 | 6/2010 | Cobb |
| 7,763,420 B2 | 7/2010 | Stritzker et al. |
| 7,981,411 B2 | 7/2011 | Nadeau et al. |
| 7,998,473 B2 | 8/2011 | Boileau et al. |
| 8,021,654 B2 | 9/2011 | Rehberger et al. |
| 8,034,601 B2 | 10/2011 | Boileau |
| 8,039,006 B2 | 10/2011 | Prato |
| 8,147,482 B2 | 4/2012 | Shimizu |
| 8,187,590 B2 | 5/2012 | Farmer |
| 8,236,508 B2 | 8/2012 | Mutharasan |
| 8,388,996 B2 | 3/2013 | Gehling |
| 8,460,648 B2 | 6/2013 | Borody |
| 8,469,648 B2 * | 6/2013 | Orgeron ............... E21B 19/155 414/22.55 |
| 8,906,668 B2 | 12/2014 | Henn et al. |
| 8,968,721 B2 | 3/2015 | Harel |
| 9,011,834 B1 * | 4/2015 | McKenzie ............ A61K 35/37 424/93.1 |

(Continued)

FOREIGN PATENT DOCUMENTS

| | | |
|---|---|---|
| CN | 102131928 A | 7/2011 |
| DE | 10 2006 062250 A1 | 6/2008 |

(Continued)

OTHER PUBLICATIONS

Maziade et al. Current Medical Research and Opinion, 29:10, 1341-1347, 2013.*

(Continued)

*Primary Examiner* — Oluwatosin A Ogunbiyi

(74) *Attorney, Agent, or Firm* — Sterne, Kessler, Goldstein & Fox P.L.L.C.

(57) ABSTRACT

Provided are therapeutic compositions containing combinations of bacteria, for the maintenance or restoration of a healthy microbiota in the gastrointestinal tract of a mammalian subject, and methods for use thereof.

17 Claims, 21 Drawing Sheets

Specification includes a Sequence Listing.

(56) References Cited

U.S. PATENT DOCUMENTS

| | | |
|---|---|---|
| 9,028,841 B2 | 5/2015 | Henn et al. |
| 9,180,147 B2 | 11/2015 | McKenzie et al. |
| 9,408,872 B2 | 8/2016 | Borody |
| 9,446,080 B2 | 9/2016 | McKenzie et al. |
| 9,610,307 B2 | 4/2017 | Berry et al. |
| 9,808,519 B2 | 11/2017 | Honda et al. |
| 2001/0036453 A1 | 11/2001 | Reid |
| 2004/0028689 A1 | 2/2004 | Borody |
| 2004/0170617 A1 | 9/2004 | Finegold |
| 2005/0048515 A1 | 3/2005 | Garner |
| 2005/0180962 A1 | 8/2005 | Raz |
| 2006/0046246 A1 | 3/2006 | Zeng et al. |
| 2006/0067924 A1 | 3/2006 | Lee et al. |
| 2006/0188523 A1 | 8/2006 | Pei |
| 2006/0233830 A1 | 10/2006 | Wong |
| 2007/0141139 A1 | 6/2007 | Vandenberg |
| 2008/0213752 A1 | 9/2008 | Stave et al. |
| 2009/0197249 A1 | 8/2009 | Gillevet |
| 2010/0074872 A1 | 3/2010 | Blaser et al. |
| 2010/0215745 A1 | 8/2010 | Lazzari et al. |
| 2011/0081320 A1 | 4/2011 | Westall et al. |
| 2011/0113863 A1 | 5/2011 | Fuhrmann et al. |
| 2011/0189132 A1 | 8/2011 | Garner et al. |
| 2011/0280840 A1 | 11/2011 | Blaser |
| 2011/0280847 A1 | 11/2011 | Sorg et al. |
| 2012/0020950 A1 | 1/2012 | Davis et al. |
| 2012/0021429 A1 | 1/2012 | Rublee |
| 2012/0021921 A1 | 1/2012 | Scott |
| 2012/0058094 A1 | 3/2012 | Blaser |
| 2012/0064592 A1 | 3/2012 | O'Mullan et al. |
| 2012/0128633 A1 | 5/2012 | Veiga et al. |
| 2012/0128634 A1 | 5/2012 | Veiga |
| 2012/0148629 A1 | 6/2012 | Holvoet et al. |
| 2012/0149584 A1 | 6/2012 | Olle |
| 2012/0165215 A1 | 6/2012 | Andersen |
| 2012/0177650 A1 | 7/2012 | Borody |
| 2012/0207726 A1 | 8/2012 | Lipkin |
| 2012/0238468 A1 | 9/2012 | Tuk |
| 2012/0264637 A1 | 10/2012 | Brodie |
| 2012/0276149 A1 | 11/2012 | Littman |
| 2012/0276201 A1 | 11/2012 | Trachtman |
| 2012/0315249 A1 | 12/2012 | Olmstead |
| 2013/0017999 A1 | 1/2013 | Fremont |
| 2013/0022575 A1 | 1/2013 | Cassity |
| 2013/0045274 A1 | 2/2013 | Hlavka |
| 2013/0045874 A1 | 2/2013 | Ehrlich |
| 2013/0065862 A1 | 3/2013 | Johnson |
| 2013/0115232 A1 | 5/2013 | Ferrara et al. |
| 2013/0121968 A1 | 5/2013 | Quay |
| 2013/0149339 A1 | 6/2013 | Honda |
| 2013/0149375 A1 | 6/2013 | Geall |
| 2013/0266539 A1 | 10/2013 | Borody |
| 2014/0045744 A1 | 2/2014 | Gordon |
| 2014/0135398 A1 | 5/2014 | Matar et al. |
| 2014/0147417 A1 | 5/2014 | Sadowsky et al. |
| 2014/0147425 A1 | 5/2014 | Henn et al. |
| 2014/0199281 A1 | 7/2014 | Henn et al. |
| 2014/0328803 A1 | 11/2014 | McKenzie et al. |
| 2014/0341921 A1 | 11/2014 | Honda et al. |
| 2014/0342438 A1 | 11/2014 | Allen-Vercoe et al. |
| 2015/0011415 A1 | 1/2015 | Levin et al. |
| 2015/0093360 A1 | 4/2015 | McKenzie et al. |
| 2015/0190435 A1 | 7/2015 | Henn et al. |
| 2016/0271188 A1 | 9/2016 | Berry et al. |
| 2017/0165302 A1 | 6/2017 | Henn et al. |

FOREIGN PATENT DOCUMENTS

| | | |
|---|---|---|
| EA | 006847 B1 | 4/2006 |
| EP | 0033584 A3 | 1/1981 |
| EP | 0446069 A1 | 9/1991 |
| EP | 0456418 A2 | 11/1991 |
| EP | 0433299 A4 | 4/1992 |
| EP | 1107772 B1 | 4/2006 |
| EP | 1631312 B1 | 9/2008 |
| EP | 2337569 A2 | 6/2011 |
| EP | 2338989 A1 | 6/2011 |
| EP | 2519108 A1 | 11/2012 |
| EP | 2684469 A1 | 1/2014 |
| EP | 0479820 B1 | 7/2014 |
| EP | 2626076 A1 | 8/2014 |
| EP | 2750682 B1 | 5/2016 |
| JP | 6-56679 A | 3/1994 |
| JP | 2007-332083 A | 12/2007 |
| JP | 2010-539179 T | 12/2010 |
| JP | 5 019563 B2 | 9/2012 |
| RU | 2035186 C1 | 5/1995 |
| RU | 2439145 C2 | 1/2012 |
| WO | WO 90/01335 A1 | 2/1990 |
| WO | WO-9408598 A1 | 4/1994 |
| WO | WO 1997/009886 A1 | 3/1997 |
| WO | WO 98/26787 A1 | 6/1998 |
| WO | WO 2000/010582 A2 | 3/2000 |
| WO | WO 01/93904 A1 | 12/2001 |
| WO | WO 2002/007741 A1 | 1/2002 |
| WO | WO 02/43649 A2 | 6/2002 |
| WO | WO 2005/017095 A2 | 2/2005 |
| WO | WO 2005/110445 A2 | 11/2005 |
| WO | WO 2006/012586 A2 | 2/2006 |
| WO | WO 2007/036230 A1 | 4/2007 |
| WO | WO 2007/136553 A2 | 11/2007 |
| WO | WO 2008/076696 A2 | 6/2008 |
| WO | WO 2008/077614 A2 | 7/2008 |
| WO | WO 2008/083157 A2 | 7/2008 |
| WO | WO 2010/030997 A1 | 3/2010 |
| WO | WO 2010/062369 A2 | 6/2010 |
| WO | WO 2010/124387 A1 | 11/2010 |
| WO | WO 2010/151842 A2 | 12/2010 |
| WO | WO 2011/005756 A1 | 1/2011 |
| WO | WO 2011/022542 A2 | 2/2011 |
| WO | WO 2011022660 A1 | 2/2011 |
| WO | WO 2011/033310 A1 | 3/2011 |
| WO | WO 2011/043654 A1 | 4/2011 |
| WO | WO 2011/046616 A3 | 4/2011 |
| WO | WO 2011/060123 A1 | 5/2011 |
| WO | WO 2011/094027 A1 | 8/2011 |
| WO | WO 2011/103123 A2 | 8/2011 |
| WO | WO 2011/107482 A2 | 9/2011 |
| WO | WO 2011/113801 A1 | 9/2011 |
| WO | WO 2011107481 A2 | 9/2011 |
| WO | WO 2011/152566 A2 | 12/2011 |
| WO | WO 2012/009712 A2 | 1/2012 |
| WO | WO 2012/016287 A2 | 2/2012 |
| WO | WO 2012/033814 A2 | 3/2012 |
| WO | WO 2012/045150 A1 | 4/2012 |
| WO | WO 2012/064981 A2 | 5/2012 |
| WO | WO 2012/108830 A1 | 8/2012 |
| WO | WO 2012/116289 A2 | 8/2012 |
| WO | WO 2012/122478 A1 | 9/2012 |
| WO | WO 2012/122522 A2 | 9/2012 |
| WO | WO 2012/142605 A1 | 10/2012 |
| WO | WO 2012/148991 A1 | 11/2012 |
| WO | WO 2012/159023 A2 | 11/2012 |
| WO | WO-2013016636 A1 | 1/2013 |
| WO | WO 2013/019896 A1 | 2/2013 |
| WO | WO 2013/032328 A1 | 3/2013 |
| WO | WO 2013/037067 A1 | 3/2013 |
| WO | WO 2013/037068 | 3/2013 |
| WO | WO 2013/050792 A1 | 4/2013 |
| WO | WO 2013/053836 A1 | 4/2013 |
| WO | WO 2013/080561 A1 | 6/2013 |
| WO | WO 2013/166031 A1 | 11/2013 |
| WO | WO 2013/171515 A1 | 11/2013 |
| WO | WO 2013/176774 A1 | 11/2013 |
| WO | WO-2013177596 A2 | 11/2013 |
| WO | WO 2014/082050 A1 | 5/2014 |
| WO | WO 2015/095241 A2 | 6/2014 |
| WO | WO 2014/121298 A2 | 8/2014 |
| WO | WO 2014/121301 A1 | 8/2014 |
| WO | WO 2014/121302 A2 | 8/2014 |
| WO | WO 2014/121304 A1 | 8/2014 |
| WO | WO 2014/145958 A2 | 9/2014 |
| WO | WO 2014/153194 A2 | 9/2014 |
| WO | WO-2014177667 A1 | 11/2014 |

(56) References Cited

FOREIGN PATENT DOCUMENTS

| WO | WO 2015/077794 A1 | 5/2015 |
| WO | WO 2017/091783 A2 | 6/2017 |
| WO | WO 2017/160711 A1 | 9/2017 |
| WO | WO 2019/089643 A1 | 5/2019 |

OTHER PUBLICATIONS

Hickson et al. BMJ 2007;335-80, 2007.*

Spinler et al. Anaerobe 41 (2016) 51-57.*

Koransky et al. Applied and Environmental Microbiology, Apr. 1978, col. 35, No. 4, p. 762-765 (Year: 1978).*

Aas, J., Gessert, C.E., and Bakken, J.S. (2003). Recurrent Clostridium difficile colitis: case series involving 18 patients treated with donor stool administered via a nasogastric tube. Clinical Infectious Diseases 36(5), 580-585.

Abrams, R.S., "Open-Label, Uncontrolled Trial of Bowel Sterilization and Repopulation with Normal Bowel Flora for Treatment of Inflammatory Bowel Disease," Current Therapeutic Research, Dec. 1997, pp. 1001-1012, vol. 58, No. 12.

Achtman, M., and Wagner, M. (2008). Microbial diversity and the genetic nature of microbial species. Nat. Rev. Microbiol. 6(6), 431-440.

Accoceberry, I. et al., "One-Step Purification of Enterocytozoon Bieneusi Spores from Human Stools by Immunoaffinity Expanded-Bed Adsorption," Journal of Clinical Microbiology, May 2001, pp. 1974-1951, vol. 39, No. 5.

Allen-Vercoe, E., Reid, G., Viner, N., Gloor, G.B., Hota, S., Kim, P., Lee, C., O'Doherty, K., Vanner, S.J., Weese, J.S., et al. (2012). A Canadian Working Group report on fecal microbial therapy: microbial ecosystems therapeutics. Can. J. Gastroenterol. 26(7), 457-462.

Allen-Vercoe, E., Strauss, J., and Chadee, K. (2011). *Fusobacterium nucleatum*: an emerging gut pathogen? Gut Microbes 2(5), 294-298.

Anderson, K.F., Lonsway, D.R., Rasheed, J.K., Biddle, J., Jensen, B., McDougal, L.K., Carey, R.B., Thompson, A., Stocker, S., Limbago, B., et al. (2007). Evaluation of Methods to Identify the Klebsiella pneumoniae Carbapenemase in Enterobacteriaceae. J. Clin. Microbiol. 45(8), 2723-2725.

Arumugam, M., Raes, J., Pelletier, E., Paslier, D.L., Yamada, T., Mende, D.R., Fernandes, G.R., Tap, J., Bruls, T., Batto, J.-M., et al. (2011). Enterotypes of the human gut microbiome. Nature 473(7346), 174-180.

Atarashi, K., Tanoue, T., Oshima, K., Suda, W., Nagano, Y., Nishikawa, H., Fukuda, S., Saito, T., Narushima, S., Hase, K., et al. (2013). Treg induction by a rationally selected mixture of Clostridia strains from the human microbiota. Nature 500(7461), 232-236.

Atarashi, K., Tanoue, T., Shima, T., Imaoka, A., Kuwahara, T., Momose, Y., Cheng, G., Yamasaki, S., Saito, T., Ohba, Y., et al. (2011). Induction of colonic regulatory T cells by indigenous *Clostridium* species. Science 331(6015), 337-341.

Australian First Examination Report, Australian Application No. 2013347805, dated Apr. 13, 2017, 3 pages.

Australian First Examination Report, Australian Application No. 2014232370, dated Oct. 19, 2017, 4 pages.

Australian First Examination Report, Australian Application No. 2014212004, dated Sep. 21, 2017, 6 pages.

Backhed, F. et al., (2004). The gut microbiota as an environmental factor that regulates fat storage, PNAS, Nov. 2, 2014, pp. 15718-15723, vol. 101, No. 44.

Bader, J., Albin, A., and Stahl, U. (2012). Spore-forming bacteria and their utilisation as probiotics. Benef Microbes 3(1), 67-75.

Bakken, J.S. (2009). Fecal bacteriotherapy for recurrent Clostridium difficile infection. Anaerobe 15(6), 285-289.

Bakken, J.S., Borody, T., Brandt, L.J., Brill, J.V., Demarco, D.C., Franzos, M.A., Kelly, C., Khoruts, A., Louie, T., Martinelli, L.P., et al. (2011). Treating Clostridium difficile infection with fecal microbiota transplantation. Clin. Gastroenterol. Hepatol. 9(12), 1044-1049.

Barreau, M., Pagnier, I., and La Scola, B. (2013). Improving the identification of anaerobes in the clinical microbiology laboratory through MALDI-TOF mass spectrometry. Anaerobe 22, 123-125.

Bauer, T.M. et al., "Derivation and Validation of Guidelines for Stool Cultures for Enteropathogenic Bacteria Other Than Clostridium difficile in Hospitalized Adults," The Journal of the American Medical Association, Jan. 17, 2001, pp. 313-319, vol. 285.

Ben-Amor, K., Heilig, H., Smidt, H., Vaughan, E.E., Abee, T., and De Vos, W.M. (2005). Genetic diversity of viable, injured, and dead fecal bacteria assessed by fluorescence-activated cell sorting and 16S rRNA gene analysis. Applied and Environmental Microbiology 71(8), 4679-4689.

Bergey's Manual of Determinative Bacteriology, Ninth Edition, John G. Holt et al., Williams & Wilkins,1994, pp. 527, 531, 577, 579 (6 pages total).

Berstad, A. et al., "Fecal Fat Determination with a Modified Titration Method," Scandinavian Journal of Gastroenterology, 2010, pp. 603-607, vol. 45.

Bhatia, A. et al., "Proionibacterium Acnes and Chronic Diseases," The Infectious Etiology of Chronic Diseases: Defining the Relationship, Enhancing the Research, and Mitigating the Effects: Workshop Summary., Knobler, S.L. et al. (eds.), 2004, pp. 74-80, may be downloaded at<URL:http://www.nap.edu/catalog/11026.html>.

Bidawid, S., Farber, J.M., Sattar, S.A., and Hayward, S. (2000). Heat inactivation of hepatitis a virus in dairy foods. J. Food Prot. 63(4), 522-528.

Bloedt, K., Riecker, M., Poppert, S., and Wellinghausen, N. (2009). Evaluation of new selective culture media and a rapid fluorescence in situ hybridization assay for identification of Clostridium difficile from stool samples. J Med Microbiol 58(7), 874-877.

Bokulich, N.A., Subramanian, S., Faith, J.J., Gevers, D., Gordon, J.I., Knight, R., Mills, D.A., and Caporaso, J.G. (2013). Quality-filtering vastly improves diversity estimates from Illumina amplicon sequencing. Nat Methods 10(1), 57-59.

Bolivar, I. et al., "Bacterial Diversity in Oral Samples of Children in Niger with Acute Noma, Acute Necrotizing Gingivitis and Healthy Controls," PLOS Neglected Tropical Diseases, Mar. 2012, pp. 1-11, vol. 6, No. 3, E1556; Uncultured *Catonella* sp. partial 16S rRNA Gene, Clone 402A04(oral): Nucleotide: NCBI: GenBank: AM420133.1, last accessed Mar. 12,2014, pp. 12-13.

Borody, T.J. et al. (2011). Fecal microbiota transplantation (FMT) in multiple sclerosis. Poster abstract at American College of Gastroenterology Annual Scientific Meeting and Postgraduate Course Oct. 28, 2011.

Borody, T.J., and Khoruts, A. (2012). Fecal microbiota transplantation and emerging applications. Nat Rev Gastroenterol Hepatol 9(2), 88-96.

Borriello, S.P. (1990). The influence of the normal flora on Clostridium difficile colonisation of the gut. Ann. Med. 22(1), 61-67.

Borriello, S.P., and Barclay, F.E. (1985). Protection of hamsters against Clostridium difficile ileocaecitis by prior colonisation with non-pathogenic strains. J Med Microbiol 19(3), 339-350.

Borriello, S.P., and Barclay, F.E. (1986). An in-vitro model of colonisation resistance to Clostridium difficile infection. Journal of Medical Microbiology 21(4), 299-309.

Borriello, S.P., and Honour, P. (1981). Simplified procedure for the routine isolation of Clostridium difficile from faeces. J Clin Pathol 34(10), 1124-1127.

Boyles, W.A., and Lincoln, R.E. (1958). Separation and concentration of bacterial spores and vegetative cells by foam flotation. Appl Microbiol 6(5), 327-334.

Brandt, L.J. (2012). Fecal Transplantation for the Treatment of Clostridium difficile Infection. Gastroenterol Hepatol (N Y) 8(3), 191-194.

Brandt, L.J., Aroniadis, O.C., Mellow, M., Kanatzar, A., Kelly, C., Park, T., Stollman, N., Rohlke, F., and Surawicz, C. (2012). Long-Term Follow-Up of Colonoscopic Fecal Microbiota Transplant for Recurrent Clostridium difficile Infection. The American Journal of Gastroenterology 107(7), 1079-1087.

Bräuniger, S., Peters, J., Borchers, U., and Kao, M. (2000). Further studies on thermal resistance of bovine parvovirus against moist and dry heat. International Journal of Hygiene and Environmental Health 203(1), 71-75.

Broda, D.M., De Lacy, K.M., and Bell, R.G. (1998). Efficacy of heat and ethanol spore treatments for the isolation of psychrotrophic

(56) References Cited

OTHER PUBLICATIONS

*Clostridium* spp. associated with the spoilage of chilled vacuum-packed meats. International Journal of Food Microbiology 39(1-2), 61-68.
Brosius, J. et al., "Complete Nucleotide Sequence of a 16S Ribosomal RNA Gene from *Eschericia coli*," Proc. Natl. Acad. Sci., Oct. 1978, pp. 4801-4805, vol. 75, No. 10.
Bueche, M., Wunderlin, T., Roussel-Delif, L., Junier, T., Sauvain, L., Jeanneret, N., and Junier, P. (2013). Quantification of Endospore-Forming Firmicutes by Quantitative PCR with the Functional Gene spo0A. Applied and Environmental Microbiology 79(17), 5302-5312.
Buffie, C.G., and Pamer, E.G. (2013). Microbiota-mediated colonization resistance against intestinal pathogens. Nature Reviews Immunology 13(11), 790-801.
Burke, C.J., Hsu, T.A., and Volkin, D.B. (1999). Formulation, stability, and delivery of live attenuated vaccines for human use. Crit Rev Ther Drug Carrier Syst 16(1), 1-83.
Cani, P.D., Possemiers, S., Wiele, T.V. De, Guiot, Y., Everard, A., Rottier, O., Geurts, L., Naslain, D., Neyrinck, A., Lambert, D.M., et al. (2009). Changes in gut microbiota control inflammation in obese mice through a mechanism involving GLP-2-driven improvement of gut permeability. Gut 58(8), 1091-1103.
Carvalho, A.S., Silva, J., Ho, P., Teixeira, P., Malcata, F.X., and Gibbs, P. (2008). Effects of Various Sugars Added to Growth and Drying Media upon Thermotolerance and Survival throughout Storage of Freeze-Dried *Lactobacillus delbrueckii* ssp. *bulgaricus*. Biotechnology Progress 20(1), 248-254.
Champagne, C.P., Mondou, F., Raymond, Y., and Roy, D. (1996). Effect of polymers and storage temperature on the stability of freeze-dried lactic acid bacteria. Food Research International 29(5-6), 555-562.
Chang, J.Y., Antonopoulos, D.A., Kalra, A., Tonelli, A., Khalife, W.T., Schmidt, T.M., and Young, V.B. (2008). Decreased diversity of the fecal Microbiome in recurrent Clostridium difficile-associated diarrhea. J. Infect. Dis. 197(3), 435-438.
Chapman, C.M.C., Gibson, G.R., and Rowland, I. (2012). In vitro evaluation of single- and multi-strain probiotics: Inter-species inhibition between probiotic strains, and inhibition of pathogens. Anaerobe 18(4), 405-413.
Chen, X., Katchar, K., Goldsmith, J.D., Nanthakumar, N., Cheknis, A., Gerding, D.N., and Kelly, C.P. (2008). A Mouse Model of Clostridium difficile-Associated Disease. Gastroenterology 135(6), 1984-1992.
Chinese First Office Action, Chinese Application No. 201480019395.8, dated Jul. 17, 2017, 13 pages.
Chinese Second Office Action, Chinese Application No. 201480019395.8, dated Apr. 4, 2018 (with concise explanation of relevance), 14 pages.
Chinese First Office Action, Chinese Application No. 201380071190.X, dated Jul. 4, 2018, 11 pages (with concise explanation of relevance).
Chiu, C-H. et al., "Rapid Identification of *Salmonella* Serovars in Feces by Specific Detection of Virulence Genes, invA and spvC, by an Enrichment Broth Culture-Multiplex PCR Combination Assay," Journal of Clinical Microbiology, Oct. 1996, pp. 2619-2622, vol. 34, No. 10.
Chow, J., Tang, H., and Mazmanian, S.K. (2011). Pathobionts of the Gastrointestinal Microbiota and Inflammatory Disease. Curr Opin Immunol 23(4), 473-480.
Claesson, M.J., Wang, Q., O'Sullivan, O., Greene-Diniz, R., Cole, J.R., Ross, R.P., and O'Toole, P.W. (2010). Comparison of two next-generation sequencing technologies for resolving highly complex microbiota composition using tandem variable 16S rRNA gene regions. Nucleic Acids Res 38(22), e200.
Clemente, J.C., Ursell, L.K., Parfrey, L.W., and Knight, R. (2012). The impact of the gut microbiota on human health: an integrative view. Cell 148(6), 1258-1270.

Coleman, W.H., "Mechanism of Killing Spores of Bacillus Cereus and Bacillus Megaterium by Wet Heat," The Society for Applied Microbiology, Letters in Applied Microbiology, 2010. pp. 507-514, vol. 50.
D'Souza, D.H., and Su, X. (2010). Efficacy of chemical treatments against murine norovirus, feline calicivirus, and MS2 bacteriophage. Foodborne Pathogens and Disease 7(3), 319-326.
David, L.A., Maurice, C.F., Carmody, R.N., Gootenberg, D.B., Button, J.E., Wolfe, B.E., Ling, A.V., Devlin, A.S., Varma, Y., Fischbach, M.A., et al. (2013). Diet rapidly and reproducibly alters the human gut microbiome. Nature advance online publication,.
De Angelis, M., Piccolo, M., Vannini, L., Siragusa, S., De Giacomo, A., Serrazzanetti, D.I., Cristofori, F., Guerzoni, M.E., Gobbetti, M., and Francavilla, R. (2013). Fecal Microbiota and Metabolome of Children with Autism and Pervasive Developmental Disorder Not Otherwise Specified. PLoS ONE 8(10), e76993.
De Vos, W.M. (2013). Fame and future of faecal transplantations—developing next-generation therapies with synthetic microbiomes: Fame and future of faecal transplantations. Microbial Biotechnology 6(4), 316-325.
Defined Fecal Microbiota Transplantation for Clostridium Difficile Diarrhea. <http://clinicaltrials.gov/ct2/show/NCT01868373> Accessed Mar. 26, 2014.
Dendukuri, N., "Probiotic Therapy for the Prevention and Treatment of Clostridium Difficile-Associated Diarrhea: A Systematic Review," Canadian Medical Association Journal, Jul. 19, 2005, pp. 167-170, vol. 173, No. 2.
Dezfulian, M. et al., "Selective Medium for Isolation of Clostridium botulinum from Human Feces," Journal of Clinical Microbiology, Mar. 1981, pp. 526-531, vol. 13, No. 3.
Derrien, M. (2004). *Akkermansia muciniphila* gen. nov., sp. nov., a human intestinal mucin-degrading bacterium. International Journal of Systematic and Evolutionary Microbiology 54(5), 1469-1476.
Dethlefsen, L., Huse, S., Sogin, M.L., and Relman, D.A. (2008). The Pervasive Effects of an Antibiotic on the Human Gut Microbiota, as Revealed by Deep 16S rRNA Sequencing. PLoS Biology 6(11), e280.
Detmer, A., and Glenting, J. (2006). Live bacterial vaccines—a review and identification of potential hazards. Microb Cell Fact 5, 23.
Dharmani, P., De Simone, C., and Chadee, K. (2013). The Probiotic Mixture VSL#3 Accelerates Gastric Ulcer Healing by Stimulating Vascular Endothelial Growth Factor. PLoS One 8(3), e58671.
Dietrich, G., Collioud, A., and Rothen, S.A. (2008). Developing and Manufacturing Attenuated Live Bacterial Vaccines. <http://www.biopharminternational.com/biopharm/Vaccine+Manufacturing+Articles/Developing-and-Manufacturing-Attenuated-Live-Bacte/ArticleStandard/Article/detail/557306> Accessed Mar. 25, 2014.
Dowell, V.R. et al., "Coproexamination for Botulinal Toxin and Clostridium botulinum," JAMA, Oct. 24, 1977, pp. 1829-1832, vol. 238, No. 7.
Dragon, D.C., and Rennie, R.P. (2001). Evaluation of spore extraction and purification methods for selective recovery of viable Bacillus anthracis spores. Lett. Appl. Microbiol. 33(2), 100-105.
Duc, L. (2003). Germination of the spore in the gastrointestinal tract provides a novel route for heterologous antigen delivery. Vaccine 21(27-30), 4215-4224.
Duc, L.H., Hong, H.A., Fairweather, N., Ricca, E., and Cutting, S.M. (2003). Bacterial Spores as Vaccine Vehicles. Infection and Immunity 71(5), 2810-2818.
Dumas, M.E. et al., (2006). Metabolic profiling reveals a contribution of gut microbiota to fatty liver phenotype in insulin-resistant mice, PNAS, Aug. 15, 2006, pp. 12511-12516, vol. 103, No. 33.
Dutta, S.K., Girotra, M., Garg, S., Dutta, A., Von Rosenvinge, E.C., Maddox, C., Song, Y., Bartlett, J.G., Vinayek, R., and Fricke, W.F. (2014). Efficacy of Combined Jejunal and Colonic Fecal Microbiota Transplantation for Recurrent Clostridium difficile Infection. Clinical Gastroenterology and Hepatology.
Edwards, A.D., and Slater, N.K.H. (2008). Formulation of a live bacterial vaccine for stable room temperature storage results in loss of acid, bile and bile salt resistance. Vaccine 26(45), 5675-5678.

(56) References Cited

OTHER PUBLICATIONS

Eiseman, B., Silen, W., Bascom, G.S., and Kauvar, A.J. (1958). Fecal enema as an adjunct in the treatment of pseudomembranous enterocolitis. Surgery 44(5), 854-859.
El-Houssieny, R. et al., "Recovery and Detection of Microbial Contaminants in Some Non-Sterile Pharmaceutical Products," Archives of Clinical Microbiology, 2013, pp. 1-14, vol. 4, No. 6: 1.
Elving, J., Emmoth, E., Albihn, A., Vinneras, B., and Ottoson, J. (2012). Composting for Avian Influenza Virus Elimination. Applied and Environmental Microbiology 78(9), 3280-3285.
Emanuelsson, F., Claesson, B.E.B., Ljungström, L., Tvede, M., and Ung, K.-A. (2014). Faecal microbiota transplantation and bacteriotherapy for recurrent Clostridium difficile infection: a retrospective evaluation of 31 patients. Scandinavian Journal of Infectious Diseases 46(2), 89-97.
Endt, K., Stecher, B., Chaffron, S., Slack, E., Tchitchek, N., Benecke, A., Van Maele, L., Sirard, J.-C., Mueller, A.J., Heikenwalder, M., et al. (2010). The Microbiota Mediates Pathogen Clearance from the Gut Lumen after Non-Typhoidal *Salmonella* Diarrhea. PLoS Pathog 6(9), e1001097.
European Extended Search Report, European Application No. 14768281.9, dated Jul. 18, 2016, 10 pages.
European Extended Search Report, European Application No. 14763266.5, dated Aug. 16, 2016, 7 pages.
European Extended Search Report, European Application No. 14746341.8, dated Sep. 28, 2016, 10 pages.
European Partial Supplementary Report, European Application No. 14745792.3, dated Sep. 20, 2016, 11 pages.
European Partial Supplementary Report, European Application No. 14745749.3, dated Oct. 14, 2016, 6 pages.
European Extended Search Report, European Application No. 14746455.6, dated Nov. 24, 2016, 10 pages.
European Extended Search Report, European Application No. 14745792.3, dated Dec. 23, 2016, 17 pages.
European Extended Search Report, European Application No. 14745749.3, dated Jan. 23, 2017, 13 pages.
European Extended Search Report, European Application No. 13856249.1, dated Jan. 26, 2017, 19 pages.
European Examination Report, European Application No. 14746341.8, dated Jun. 13, 2017, 11 pages.
European Partial Supplementary Search Report, European Application No. 14870947.0, dated Jul. 11, 2017, 14 pages.
European Extended Search Report, European Application No. 14870947.0, dated Oct. 17, 2017, 11 pages.
European Examination Report, European Application No. 14745749.3, dated Oct. 31, 2017, 3 pages.
European Examination Report, European Application No. 14746455.6, dated Oct. 31, 2017, 6 pages.
European Examination Report, European Application No. 14763266.5, dated Nov. 13, 2017, 4 pages.
European Examination Report, European Application No. 14768281.9, dated Dec. 18, 2017, 4 pages.
European Examination Report, European Application No. 14745792.3, dated Dec. 21, 2017, 6 pages.
European Examination Report, European Application No. 14821918.1, dated Jan. 29, 2018, 4 pages.
European Examination Report, European Application No. 14746341.8, dated Apr. 18, 2018, 8 pages.
European Examination Report, European Application No. 13856249.1, dated May 23, 2018, 6 pages.
European Summons to Attend Oral Proceedings Pursuant to Rule 115(1) EPC, European Application No. 14768281.9, Jul. 11, 2018, 9 pages.
Everard, A., Belzer, C., Geurts, L., Ouwerkerk, J.P., Druart, C., Bindels, L.B., Guiot, Y., Derrien, M., Muccioli, G.G., Delzenne, N.M., et al. (2013). Cross-talk between Akkermansia muciniphila and intestinal epithelium controls diet-induced obesity. Proceedings of the National Academy of Sciences 110(22), 9066-9071.
Fairhead, H., Setlow, B., Waites, W.M., and Setlow, P. (1994). Small, acid-soluble proteins bound to DNA protect Bacillus subtilis spores from being killed by freeze-drying. Applied and Environmental Microbiology 60(7), 2647-2649.
Faith, J.J., Ahern, P.P., Ridaura, V.K., Cheng, J., and Gordon, J.I. (2014). Identifying Gut Microbe—Host Phenotype Relationships Using Combinatorial Communities in Gnotobiotic Mice. Sci Transl Med 6(220), 220ra11-220ra11.
Fakhry, S., Sorrentini, I., Ricca, E., De Felice, M., and Baccigalupi, L. (2008). Characterization of spore forming Bacilli isolated from the human gastrointestinal tract. Journal of Applied Microbiology 105(6), 2178-2186.
Faust, et al., "Microbial Co-occurrence Relationships in the Human Microbiome," PLoS Computational Biology, Jul. 2012, e1002606, 17 pages, vol. 8, No. 7.
Fell JR., N.F., Pellegrino, P.M., and Gillespie, J.B. (2001). Mitigating phosphate interference in bacterial endospore detection by Tb dipicolinate photoluminescence. Analytica Chimica Acta 426(1), 43-50.
Fichtel, J., Köster, J., Rullkötter, J., and Sass, H. (2007). Spore dipicolinic acid contents used for estimating the number of endospores in sediments. FEMS Microbiology Ecology 61(3), 522-532.
Fischbach, M.A., Bluestone, J.A., and Lim, W.A. (2013). Cell-Based Therapeutics: The Next Pillar of Medicine. Sci Transl Med 5(179), 179ps7.
Fonseca, F., Béal, C., and Corrieu, G. (2001). Operating Conditions That Affect the Resistance of Lactic Acid Bacteria to Freezing and Frozen Storage. Cryobiology 43(3), 189-198.
Franz, C.M.A.P., Huch, M., Abriouel, H., Holzapfel, W., and Gálvez, A. (2011). Enterococci as probiotics and their implications in food safety. International Journal of Food Microbiology 151(2), 125-140.
Friedman-Moraco, R.J., Mehta, A.K., Lyon, G.M., and Kraft, C.S. (2014). Fecal Microbiota Transplantation for Refractory Clostridium difficile Colitis in Solid Organ Transplant Recipients: Fecal Microbiota Transplantation in Solid Organ Transplant Recipients. American Journal of Transplantation 14(2), 477-480.
Fuentes, S., Van Nood, E., Tims, S., Heikamp-De Jong, I., Ter Braak, C.J., Keller, J.J., Zoetendal, E.G., and De Vos, W.M. (2014). Reset of a critically disturbed microbial ecosystem: faecal transplant in recurrent Clostridium difficile infection. The ISME Journal.
GenBank HQ819637, "Uncultured Organism Clone ELU0180-T56-S-NIPCRAMgANa_000311 Small Subunit Ribosomal RNA Gene, Partial Sequence," Jul. 30, 2012, 1 page, [Online] [Retrieved on Aug. 21, 2014] Retrieved from the Internet<URL:http://www.ncbi.nlm.nih.gov/nuccore/HQ819637>.
Gevers, D., Kugathasan, S., Denson, L.A., Vázquez-Baeza, Y., Van Treuren, W., Ren, B., Schwager, E., Knights, D., Song, S.J., Yassour, M., et al. (2014). The Treatment-Naive Microbiome in New-Onset Crohn's Disease. Cell Host & Microbe 15(3), 382-392.
Gilligan, P.H. (2013). Identification of Pathogens by Classical Clinical Tests. In the Prokaryotes, E. Rosenberg, E.F. DeLong, S. Lory, E. Stackebrandt, and F. Thompson, eds. (Springer Berlin Heidelberg), pp. 57-89.
Goodman, A.L., Kallstrom, G., Faith, J.J., Reyes, A., Moore, A., Dantas, G., and Gordon, J.I. (2011). From the Cover: Extensive personal human gut microbiota culture collections characterized and manipulated in gnotobiotic mice. Proceedings of the National Academy of Sciences 108(15), 6252-6257.
Goodman, N.S., Gottfried, R.J., and Rogoff, M.H. (1967). Biphasic system for separation of spores and crystals of Bacillus thuringiensis. Journal of Bacteriology 94(2), 485.
Gough, E. et al., "Systematic Review of Intestinal Microbiota Transplantation (Fecal Bacteriotherapy) for Recurrent Clostridium Dfficile Infection," Clin. Infect. Dis., Nov. 15, 2011, pp. 994-1002, vol. 53, No. 10.
Gould, G.W., and Sale, A.J. (1970). Initiation of germination of bacterial spores by hydrostatic pressure. J. Gen. Microbiol. 60(3), 335-346.
Grabow, W.O., Clay, C.G., Dhaliwal, W., Vrey, M.A., and Müller, E.E. (1999). Elimination of viruses, phages, bacteria and Cryptosporidium by a new generation Aquaguard point-of-use water treatment unit. Zentralbl Hyg Umweltmed 202(5), 399-410.

(56) References Cited

OTHER PUBLICATIONS

Greenway, F., Wang, S., and Heiman, M. (2014). A novel cobiotic containing a prebiotic and an antioxidant augments the glucose control and gastrointestinal tolerability of metformin: a case report. Beneficial Microbes 5(1), 29-32.

Grehan, M.J., Borody, T.J., Leis, S.M., Campbell, J., Mitchell, H., and Wettstein, A. (2010). Durable alteration of the colonic microbiota by the administration of donor fecal flora. J. Clin. Gastroenterol. 44(8), 551-561.

Grimoud, J. et al., "In Vitro Screening of Probiotic Lactic Acid Bacteria and Prebiotic Glucooligosaccharides to Select Effective Synbiotics," Anaerobe, Clinical Microbiology, Oct. 2010, pp. 493-500, vol. 16, No. 5.

Gupta, R.K. et al., "Differentiation Between Heat Resistance and Octyl Alcohol Resistance of the Cells of Bacillus Cereus T.," Biochemical and Biophysical Research Communications, 1970, pp. 23-30, vol. 38, No. 1.

Halmann, M. et al., "Stages in Germination of Spores of Bacillus Lichenformis," J. Bacteriol., 1962, pp. 1187-1193, vol. 84.

Hamilton, M.J., Weingarden, A.R., Sadowsky, M.J., and Khoruts, A. (2012). Standardized frozen preparation for transplantation of fecal microbiota for recurrent Clostridium difficile infection. Am. J. Gastroenterol. 107(5), 761-767.

Hamilton, M.J., Weingarden, A.R., Unno, T., Khoruts, A., and Sadowsky, M.J. (2013). High-throughput DNA sequence analysis reveals stable engraftment of gut microbiota following transplantation of previously frozen fecal bacteria. Gut Microbes 4(2), 125-135.

Harmsen, H. J. M., Gibson, G. R., Elfferich, P., Raangs, G. C., Wildeboer-Veloo, A. C. M., Argaiz, A., Roberfroid, M. B., and Welling, G. W. (2000). Comparison of viable cell counts and fluorescence in situ hybridization using specific rRNA-based probes for the quantification of human fecal bacteria. FEMS Microbiology Letters 183(1), 125-129.

Harrison, F., "Bacterial Cooperation in the Wild and in the Clinic: Are Pathogen Social Behaviours Relevant Outside the Laboratory?" Bioessays, Dec. 27, 2012, pp. 108-112, vol. 35, No. 2.

Hasan, J.A., Japal, K.M., Christensen, E.R., and Samalot-Freire, L.C. (2011). In vitro production of Clostridium difficile spores for use in the efficacy evaluation of disinfectants: a precollaborative investigation. J AOAC Int 94(1), 259-272.

Hayashi, Y. et al., "Western Blot (Immunoblot) Assay of Small Round-Structured Virus Associated with an Acute Gastroenteritis Outbreak in Tokyo," Journal of Clinical Microbiology, Aug. 1989, pp. 1728-1733, vol. 27.

Hell, M., Bernhofer, C., Stalzer, P., Kern, J.M., and Claassen, E. (2013). Probiotics in Clostridium difficile infection: reviewing the need for a multistrain probiotic. Beneficial Microbes 4(1), 39-51.

Hemmerling, A., Harrison, W., Schroeder, A., Park, J., Korn, A., Shiboski, S., Foster-Rosales, A., and Cohen, C.R. (2010). Phase 2a Study Assessing Colonization Efficiency, Safety, and Acceptability of Lactobacillus crispatus CTV-05 in Women With Bacterial Vaginosis: Sexually Transmitted Diseases 37(12), 745-750.

Herron, P.R., and Wellington, E.M.H. (1990). New Method for Extraction of Streptomycete Spores from Soil and Application to the Study of Lysogeny in Sterile Amended and Nonsterile Soil. Appl Environ Microbiol 56(5), 1406-1412.

Hewitt, J., Rivera-Aban, M., and Greening, G.E. (2009). Evaluation of murine norovirus as a surrogate for human norovirus and hepatitis A virus in heat inactivation studies. Journal of Applied Microbiology 107(1), 65-71.

Hickson, M. et al., "Probiotics in the Prevention of Antibiotic-Associated Diarrhoea and Clostridium Difficile Infection," Therapeutic Advances in Gastroenterology, 2011, pp. 185-197, vol. 4, No. 3.

Hindle, A.A., and Hall, E.A.H. (1999). Dipicolinic acid (DPA) assay revisited and appraised for spore detection. The Analyst 124(11), 1599-1604.

Hirsch, E.B., and Tam, V.H. (2010). Detection and treatment options for Klebsiella pneumoniae carbapenemases (KPCs): an emerging cause of multidrug-resistant infection. J. Antimicrob. Chemother. 65(6), 1119-1125.

Hofsten, B.V. (1966). Partition of *Escherichia coli* in an aqueous polymer two-phase system. Experimental Cell Research 41(1), 117-123.

Holdeman, L.V. et al., "Human Fecal Flora: Variation in Bacterial Composition Within Individuals and a Possible Effect of Emotional Stress," Applied and Environmental Microbiology, Mar. 1976, pp. 359-375, vol. 31, No. 3.

Holmes, E., Kinross, J., Gibson, G.R., Burcelin, R., Jia, W., Pettersson, S., and Nicholson, J.K. (2012). Therapeutic Modulation of Microbiota-Host Metabolic Interactions. Science Translational Medicine 4(137), 137rv6-137rv6.

Hoppe, B., Groothoff, J.W., Hulton, S.-A., Cochat, P., Niaudet, P., Kemper, M.J., Deschênes, G., Unwin, R., and Milliner, D. (2011). Efficacy and safety of Oxalobacter formigenes to reduce urinary oxalate in primary hyperoxaluria. Nephrol. Dial. Transplant. 26(11), 3609-3615.

Hoyles, L., Honda, H., Logan, N.A., Halket, G., La Ragione, R.M., and McCartney, A.L. (2012). Recognition of greater diversity of *Bacillus* species and related bacteria in human faeces. Res. Microbiol. 163(1), 3-13.

Hurst, C.J., and Gerba, C.P. (1989). Fate of viruses during wastewater sludge treatment processes. Critical Reviews in Environmental Control 18(4), 317-343.

Iizuka, M. et al., "Elemental Diet Modulates the Growth of Clostridium difficile in the Gut Flora," Aliment Pharmacol. Ther., Jul. 2004, pp. 151-157, vol. 20, Suppl. 1.

Israel Office Action, Israel Application No. 238973, dated Apr. 20, 2017, 4 pages (with concise explanation of relevance).

Itoh, K., and Mitsuoka, T. (1985). Characterization of clostridia isolated from faeces of limited flora mice and their effect on caecal size when associated with germ-free mice. Laboratory Animals 19(2), 111-118.

Itoh, K., Lee, W.K., Kawamura, H., Mitsuoka, T., and Magaribuchi, T. (1987). Intestinal bacteria antagonistic to Clostridium difficile in mice. Lab Anim 21(1), 20-25.

Itoh, K., Urano, T., and Mitsuoka, T. (1986). Colonization resistance against Pseudomonas aeruginosa in gnotobiotic mice. Lab Anim 20(3), 197-201.

Jalanka-Tuovinen, J., Salojarvi, J., Salonen, A., Immonen, O., Garsed, K., Kelly, F.M., Zaitoun, A., Palva, A., Spiller, R.C., and De Vos, W.M. (2013). Faecal microbiota composition and host-microbe cross-talk following gastroenteritis and in postinfectious irritable bowel syndrome. Gut 0, 1-9.

Janda, J.M. et al., "16S rRNA Gene Sequencing for Bacterial Identification in the Diagnostic Laboratory: Pluses, Perils and Pitfalls," Journal of Clinical Microbiology, Sep. 2007, pp. 2761-2764, vol. 45, No. 9.

Japanese First Office Action, Japanese Application No. P2015-544179, dated Sep. 19, 2017, 8 pages.

Japanese Office Action, Japanese Application No. 2015-556241, dated Sep. 26, 2017, 12 pages.

Japanese Office Action, Japanese Application No. 2015-556240, dated Oct. 3, 2017, 8 pages.

Japanese Office Action, Japanese Application No. P2016-502561, dated Feb. 6, 2018, 10 pages.

Japanese Office Action, Japanese Application No. 2015-556240, dated Jun. 5, 2018, 5 pages.

Jeffs, L.B., and Khachatourians, G.G. (1997). Estimation of spore hydrophobicity for members of the genera *Beauveria*, *Metarhizium*, and *Tolypocladium* by salt-mediated aggregation and sedimentation. Canadian Journal of Microbiology 43(1), 23-28.

Jensen, N.S., and Canale-Parola, E. (1986). *Bacteroides pectinophilus* sp. nov. and *Bacteroides galacturonicus* sp. nov.: two pectinolytic bacteria from the human intestinal tract. Appl. Environ. Microbiol. 52(4), 880-887.

Johnson, S. et al., "Is Primary Prevention of Clostridium Difficile Infection Possible with Specific Probiotics?" International Journal of Infectious Diseases, Nov. 2012, pp. e786-e792, vol. 16, No. 11.

(56) References Cited

OTHER PUBLICATIONS

Johnston, R. et al., "Method to Facilitate the Isolation of Clostridium botulinum Type E," J. Bacteriol., 1964, pp. 1521-1522, vol. 88.

Jones, M.L., Martoni, C.J., and Prakash, S. (2012a). Cholesterol lowering and inhibition of sterol absorption by Lactobacillus reuteri NCIMB 30242: a randomized controlled trial. Eur J Clin Nutr 66(11), 1234-1241.
Jones, M.L., Martoni, C.J., Parent, M., and Prakash, S. (2012b). Cholesterol-lowering efficacy of a microencapsulated bile salt hydrolase-active Lactobacillus reuteri NCIMB 30242 yoghurt formulation in hypercholesterolaemic adults. British Journal of Nutrition 107(10), 1505-1513.
Joosten, H. et al., "Salmonelle Detection in Probiotic Products," International Journal of Food Microbiology, Jul. 2006, pp. 104-107, vol. 110, No. 1.
Jordan, F. et al., "Network Ecology: Topological Constraints on Ecosystem Dynamics," Physics of Life Reviews, Dec. 2004, pp. 139-172, vol. 1, Issue 3 (Abstract Only).
Jorgensen, J.H., and Ferraro, M.J. (2009). Antimicrobial Susceptibility Testing: A Review of General Principles and Contemporary Practices. Clin Infect Dis., Medical Microbiology, 49(11), 1749-1755.
Jorup-Rönström, C., Håkanson, A., Sandell, S., Edvinsson, O., Midtvedt, T., Persson, A.-K., and Norin, E. (2012). Fecal transplant against relapsing Clostridium difficile-associated diarrhea in 32 patients. Scand. J. Gastroenterol. 47(5), 548-552.
Jousimies-Somer, H., Summanen, P., Citron, D.M., Baron, E.J., Wexler, H.M., and Finegold, S.M. (2002). Wadsworth-KLT Anaerobic Bacteriology Manual, 6th edition (California: Star), pp. 55-74, 81-132, 165-185.
Kailasapathy, K. (2002). Microencapsulation of probiotic bacteria: technology and potential applications. Curr Issues Intest Microbiol 3(2), 39-48.
Kamiya, S., Yamakawa, K., Ogura, H., and Nakamura, S. (1989). Recovery of spores of Clostridium difficile altered by heat or alkali. J Med Microbiol 28(3), 217-221.
Kanamoto, T. et al., "Genetic Heterogeneities and Phenotypic Characteristics of Strains of the Genus *Abiotrophia* and Proposal of *Abiotrophia para-adiacens* sp. nov.," Journal of Clinical Microbiology, Feb. 2000, pp. 492-498, vol. 38, No. 2; Abiotropia para-adjacens gene for 16S rRNA, partial sequence, strain: Nucleotide: NCBI: GenBank: AB022027.1, last accessed Mar. 12, 2014, p. 8.
Kanehisa Laboratories. KEGG: Kyoto encyclopedia of genes and genomes. <http://www.genome.jp/kegg/> Accessed Mar. 27, 2014.
Karasawa, T. et al., "A Defined Growth Medium for Clostridium difficile," Microbiology, Feb. 1995, pp. 371-375, vol. 151, No. 2.
Kazamias, M. et al., "Enhanced Fermentation of Mannitol and Release of Cytotoxin by Clostridium difficile in Alkaline Culture Media," Applied and Environmental Microbiology, Jun. 1995, pp. 2425-2427, vol. 61, No. 6.
Kelly, D., Campbell, J.I., King, T.P., Grant, G., Jansson, E.A., Coutts, A.G.P., Pettersson, S., and Conway, S. (2003). Commensal anaerobic gut bacteria attenuate inflammation by regulating nuclear-cytoplasmic shuttling of PPAR-γ and ReIA. Nature Immunology 5(1), 104-112.
Khoruts, A. (2013). How Does Fecal Microbiota Transplantation Treat Clostridium difficile Infection? <https://www.genome.gov/Multimedia/Slides/HumanMicrobiomeScience2013/39_Khoruts.pdf> Accessed Mar. 21, 2014.
Khoruts, A., and Sadowsky, M.J. (2011). Therapeutic transplantation of the distal gut microbiota. Mucosal Immunol 4(1), 4-7.
Khoruts, A., Dicksved, J., Jansson, J.K., and Sadowsky, M.J. (2010). Changes in the composition of the human fecal microbiome after bacteriotherapy for recurrent Clostridium difficile-associated diarrhea. J. Clin. Gastroenterol. 44(5), 354-360.
Kim, B., Kim, N.J., Kim, M., Kim, Y.S., Woo, J., and Ryu, J. (2003). Bacteraemia Due to Tribe Proteeae: A Review of 132 Cases During a Decade (1991-2000). Scandinavian Journal of Infectious Diseases 35(2), 98-103.
Kim, J.Y. et al., "Effect of Oral Probiotics (Bifidobacterium lactis AD011 and Lactobacillus acidophilus AD031) Administration on Ovalbumin-Induced Food Allergy Mouse Model," J. Microbiol. Biotechnol., 2008, pp. 1393-1400, vol. 18, No. 8.
Klayraung, S., Viernstein, H., and Okonogi, S. (2009). Development of tablets containing probiotics: Effects of formulation and processing parameters on bacterial viability. International Journal of Pharmaceutics 370(1-2), 54-60.
Kollmann, M. et al., Design Principles of a Bacterial Signalling Network, Nature, Nov. 24, 2005, pp. 504-507, vol. 438, No. 7067.
Kong, Q., He, G.-Q., Jia, J.-L., Zhu, Q.-L., and Ruan, H. (2011). Oral Administration of Clostridium butyricum for Modulating Gastrointestinal Microflora in Mice. Curr Microbiol 62(2), 512-517.
Konstantinidis, K.T., Ramette, A., and Tiedje, J.M. (2006). The bacterial species definition in the genomic era. Philos Trans R Soc Lond B Biol Sci 361(1475), 1929-1940.
Koonin, E.V. (2002). Chapter 22 The clusters of orthologous groups (COGS) database: Phylogenetic classification of proteins from complete genomes. <http://www.ncbi.nlm.nih.gov/books/NBK21090/pdf/ch22.pdf> Accessed Mar. 27, 2014.
Koransky, J.R., Allen, S.D., and Dowell, V.R., JR (1978). Use of ethanol for selective isolation of sporeforming microorganisms. Appl. Environ. Microbiol. 35(4), 762-765.
Kort, R., O'Brien, A.C., Stokkum, I.H.M. Van, Oomes, S.J.C.M., Crielaard, W., Hellingwerf, K.J., and Brul, S. (2005). Assessment of Heat Resistance of Bacterial Spores from Food Product Isolates by Fluorescence Monitoring of Dipicolinic Acid Release. Appl. Environ. Microbiol. 71(7), 3556-3564.
Kucerova, Z., Moura, H., Leitch, G.J., Sriram, R., Bern, C., Kawai, V., Vargas, D., Gilman, R.H., Ticona, E., and Vivar, A. (2004). Purification of Enterocytozoon bieneusi spores from stool specimens by gradient and cell sorting techniques. Journal of Clinical Microbiology 42(7), 3256-3261.
Kumar, M. et al., "Cholesterol-Lowering Probiotics as Potential Biotherapeutics for Metabolic Diseases," Experimental Diabetes Research, 2012, Article ID 902917, 14 pages, vol. 2012.
Kump, P.K., Gröchenig, H.-P., Lackner, S., Trajanoski, S., Reicht, G., Hoffmann, K.M., Deutschmann, A., Wenzl, H.H., Petritsch, W., Krejs, G.J., et al. (2013). Alteration of intestinal dysbiosis by fecal microbiota transplantation does not induce remission in patients with chronic active ulcerative colitis. Inflamm. Bowel Dis. 19(10), 2155-2165.
Kunde, S., Pham, A, Bonczyk, S., Crumb, T., Duba, M., Conrad, H., JR, Cloney, D., and Kugathasan, S. (2013). Safety, tolerability, and clinical response after fecal transplantation in children and young adults with ulcerative colitis. J. Pediatr. Gastroenterol. Nutr. 56(6), 597-601.
Landy, J., Al-Hassi, H.O., McLaughlin, S.D., Walker, A.W., Ciclitira, P.J., Nicholls, R.J., Clark, S.K., and Hart, A.L. (2011). Review article: faecal transplantation therapy for gastrointestinal disease. Alimentary Pharmacology & Therapeutics 34(4), 409-415.
Lawley, T.D., Clare, S., Walker, A.W., Stares, M.D., Connor, T.R., Raisen, C., Goulding, D., Rad, R., Schreiber, F., Brandt, C., et al. (2012). Targeted Restoration of the Intestinal Microbiota with a Simple, Defined Bacteriotherapy Resolves Relapsing Clostridium difficile Disease in Mice. PLoS Pathog 8(10), e1002995.
Lawson, P.A., Song, Y., Liu, C., Molitoris, D.R., Vaisanen, M.-L., Collins, M.D., and Finegold, S.M. (2004). *Anaerotruncus colihominis* gen. nov., sp. nov., from human faeces. Int J Syst Evol Microbiol 54(2), 413-417.
Lee, I.-K., and Liu, J.-W. (2006). Clinical characteristics and risk factors for mortality in Morganella morganii bacteremia. J Microbiol Immunol Infect 39(4), 328-334.
Lee, J.S., Cha, D.S., and Park, H.J. (2004). Survival of Freeze-Dried Lactobacillus bulgaricus KFRI 673 in Chitosan-Coated Calcium Alginate Microparticles. J. Agric. Food Chem. 52(24), 7300-7305.
Lee, M., Hesek, D., Shah, I.M., Oliver, A.G., Dworkin, J., and Mobashery, S. (2010). Synthetic peptidoglycan motifs for germination of bacterial spores. Chembiochem 11(18), 2525-2529.
Lehar, J. (2007). Chemical combination effects predict connectivity in biological systems, Molecular Systems Biology, pp. 1-14, vol. 3, Article No. 80.

(56) References Cited

OTHER PUBLICATIONS

Lemon, K.P., Armitage, G.C., Relman, D.A., and Fischbach, M.A. (2012). Microbiota-Targeted Therapies: An Ecological Perspective. Science Translational Medicine 4(137), 137rv5-137rv5.

Leslie, S.B., Israeli, E., Lighthart, B., Crowe, J.H., and Crowe, L.M. (1995). Trehalose and sucrose protect both membranes and proteins in intact bacteria during drying. Applied and Environmental Microbiology 61(10), 3592-3597.

Li, A-D. et al., "Clinical Features and Bacterial Culture on Stools of Patients with Acute Diarrhea," Chinese Journal of Health Laboratory Technology, Mar. 10, 2012, pp. 559-561, vol. 2, No. 6.

Liggins, M., Ramirez, N., Magnuson, N., and Abel-Santos, E. (2011). Progesterone analogs influence germination of Clostridium sordellii and Clostridium difficile spores in vitro. J. Bacteriol. 193(11), 2776-2783.

Lindsay, J.A., Beaman, T.C., and Gerhardt, P. (1985). Protoplast water content of bacterial spores determined by buoyant density sedimentation. J. Bacteriol. 163(2), 735-737.

Liu, K., Linder, C.R., and Warnow, T. (2011). RAxML and FastTree: Comparing Two Methods for Large-Scale Maximum Likelihood Phylogeny Estimation. PLoS ONE 6(11), e27731.

Livingston, S.J., Kominos, S.D., and Yee, R.B. (1978). New medium for selection and presumptive identification of the Bacteroides fragilis group. J. Clin. Microbiol. 7(5), 448-453.

Logan, N.A., "Bacillus and Relatives in Foodborne Illness," Journal of Applied Microbiology, Mar. 20, 2012, pp. 417-429, vol. 112, No. 3.

Lopetuso, L.R., Scaldaferri, F., Petito, V., and Gasbarrini, A. (2013). Commensal Clostridia: leading players in the maintenance of gut homeostasis. Gut Pathogens 5(1), 23.

Lodish, H. et al., "Viruses: Structure, Function, and Uses," Molecular Cell Biology, 4th Edition, 2000, pp. 1-12.

Lozupone, C., Faust, K., Raes, J., Faith, J.J., Frank, D.N., Zaneveld, J., Gordon, J.I., and Knight, R. (2012). Identifying genomic and metabolic features that can underlie early successional and opportunistic lifestyles of human gut symbionts. Genome Res 22(10), 1974-1984.

Malik, K.A. (1988). A new freeze-drying method for the preservation of nitrogen-fixing and other fragile bacteria. Journal of Microbiological Methods 8(5), 259-271.

Manafi, M. Handbook of Culture Media for Food and Water Microbiology, 3rd Edition, Janet E.L. Corry et al., 2012, pp. 223-260.

Manichanh, C. (2006). Reduced diversity of faecal microbiota in Crohn's disease revealed by a metagenomic approach. Gut 55(2), 205-211.

Matsuda, K. et al., "Sensitive Quantitative Detection of Commensal Bacteria by rRNA-Targeted Reverse Transcription-PCR," Applied and Environmental Microbiology, Jan. 2007, pp. 32-39, vol. 73, No. 1.

Mbithi, J.N., Springthorpe, V.S., and Sattar, S.A. (1990). Chemical disinfection of hepatitis A virus on environmental surfaces. Applied and Environmental Microbiology 56(11), 3601-3604.

McFarland, L.V., "Use of Probiotics to Correct Dysbiosis of Normal Microbiota Following Disease or Disruptive Events: A Systematic Review," BMJ Open, 2014, pp. 1-18, vol. 4.

McFarland, L.V. et al., "Pharmaceutical Probiotics for the Treatment of Anaerobic and Other Infections," Anaerobe, Jan. 1997, pp. 73-78, vol. 3, No. 2-3.

McGuire, G., Denham, M.C., and Balding, D.J. (2001). Models of Sequence Evolution for DNA Sequences Containing Gaps. Mol Biol Evol 18(4), 481-490.

McNulty, N.P., Yatsunenko, T., Hsiao, A., Faith, J.J., Muegge, B.D., Goodman, A.L., Henrissat, B., Oozeer, R., Cools-Portier, S., Gobert, G., et al. (2011). The impact of a consortium of fermented milk strains on the gut microbiome of gnotobiotic mice and monozygotic twins. Sci Transl Med 3(106), 106ra106.

Mevissen-Verhage, E.A., Marcelis, J.H., Vos, M.N. De, Amerongen, W.C.H., and Verhoef, J. (1987). Bifidobacterium, Bacteroides, and Clostridium spp. in fecal samples from breast-fed and bottle-fed infants with and without iron supplement. J. Clin. Microbiol. 25(2), 285-289.

Mexican Office Action, Mexican Application No. MX/a/2015/006491, dated Jun. 25, 2018, 8 pages, (with concise explanation of relevance).

Mexican Office Action, Mexican Application No. MX/a/2015/009991, dated Jul. 16, 2018, (with concise explanation of relevance).

Miller, R.S., and Hoskins, L.C. (1981). Mucin degradation in human colon ecosystems. Fecal population densities of mucin-degrading bacteria estimated by a "most probable number" method. Gastroenterology 81(4), 759-765.

Mireau, I. et al., "Industrial-Scale Production and Purification of a Heterologous Protein in Lactococcus Lactis Using the Nisin-Controlled Gene Expression System NICE: The Case of Lysostaphin," Microbial Cell Factories, May 27, 2005, pp. 1-9, vol. 4, No. 15.

Miyamoto-Shinohara, Y., Sukenobe, J., Imaizumi, T., Nakahara, T., and Others (2008). Survival of freeze-dried bacteria. The Journal of General and Applied Microbiology 54(1), 9.

Momose, Y. et al., "16S rRNA Gene Sequence-Based Analysis of Clostridia Related to Conversion of Germfree Mice to the Normal State," Journal of Applied Microbiology, 2009, pp. 2088-2097, vol. 107.

Morgan, C.A., Herman, N., White, P.A., and Vesey, G. (2006). Preservation of micro-organisms by drying; A review. Journal of Microbiological Methods 66(2), 183-193.

Murri, M., Leiva, I., Gomez-Zumaquero, J.M., Tinahones, F.J., Cardona, F., Soriguer, F., and Queipo-Ortuño, M.I. (2013). Gut microbiota in children with type 1 diabetes differs from that in healthy children: a case-control study. BMC Med 11(1), 1-12.

Myllyluoma, E. et al., "Effects of Multispecies Probiotic Combination on Helicobacter pylori Infection in Vitro," Clinical and Vaccine Immunology, Sep. 2008, pp. 1472-1482, vol. 15, No. 9.

Naaber P et al "Inhibition of Clostridium difficile strains by intestinal *Lactobacillus* species" Journal of Medical Microbiology, 2004, pp. 551-554, vol. 53.

New Zealand First Examination Report, New Zealand Application No. 709392, dated Oct. 5, 2015, 7 pages.

New Zealand First Examination Report, New Zealand Application No. 711771, dated Nov. 23, 2015, 6 pages.

New Zealand First Examination Report, New Zealand Application No. 711773, dated Nov. 24, 2015, 6 pages.

New Zealand Second Examination Report, New Zealand Application No. 709392, dated Jun. 9, 2016, 7 pages.

New Zealand Third Examination Report, New Zealand Application No. 711771, dated Nov. 4, 2016, 4 pages.

New Zealand First Examination Report, New Zealand Application No. 713298, dated Feb. 28, 2017, 6 pages.

New Zealand Examination Report, New Zealand Application No. 713298, dated Sep. 26, 2017, 5 pages.

New Zealand Third Examination Report, New Zealand Application No. 713298, dated Feb. 15, 2018, 6 pages.

New Zealand Fourth Examination Report, New Zealand Application No. 713298, dated Mar. 15, 2018, 2 pages.

Nicholson, W.L., and Law, J.F. (1999). Method for purification of bacterial endospores from soils: UV resistance of natural Sonoran desert soil populations of< i> Bacillus</i> spp. with reference to< i> B. subtilis</i> strain 168. Journal of Microbiological Methods 35(1), 13-21.

NIH human microbiome project. <http://www.hmpdacc.org/> Accessed Mar. 27, 2014.

Nishio, J., Atarashi, K., Tanoue, T., Baba, M., Negishi, H., Yanai, H., Honda, K., Benoist, C., Mathis, D., and Taniguchi, T. (2013). Impact of TCR repetoire on intestinal homeostasis (Taos, NM).

Nitert, M.D., Barrett, H.L., Foxcroft, K., Tremellen, A., Wilkinson, S., Lingwood, B., Tobin, J.M., McSweeney, C., O'Rourke, P., McIntyre, H.D., et al. (2013). Spring: an RCT study of probiotics in the prevention of gestational diabetes mellitus in overweight and obese women. BMC Pregnancy and Childbirth 13(1), 50.

Noack, J., Kleessen, B., Proll, J., Dongowski, G., and Blaut, M. (1998). Dietary guar gum and pectin stimulate intestinal microbial polyamine synthesis in rats. J. Nutr. 128(8), 1385-1391.

(56) References Cited

OTHER PUBLICATIONS

Nyangale, et al., "Gut Microbial Activity, Implications for Health and Disease: the Potential Role of Metabolite Analysis," J. Proteome Res., 2012, pp. 5573-5585. vol. 11, No. 12.

O'Hara, C.M., Brenner, F.W., and Miller, J.M. (2000). Classification, identification, and clinical significance of Proteus, Providencia, and Morganella. Clin. Microbiol. Rev. 13(4), 534-546.

Okada, Y., Setoyama, H., Matsumoto, S., Imaoka, A., Nanno, M., Kawaguchi, M., and Umesaki, Y. (1994). Effects of fecal microorganisms and their chloroform-resistant variants derived from mice, rats, and humans on immunological and physiological characteristics of the intestines of ex-germfree mice. Infect. Immun. 62(12), 5442-5446.

Olle, B. (2013). Medicines from microbiota. Nat. Biotechnol. 31(4), 309-315.

Openbiome. Quality metrics. <http://static.squarespace.com/static/50e0c29ae4b0a05702af7e6a/t/52e19689e4b0b28f802c9b4e/1390517129976/OpenBiome%20Quality%20Metrics.pdf> Accessed Mar. 21, 2014.

Owens, C., Broussard, E., and Surawicz, C. (2013). Fecal microbiota transplantation and donor standardization. Trends in Microbiology 21(9), 443-445.

Paine, R.T. (1969). A note on trophic complexity and community stability. American Naturalist 103(929), 91-93.

Palmfeldt, J., and Hahn-Hägerdal, B. (2000). Influence of culture pH on survival of <i> Lactobacillus reuteri</i> subjected to freeze-drying. International Journal of Food Microbiology 55(1), 235-238.

Pamer, E.G. (2014). Fecal microbiota transplantation: effectiveness, complexities, and lingering concerns. Mucosal Immunology 7(2), 210-214.

Papadimitriou, K. et al., "Discovering Probiotic Microorganisms: In Vitro, In Vivo, Genetic and Omics Approaches," Frontiers in Microbiology, Feb. 17, 2015, pp. 1-28, vol. 6, Article 58.

Paredes-Sabja, D., Udompijitkul, P., and Sarker, M.R. (2009). Inorganic phosphate and sodium ions are cogerminants for spores of Clostridium perfringens type A food poisoning-related isolates. Appl. Environ. Microbiol. 75(19), 6299-6305.

Path Vaccine and Pharmaceutical Technologies Group. Summary of stability data for investigational formulations of vaccines. <http://www.path.org/publications/files/TS_vaccine_stability_table_invest.pdf> Accessed Mar. 21, 2014.

PCT International Search Report and Written Opinion, PCT Application No. PCT/US14/14744, dated May 21, 2014, 36 pages.

PCT International Search Report and Written Opinion, PCT Application No. PCT/US14/14747, dated Jun. 13, 2014, 27 pages.

PCT International Search Report and Written Opinion, PCT Application No. PCT/US14/14738, dated Jul. 30, 2014, 32 pages.

PCT International Search Report and Written Opinion, PCT Application No. PCT/US14/14745, dated Jul. 30, 2014, 31 pages.

PCT Invitation to Pay Additional Fees, PCT Application No. PCT/US14/14745, dated May 16, 2014, 2 pages.

PCT International Search Report and Written Opinion, PCT Application No. PCT/US13/71758, dated May 5, 2014, 45 pages.

PCT Invitation to Pay Additional Fees, PCT Application No. PCT/US14/70684, dated Mar. 24, 2015, 2 pages.

PCT International Search Report and Written Opinon, PCT Application No. PCT/US2014/067491, dated Apr. 2, 2015, 14 pages.

PCT International Search Report and Written Opinion, PCT Application No. PCT/US14/70684, dated Jun. 10, 2015, 24 pages.

PCT Invitation to Pay Additional Fees, PCT Application No. PCT/US13/71758, dated Feb. 25, 2014, 4 pages.

PCT Invitation to Pay Additional Fees, PCT Application No. PCT/US2014/014738, dated May 16, 2014, 2 pages.

PCT International Search Report and Written Opinion, PCT Application No. PCT/US2014/030817, dated Dec. 5, 2014, 16 pages.

PCT Invitation to Pay Additional Fees, PCT Application No. PCT/US2014/030817, dated Sep. 8, 2014, 5 pages.

PCT International Search Report and Written Opinion, PCT Application No. PCT/US2014/029539, dated Oct. 10, 2014, 17 pages.

PCT Invitation to Pay Additional Fees, PCT Application No. PCT/US14/29539, dated Jul. 31, 2014, 3 pages.

Peck, M.W. et al., "Development and Application of a New Method for Specific and Sensitive Enumeration of Spores of Nonproteolytic Clostridium Botulinum Types B, E and F in Foods and Food Materials," Applied and Environmental Microbiology, Oct. 2010, pp. 6607-6614, vol. 76, No. 19.

Pehkonen, K.S., Roos, Y.H., Miao, S., Ross, R.P., and Stanton, C. (2008). State transitions and physicochemical aspects of cryoprotection and stabilization in freeze-drying of Lactobacillus rhamnosus GG (LGG). Journal of Applied Microbiology 104(6), 1732-1743.

Peighambardoust, S.H., Golshan Tafti, A., and Hesari, J. (2011). Application of spray drying for preservation of lactic acid starter cultures: a review. Trends in Food Science & Technology 22(5), 215-224.

Pellegrino, P.M., Fell Jr., N.F., and Gillespie, J.B. (2002). Enhanced spore detection using dipicolinate extraction techniques. Analytica Chimica Acta 455(2), 167-177.

Perez, F., Pultz, M.J., Endimiani, A., Bonomo, R.A., and Donskey, C.J. (2011). Effect of antibiotic treatment on establishment and elimination of intestinal colonization by KPC-producing Klebsiella pneumoniae in mice. Antimicrob. Agents Chemother. 55(6), 2585-2589.

Perez, J., Springthorpe, V.S., and Sattar, S.A. (2011). Clospore: a liquid medium for producing high titers of semi-purified spores of Clostridium difficile. J AOAC Int 94(2), 618-626.

Peterson, D.A. et al., "Metagenomic Approaches for Defining the Pathogenesis of Inflammatory Bowel Diseases," Cell Host Microbe, Jun. 2008, pp. 417-427, vol. 3, No. 6.

Petrof, E.O., Claud, E.C., Gloor, G.B., and Allen-Vercoe, E. (2013a). Microbial ecosystems therapeutics: a new paradigm in medicine? Beneficial Microbes 4(1), 53-65.

Petrof, E.O., Gloor, G.B., Vanner, S.J., Weese, S.J., Carter, D., Daigneault, M.C., Brown, E.M., Schroeter, K., and Allen-Vercoe, E. (2013b). Stool substitute transplant therapy for the eradication of Clostridium difficile infection: "RePOOPulating" the gut, Microbiome, Jan. 9, 2013, p. 3, vol. 1, No. 1.

Pharmacy, 2011, pp. 79-86, vol. 62, No. 3. [With English Main Sub-Points].

Picot, A., and Lacroix, C. (2004). Encapsulation of bifidobacteria in whey protein-based microcapsules and survival in simulated gastrointestinal conditions and in yoghurt. International Dairy Journal 14(6), 505-515.

Pillai, A. et al., "Probiotics for Treatment of Clostridium Difficile-Associated Colitis in Adults (Review)," Cochrane Database of Systematic Reviews, The Cochrane Collaboration, John Wiley & Sons, Ltd., 2010, 18 pages.

Pinn, D. et al. (2013). Follow-up Study of Fecal Microbiota Transplantation (FMT) for the Treatment of Refractory Irritable Bowel Syndrome (IBS). Abstract ACG 2013.

Plassart, C. et al., "First Case of Intra-Abdominal Infection with Clostridium Disporicum," Anaerobe, 2013, pp. 77-78, vol. 19.

Postgate, J.R., and Hunter, J.R. (1961). On the Survival of Frozen Bacteria. J Gen Microbiol 26(3), 367-378.

"Potentials of Probiotics in Pig Nutrition," AllAboutFeed News, Jan. 31, 2007, 6 pages.

Prilassnig, M. et al., "Are Probiotics Detectable in Human Feces After Oral Uptake by Healthy Volunteers?" The Middle European Journal of Medicine, Aug. 2007, pp. 456-462, vol. 119, Nos. 15-16.

Prioult, G. et al., "Effect of Probiotic Bacteria on Induction and Maintenance of Oral Tolerance to β-Lactoglobulin in Gnotobiotic Mice," Clinical and Diagnostic Laboratory Immunology, Sep. 2003, pp. 787-792, vol. 10, No. 5.

Pultz, N.J., Hoyen, C.K., and Donskey, C.J. (2004). Inhibition of methicillin-resistant *Staphylococcus aureus* by an in vitro continuous-flow culture containing human stool microflora. FEMS Microbiology Letters 241(2), 201-205.

Queenan, A.M., and Bush, K. (2007). Carbapenemases: the Versatile β-Lactamases. Clin. Microbiol. Rev. 20(3), 440-458.

Quigley, E.M.M. et al., "Small Intestinal Bacterial Overgrowth: Roles of Antibiotics, Prebiotics and Probiotics," Gastroenterology, Feb. 2006, pp. 78-90, vol. 130.

(56) References Cited

OTHER PUBLICATIONS

Raibaud, P., Ducluzeau, R., Dubos, F., Hudault, S., Bewa, H., and Muller, M.C. (1980). Implantation of bacteria from the digestive tract of man and various animals into gnotobiotic mice. Am J Clin Nutr 33(11), 2440-2447.
Ramirez, N., and Abel-Santos, E. (2010). Requirements for germination of Clostridium sordellii spores in vitro. J. Bacteriol. 192(2), 418-425.
Rao, A.V., Shiwnarain, N., and Maharaj, I. (1989). Survival of Microencapsulated Bifidobacterium pseudolongum in Simulated Gastric and Intestinal Juices. Canadian Institute of Food Science and Technology Journal 22(4), 345-349.
Reeves, A.E., Koenigsknecht, M.J., Bergin, I.L., and Young, V.B. (2012). Suppression of Clostridium difficile in the Gastrointestinal Tracts of Germfree Mice Inoculated with a Murine Isolate from the Family Lachnospiraceae. Infection and Immunity 80(11), 3786-3794.
Rehman, A. et al., "Effect of Probiotics and Antibiotics on the Intestinal Homeostasis in a Computer Controlled Model of the Large Intestine," BMC Microbiology, 2012, 10 pages, vol. 12, No. 47.
Rexroad, J., Wiethoff, C.M., Jones, L.S., and Middaugh, C.R. (2002). Lyophilization and the thermostability of vaccines. Cell Preservation Technology 1(2), 91-104.
Ridaura, V.K., Faith, J.J., Rey, F.E., Cheng, J., Duncan, A.E., Kau, A.L., Griffin, N.W., Lombard, V., Henrissat, B., Bain, J.R., et al. (2013). Gut Microbiota from Twins Discordant for Obesity Modulate Metabolism in Mice. Science 341(6150), 1241214-1241214.
Robinson, I.M. et al., "Emendation of Acetivibrio and Description of Acetivibrio ethanolgignens, a New Species from the Colons of Pigs with Dysentery," International Journal of Systematic Bacteriology, Jul. 1981, pp. 333-338, vol. 31, No. 3.
Rode, L.J., and Foster, J.W. (1961). Germination of bacterial spores with alkyl primary amines1. J Bacteriol 81(5), 768-779.
Roffe, C. (1996). Biotherapy for antibiotic-associated and other diarrhoeas. J. Infect. 32(1), 1-10.
Rohlke, F., Surawicz, C.M., and Stollman, N. (2010). Fecal flora reconstitution for recurrent Clostridium difficile infection: results and methodology. J. Clin. Gastroenterol. 44(8), 567-570.
Rosen, D.L., Sharpless, C., and McGown, L.B. (1997). Bacterial Spore Detection and Determination by Use of Terbium Dipicolinate Photoluminescence. Anal. Chem. 69(6), 1082-1085.
Russell, A.D., "The Destruction of Bacterial Spores," 1982, pp. 191-193.
Russian Office Action, Russian Application No. 2015137399, dated Mar. 22, 2016, 8 pages.
Russian Office Action, Russian Application No. 201537399, dated Aug. 15, 2016, 8 pages.
Russian First Office Action, Russian Patent Application No. 2015124366, dated Dec. 13, 2016, 12 pages.
Russian Second Office Action, Russian Patent Application No. 2015137399, dated Mar. 14, 2017, 8 pages.
Russian Second Office Action, Russian Application No. 2015124366, dated Feb. 12, 2018, 10 pages.
Sack, D.A., Shimko, J., Sack, R.B., Gomes, J.G., MacLeod, K., O'Sullivan, D., and Spriggs, D. (1997). Comparison of alternative buffers for use with a new live oral cholera vaccine, Peru-15, in outpatient volunteers. Infect. Immun. 65(6), 2107-2111.
Sacks, L.E., and Alderton, G. (1961). Behavior of bacterial spores in aqueous polymer two-phase systems. J. Bacteriol. 82, 331-341.
Sahlström, L., Bagge, E., Emmoth, E., Holmqvist, A., Danielsson-Tham, M.-L., and Albihn, A. (2008). A laboratory study of survival of selected microorganisms after heat treatment of biowaste used in biogas plants. Bioresour. Technol. 99(16), 7859-7865.
Santivarangkna, C., Kulozik, U., and Foerst, P. (2007). Alternative Drying Processes for the Industrial Preservation of Lactic Acid Starter Cultures. Biotechnology Progress 23(2), 302-315.
Sattar, S.A., Jason, T., Bidawid, S., and Farber, J. (2000). Foodborne spread of hepatitis A: recent studies on virus survival, transfer and inactivation. The Canadian Journal of Infectious Diseases 11(3), 159.
Savaiano, D.A., Ritter, A.J., Klaenhammer, T., Walker, M.R., Carlson, H.L.F., and Ruckle, J. (2012). A Novel High Purity Short-Chain Galacto-Oligosaccharide (RP-G28) Improves Lactose Digestion and Symptoms of Lactose Intolerance. Gastroenterology 142(5), S-182.
Savaiano, D.A., Ritter, A.J., Klaenhammer, T.R., Walker, W.A., James, G.M., Longcore, A.T., Chandler, J.R., and Foyt, H.L. (2013). Improving lactose digestion and symptoms of lactose intolerance with a novel galacto-oligosaccharide (RP-G28): a randomized, double-blind clinical trial. Nutrition Journal 12(1), 160.
Seale, R.B., Flint, S.H., McQuillan, A.J., and Bremer, P.J. (2008). Recovery of Spores from Thermophilic Dairy Bacilli and Effects of Their Surface Characteristics on Attachment to Different Surfaces. Appl Environ Microbiol 74(3), 731-737.
Seo, M., Inoue, I., Tanaka, M., Matsuda, N., Nakano, T., Awata, T., Katayama, S., Alpers, D.H., and Komoda, T. (2013). Clostridium butyricum MIYAIRI 588 improves high-fat diet-induced non-alcoholic fatty liver disease in rats. Dig. Dis. Sci. 58(12), 3534-3544.
Setlow, B., Cowan, A. E., and Setlow, P. (2003). Germination of spores of Bacillus subtilis with dodecylamine. Journal of Applied Microbiology 95(3), 637-648.
Setlow, B., Yu, J., Li, Y.-Q., and Setlow, P. (2013). Analysis of the germination kinetics of individual Bacillus subtilis spores treated with hydrogen peroxide or sodium hypochlorite. Letters in Applied Microbiology 57(4), 259-265.
Setlow, B. et al., "Mechanisms of Killing Spores of Bacillus Subtilis by Acid, Alkali and Ethanol," Journal of Applied Microbiology, 2002, pp. 362-375, vol. 92.
Shafaat, H.S., and Ponce, A. (2006). Applications of a Rapid Endospore Viability Assay for Monitoring UV Inactivation and Characterizing Arctic Ice Cores. Appl Environ Microbiol 72(10), 6808-6814.
Shah, I.M., Laaberki, M.-H., Popham, D.L., and Dworkin, J. (2008). A eukaryotic-like Ser/Thr kinase signals bacteria to exit dormancy in response to peptidoglycan fragments. Cell 135(3), 486-496.
Shah, N.P., "Symposium: Probiotic Bacteria: Probiotic Bacteria: Selective Enumeration and Survival in Dairy Foods," Oct. 7, 1999, 14 pages.
Shah, N.P. et al., "Microencapsulation of Probiotic Bacteria and Their Survival in Frozen Fermented Dairy Desserts," The Australian Journal of Dairy Technology, Oct. 2000, pp. 139-144, vol. 55, No. 3.
Shah, S. (2012). Clostridium difficile in inflammatory Bowel Disease: a dangerous mix (Clostridium difficile Symposium, Miriam Hospital, Providence, RI).
Shahinas, D., Silverman, M., Sittler, T., Chiu, C., Kim, P., Allen-Vercoe, E., Weese, S., Wong, A., Low, D.E., and Pillai, D.R. (2012). Toward an Understanding of Changes in Diversity Associated with Fecal Microbiome Transplantation Based on 16S rRNA Gene Deep Sequencing. mBio 3(5), e00338-12-e00338-12.
Sharpe, E.S., Nickerson, K.W., Bulla Jr, L.A., and Aronson, J.N. (1975). Separation of spores and parasporal crystals of Bacillus thuringiensis in gradients of certain x-ray contrasting agents. Applied Microbiology 30(6), 1052.
Sheptulin, A.A., "Refractory and Relapsing Forms of Clostridium difficile—Associated Colitis," www.gastro-j.ru, 2011, pp. 50-53 (with English abstract).
Sheu, T.-Y., Marshall, R.T., and Heymann, H. (1993). Improving Survival of Culture Bacteria in Frozen Desserts by Microentrapment. Journal of Dairy Science 76(7), 1902-1907.
Siaterlis, A., Deepika, G., and Charalampopoulos, D. (2009). Effect of culture medium and cryoprotectants on the growth and survival of probiotic lactobacilli during freeze drying. Letters in Applied Microbiology 48(3), 295-301.
Sigma-Tau. VSL#3. <http://www.vsl3.com/> Accessed Mar. 21, 2014.

(56) References Cited

OTHER PUBLICATIONS

Skaar, E., "The Battle for Iron Between Bacterial Pathogens and Their Vertebrate Hosts," PLoS Pathog., Aug. 12, 2010, pp. 1-4, vol. 6, No. 8.

Sleator, R.D. et al.,"Designer Probiotics: A Potential Therapeutic for Clostridium difficile?" Journal of Medical Microbiology, Jun. 2008, pp. 793-794, vol. 57, No. 6.

Snitkin, E.S., Zelazny, A.M., Thomas, P.J., Stock, F., Henderson, D.K., Palmore, T.N., and Segre, J.A. (2012). Tracking a Hospital Outbreak of Carbapenem-Resistant Klebsiella pneumoniae with Whole-Genome Sequencing. Sci Transl Med 4(148), 148ra116-148ra116.

Solanki, H.K., Pawar, D.D., Shah, D.A., Prajapati, V.D., Jani, G.K., Mulla, A.M., and Thakar, P.M. (2013). Development of Microencapsulation Delivery System for Long-Term Preservation of Probiotics as Biotherapeutics Agent. BioMed Research International 2013, 1-21.

SOP No. MB-28-00. <http://www.epa.gov/pesticides/methods/MB-28-00.pdf> Accessed Mar. 27, 2014.

Sorg, J.A., and Sonenshein, A.L. (2008). Bile Salts and Glycine as Cogerminants for Clostridium difficile Spores. J Bacteriol 190(7), 2505-2512.

Sow, H., Desbiens, M., Morales-Rayas, R., Ngazoa, S.E., and Jean, J. (2011). Heat Inactivation of Hepatitis A Virus and a Norovirus Surrogate in Soft-Shell Clams (*Mya arenaria*). Foodborne Pathogens and Disease 8(3), 387-393.

Stams, A.J.M., Van Dijk, J.B., Dijkema, C., and Plugge, C.M. (1993). Growth of Syntrophic Propionate-Oxidizing Bacteria with Fumarate in the Absence of Methanogenic Bacteria. Appl Environ Microbiol 59(4), 1114-1119.

Stefka, A.T. et al., "Commensal Bacteria Protect Against Food Allergen Sensitization," PNAS, Sep. 9, 2014, pp. 13145-13150, vol. 111, No. 36.

Stevens, K.A., and Jaykus, L.-A. (2004). Bacterial Separation and Concentration from Complex Sample Matrices: A Review. Critical Reviews in Microbiology 30(1), 7-24.

Su, W.J., Waechter, M.J., Bourlioux, P., Dolegeal, M., Fourniat, J., and Mahuzier, G. (1987). Role of volatile fatty acids in colonization resistance to Clostridium difficile in gnotobiotic mice. Infect. Immun. 55(7), 1686-1691.

Talwalkar, A., and Kailasapathy, K. (2003). Effect of microencapsulation on oxygen toxicity in probiotic bacteria. Australian Journal of Dairy Technology 58(1), 36-39.

Tamir, H., and Gilvarg, C. (1966). Density Gradient Centrifugation for the Separation of Sporulating Forms of Bacteria. J. Biol. Chem. 241(5), 1085-1090.

Tanaka, M. et al., "Increased Fasting Plasma Ghrelin Levels in Patients with Bulimia Nervosa," European Journal of Endocrinology, Jun. 2002, pp. 1-3, vol. 146.

Taur, Y., and Pamer, E.G. (2014). Harnessing Microbiota to Kill a Pathogen: Fixing the microbiota to treat Clostridium difficile infections. Nature Medicine 20(3), 246-247.

Taur, Y., Xavier, J.B., Lipuma, L., Ubeda, C., Goldberg, J., Gobourne, A., Lee, Y.J., Dubin, K.A., Socci, N.D., Viale, A., et al. (2012). Intestinal Domination and the Risk of Bacteremia in Patients Undergoing Allogeneic Hematopoietic Stem Cell Transplantation. Clin Infect Dis 55(7), 905-914.

Technical Data, HiMedia Laboratories Pvt. Ltd., M581BP, 2011, pp. 1-2.

The Human Microbiome Project Consortium (2012). Structure, function and diversity of the healthy human microbiome. Nature 486(7402), 207-214.

Theriot, C.M. et al., "Antibiotic-Induced Shifts in the Mouse Gut Microbiome and Metabolome Increase Susceptibility to Clostridium difficile Infection," Nature Communications, Jan. 20, 2014, pp. 1-10, vol. 5.

Tisa, L.S., Koshikawa, T., and Gerhardt, P. (1982). Wet and dry bacterial spore densities determined by buoyant sedimentation. Applied and Environmental Microbiology 43(6), 1307-1310.

Tvede, M., and Rask-Madsen, J. (1989). Bacteriotherapy for chronic relapsing Clostridium difficile diarrhoea in six patients. Lancet 1(8648), 1156-1160.

Ubeda, C., Bucci, V., Caballero, S., Djukovic, A., Toussaint, N.C., Equinda, M., Lipuma, L., Ling, L., Gobourne, A., No, D., et al. (2013). Intestinal Microbiota Containing *Barnesiella* Species Cures Vancomycin-Resistant Enterococcus faecium Colonization. Infect. Immun. 81(3), 965-973.

Ubeda, C., Taur, Y., Jenq, R.R., Equinda, M.J., Son, T., Samstein, M., Viale, A., Socci, N.D., Van Den Brink, M.R.M., Kamboj, M., et al. (2010). Vancomycin-resistant Enterococcus domination of intestinal microbiota is enabled by antibiotic treatment in mice and precedes bloodstream invasion in humans. Journal of Clinical Investigation 120(12), 4332-4341.

United States Office Action, U.S. Appl. No. 14/313,828, dated Aug. 13, 2014, 5 pages.

United States Office Action, U.S. Appl. No. 14/313,828, dated Dec. 10, 2014, 7 pages.

United States Office Action, U.S. Appl. No. 14/313,828, dated May 15, 2015, 11 pages.

United States Office Action, U.S. Appl. No. 14/221,190, dated Jul. 22, 2014, 19 pages.

United States Office Action, U.S. Appl. No. 14/091,201, dated Mar. 25, 2014, 19 pages.

United States Office Action, U.S. Appl. No. 14/197,044, dated Aug. 13, 2014, 5 pages.

United States Office Action, U.S. Appl. No. 14/592,481, dated Dec. 22, 2015, 21 pages.

United States Office Action, U.S. Appl. No. 15/068,438, dated Apr. 28, 2016, 9 pages.

United States Office Action, U.S. Appl. No. 14/884,655, dated May 5, 2016, 10 pages.

United States Office Action, U.S. Appl. No. 14/884,655, dated Aug. 17, 2016, 9 pages.

United States Office Action, U.S. Appl. No. 14/765,812, dated Aug. 25, 2016, 10 pages.

United States Office Action, U.S. Appl. No. 14/777,252, dated Nov. 3, 2016, 16 pages.

United States Office Action, U.S. Appl. No. 14/765,810, dated Jan. 23, 2017, 20 pages.

United States Office Action, U.S. Appl. No. 14/776,676, dated Mar. 23, 2017, 9 pages.

United States Office Action, U.S. Appl. No. 14/777,252, dated May 11, 2017, 9 pages.

United States Office Action, U.S. Appl. No. 14/777,252, dated Aug. 29, 2017, 16 pages.

United States Office Action, U.S. Appl. No. 15/104,873, dated Oct. 17, 2017, 7 pages.

United States Office Action, U.S. Appl. No. 15/039,007, dated Nov. 1, 2017, 13 pages.

United States Office Action, U.S. Appl. No. 14/765,812, dated Dec. 7, 2017, 10 pages.

United States Office Action, U.S. Appl. No. 14/765,810, dated Jan. 8, 2018, 8 pages.

United States Office Action, U.S. Appl. No. 14/765,810, dated Jan. 25, 2018, 11 pages.

United States Office Action, U.S. Appl. No. 14/765,814, dated Apr. 17, 2018, 15 pages.

United States Office Action, U.S. Appl. No. 15/359,439, dated Jun. 15, 2018, 14 pages.

United States Office Action, U.S. Appl. No. 14/776,676, dated Jun. 22, 2018, 16 pages.

United States Office Action, U.S. Appl. No. 15/039,007, dated Jun. 12, 2018, 9 pages.

Van Der Woude, M.W., and Baumler, A.J. (2004). Phase and Antigenic Variation in Bacteria. Clin Microbiol Rev 17(3), 581-611.

Van Immerseel, F. et al., "Butyric Acid-Producing Anaerobic Bacteria as a Novel Probiotic Treatment Approach for Inflammatory Bowel Disease," Journal of Medical Microbiology, JMM Editorial, 2010, pp. 141-143.

(56) References Cited

OTHER PUBLICATIONS

Van Kregten, E., Westerdaal, N.A., and Willers, J.M. (1984). New, simple medium for selective recovery of Klebsiella pneumoniae and Klebsiella oxytoca from human feces. J Clin Microbiol 20(5), 936-941.

Van Nood, E., Vrieze, A., Nieuwdorp, M., Fuentes, S., Zoetendal, E.G., De Vos, W.M., Visser, C.E., Kuijper, E.J., Bartelsman, J.F.W. M., Tijssen, J.G.P., et al. (2013). Duodenal Infusion of Donor Feces for Recurrent Clostridium difficile. New England Journal of Medicine 368(5), 407-415.

Vandenplas, Y., Veereman, G., Van Der Werff Ten Bosch, J., Goossens, A., Pierard, D., Samsom, J.N., and Escher, J.C. (2014). Fecal Microbial Transplantation in a One-Year-Old Girl with Early Onset Colitis—Caution Advised: Journal of Pediatric Gastroenterology and Nutrition 1.

Vidal, M., Forestier, C., Charbonnel, N., Henard, S., Rabaud, C., and Lesens, O. (2010). Probiotics and Intestinal Colonization by Vancomycin-Resistant Enterococci in Mice and Humans. J Clin Microbiol 48(7), 2595-2598.

Villano, S.A., Seiberling, M., Tatarowicz, W., Monnot-Chase, E., and Gerding, D.N. (2012). Evaluation of an Oral Suspension of VP20621, Spores of Nontoxigenic Clostridium difficile Strain M3, in Healthy Subjects. Antimicrobial Agents and Chemotherapy 56(10), 5224-5229.

Wagman, J., and Weneck, E.J. (1963). Preservation of bacteria by circulating-gas freeze drying. Applied Microbiology 11(3), 244-248.

Waites, W.M., and Wyatt, L.R. (1971). Germination of spores of Clostridium bifermentans by certain amino acids, lactate and pyruvate in the presence of sodium or potassium ions. J. Gen. Microbiol. 67(2), 215-222.

Waites, W.M., and Wyatt, L.R. (1974). The effect of pH, germinants and temperature on the germination of spores of Clostridium bifermentans. J. Gen. Microbiol. 80(1), 253-258.

Walker, A.W., and Lawley, T.D. (2012). Therapeutic modulation of intestinal dysbiosis. Pharmacological Research 69(1), 75-86.

Wang, M. et al., "Comparison of Bacterial Diversity Along the Human Intestinal Tract by Direct Cloning and Sequencing of 16S rRNA Genes," FEMS Microbiology Ecology, 2005, pp. 219-231, vol. 54.

Wang, S., and Curtiss III, R. (2014). Development of *Streptococcus pneumoniae* Vaccines Using Live Vectors. Vaccines 2(1), 49-88.

Weingarden, A.R., Chen, C., Bobr, A., Yao, D., Lu, Y., Nelson, V.M., Sadowsky, M.J., and Khoruts, A. (2013). Microbiota transplantation restores normal fecal bile acid composition in recurrent Clostridium difficile infection. AJP: Gastrointestinal and Liver Physiology 306(4), G310-G319.

Wiencek, K.M. et al., "Hydrophobicity of Bacillus and Clostridium Spores," Applied and Environmental Microbiology, Sep. 1990, pp. 2600-2605, vol. 56, No. 9.

Wilson, K.H., and Sheagren, J.N. (1983). Antagonism of toxigenic Clostridium difficile by nontoxigenic C. difficile. Journal of Infectious Diseases 147(4), 733.

Wilson, K.H., Silva, J., and Fekety, F.R. (1981). Suppression of Clostridium difficile by Normal Hamster Cecal Flora and Prevention of Antibiotic-Associated Cecitis. Infect Immun 34(2), 626-628.

Wilson, K. et al., "Role of Competition for Nutrients in Suppression of Clostridium difficile by the Colonic Microflora," Infection and Immunity, Oct. 1988, pp. 2610-2614, vol. 56, No. 10.

Woo, T.D.H., Oka, K., Takahashi, M., Hojo, F., Osaki, T., Hanawa, T., Kurata, S., Yonezawa, H., and Kamiya, S. (2011). Inhibition of the cytotoxic effect of Clostridium difficile in vitro by Clostridium butyricum MIYAIRI 588 strain. J. Med. Microbiol. 60(Pt 11), 1617-1625.

Wróbel, B. (2008). Statistical measures of uncertainty for branches in phylogenetic trees inferred from molecular sequences by using model-based methods. J. Appl. Genet. 49(1), 49-67.

Wroblewski, D., Hannett, G.E., Bopp, D.J., Dumyati, G.K., Halse, T.A., Dumas, N.B., and Musser, K.A. (2009). Rapid Molecular Characterization of Clostridium difficile and Assessment of Populations of C. difficile in Stool Specimens. Journal of Clinical Microbiology 47(7), 2142-2148.

Yamakawa, K. et al., "Enhancement of Clostridium difficile Toxin Production in Biotin-Limited Conditions," J. Med. Microbiol., Feb. 1996, pp. 111-114, vol. 44, No. 2.

Yamamura, H., Hayakawa, M., and Iimura, Y. (2003). Application of sucrose-gradient centrifugation for selective isolation of *Nocardia* spp. from soil. Journal of Applied Microbiology 95(4), 677-685.

Yang, W.-W., and Ponce, A. (2009). Rapid endospore viability assay of Clostridium sporogenes spores. International Journal of Food Microbiology 133(3), 213-216.

Yang, W.-W., and Ponce, A. (2011). Validation of a Clostridium Endospore Viability Assay and Analysis of Greenland Ices and Atacama Desert Soils. Appl. Environ. Microbiol. 77(7), 2352-2358.

Yang, W.-W., Crow-Willard, E.N., and Ponce, A. (2009). Production and characterization of pure Clostridium spore suspensions. J. Appl. Microbiol. 106(1), 27-33.

Yang, W.W. (2010). Fast Viability Assessment of Clostridium Spores Survival in Extreme Environments. PhD thesis California Institute of Technology.

Yi, X., and Setlow, P. (2010). Studies of the Commitment Step in the Germination of Spores of *Bacillus* Species. J. Bacteriol. 192(13), 3424-3433.

Yuguchi Hiroya et al., "Hakkonyuu/nyuusankin inryou to chounaikinsou "Fermented Milk/Lactic Acid Bacteria Beverages and Intestinal Bacterial Flora,"" New Food Industry, UDA, Moritaka, New Food Industry K.K., 1987, pp. 71-88, vol. 29, No. 7. [With English Subtitle Translations].

Yung, P.T., and Ponce, A. (2008). Fast Sterility Assessment by Germinable-Endospore Biodosimetry. Appl. Environ. Microbiol. 74(24), 7669-7674.

Yunoki, M., Tsujikawa, M., Urayama, T., Sasaki, Y., Morita, M., Tanaka, H., Hattori, S., Takechi, K., and Ikuta, K. (2003). Heat sensitivity of human parvovirus B19. Vox Sanguinis 84(3), 164-169.

Zeng, Y., Fan, H., Chiueh, G., Pham, B., Martin, R., Lechuga-Ballesteros, D., Truong, V.L., Joshi, S.B., and Middaugh, C.R. (2009). Towards development of stable formulations of a live attenuated bacterial vaccine: a preformulation study facilitated by a biophysical approach. Hum Vaccin 5(5), 322-331.

Zhao, J., Krishna, V., Moudgil, B., and Koopman, B. (2008). Evaluation of endospore purification methods applied to Bacillus cereus. Separation and Purification Technology 61(3), 341-347.

Abubucker, S.,et al., "Metabolic Reconstruction for Metagenomic Data and Its Application to the Human Microbiome.," Plos Computational Biology, 8(6):1002358, Public Library of Science,United States, (2012).

Ahmad, T.,et al., "Biomarkers of Myocardial Stress and Fibrosis as Predictors of Mode of Death in Patients With Chronic Heart Failure.," Jacc. Heart Failure, 2(3):260-268, Elsevier, United States, (Jun. 2014).

Arpaia et al., "Metabolites produced by commensal bacteria promote peripheral regulatory T-cell generation," Nature 504:451-455 (2013).

Arpaia, N., et al., "Metabolites Produced by Commensal Bacteria Promote Peripheral Regulatory T-cell Generation," Nature 504(7480):451-455, Nature Publishing Group, England (Dec. 2013).

ASBMT RFI 2016—Disease Classifications Corresponding to CIBMTR Classifications. 2016.

Atarashi et al., "Treg induction by a rationally selected mixture of Clostridia strains from the human microbiota," Nature 500:232-236 (2013).

Atta, "Gene therapy for liver regeneration: Experimental studies and prospects for clinical trials," World J Gastroenterol., 16(32):4019-4030 (2010).

Bacigalupo, A.,et al., "Defining the Intensity of Conditioning Regimens: Working Definitions.," Biology of Blood and Marrow Transplantation : Journal of the American Society for Blood and Marrow Transplantation, 15(12):1628-1633, Carden Jennings Publishing, United States, (Dec. 2009).

Bajaj, J.S.,et al., "Colonic Mucosal Microbiome Differs From Stool Microbiome in Cirrhosis and Hepatic Encephalopathy and is Linked to Cognition and Inflammation.," American Journal of Physiology.

(56) References Cited

OTHER PUBLICATIONS

Gastrointestinal and Liver Physiology, 303(6):75-85, American Physiological Society, United States, (Sep. 2012).
Barrasa, J.I., et al., "Bile Acids in the Colon, From Healthy to Cytotoxic Molecules.," Toxicology in Vitro : an International Journal Published in Association With Bibra, 27(2):964-977, Pergamon Press , England, (Mar. 2013).
Barrell, C.,et al., "Reduced-intensity Conditioning Allogeneic Stem Cell Transplantation in Pediatric Patients and Subsequent Supportive Care.," Oncology Nursing Forum, 39(6):451-458, Oncology Nursing Society,United States, (Nov. 2012).
Bartlett, J.G., et al., "Antibiotic-associated Pseudomembranous Colitis Due to Toxin-Producing Clostridia," The New England journal of medicine, 298(10):531-534, Massachusetts Medical Society, United States , (Mar. 1978).
Basler, M., et al., "Type Vi Secretion Requires a Dynamic Contractile Phage Tail-like Structure," Nature, 483(7388):182-186, Nature Publishing Group, England, (Feb. 2012 ).
Beelen et al., "Influence of Intestinal Bacterial Decontamination Using Metronidazole and Ciprofloxacin or Ciprofloxacin Alone on the Development of Acute Graft-Versus-Host Disease After Marrow Transplantation in Patients with Hematologic Malignancies: Final Results and Long-Term Follow-Up of an Open-Label Prospective Randomized Trial," Blood 93(10):3267-3275 (1999).
Begley et al., "Bile Salt Hydrolase Activity in Probiotics," Appl. Environ Microbial. 72(3): 1729-173 8 (2006).
Bernstein, H., et al., "Bile Acids as Carcinogens in Human Gastrointestinal Cancers.," Mutation research, 589(1):47-65, Elsevier, Netherlands, (Jan. 2005).
Bolger, A.M.,et al., "Trimmomatic: a Flexible Trimmer for Illumina Sequence Data.," Bioinformatics (Oxford, England), 30(15):2114-2120, Oxford University Press,England, (Aug. 2014).
Brandl et al., "Vancomycin-resistant enterococci exploit anti biotic-induced innate immune deficit,". Nature 455(7214):804-807, Nature Publishing Group, England (2008).
Britton, R.A., et al., "Role of the Intestinal Microbiota in Resistance to Colonization by Clostridium Difficile," Gastroenterology 146(6):1547-1553, W.B. Saunders, United States (May 2014).
Buffie, C. G., et al. , "Precision Microbiome Reconstitution Restores Bile Acid Mediated Resistance to Clostridium Difficile," Nature 517(7533):205-208, Nature Publishing Group, England (Jan. 2015).
Buffie, C.G., et al., "Profound Alterations of Intestinal Microbiota Following a Single Dose of Clindamycin Results in Sustained Susceptibility to Clostridium Difficile-induced Colitis," Infection and Immunity, 80(1):62-73, American Society for Microbiology, United States, (Jan. 2012 ).
Caporaso, J.G., et al., "QIIMEAllows Analysis of High-throughput Community Sequencing Data," Nature Methods, 7(5):335-336, Nature Publishing Group, United States, (May 2010 ).
Caporaso, J.G., et al., "Ultra-high-throughput Microbial Community Analysis on the Illumina Hiseq and Miseq Platforms," The Isme Journal, 6(8):1621-1624, Nature Publishing Group, England, (Aug. 2012).
Carlier, J.P., et al., "Proposal to Unify Clostridium Orbiscindens Winter et al. 1991 and Eubacterium Plautii (Séguin 1928) Hofstad and Aasjord 1982, With Description of *Flavonifractor plautii* Gen. Nov., Comb. Nov., and Reassignment of *Bacteroides capillosus* to *Pseudoflavonifractor capillosus* Gen. Nov., Comb. Nov.," International Journal of Systematic and Evolutionary Microbiology 60(Pt 3):585-590, Microbiology Society, England (Mar. 2010).
Chen, X., et al., "Overview of Clostridium Difficile Infection: Implications for China," Gastroenterology Report, 1(3):153-158, Oxford University Press and Science Digestive, England, (Nov. 2013).
Chen, W.,et al., "Human Intestinal Lumen and Mucosa-associated Microbiota in Patients With Colorectal Cancer.," Plos One, 7(6):39743, Public Library of Science,United States, (2012).
Chromek, M.,et al., "The Antimicrobial Peptide Cathelicidin Protects Mice From *Escherichia coli* 0157:h7-mediated Disease.," Plos One, 7(10):46476, Public Library of Science,United States, (2012).

Chung, H., et al., "Gut Immune Maturation Depends on Colonization With a Host-specific Microbiota," Cell 149(7):1578-1593, Cell Press, United States (Jun. 2012).
Clifford, R.J.,et al., "Detection of Bacterial 16s Rrna and Identification of Four Clinically Important Bacteria by Real-time Pcr.," Plos One, 7(11):48558, Public Library of Science,United States, (2012).
Cline, M.J., "Perspectives for Gene Therapy: Inserting New Genetic Information Into Mammalian Cells by Physical Techniques and Viral Vectors," Pharmacology & Therapeutics 29(1):69-92, Pergamon Press, England (1985).
Cohen, Statistical Power Analysis for the Behavioral Sciences, Second Edition (Routledge, Hillsdale, NJ, 1988).
Collins et al., "The Phylogeny of the Genus *Clostridium*: Proposal of Five New Genera and Eleven New Species Combinations," Int. J Syst Bacterial44(4):812-826 (1994).
Cooke et al., "LPS antagonism reduces graft-versus-host disease and preserves graftversus-leukemia activity after experimental bone marrow transplantation," J. Clin. Invest. 107:1581-1589 (2001).
Cooke, K.R.,et al., "An Experimental Model of Idiopathic Pneumonia Syndrome After Bone Marrow Transplantation: I. The Roles of Minor H Antigens and Endotoxin.," Blood, 88(8):3230-3239, American Society of Hematology,United States, (Oct. 1996).
Copelan, E.,et al., "A Scheme for Defining Cause of Death and Its Application in the T Cell Depletion Trial.," Biology of Blood and Marrow Transplantation : Journal of the American Society for Blood and Marrow Transplantation, 13(12):1469-1476, Carden Jennings Publishing,United States, (Dec. 2017).
Cotten, M., et al., "Receptor-mediated Transport of DNA Into Eukaryotic Cells," Methods in Enzymology 217:618-644, Academic Press, United States (1993).
Current Uses and Outcomes of Hematopoietic Stem Cell Transplantation 2012 CIBMTR Summary Slides, 2012.
Das, R.,et al., "Interleukin-23 Secretion by Donor Antigen-presenting Cells is Critical for Organ-specific Pathology in Graft-versus-host Disease.," Blood, 113(10):2352-2362, American Society of Hematology,United States, (Mar. 2009).
Das et al., "Blockade ofinterleukin-23 signaling results in targeted protection ofthe colon and allows for separation of graft-versus-host and graft-versus-leukemia responses," Blood 115(25):5249-5258 (2010).
De Aguiar Vallim, T.Q., et al., "Pleiotropic Roles of Bile Acids in Metabolism," Cell Metabolism, 17(5):657-669, Cell Press, United States, (May 2013).
Delay, M.L.,et al., "Hla-b27 Misfolding and the Unfolded Protein Response Augment Interleukin-23 Production and Are Associated With Th17 Activation in Transgenic Rats. ," Arthritis and Rheumatism, 60(9):2633-2643, Hoboken, N.J. : Wiley-Blackwell,United States, (Sep. 2009).
Derrien, M.,et al., "Mucin-bacterial Interactions in the Human Oral Cavity and Digestive Tract.," Gut Microbes, 1(4):254-268, PA : Taylor & Francis, United States, (Jul. 2010).
Desantis, T.Z.,et al., "Greengenes, A Chimera-Checked 16S RRNA Gene Database and Workbench Compatible With ARB.," Applied and Environmental Microbiology, 72(7):5069-5072, American Society for Microbiology, United States, (Jul. 2006).
Dethlefsen, L., et al., "Incomplete Recovery and Individualized Responses of the Human Distal Gut Microbiota to Repeated Antibiotic Perturbation," Proceedings of the National Academy of Sciences of the United States of America, 108 Suppl 1:4554-4561, National Academy of Sciences, United States, (Mar. 2011).
Diehl, G.E., et al., "Microbiota Restricts Trafficking of Bacteria to Mesenteric Lymph Nodes by Cx(3)cr1(Hi) Cells," Nature, 494(7435):116-120, Nature Publishing Group, England, (Feb. 2013).
Duan, J., et al., "Microbial Colonization Drives Expansion of Il-1 Receptor 1-expressing and Il-17-producing Gamma/delta T Cells," Cell host & microbe, 7(2):140-150, Cell Press, United States, (Feb. 2010).
Duncker, S.C.,et al., "The D-alanine Content of Lipoteichoic Acid is Crucial for Lactobacillus Plantarum-mediated Protection From Visceral Pain Perception in a Rat Colorectal Distension Model.," Neurogastroenterology and Motility : the Official Journal of the

(56) References Cited

OTHER PUBLICATIONS

European Gastrointestinal Motility Society, 20(7):843-850, Blackwell Scientific Publications, c1994, England, (Jul. 2008).
Edgar, R.C., et al., "Uchime Improves Sensitivity and Speed of Chimera Detection," Bioinformatics, 27(16):2194-2200, Oxford University Press, England, (Aug. 2011).
Eriguchi et al., "Graft versus-host disease disrupts intestinal microbial ecology by inhibiting Paneth cell production of a-defensins," Blood 120(1):223-231 (2012).
Ezaki, T., et al., "16s Ribosomal Dna Sequences of Anaerobic Cocci and Proposal of *Ruminococcus hansenii* Comb. Nov. and *Ruminococcus productus* Comb. Nov," International Journal of Systematic Bacteriology 44(1):130-136, Society for General Microbiology, England (Jan. 1994).
Farache, J., et al., "Luminal Bacteria Recruit Cd103+ Dendritic Cells Into the Intestinal Epithelium to Sample Bacterial Antigens for Presentation," Immunity, 38(3):581-595, Cell Press, United States, (Mar. 2013).
Ferreira, R.B., et al., "The Intestinal Microbiota Plays a Role in *Salmonella*-induced Colitis Independent of Pathogen Colonization," Plos One, 6(5):e20338, Public Library of Science, United States, (May 2011).
Freifeld et al., "Clinical Practice Guideline for the Use of Antimicrobial Agents in Neutropenic Patients with Cancer: 2010 Update by the Infectious Diseases Society of America," Clinical Infectious Diseases 52(4):e56-e93 (2011).
Furusawa, Y., et al., "Commensal Microbe-derived Butyrate Induces the Differentiation of Colonic Regulatory T Cells ," Nature 504(7480):446-450, Nature Publishing Group, England (Dec. 2013).
Gallo, R.L and Hooper, L.V, "Epithelial Antimicrobial Defence of the Skin and Intestine," Nature Reviews Immunology , 12(7):503-516, Nature Publishing Group, England, (Jun. 2012).
Ganesh et al., "Commensal Akkermansia muciniphila Exacerbates Gut Inflammation in *Salmonella typhimurium*-Infected Gnotobiotic Mice," PLoS One 8(9):e74963 (2013).
Gennaro, A., Editor "Remington's Pharmaceutical Sciences", 18th Edition, Mack Publishing Co., 5 pages, 1990 (Table of Contents).
Giel, J.L., et al., "Metabolism of Bile Salts in Mice Influences Spore Germination in Clostridium Difficile," Plos One, 5(1):e8740, Public Library of Science, United States, (Jan. 2010).
Goldberg et al., "T Cell-Depleted Stem Cell Transplantation for Adults with High-Risk Acute Lymphoblastic Leukemia: Long-Term Survival for Patients in First Complete Remission with a Decreased Risk of Graft-versus-Host Disease," Biol. Blood Marrow Transplant 19:208-213 (2013).
Goldspiel, B.R., et al., "Human Gene Therapy," Clinical Pharmacy 12(7):488-505, American Society of Hospital Pharmacists, United States (1993).
Grangette et al., "Enhanced anti-inflammatory capacity of a Lactobacillus plantarum mutant synthesizing modified teichoic acids," PNAS 102(29): 10321-10326 (2005).
Hahn et al., "Risk factors for Acute Graft-Versus-Host Disease after Human Leukocyte Antigen-Identical Sibling Transplants for Adults With Leukemia," J Clin. Oncol. 26(35):5728-5734 (2008).
Hall, B.G., et al., "Building Phylogenetic Trees From Molecular Data With Mega," Molecular biology and Evolution, 30(5):1229-1235, Oxford University Press, United States, (May 2013).
Hamilton, M.J., et al., "High-throughput Dna Sequence Analysis Reveals Stable Engraftment of Gut Microbiota Following Transplantation of Previously Frozen Fecal Bacteria," Gut Microbes, 4(2):125-135, Philadelphia, United States, (Mar.-Apr. 2013).
Hand, T.W., et al., "Acute Gastrointestinal Infection Induces Long-lived Microbiota-specific T Cell Responses," Science, 337(6101):1553-1556, American Association for the Advancement of Science, United States, (Sep. 2012).
Heeg, D et al., "Spores of Clostridium dif.ficile Clinical Isolates Display a Diverse Germination Response to Bile Salts," PLoS One 7(2):e32381 (2012).

Hiemenz, "Management of Infections Complicating Allogeneic Hematopoietic Stem Cell Transplantation," Semin Hematol 46:289-312 (2009).
Hill, D.A., et al., "Commensal bacteria-derived signals regulate basophil hematopoiesis and allergic inflammation," Nat Med., 18(4):538-546 (2012).
Holler et al., "Metagenomic Analysis of the Stool Microbiome in Patients Receiving Allogeneic Stem Cell Transplantation: Loss of Diversity Is Associated with Use of Systemic Antibiotics and More Pronounced m Gastrointestinal Graft-versus-Host Disease," Biol. Blood Marrow Transplant. 20:640-645 (2014).
Hong et al., "1H NMR-based Metabonomic Assessment of Probiotic Effects in a Colitis Mouse Model," Arch Pharm Res 33(7): 1091-1101 (2010).
Hue et al., "Interleukin-23 drives innate and T cell-mediated intestinal inflammation," JEM 203(11):2473-2483 (2006).
Huse, S.M., et al., "Exploring Microbial Diversity and Taxonomy Using SSU rRNA Hypervariable Tag Sequencing," PLoS Genetics 4(11):e1000255, Public Library of Science, United States (Nov. 2008).
International Search Report for International Application No. PCT/US2015/31627, ISA/US, Commissioner for Patents, Alexandria, Virginia, dated Sep. 8, 2015.
International Search Report dated Mar. 9, 2017 in International Application No. PCT/US2016/063643.
International Search Report dated Apr. 14, 2016 in International Application No. PCT/US2015/062734.
Ivanov, I.I., et al., "Induction of intestinal Th 17 cells by segmented filamentous bacteria," Cell, 139(3):485-498 (2009).
Jacobs et al., "1H NMR metabolite profiling of feces as a tool to assess the impact of nutrition on the human microbiome," NMR in Biomedicine 21:615-626 (2008).
Jaffe et al., "Prevention of Peritransplantation Viridans Streptococcal Bacteremia with Early Vancomycin Administration: A Single-Center Observational Cohort Study," Clin Infect Dis. 39:1625-1632 (2004).
Jagasia et al., "Risk factors for acute GVHD and survival after hematopoietic cell transplantation," Blood 119(1):296-307 (2012).
Jakubowski et al., "T Cell-Depleted Unrelated Donor Stem Cell Transplantation Provides Favorable Disease-Free Survival for Adults with Hematologic Malignancies," Biol. Blood Marrow Transplant 17:1335-1342 (2011).
Jenq et al., "Intestinal Blautia Is Associated with Reduced Death from Graft-versus-Host Disease," Biology ofBlood and Marrow Transplantation 21:1373-1383 (2015).
Jenq et al., "Regulation of intestinal inflammation by microbiota following allogeneic bone marrow transplantation," J Exp. Med. 209(5):903-911 (2012).
Johansson et al., "The two mucus layers of colon are organized by the MUC2 mucin, whereas the outer layer is a legislator of host-microbial interactions," PNAS 108(Suppl. 1):4659-4665 (2011).
Jones et al., "Mortality and Gross Pathology of Secondary Disease in Germfree Mouse Radiation Chimeras," Radiat Res. 45(3):577-588 (1971).
Kamboj et al., "Clostridium difficile Infection after Allogeneic Hematopoietic Stem Cell Transplant: Strain Diversity and Outcomes Associated with NAP1/027," Biol. Blood Marrow Transplant 20:1626-1633 (2014).
Kamboj et al., "The Changing Epidemiology of Vancomycin-Resistant Enterococcus (VRE) Bacteremia m Allogeneic Hematopoietic Stem Cell Transplant (HSCT) Recipients," Biol Blood Marrow Transplant 16:1576-1581 (2010).
Kang, D.J., et al., "Clostridium scindens baiCD and baiH genes encode stereo-specific 7a/7~-hydroxy-3-oxo-114-cholenoic acid oxidoreductases," Biochim Biophys Acta 1781(1-2): 16-25 (2008).
Kim, S.W.,et al., "Treatment of Refractory or Recurrent Clostridium Difficile Infection," The Korean Journal of Gastroenterology= Taehan Sohwagi Hakhoe Chi, 60(2):71-78, Korean Society of Gastroenterology, [2003],Korea (South), (Aug. 2012).
Kinnebrew, M.A., et al., "Early Clostridium Difficile Infection During Allogeneic Hematopoietic Stem Cell Transplantation," Plos One, 9(3):e90158, Public Library of Science, United States, (Mar. 2014).

(56) References Cited

OTHER PUBLICATIONS

Kitahara, M., et al., "Assignment of *Eubacterium* sp. VPI 12708 and Related Strains with High Bile Acid 7alpha-dehydroxylating Activity to Clostridium Scindens and Proposal of *Clostridium hylemonae* sp. nov., Isolated from Human Faeces," International Journal of Systematic and Evolutionary Microbiology 50(3):971-978, Microbiology Society, England (May 2000).
Koeth, R.A., et al., "Intestinal Microbiota Metabolism of L-carnitine, a Nutrient in Red Meat, Promotes Atherosclerosis," Nature Medicine, 19(5):576-585, Nature Publishing Company, United States, (May 2013).
Krafft et al., "Purification and Characterization of a Novel Form of 20a-Hydroxysteroid Dehydrogenase from Clostridium scindens," J Bacterial., 171(6):2925-2932 (1989).
Zilberberg, M.D.,et al., "Increase in Adult Clostridium Difficilerelated Hospitalizations and Case-fatality Rate, United States, 2000-2005.," Emerging Infectious Diseases, 14(6):929-931, National Center for Infectious Diseases, Centers for Disease Control and Prevention (CDC),United States., (Jun. 2008).
Krishna, S.G., et al., "Risk Factors, Preemptive Therapy, and Antiperistaltic Agents for Clostridium Difficile Infection in Cancer Patients," Transplant Infectious Disease, 15(5):493-501, Munksgaard, Denmark, (Oct. 2013 ).
Kron et al., "Adenovirus Vectors and Subviral Particles for Protein and Peptide Delivery," Curr Gene Ther 12:362-373 (2012).
Kyne, L., et al., "Health Care Costs and Mortality Associated With Nosocomial Diarrhea Due to Clostridium Difficile," Clinical Infectious Diseases, 34(3):346-353, Oxford University Press, United States, (Feb. 2002 ).
Langille, M.G., et al., "Predictive Functional Profiling of Microbial Communities Using 16s Rrna Marker Gene Sequences," Nature biotechnology, 31(9):814-821, Nature America Publishing, United States, (Sep. 2013).
Langrish et al., "IL-12 and IL-23: master regulators of innate and adaptive immunity," Immunological Reviews 202:96-105 (2004).
Larocco et al., "Infection in the Bone Marrow Transplant Recipient and Role of the Microbiology Laboratory in Clinical Transplantation," Clinical Microbiology Reviews 1 0(2):277-297 (1997).
Lathrop, S.K., et al., "Peripheral Education of the Immune System by Colonic Commensal Microbiota," Nature, 478(7368):250-254, Nature Publishing Group, England, (Sep. 2011 ).
Lindner et al., "Diversification of memory B cells drives the continuous adaptation of secretory antibodies to gut microbiota," Nature Immunology 16(8):880-890 (2015).
Liu, C., et al., "Reclassification of Clostridium Coccoides, Ruminococcus Hansenii, Ruminococcus Hydrogenotrophicus, Ruminococcus Luti, Ruminococcus Productus and Ruminococcus Schinkii as *Blautia coccoides* Gen. Nov., Comb. Nov., *Blautia Hhansenii* Comb. Nov., *Blautia hydrogenotrophica* Comb. Nov., *Blautia luti* Comb. Nov., *Blautia producta* Comb. Nov., *Blautia schinkii* Comb. Nov. and Description of *Blautia wexlerae* Sp. Nov., Isolated From Human Faeces," International Journal of Systematic and Evolutionary Microbiology 58(Pt 8):1896-1902, Microbiology Society, England (Aug. 2008).
Loeffler, J.P., et al., "Gene Transfer Into Primary and Established Mammalian Cell Lines With Lipopolyamine-coated DNA," Methods in Enzymology 217:599-618, Academic Press, United States (1993).
Louie, T.J., et al., "Tolevamer, a Novel Nonantibiotic Polymer, Compared With Vancomycin in the Treatment of Mild to Moderately Severe Clostridium Difficile-associated Diarrhea," Clinical Infectious Diseases, 43(4):411-420, Oxford University Press, United States, (Aug. 2006).
Lozupone et al., "UniFrac—An online tool for comparing microbial community diversity in a phylogenetic context," BMC Bioinformatics 7:371 (2006).
Lozupone, C and Knight, R., "UniFrac: a New Phylogenetic Method for Comparing Microbial Communities," Applied and Environmental Microbiology 71(12):8228-8235, American Society for Microbiology, United States (Dec. 2005).

MacPherson, A.J and Uhr, T., "Induction of Protective Iga by Intestinal Dendritic Cells Carrying Commensal Bacteria," Science, 303(5664):1662-1665, American Association for the Advancement of Science, United States, (Mar. 2004).
MacMillan et al., "What predicts high risk acute graft-versus-host disease (GVHD) at onset?: identification of those at highest risk by a novel acute GVHD risk score," Br. J. Haematol 157:732-741 (2012).
Magurran, "Measuring Biological Diversity," Malden, MA: Blackwell Publishing; 2004.
Malard et al., "Impact of Cyclosporine—A Concentration on the Incidence of Severe Acute Graft-Versus-Host Disease after Allogeneic Stem Cell Transplantation," Biol. Blood Marrow Transplant 16:28-34 (2010).
Manges, A.R., et al., "Comparative Metagenomic Study of Alterations to the Intestinal Microbiota and Risk of Nosocomial Clostridum Difficile-associated Disease," The Journal of Infectious Diseases, 202(12):1877-1884, Oxford University Press, United States, (Dec. 2010).
Marsh, J.W., et al., "Association of Relapse of Clostridium Difficile Disease With Bi/nap1/027," Journal of Clinical Microbiology, 50(12):4078-4082, American Society for Microbiology, United States, (Dec. 2012).
Martin et al., "Increasingly Frequent Diagnosis of Acute Gastrointestinal Graft-versus-Host Disease after Allogeneic Hematopoietic Cell Transplantation," Biol. Blood Marrow Transplant. 10:320-327 (2004).
Maynard et al., "Reciprocal interactions of the intestinal microbiota and immune system," Nature 489:231-241 (2012).
McAuliffe et al., "Genetic Analysis of Two Bile Salt Hydrolase Activities in Lactobacillus acidophilus NCFM," Appl. Environ Microbial., 71(8):4925-4929 (2005).
Meyers, "Infection in Bone Marrow Transplant Recipients," The American Journal of Medicine 81(Suppl. 1A):27-38 (1986).
Morgan, R.A. And Anderson, W.F., "Human Gene Therapy," Annual Review of Biochemistry 62:191-217, Annual Reviews, United States (1993).
Morris, G.N., et al., "*Clostridium scindens* sp. nov., A Human Intestinal Bacterium with Desmolytic Activity on Corticoids," International Journal of Systematic and Evolutionary Microbiology 35(4):478-481, (Oct. 1985).
Mulligan, R.C., "The Basic Science of Gene Therapy," Science 260(5110):926-932, American Association for the Advancement of Science, United States (1993).
Narushima, S., et al., "Characterization of the 17 Strains of Regulatory T Cell-Inducing Human-Derived Clostridia," Gut Microbes 5(3):333-339, Taylor & Francis, United States (May-Jun. 2014).
Olszak, T., et al., "Microbial Exposure During Early Life Has Persistent Effects on Natural Killer T Cell Function," Science (New York, N.Y.), 336(6080):489-493, American Association for the Advancement of Science, United States, (Apr. 2012).
Ott, S.J., et al., "Quantification of Intestinal Bacterial Populations by Real-time Pcr With a Universal Primer Set and Minor Groove Binder Probes: a Global Approach to the Enteric Flora," Journal of Clinical Microbiology, 42(6):2566-2572, American Society for Microbiology,United States, (Jun. 2004).
Out, C., et al., "Bile Acid Sequestrants: More Than Simple Resins," Current opinion in lipidology, 23(1):43-55, Lippincott Williams & Wilkins, England, (Feb. 2012).
Pamer, "Fecal microbiota transplantation: effectiveness, complexities, and lingering concerns," Mucosal Immunol 7(2):210-214 (2014).
Parham et al., "A Receptor for the Heterodimeric Cytokine IL-23 is Composed of IL-12R~1 and a Novel Cytokine Receptor Subunit, IL-23R1," J Immunol 168:5699-5708—2002.
Park et al., "*Blautia faecis* sp. nov., isolated from human faeces," Int J Syst Evol Microbial. 63:599-603 (2013).
Passweg et al., "Influence of protective isolation on outcome of allogeneic bone marrow transplantation for leukemia," Bone Marrow Transplantation 21:1231-1238 (1998).
Partial Supplementary European Search Report dated Jan. 4, 2018 in Application No. 15796000.6.

(56) References Cited

OTHER PUBLICATIONS

Pelaseyed et al., "The mucus and mucins of the goblet cells and enterocytes provide the first defense line of the gastrointestinal tract and interact with the immune system," Immunological Reviews 260:8-20 (2014).
Petersen et al., "Infectious Complications m Patients Undergoing Marrow Transplantation: A Prospective Randomized Study of the Additional Effect of Decontamination and Laminar Airflow Isolation among Patients Receiving Prophylactic Systemic Antibiotics," Scand J. Infect Dis. 19(5):559-567 (1987).
Petrof et al., "Stool substitute transplant therapy for the eradication of Clostridium dif.ficile infection: 'RePOOPulating' the gut," Microbiome 1:3, pp. 1-12 (2013).
Pittelkow, M.R. and Scott, R.E., "New Techniques for the in Vitro Culture of Human Skin Keratinocytes and Perspectives on Their Use for Grafting of Patients With Extensive Burns," Mayo Clinic Proceedings 61(10):771-777, Elsevier, England (Oct. 1986).
Ponce et al., "Graft-versus-Host Disease after Double-Unit Cord Blood Transplantation Has Unique Features and an Association with Engrafting Unit-To-Recipient HLA Match," Biol. Blood Marrow Transplant 19:904-911 (2013).
Porada et al., "Treatment of Hemophilia A in Utero and Postnatally using Sheep as a Model for Cell and Gene Delivery," J. Genet Syndr Gene Ther., 25:Suppl. 1, 26 pages 2012).
Rakoff-Nahoum, S., et al., "Recognition of Commensal Microflora by Toll-like Receptors is Required for Intestinal Homeostasis," Cell, 118(2):229-241, Cell Press, United States, (Jul. 2004).
Rawlings et al., "IBMTR Severity Index for grading acute graft-versus-host disease: retrospective comparison with Glucksberg grade," Br J Haematol. 97:855-864 (1997).
Rea, M.C., et al., "Effect of Broad- and Narrow-spectrum Antimicrobials on Clostridium Dif.ficile and Microbial Diversity in a Model of the Distal Colon," Proceedings of the National Academy of Sciences of the United States of America, 108 Suppl 1:4639-4644, National Academy of Sciences, United States, ( Mar. 2011 ).
Rea, M.C.,et al., "Thuricin Cd, a Posttranslationally Modified Bacteriocin With a Narrow Spectrum of Activity Against Clostridium Dif.ficile," Proceedings of the National Academy of Sciences of the United States of America, 107(20):9352-9357, National Academy of Sciences, (May 2010).
Reeves, A.E.,et al., "The Interplay Between Microbiome Dynamics and Pathogen Dynamics in a Murine Model of Clostridium Difficile Infection.," Gut Microbes, 2(3):145-158, Philadelphia, PA : Taylor & Francis, (May 2011).
Rheinwald, J.G., "Chapter 15 Serial Cultivation of Normal Human Epidermal Keratinocytes," Methods in Cell Biology 21A:229-254, Academic Press, United States (1980).
Ridlon, J.M and Hylemon, P.B., "Identification and Characterization of Two Bile Acid Coenzyme a Transferases From Clostridium Scindens, a Bile Acid 7α-dehydroxylating Intestinal Bacterium.," Journal of Lipid Research, 53(1):66-76, American Society for Biochemistry and Molecular Biology, United States, (Jan. 2012).
Ridlon, J.M., "Enzymology and Molecular Biology of Bile Acid 7alpha- and 7beta-Dehydroxylation by the Intestinal Bacteria Clostridium Scindens and Clostridium Hylemonae," VCU Theses and Dissertations, Paper 736 (2008).
Ridlon, J.M.,et al., "Clostridium Scindens: a Human Gut Microbe With a High Potential to Convert Glucocorticoids Into Androgens.," Journal of Lipid Research, 54(9):2437-2449, American Society for Biochemistry and Molecular Biology, United States, (Sep. 2013).
Ridlon,J.M,.et al, "Bile Salt Biotransformations by Human Intestinal Bacteria.," Journal of Lipid Research, 47(2):241-259, American Society for Biochemistry and Molecular Biology, (Feb. 2006).
Rupnik, M.,et al., "Clostridium Difficile Infection: New Developments in Epidemiology and Pathogenesis.," Nature Reviews. Microbiology, 7(7):526-536, Nature Pub. Group, c2003-, England, (Jul. 2009).
Russell et al., "Early Outcomes After Allogeneic Stem Cell Transplantation for Leukemia and Myelodysplasia Without Protective Isolation: A 1 0-year Experience," Biol. Blood Marrow Transplant 6(2): 109-114 (2000).
Sakamoto et al., "Eubacterium limosum strain JCM 6421 16S ribosomal RNA gene, partial sequence" NCBI Reference Sequence, 2 pages, Nov. 23, 2016.
Salzman et al., "Analysis of 16S libraries of mouse gastrointestinal microflora reveals a large new group of mouse intestinal bacteria," Microbiology 148:3651-3660 (2002).
Schloss, P.D., et al., "Introducing Mothur: Open-source, Platform-independent, Community-supported Software for Describing and Comparing Microbial Communities," Applied and Environmental Microbiology 75(23):7537-7541, American Society for Microbiology, United States (Dec. 2009).
Schloss, P.D., et al., "Reducing the Effects of Pcr Amplification and Sequencing Artifacts on 16s Rrna-based Studies," PLoS One 6(12):e27310, Public Library of Science, United States (Dec. 2011).
Schwab et al., "Neutrophil granulocytes recruited upon translocation of intestinal bacteria enhance graft-versus-host disease via tissue damage," Nature Medicine 20(6):648-654—2014.
Segata et al., "Metagenomic biomarker discovery and explanation," Genome Biol. 12:R60—2011.
Seguy et al., "Enteral Feeding and Early Outcomes of Patients Undergoing Allogeneic Stem Cell Transplantation following Myeloablative Conditioning," Transplantation 82:835-839 (2006).
Shannon, "The Mathematical Theory of Communication," M.D. Computing 14( 4): 3 06-317 (1997).
Sheneman, L.,et al., "Clearcut: a Fast Implementation of Relaxed Neighbor Joining.," Bioinformatics (Oxford, England), 22(22):2823-2824, Oxford University Press, c1998,England, (Nov. 2006).
Shono et al., "A Small-Molecule c-Rel Inhibitor Reduces Alloactivation of T Cells without Compromising Antitumor Activity," Cancer Discovery 4(5):578-591 (2014).
Solomkin et al., "Diagnosis and Management of Complicated Intra-abdominal Infection in Adults and Children: Guidelines by the Surgical Infection Society and the Infectious Diseases Society of America," Clin Infect Dis. 50:133-164 (2010).
Smith, P.M., et al., "The Microbial Metabolites, Short-Chain Fatty Acids, Regulate Colonic Treg Cell Homeostasis," Science 341(6145):569-573, American Association for the Advancement of Science, United States (Aug. 2013 ).
Sorg et al., "Bile Salts and Glycine as Cogerminants for Clostridium dif.ficile Spores," J. Bacteriology 190(7):2505-2512 (2008).
Sorg, J.A and Sonenshein, A.L., "Chenodeoxycholate is an Inhibitor of Clostridium Difficile Spore Germination.," Journal of Bacteriology, 191(3):1115-1117, American Society for Microbiology,United States, (Feb. 2009).
Stein, R.R.,et al., "Ecological Modeling From Time-series Inference: Insight Into Dynamics and Stability of Intestinal Microbiota.," Plos Computational Biology, 9(12):1003388, Public Library of Science, [2005], United States , (Sep. 2013).
Stemple et al., "Isolation of a Stem Cell for Neurons and Glia from the Mammalian Neural Crest," Cell 71:973-985 (1992).
Storb et al., "Graft-Versus-Host Disease and Survival in Patients with Aplastic Anemia Treated by Marrow Grafts from HLA-Identical Siblings. Beneficial Effect of a Protective Environment," N Engl J Med. 308:302-307 (1983).
Supplementary Partial European Search Report dated Jun. 14, 2018 in Application No. EP 15862844.
Swidsinski et al., "Spatial Organization and Composition of the Mucosal Flora in Patients with Inflammatory Bowel Disease," Journal of Clinical Microbiology 43(7):3380-3389—2005.
Taur et al., "The effects of intestinal tract bacterial diversity on mortality following allogeneic hematopoietic stem cell transplantation," Blood 124(7): 1174-1182 (2014).
The Human Microbiome Project Consortium: "Structure, Function and Diversity of the Healthy Human Microbiome," Nature 486(7402):207-214 (2013).
Theriot et al., "Antibiotic-induced shifts in the mouse gut microbiome and metabolome increase susceptibility to Clostridium dif.ficile infection," Nature Communications 5:3114 pp. 1-22 (2014).

(56) References Cited

OTHER PUBLICATIONS

Tolstoshev, P., "Gene Therapy, Concepts, Current Trials and Future Directions," Annual Review of Pharmacology and Toxicology 33:573-596, Annual Reviews, United States (1993).
Trends in Biotechnology, TIBTECH 11(5): 155-215 (1993) (Table of Contents).
Turnbaugh, P.J.,et al., "A Core Gut Microbiome in Obese and Lean Twins.," Nature, 457(7228):480-484, Nature Publishing Group, England, (Jan. 2009).
Vigorito et al., "Evaluation of NIH consensus criteria for classification of late acute and chronic GVHD," Blood 114(3):702-708 (2009).
Vossen et al., "Complete Suppression of the Gut Microbiome Prevents Acute Graft-Versus Host Disease following Allogeneic Bone Marrow Transplantation," PLoS ONE 9(9):e105706 (2014).
Wang, Q., et al., "Naive Bayesian Classifier for Rapid Assignment of Rrna Sequences Into the New Bacterial Taxonomy," Applied and Environmental Microbiology 73(16):5261-5267, American Society for Microbiology, United States (Aug. 2007).
Weber et al., "Low urinary indoxyl sulfate levels early after transplantation reflect a disrupted microbiome and are associated with poor outcome," Blood 126(14): 1723-1728—2015.
Wells, J.E and Hylemon, P.B., "Identification and Characterization of a Bile Acid 7alpha-dehydroxylation Operon in *Clostridium* Sp. Strain to-931, a Highly Active 7alpha-dehydroxylating Strain Isolated From Human Feces.," Applied and Environmental Microbiology, 66(3):1107-1113, American Society for Microbiology,United States, (Mar. 2000).
Wells, J.E.,et al., "Development and Application of a Polymerase Chain Reaction Assay for the Detection and Enumeration of Bile Acid 7alpha-dehydroxylating Bacteria in Human Feces.," Clinica chimica acta; international journal of clinical chemistry, 331(1-2):127-134, Elsevier,Netherlands, (May 2003).
Wingender, G.,et al., "Intestinal Microbes Affect Phenotypes and Functions of Invariant Natural Killer T Cells in Mice," Gastroenterology, 143(2):418-428, PA : W.B. Saunders,United States, (Aug. 2012).
Wood et al., "Kraken: ultrafast metagenomic sequence classification usmg exact alignments," Genome Biology 15:R46 (2014).
Wu, G.Y. and Wu, C.H., "Delivery Systems for Gene Therapy," Biotherapy 3(1):87-95, Kluwer Academic Publishers, Netherlands (1991).
Yen et al., "IL-23 is essential for T cell-mediated colitis and promotes inflammation via IL-17 and IL-6," The Journal of Clinical Investigation 116( 5): 1310-1316 (2006).
Yi, Y., et al., "Current Advances in Retroviral Gene Therapy," Current Gene Therapy 11(3):218-228, Bentham Science Publishers, Netherlands (2011).
Yutin, N. and Galperin, M.Y., "A Genomic Update on Clostridial Phylogeny: Gram-negative Spore Formers and Other Misplaced Clostridia," Environmental Microbiology 15(10):2631-2641, Blackwell Science, England (Oct. 2013).
Zar, F.A., "A Comparison of Vancomycin and Metronidazole for the Treatment of Clostridium Difficile-associated Diarrhea, Stratified by Disease Severity.," Clinical Infectious Diseases : an Official Publication of the Infectious Diseases Society of America, 45(3):302-307, Oxford University Press, United States, (Aug. 2007).
Zhao, Y.,et al., "Rapsearch2: a Fast and Memory-efficient Protein Similarity Search Tool for Next-generation Sequencing Data.," Bioinformatics (Oxford, England), 28(1):125-126, Oxford University Press,England, (Jan. 2012).
Andoh, A. et al., "Terminal Restriction Fragment Polymorphism Analyses of Fecal Microbiota in Five Siblings Including Two with Ulcerative Colitis," Clin. J. Gastroenterol., 2009, pp. 343-345, vol. 2.
Application as Filed WO 2011/152566, Filed Jun. 3, 2011, 151 pages.
Abstract of Atarashi, K. et al., "Induction of Colonic Regulatory T Cells by Indigenous *Clostridium* Species," Science, Jan. 21, 2011, pp. 337-341, vol. 331, No. 6015—1 page.

Atarashi, K. et al., "Induction of Colonic Regulatory T Cells by Indigenous *Clostridium* Species," Science, Jan. 21, 2011, pp. 337-341, vol. 331.
Atarashi, K. et al., Supporting Online Material for "Induction of Colonic Regulatory T Cells by Indigenous *Clostridium* Species," Science Express, Dec. 23, 2010, 26 pages.
Atarashi, K. et al., "$T_{reg}$ Induction by a Rationally Selected Mixture of Clostridia Strains from the Human Microbiota," Nature, Macmillan Publishers Limited, 2013, pp. 1-17.
Autoimmune Disease List, There Are More Than 100 Autoimmune Diseases, American Autoimmune Related Diseases Association, AARDA, Inc., 2014, 4 pages.
Babel, N. et al., "Analysis of T Cell Receptor Repertoire by Newly Established CDR3 High-Throughput Sequencing Allows for Monitoring/Tracing of Antigen-Specific T Cells in Peripheral Blood and Tissue," PP-063-40, 14th ICI Abstract Book, 14th International Congress of Immunology, 2010, 3 pages.
Belkaid, Y. et al., "Natural Regulatory T Cells in Infectious Disease," Nature Immunology, Apr. 2005, pp. 353-360, vol. 6, No. 4.
Borody, T.J. et al., "Treatment of Ulcerative Colitis Using Fecal Bacteriotherapy," J. Clin. Gastroenterol., 2003, pp. 42-47, vol. 37, No. 1.
Browne, H.P. et al., "Culturing of 'Unculturable' Human Microbiota Reveals Novel Taxa and Extensive Sporulation," Nature, Macmillan Publishers Limited, 2016, pp. 1-15.
Cato, E.P. et al., "*Clostridium oroticum* Comb. Nov. Amended Description," International Journal of Systematic Bacteriology, Jan. 1968, pp. 9-13, vol. 17, No. 1.
Certified translation of second priority document, PCT/JP2010/071746, 117 pages.
Collins, M.D. et al., "The Phylogeny of the Genus *Clostridium*: Proposal of Five New Genera and Eleven New Species Combinations," International Journal of Systematic Bacteriology, Oct. 1994, pp. 812-826, vol. 44, No. 4.
Dewhirst, F.E. et al., "Phylogeny of the Defined Murine Microbiota: Altered Schaedler Flora," Applied and Environmental Microbiology, Aug. 1999, pp. 3287-3292, vol. 65, No. 8.
Eeckhaut, V. et al., "The Anaerobic Butyrate-Producing Strain Butyricicoccus Pullicaecorum Decreases Colonic Inflammation and Ulceration in a TNBS-Induced Colitis Rat Model," 5th Probiotics, Prebiotics and New Foods Congress, 2009, 1 page.
El Hage, R. et al., "Emerging Trends in "Smart Probiotics": Functional Consideration for the Development of Novel Health and Industrial Applications," Frontiers in Microbiology, Sep. 2017, pp. 1-11, vol. 8, Article 1889.
European Examination Report, European Application No. 11728077.6, dated Sep. 18, 2015, 2 pages.
Foditsch, C. et al., "Isolation and Characterization of Faecalibacterium prausnitzii from Calves and Piglets," PLOS One, Dec. 31, 2014, pp. 1-19.
Frank, D.N. et al., "Molecular-Phylogenetic Characterization of Microbial Community Imbalances in Human Inflammatory Bowel Diseases," PNAS, Aug. 21, 2007, pp. 13780-13785, vol. 104, No. 34.
Gaboriau-Routhiau, V. et al., "The Key Role of Segmented Filamentous Bacteria in the Coordinated Maturation of Gut Helper T Cell Responses," Immunity, Oct. 16, 2009, pp. 677-689, vol. 31.
Geuking, M.B. et al., "Intestinal Bacterial Colonization Induces Mutualistic Regulatory T Cell Responses," Immunity, May 27, 2011, pp. 794-806, vol. 34.
Hansen, A.K. et al., Handbook of Laboratory Animal Bacteriology, Second Edition, CRC Press, 2015, p. 158 (3 total pages).
Hata, D.J. et al., "Blood Group B Degrading Activity of Ruminococcus Gnavus Alpha-Galactosidase," Artif. Cells Blood Substit. Immobil. Biotechnol., May 2004, pp. 263-274, vol. 32, No. 2.
Hayashi, H. et al., "Phylogenetic Analysis of the Human Gut Microbiota Using 16S rDNA Clone Libraries and Strictly Anaerobic Culture-Based Methods," Microbiol. Immunol., 2002, pp. 535-548, vol. 46, No. 8.
Honda, K. et al., "Regulation of T Cell Responses by Intestinal Commensal Bacteria," Proceedings of the 15th Annual Meeting for Intestinal Microbiology, Apr. 2011, pp. 103-104, vol. 25, No. 2.

(56) References Cited

OTHER PUBLICATIONS

International Statistical Classification of Diseases and Related Health Problems 10th Review, Chapter I: Certain Infectious and Parasitic Diseases (A00-B99), 2016, 2 pages.
14th International Congress of Immunology, Kobe, Japan, International Immunology, Aug. 2010, 3 pages, vol. 22, Issue Suppl 1 Pt 3.
14th International Congress of Immunology, Kobe, Japan, ICI 2010 Wrap-up Report, Immunology in the 21st Century: Defeating Infection, Autoimmunity, Allergy and Cancer, Aug. 22-27, 2010, 1 page.
Ivanov, I.K. et al., "Specific Microbiota Direct the Differentiation of IL-17-Producing T-Helper Cells in the Mucosa of the Small Intestine," Cell Host & Microbe, Oct. 16, 2008, pp. 337-349, vol. 4.
Janeway, C.A. et al., Immuno Biology, 6th Edition, Garland Science Publishing, 2005, p. 414.
Janeway, C.A. et al., "Autoimmune Responses are Directed Against Self Antigens," Immunobiology: The Immune System in Health and Disease, 5th Edition, Garland Science, 2001, pp. 1-14.
Jarry, A. et al., "Mucosal IL-10 and TGF-β Play Crucial Roles in Preventing LPS-Driven, IFN-γ-Mediated Epithelial Damage in Human Colon Explants," The Journal of Clinical Investigation, Mar. 2008, pp. 1132-1142, vol. 118, No. 3.
Chapter 11: Spore-Forming Gram-Positive Bacilli: *Bacillus* and *Clostridium* Species, Jawetz, Melnick & Adelberg's Medical Microbiology, 26e, Mar. 7, 2017, pp. 1-15.
Kakihana, K. et al., "Fecal Microbiota Transplantation for Patients with Steroid-Resistant Acute Graft-Versus-Host Disease of the Gut," Blood, Oct. 20, 2016, pp. 2083-2088, vol. 128, No. 16.
Kelly, D. et al., "Commensal Gut Bacteria: Mechanisms of Immune Modulation," Trends in Immunology, Jun. 2005, pp. 326-333, vol. 26, No. 6.
Keynan, Y. et al., "The Role of Regulatory T Cells in Chronic and Acute Viral Infections," CID, Apr. 1, 2008, pp. 1046-1052, vol. 46.
Krogius-Kurikka, L. et al., "Sequence Analysis of Percent G+C Fraction Libraries of Human Fecal Bacterial DNA Reveals a High Number of Actinobacteria," BMC Microbiology, 2009, pp. 1-13, vol. 9, No. 68.
Lau, S.K.P. et al., "Bacteraemia Caused by Anaerotruncus Colihominis and Emended Description of the Species," J. Clin. Pathol., 2006, pp. 748-752, vol. 59.
Lawson, P.A., "Anaerotruncus," Bergey's Manual of Systematics of Archaea and Bacteria, Bergey's Manual Trust, 2009, pp. 1-4.
Louis, P. et al., "Diversity, Metabolism and Microbial Ecology of Butyrate-Producing Bacteria from the Human Large Intestine," FEMS Microbiol. Lett., 2009, pp. 1-8, vol. 294.
Maizels, R.M. et al., Chapter 3: Regulatory T Cells in Infection, Advances in Immunology, 2011, pp. 73-136, vol. 112.
Maslowski, K.M. et al., "Diet, Gut Microbiota and Immune Responses," Nature Immunology, Jan. 2011, pp. 5-9, vol. 12, No. 1.
Nitzan, O. et al., "Role of Antibiotics for Treatment of Inflammatory Bowel Disease," World Journal of Gastroenterology, Jan. 21, 2016, pp. 1078-1087, vol. 22, No. 3.
O'Garra, A. et al., "IL-10-Producing and Naturally Occurring CD4+ Tregs: Limiting Collateral Damage," The Journal of Clinical Investigation, Nov. 2004, pp. 1372-1378, vol. 114, No. 10.
Non-Patent Literature Submitted with Notice of Opposition to a European Patent, Jul. 18, 2017, European Patent No. EP2575835: Other Evidence, E 102635, 1 page.
Priority Document PCT/JP2010/071746 for PCT Application No. PCT/JP2011/063302, Filed Dec. 3, 2010, 107 pages.
Machine Translation of PCT Specification, PCT Application No. PCT/JP2010/071746, Filed Dec. 3, 2010, 79 pages.
Priority Document JP 2010-129134 for PCT Application No. PCT/JP2011/063302, Filed Jun. 4, 2010, 42 pages.
Preamble and Precautionary Statements Regarding Amendment and Argument, European Application No. 11728077.6, Feb. 25, 2014, 6 pages.
Qiu, X. et al., "Faecalibacterium prausnitzii Upregulates Regulatory T Cells and Anti-Inflammatory Cytokines in Treating TNBS-Induced Colitis," Journal of Crohn's and Colitis, 2013, pp. e558-e568, vol. 7.
Response to Official Communication dated Sep. 18, 2018, European Application No. 11728077.6, dated Nov. 18, 2015, 2 pages.
Response of Jan. 28, 2015 in Examination, European Application No. 11728077.6, 3 pages.
Roberts, B., Presentation: "Generation and Development of Defined Microbial Drug Products," Vendata Biosciences, 2016, 17 pages.
Rosero, J.A. et al., Abstract: "Reclassification of Eubacterium Rectale (Hauduroy et al. 1937) Prevot 1938 in a New Genus *Agathobacter* gen. nov. as *Agathobacter rectalis* comb. nov., and Description of *Agathobacter ruminis* sp. nov., Isolated from the Rumen Contents of Sheep and Cows," Int. J. Sys. Evol. Microbiol., Feb. 2016, pp. 768-773, vol. 66, No. 2.
Rossen, N.G. et al., "Findings From a Randomized Controlled Trial of Fecal Transplantation for Patients with Ulcerative Colitis," Gastroenterology, 2015, pp. 110-118, vol. 149.
Rossi, O. et al., "Faecalibacterium prausnitzii A2-165 Has a High Capacity to Induce IL-10 in Human and Murine Dendritic Cells and Modulates T Cell Responses," Scientific Reports, Jan. 4, 2015, pp. 1-12, vol. 6.
Sanchez, A.M. et al., "The Role of Natural Regulatory T Cells in Infection," Immunol. Res., Apr. 2011, pp. 124-134, vol. 49.
Sartor, R.B., "Therapeutic Correction of Bacterial Dysbiosis Discovered by Molecular Techniques," PNAS, Oct. 28, 2008, pp. 16413-16414, vol. 105, No. 43.
Cover Page of Science, Jan. 21, 2011, 1 page.
Sequence Listing, PCT Application No. PCT/JP2011/063302, 43 pages.
Sghir, A. et al., "Quantification of Bacterial Groups within Human Fecal Flora by Oligonucleotide Probe Hybridization," Applied and Environmental Microbiology, May 2000, pp. 2263-2266, vol. 66, No. 5.
Sokol, H. et al., "Faecalibacterium prausnitzii is an Anti-Inflammatory Commensal Bacterium Identified by Gut Microbiota Analysis of Crohn Disease Patients," PNAS, Oct. 28, 2008, pp. 16731-16736, vol. 105, No. 43.
Sokol, H. et al., "Low Counts of Faecalibacterium prausnitzii in Colitis Microbiota," Inflamm. Bowel Dis., 2009, pp. 1183-1189, vol. 15, No. 8.
Takaishi, H. et al., "Imbalance in Intestinal Microflora Constitution Could be Involved in the Pathogenesis of Inflammatory Bowel Disease," International Journal of Medical Microbiology, 2008, pp. 463-472, vol. 298.
Wachsman, J.T. et al., "Characterization of an Orotic Acid Fermenting Bacterium *Zymobacterium oroticum*, Nov. Gen., Nov. Spec.," Research Contract with United States Atomic Energy Commission, 1954, pp. 400-404, vol. 68, No. 4.
Warren, Y.A. et al., "*Clostridium aldenese* sp. nov. and *Clostridium citroniae* sp. nov. Isolated from Human Clinical Infections," Journal of Clinical Microbiology, Jul. 2006, pp. 2416-2422, vol. 44, No. 7.
Wells, C.L. et al., Chapter 18: Clostridia: Sporeforming Anaerobic Bacilli, Medical Microbiology, 4th Edition, 1996, pp. 1-20.
Zhou, D. et al., "Total Fecal Microbiota Transplantation Alleviates High-Fat Diet-Induced Steatohepatitis in Mice Via Beneficial Regulation of Gut Microbiota," Scientific Reports, May 8, 2017, pp. 1-11, vol. 7.
Hazenberg, M.P. et al., "Conversion of Germ-Free Mice to the Normal State by Clostridia," Zeitschrift fur Versuchstierkunde, 1976, pp. 185-190, vol. 18, No. 4.
Manichanh, C. et al., "Reshaping the Gut Microbiome with Bacterial Transplantation and Antibiotic Intake," Genome Research, 2010, pp. 1411-1419, vol. 20.
Thompson-Chagoyan, O.C. et al., "Aetiology of Inflammatory Bowel Disease (IBD): Role of Intestinal Microbiota and Gut-Associated Lymphoid Tissue Immune Response," Clinical Nutrition, Feb. 2005, pp. 339-352, vol. 24, No. 3.
Wilson, K.H. et al., "Interaction of Clostridium difficile and *Escherichia coli* with Microfloras in Continuous-Flow Cultures and Gnotobiotic Mice," Infection and Immunity, Nov. 1986, pp. 354-358, vol. 54, No. 2.
Dabard et al., "Ruminococcin A, a New Lantibiotic Produced by a Ruminococcus gnavus Strain Isolated from Human Feces," Appl Envr MicroBiol 67(9):4111-8, American Society for Microbiology, United States (2001).

(56) References Cited

OTHER PUBLICATIONS

Evidence of Effects of Probiotics Against Antimicrobial-Related Diarrhea, Pharmacy, Paper 62(3): 12 pages (2011).
Fitzpatrick, L.R. et al., "Probiotics for the treatment of Clostridium difficile associated disease," World Journal of Gastrointestinal Pathophysiology 4(3):47-52, Baishideng Publishing Group, United States (2008).
International Search Report and Written Opinion for International Application No. PCT/US2016/063697, European Patent Office, H V Rijswijk, dated May 19, 2017, 24 pages.
International Search Report and Patentability for Application No. PCT/US2016/063697, dated May 29, 2018, Button et al., "Designed Bacterial Compositions," filed Nov. 23, 2016, 27 pages.
Office Action dated Aug. 19, 2016, in U.S. Appl. No. 14/592,481, Henn, M.R., et al., filed Jan. 8, 2015.
Seki, H., et al., "Prevention of Antibiotic-Associated Diarrhea in Children by Clostridium Butyricuin MAYAIRI," Pediatrics International, 45(1):86-90, Blackwell Science Asia, Australia (Feb. 2003).
Ze, et al, "Ruminococcus bromii is a keystone species for the degradation of resistant starch in the human colon," SIME J 6(8):1535-43, International Society for Microbial Ecology, United States (2012).
Office action dated Dec. 31, 2019, in U.S. Appl. No. 16/051,747, Maltzahn; G. et al., filed Aug. 1, 2018, 47 pages.
Office action dated Mar. 15, 2019, in U.S. Appl. No. 16/054,864, McKenzie; G. et al., filed Aug. 3, 2018, 10 pages.
Office action dated Nov. 11, 2019, in U.S. Appl. No. 16/054,864, McKenzie; G. et al., filed Aug. 3, 2018, 11 pages.
Office action dated Dec. 21, 2018, in U.S. Appl. No. 15/986,369, Pamer; E. et al., filed May 22, 2018, 15 pages.
Office action dated Sep. 20, 2019, in U.S. Appl. No. 15/986,369, Pamer; E. et al., filed May 22, 2018, 10 pages.
Office action dated Jan. 13, 2020, in U.S. Appl. No. 15/986,369, Pamer; E. et al., filed May 22, 2018, 10 pages.
Office action dated Jan. 18, 2019, in U.S. Appl. No. 14/765,814, Cook; D. et al., filed Aug. 4, 2015, 14 pages.
Office action dated Nov. 14, 2019, in U.S. Appl. No. 14/765,814, Cook; D. et al., filed Aug. 4, 2015, 18 pages.
Office action dated Oct. 22, 2019, in U.S. Appl. No. 15/742,732, Cook; D. et al., filed Jan. 8, 2018, 10 pages.
Office action dated Mar. 21, 2019, in U.S. Appl. No. 14/765,812, Afeyan; N. et al., filed Aug. 4, 2015, 10 pages.
Office action dated Dec. 11, 2019, in U.S. Appl. No. 14/765,812, Afeyan; N. et al., filed Aug. 4, 2015, 10 pages.
Abt, M.C., et al., "Commensal Bacteria Calibrate the Activation Threshold of Innate Antiviral Immunity," Immunity, 37(1):158-170, Cell Press, United States, (Jul. 2012).
Ahern et al., "The interleukin-23 axis in intestinal inflammation," Immunological Reviews 226:147-159 (Dec. 2008).
Anonymous, "Microbiome Therapeutics Platform," Seres Therapeutics, Retrieved on [Oct. 23, 2015], Retrieved from (http:/ /web.arch ive.org/web/20 151023063153/), Retrieved from (http://www.serestherapeutics.com/ourscience/ microbiome-therapeutics-platform), Retrieved on [Mar. 7, 2017], 3 pages.
Anonymous, "Product Pipeline," Seres Therapeutics, Oct. 22, 2015], Retrieved from (www.serestherapeutics.com/pipeline/products), Retrieved on[Mar. 7, 2017], (3 pages).
Caballero, S. et al. "Distinct but Spatially Overlapping Intestinal Niches for Vancomycin-Resistant Enterococcus faecium and Carbapenem-Resistant Klebsiella Pneumoniae" PLOS Pathogens 11(9):e1005132, Public Library of Science, United States (Sep. 2015).
Cruz et al., "Immunosuppressive and Nonimmunosuppressive Cyclosporine Analogs Are Toxic to the Opportunistic Fungal Pathogen *Cryptococcus neoformans* via Cyclophilin-Dependent Inhibition of Calcineurin," Antimicrob. Agents Chemother. 44(1):143-149, American Society for Microbiology (Jan. 2000).
Derrien, M.,et al., "Modulation of Mucosal Immune Response, Tolerance, and Proliferation in Mice Colonized by the Mucin-degrader Akkermansia Muciniphila.," Frontiers in Microbiology, 2:166, Frontiers Research Foundation, Switzerland., (Aug. 2011).
Final Office Action dated Nov. 1, 2019, in U.S. Appl. No. 16/054,864, Gregory McKenzie et al., filed Aug. 3, 2018, 10 pages.
Final Office Action dated Apr. 14, 2020, in U.S. Appl. No. 16/223,008, Henn, M.R. et al., filed Dec. 17, 2018, 11 pages.
Final Office Action dated May 5, 2020, in U.S. Appl. No. 14/765,814, Cook, D. et al., filed Aug. 4, 2015, 16 pages.
Gut definition. Merriam Webster Dictionary. https://www.merriamwebster.com/dictionary/gut, retrieved Mar. 9, 2020.
International Search Report and Written Opinion for Application No. PCT/US2016/041538, dated Sep. 23, 2016, Cook., et al., "Methods of Treating Colitis," filed Jul. 8, 2016, 12 Pages.
Non Final Office Action dated Mar. 15, 2019, in U.S. Appl. No. 16/054,864, Gregory McKenzie et al., filed Aug. 3, 2018, 9 pages.
Non Final Office Action dated Apr. 7, 2020, in U.S. Appl. No. 16/054,864, Gregory McKenzie et al., filed Aug. 3, 2018, 15 pages.
Non-Final Office Action dated Dec. 9, 2019, in U.S. Appl. No. 16/223,008, Matthew R. Henn et al., filed Dec. 17, 2018, 17 pages.
Final Office Action dated Apr. 14, 2020, in U.S. Appl. No. 16/223,008, Matthew R. Henn et al., filed Dec. 17, 2018, 11 pages.
Non-Final Office Action dated Mar. 10, 2020, in U.S. Appl. No. 15/778,095, Button, J. et al., filed May 22, 2018, 28 pages.
Office Action dated Feb. 26, 2019, in U.S. Appl. No. 15/312,610, Pamer, E. et al., filed Nov. 18, 2016, 22 pages.
Office Action dated Jun. 6, 2020, in U.S. Appl. No. 16/523,414, Pamer, E. et al., filed Jul. 26, 2019, 10 pages.
Office Action dated Jul. 10, 2018, in U.S. Appl. No. 15/312,610, Pamer,E. et al., filed Nov. 18, 2016, 16 pages.
Rasti et al., "Inhibition of Clostridium scindens and Clostridium hiranonis growth by Bifidobacterium pseudocatenulatum G4 in simulated colonic pH," Journal of Food Agriculture and Environment 11 (2): 127-131, WFL Publisher Ltd, Poland (2013).
Stackebrandt, E., et al., "Taxonomic Note: A Place for DNA-DNA Reassociation and 16s rRNA Sequence Analysis in the Present Species Definition in Bacteriology ," International Journal of Systematic Bacteriology 44 (4):846-849, (Oct. 1994).
Surawicz, C.M and Alexander, J., "Treatment of Refractory and Recurrent Clostridium Difficile Infection, " Nature Reviews Gastroenterology & Hepatology, 8(6):330-339, Nature Publishing Group, England (Jun. 2011).
Vogt et al. "Chemical communication in the gut: Effects of microbiota-generated metabolites on gastrointestinal bacterial pathogens," Anaerobe 34 106-115, Elsevier, Netherlands (May 2015).
Wortman et al., "Design and evaluation of SER-262: A fermentation-derived microbiometherapeutic for the prevention of recurrence in patients with primary clostridium difficile infection," Seres Therapeutics, Cambridge, MA, Jun. 1, 2016, Retrived from (http://serestherapeutics.com/sites/default/files/wortman_asm_poster_final_poster ser_262.pdf), Retrieved on [Mar. 6, 2017], 1 page.

\* cited by examiner

```
   1 AAATGAAGAGTTTGATCATGGCTCAGATTGAACGCTGGCGGCAGGCCTA
  51 ACACATGCAAGTCGAACGGTAACAGGAAGAAGCTTGCTCTTTGCTGACGA
 101 GTGGCGGACGGGTGAGTAATGTCTGGGAAACTGCCTGATGGAGGGGGATA
 151 ACTACTGGAAACGGTAGCTAATACCGCATAACGTCGCAAGACCAAAGAGG
 201 GGGACCTTCGGGCCTCTTGCCATCGATGTGCCCAGATGGGATTAGCTAG
 251 TAGGTGGGGTAACGGCTCACCTAGGCGACGATCCCTAGCTGGTCTGAGAG
 301 GATGACCAGCCACACTGGAACTGAGACACGGTCCAGACTCCTACGGGAGG
 351 CAGCAGTGGGGAATATTGCACAATGGGCGCAAGCCTGATGCAGCCATGCC
 401 GCGTGTATGAAGAAGGCCTTCGGGTTGTAAAGTACTTTCAGCGGGGAGGA
 451 AGGGAGTAAAGTTAATACCTTTGCTCATTGACGTTACCCGCAGAAGAAGC
 501 ACCGGCTAACTCGTGCCAGCAGCCGCGGTAATACGGAGGGTGCAAGCGT
 551 TAATCGGAATTACTGGGCGTAAAGCGCACGCAGGCGGTTTGTTAAGTCAG
 601 ATGTGAAATCCCCGGGCTCAACCTGGGAACTGCATCTGATACTGGCAAGC
 651 TTGAGTCTCGTAGAGGGGGGTAGAATTCCAGGTGTAGCGGTGAAATGCGT
 701 AGAGATCTGGAGGAATACCGGTGGCGAAGGCGGCCCCCTGGACGAAGACT
 751 CACGCTCAGGTGCGAAAGCGTGGGGAGCAAACAGGATTAGATACCCTGGT
 801 AGTCCACGCCGTAAACGATGTCGACTTGGAGGTTGTGCCCTTGAGGCGTG
 851 GCTTCCGGAGCTAACGCGTTAAGTCGACCGCCTGGGGAGTACGGCCGCAA
 901 GGTTAAAACTCAAATGAATTGACGGGGGCCCGAAGAACCTTACCTGGTCTTGACATCCAC
 951 TGGTTAATTCGATGCAACGCGAAGAACCTTACCTGGTCTTGACATCCAC
1001 GGAAGTTTCAGAGATGAGAATGTGCCTTCGGGAACGGTGAGACAGGTGC
1051 TGCATGGCTGTCGTCAGCTCGTGTTGTGAAAGTTGGGTTAAGTCCCGCA
1101 ACGAGCGCAACCCTTATCCTTTGTTGCCAGCGGTCCGGCCGGGAACTCAA
1151 AGGAGACTGCCAGTGATAAACTGGAGGAAGGTGGGGATGACGTCAAGTCA
1201 TCATGGCCCTTACGACCAGGGCTACACACGTGCTACAATGGCGCATACAA
1251 AGAGAAGCGACCTCGCGAGAGCAAGCGGACCTCATAAAGTGCGTCGTAGT
1301 CCGGATTGGAGTCTGCAACTCGACTCCATGAAGTCGGAATCGCTAGTAAT
1351 CGTGGATCAGAATGCCACGGTGAATACGTTCCCGGGCCTTGTACACACCG
1401 CCCGMCACACCATGGGAGTAGGTTGCAAAAGAAGTAGGTAGCTTAACCTT
1451 CGGGAGGGCGCTTACCACTTTGTGATTCATGACTGGGGTGAAGTCGTAAC
1501 AAGGTAACCGTAGGGGAACCTGCGGTTGGATCACCTCCTTA
```

Figure 2

NETWORK-BASED MICROBIAL COMPOSITIONS AND METHODS

RELATED APPLICATIONS

This application is a divisional of U.S. application Ser. No. 14/777,252, filed Sep. 15, 2015, which is the National Stage of International Application No. PCT/US2014/030817, filed Mar. 17, 2014, which claims the benefit of U.S. Provisional Application No. 61/798,666, filed Mar. 15, 2013, all of which are incorporated by reference in their entirety.

REFERENCE TO A SEQUENCE LISTING

This application includes a Sequence Listing submitted electronically as a text file named 40681_US_sequencelisting.txt, created on May 21, 2018, with a size of 4,166,333 bytes. The sequence listing is incorporated by reference.

BACKGROUND

Mammals are colonized by microbes in the gastrointestinal (GI) tract, on the skin, and in other epithelial and tissue niches such as the oral cavity, eye surface and vagina. The gastrointestinal tract harbors an abundant and diverse microbial community. It is a complex system, providing an environment or niche for a community of many different species or organisms, including diverse strains of bacteria. Hundreds of different species can form a commensal community in the GI tract in a healthy person, and this complement of organisms evolves from birth to ultimately form a functionally mature microbial population by about 3 years of age. Interactions between microbial strains in these populations and between microbes and the host (e.g. the host immune system) shape the community structure, with availability of and competition for resources affecting the distribution of microbes. Such resources may be food, location and the availability of space to grow or a physical structure to which the microbe may attach. For example, the host's diet is involved in shaping the GI tract flora.

A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of dysbiosis' or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the intestinal microbiota plays a significant role in the pathogenesis of many diseases and disorders. Many of these diseases and disorders are chronic conditions that significantly decrease a subject's quality of life and can be ultimately fatal.

Manufacturers of probiotics have asserted that their preparations of bacteria promote mammalian health by preserving the natural microflora in the GI tract and reinforcing the normal controls on aberrant immune responses. See, e.g., U.S. Pat. No. 8,034,601. Probiotics, however, have been limited to a very narrow group of genera and a correspondingly limited number of species. As such, they do not adequately replace the missing natural microflora nor correct dysbioses of the GI tract in many situations.

Therefore, in response to the need for durable, efficient, and effective compositions and methods for prevention, diagnosis and/or treatment of prediabetes and diabetes by way of restoring or enhancing microbiota functions, we address these and other shortcomings of the prior art by providing compositions and methods for treating subjects.

SUMMARY OF THE INVENTION

Disclosed herein are methods for treating, preventing, or reducing the severity of a disorder selected from the group consisting of *Clostridium difficile* Associated Diarrhea (CDAD), Type 2 Diabetes, Obesity, Irritable Bowel Disease (IBD), colonization with a pathogen or pathobiont, and infection with a drug-resistant pathogen or pathobiont, comprising: administering to a mammalian subject in need thereof an effective amount of a therapeutic bacterial composition, said therapeutic bacterial composition comprising a plurality of isolated bacteria or a purified bacterial preparation, the plurality of isolated bacteria or the purified bacterial preparation capable of forming a network ecology selected from the group consisting of N262.S, N290.S, N284.S, N271.S, N282.S, N288.S, N302.S, N279.S, N310.S, N323.S, N331.S, N332.S, N301.S, N312.S, N339.S, N325.S, N340.S, N341.S, N346.S, N338.S, N336.S, N345.S, N355.S, N356.S, N343.S, N329.S, N361.S, N353.S, N381.S, N344.S, N352.S, N357.S, N358.S, N369.S, N372.S, N375.S, N380.S, N374.S, N377.S, N368.S, N370.S, N373.S, N376.S, N389.S, N394.S, N431.S, N434.S, N390.S, N397.S, N387.S, N440.S, N396.S, N399.S, N403.S, N414.S, N430.S, N432.S, N436.S, N437.S, N457.S, N545, N386.S, N402.S, N405.S, N415.S, N421.S, N422.S, N423.S, N458.S, N459.S, N493.S, N416.S, N439.S, N447.S, N490.S, N526, N429.S, N433.S, N448.S, N488.S, N508.S, N509.S, N510.S, N511.S, N408.S, N446.S, N451.S, N474.S, N520.S, N521.S, N535.S, N516.S, N463.S, N518.S, N586, N450.S, N465.S, N519.S, N537.S, N419.S, N468.S, N477.S, N514.S, N382.S, N460.S, N462.S, N512.S, N517.S, N523.S, N547.S, N548.S, N577.S, N581.S, N585.S, N616.S, N466.S, N469.S, N480.S, N482.S, N484.S, N515.S, N533.S, N709, N730, N478.S, N572.S, N400.S, N543.S, N582.S, N621.S, N689, N769, N481.S, N525.S, N528.S, N534.S, N574.S, N580.S, N590.S, N591.S, N597.S, N664, N693, N530.S, N687, N470.S, N529.S, N539.S, N546.S, N570.S, N579.S, N602.S, N614.S, N648.S, N652.S, N655.S, N672.S, N681.S, N690.S, N692.S, N698.S, N737.S, N738.S, N785, N841, N878, N880, N881, N987, N988, N996, N1061, N479.S, N538.S, N542.S, N578.S, N609.S, N611.S, N617.S, N666.S, N675.S, N682.S, N844, N845, N846, N852, N876, N982, N1008, N649.S, N657.S, N678.S, N686.S, N710.S, N522.S, N651.S, N653.S, N654.S, N680.S, N712.S, N792, N802, N804, N807, N849, N858, N859, N875, N885, N942, N961, N972, N1051, N587.S, N589.S, N612.S, N625.S, N656.S, N714.S, N779, N781, N828, N829, N860, N894, N925, N927, N935, N947, N983, N1023, N441.S, N584.S, N794, N788, N524.S, N604.S, N610.S, N623.S, N663.S, N669.S, N676.S, N703.S, N775.S, N777.S, N780.S, N817.S, N827.S, N836.S, N871.S, N874.S, N898.S, N907.S, N998.S, N1088, N1089, N660.S, N665.S, N667.S, N733.S, N734.S, N739.S, N741.S, N782.S, N789.S, N796.S, N798.S, N800.S, N809.S, N816.S, N842.S, N843.S, N869.S, N986.S, N995.S, N1002.S, N1004.S, N1019.S, N1093, N668.S, N685.S, N835.S, N851.S, N464.S, N695.S, N776.S, N793.S, N815.S, N833.S, N891.S, N1070.S, N1092, N795.S, N797.S, N808.S, N811.S, N826.S, N830.S, N832.S, N840.S, N945.S, N960.S, N968.S, N1091, N805.S, N822.S, N928.S, N936.S, N1078.S, and N913.S.

In some embodiments, the therapeutic bacterial composition comprises at least one bacterial entity, wherein said bacterial entity is capable of forming the network ecology in combination with one more bacterial entities present in the gastrointestinal tract of the mammalian subject at the time of the administering or thereafter. In certain embodiments, the network ecology is selected from the group consisting of N1008, N1023, N1051, N1061, N1070.S, N1088, N1089, N1092, N381.S, N382.S, N387.S, N399.S, N400.S, N402.S, N403.S, N414.S, N429.S, N430.S, N432.S, N433.S, N436.S, N437.S, N439.S, N441.S, N447.S, N448.S, N457.S, N460.S, N462.S, N463.S, N464.S, N470.S, N474.S, N488.S, N490.S, N493.S, N508.S, N509.S, N510.S, N511.S, N512.S, N514.S, N515.S, N517.S, N518.S, N519.S, N520.S, N523.S, N524.S, N529.S, N539.S, N543.S, N546.S, N547.S, N548.S, N570.S, N574.S, N577.S, N579.S, N580.S, N582.S, N584.S, N585.S, N589.S, N591.S, N597.S, N602.S, N604.S, N609.S, N610.S, N611.S, N612.S, N614.S, N616.S, N621.S, N623.S, N625.S, N648.S, N651.S, N652.S, N653.S, N654.S, N655.S, N660.S, N663.S, N664, N665.S, N666.S, N669.S, N672.S, N676.S, N681.S, N687, N689, N690.S, N692.S, N693, N695.S, N698.S, N703.S, N709, N712.S, N714.S, N730, N734.S, N737.S, N738.S, N769, N775.S, N777.S, N779, N780.S, N781, N785, N788, N792, N793.S, N794, N797.S, N798.S, N802, N804, N807, N817.S, N827.S, N828, N830.S, N832.S, N833.S, N836.S, N840.S, N841, N844, N845, N849, N852, N858, N859, N860, N869.S, N871.S, N874.S, N875, N878, N880, N881, N885, N894, N898.S, N907.S, N913.S, N925, N927, N942, N947, N961, N968.S, N972, N982, N983, N986.S, N987, N988, N996, and N998.S.

In one embodiment, the network ecology consists essentially of N1008, N1023, N1051, N1061, N1070.S, N1088, N1089, N1092, N381.S, N382.S, N387.S, N399.S, N400.S, N402.S, N403.S, N414.S, N429.S, N430.S, N432.S, N433.S, N436.S, N437.S, N439.S, N441.S, N447.S, N448.S, N457.S, N460.S, N462.S, N463.S, N464.S, N470.S, N474.S, N488.S, N490.S, N493.S, N508.S, N509.S, N510.S, N511.S, N512.S, N514.S, N515.S, N517.S, N518.S, N519.S, N520.S, N523.S, N524.S, N529.S, N539.S, N543.S, N546.S, N547.S, N548.S, N570.S, N574.S, N577.S, N579.S, N580.S, N582.S, N584.S, N585.S, N589.S, N591.S, N597.S, N602.S, N604.S, N609.S, N610.S, N611.S, N612.S, N614.S, N616.S, N621.S, N623.S, N625.S, N648.S, N651.S, N652.S, N653.S, N654.S, N655.S, N660.S, N663.S, N664, N665.S, N666.S, N669.S, N672.S, N676.S, N681.S, N687, N689, N690.S, N692.S, N693, N695.S, N698.S, N703.S, N709, N712.S, N714.S, N730, N734.S, N737.S, N738.S, N769, N775.S, N777.S, N779, N780.S, N781, N785, N788, N792, N793.S, N794, N797.S, N798.S, N802, N804, N807, N817.S, N827.S, N828, N830.S, N832.S, N833.S, N836.S, N840.S, N841, N844, N845, N849, N852, N858, N859, N860, N869.S, N871.S, N874.S, N875, N878, N880, N881, N885, N894, N898.S, N907.S, N913.S, N925, N927, N942, N947, N961, N968.S, N972, N982, N983, N986.S, N987, N988, N996, or N998. S.

In another embodiment, the network ecology is selected from the group consisting of N387.S, N399.S, N512.S, N462.S, N651.S, N982, and N845. In one embodiment, network ecology comprises N387.S and the therapeutic bacterial composition comprises at least one bacterium selected from each of clade_262, clade_396, clade_444, clade_478, clade_500, and clade_553. In another embodiment, the network ecology comprises N387.S and the therapeutic bacterial composition consists essentially of at least one bacterium selected from each of clade_262, clade_396, clade_444, clade_478, clade_500, and clade_553. In certain embodiments, clade_262 comprises one or more bacteria selected from the group consisting *Clostridium glycyrrhizinilyticum*, *Clostridium nexile*, *Coprococcus comes*, Lachnospiraceae bacterium 1_1_57FAA, Lachnospiraceae bacterium 1_4_56FAA, Lachnospiraceae bacterium 8_1_57FAA, *Ruminococcus lactaris*, and *Ruminococcus torques*, wherein clade_396 comprises one or more bacteria selected from the group consisting *Acetivibrio ethanolgignens*, *Anaerosporobacter mobilis*, *Bacteroides pectinophilus*, *Clostridium aminovalericum*, *Clostridium phytofermentans*, *Eubacterium hallii*, and *Eubacterium xylanophilum*, wherein clade_444 comprises one or more bacteria selected from the group consisting *Butyrivibrio fibrisolvens*, *Eubacterium rectale*, *Eubacterium* sp. oral clone GI038, *Lachnobacterium bovis*, *Roseburia cecicola*, *Roseburia faecalis*, *Roseburia faecis*, *Roseburia hominis*, *Roseburia intestinalis*, *Roseburia inulinivorans*, *Roseburia* sp. 11SE37, *Roseburia* sp. 11SE38, *Shuttleworthia satelles*, *Shuttleworthia* sp. MSX8B, and *Shuttleworthia* sp. oral taxon G69, wherein clade_478 comprises one or more bacteria selected from the group consisting *Faecalibacterium prausnitzii*, *Gemmiger formicilis*, and *Subdoligranulum variabile*, wherein clade_500 comprises one or more bacteria selected from the group consisting *Alistipes finegoldii*, *Alistipes onderdonkii*, *Alistipes putredinis*, *Alistipes shahii*, *Alistipes* sp. HGB5, *Alistipes* sp. JC50, and *Alistipes* sp. RMA 9912, and wherein clade_553 comprises one or more bacteria selected from the group consisting *Collinsella aerofaciens*, *Collinsella intestinalis*, *Collinsella stercoris*, and *Collinsella tanakaei*.

In one embodiment, clade_262 comprises one or more bacteria of *Ruminococcus torques*, wherein clade_396 comprises one or more bacteria of *Eubacterium hallii*, wherein clade_444 comprises one or more bacteria selected from the group consisting of *Eubacterium rectale* and *Roseburia inulinivorans*, wherein clade_478 comprises one or more bacteria of *Faecalibacterium prausnitzii*, wherein clade_500 comprises one or more bacteria of *Alistipes putredinis*, and wherein clade_553 comprises one or more bacteria of *Collinsella aerofaciens*.

In another embodiment, clade_262 comprises one more bacteria selected from the group consisting of bacteria having 16S sequences having 97% or greater identity to Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_396 comprises one more bacteria selected from the group consisting of bacteria having 16S sequences having 97% or greater identity to Seq. ID No.: 161, Seq. ID No.: 288, Seq. ID No.: 551, Seq. ID No.: 6, Seq. ID No.: 613, Seq. ID No.: 848, and Seq. ID No.: 875, wherein clade_444 comprises one more bacteria selected from the group consisting of bacteria having 16S sequences having 97% or greater identity to Seq. ID No.: 1045, Seq. ID No.: 1634, Seq. ID No.: 1635, Seq. ID No.: 1636, Seq. ID No.: 1637, Seq. ID No.: 1638, Seq. ID No.: 1639, Seq. ID No.: 1640, Seq. ID No.: 1641, Seq. ID No.: 1728, Seq. ID No.: 1729, Seq. ID No.: 1730, Seq. ID No.: 456, Seq. ID No.: 856, and Seq. ID No.: 865, wherein clade_478 comprises one more bacteria selected from the group consisting of bacteria having 16S sequences having 97% or greater identity to Seq. ID No.: 1896, Seq. ID No.: 880, and Seq. ID No.: 932, wherein clade_500 comprises one more bacteria selected from the group consisting of bacteria having 16S sequences having 97% or greater identity to Seq. ID No.: 129, Seq. ID No.: 131, Seq. ID No.: 132, Seq. ID No.: 133, Seq. ID No.: 134, Seq. ID No.: 135, and Seq. ID No.: 136, and wherein clade_553 comprises one more bacteria selected from the group consisting of bacteria having 16S sequences having 97% or greater identity to Seq. ID No.: 659, Seq. ID No.: 660, Seq. ID No.: 661, and Seq. ID No.: 662.

In other embodiments, clade_262 comprises one more bacteria selected from the group consisting of bacteria having 16S sequences Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_396 comprises one more bacteria selected from the group consisting of bacteria having 16S sequences Seq. ID No.: 161, Seq. ID No.: 288, Seq. ID No.: 551, Seq. ID No.: 6, Seq. ID No.: 613, Seq. ID No.: 848, and Seq. ID No.: 875, wherein clade_444 comprises one more bacteria selected from the group consisting of bacteria having 16S sequences Seq. ID No.: 1045, Seq. ID No.: 1634, Seq. ID No.: 1635, Seq. ID No.: 1636, Seq. ID No.: 1637, Seq. ID No.: 1638, Seq. ID No.: 1639, Seq. ID No.: 1640, Seq. ID No.: 1641, Seq. ID No.: 1728, Seq. ID No.: 1729, Seq. ID No.: 1730, Seq. ID No.: 456, Seq. ID No.: 856, and Seq. ID No.: 865, wherein clade_478 comprises one more bacteria selected from the group consisting of bacteria having 16S sequences Seq. ID No.: 1896, Seq. ID No.: 880, and Seq. ID No.: 932, wherein clade_500 comprises one more bacteria selected from the group consisting of bacteria having 16S sequences Seq. ID No.: 129, Seq. ID No.: 131, Seq. ID No.: 132, Seq. ID No.: 133, Seq. ID No.: 134, Seq. ID No.: 135, and Seq. ID No.: 136, and wherein clade_553 comprises one more bacteria selected from the group consisting of bacteria having 16S sequences Seq. ID No.: 659, Seq. ID No.: 660, Seq. ID No.: 661, and Seq. ID No.: 662.

In one embodiment, clade_262 comprises one or more bacteria selected from the group consisting of bacteria having 16S sequences having 97% or greater identity to Seq. ID No.: 1670, wherein clade_396 comprises one or more bacteria selected from the group consisting of bacteria having 16S sequences having 97% or greater identity to Seq. ID No.: 848, wherein clade_444 comprises one or more bacteria selected from the group consisting of bacteria having 16S sequences having 97% or greater identity to Seq. ID No.: 1639 and Seq. ID No.: 856, wherein clade_478 comprises one or more bacteria selected from the group consisting of bacteria having 16S sequences having 97% or greater identity to Seq. ID No.: 880, wherein clade_500 comprises one or more bacteria selected from the group consisting of bacteria having 16S sequences having 97% or greater identity to Seq. ID No.: 132, and wherein clade_553 comprises one or more bacteria selected from the group consisting of bacteria having 16S sequences having 97% or greater identity to Seq. ID No.: 659.

In other embodiments, clade_262 comprises one or more bacteria selected from the group consisting of bacteria having 16S sequences Seq. ID No.: 1670, wherein clade_396 comprises one or more bacteria selected from the group consisting of bacteria having 16S sequences Seq. ID No.: 848, wherein clade_444 comprises one or more bacteria selected from the group consisting of bacteria having 16S sequences Seq. ID No.: 1639 and Seq. ID No.: 856, wherein clade_478 comprises one or more bacteria selected from the group consisting of bacteria having 16S sequences Seq. ID No.: 880, wherein clade_500 comprises one or more bacteria selected from the group consisting of bacteria having 16S sequences Seq. ID No.: 132, and wherein clade_553 comprises one or more bacteria selected from the group consisting of bacteria having 16S sequences Seq. ID No.: 659.

In another embodiment, network ecology comprises N399.S and the therapeutic bacterial composition comprises at least one bacterium selected from each of clade_262, clade_360, clade_396, clade_444, clade_478, and clade_494. In yet another embodiment, the network ecology comprises N399.S and the therapeutic bacterial composition consists essentially of at least one bacterium selected from each of clade_262, clade_360, clade_396, clade_444, clade_478, and clade_494.

In some embodiments, clade_262 comprises one or more bacteria selected from the group consisting of *Clostridium glycyrrhizinilyticum*, *Clostridium nexile*, *Coprococcus comes*, Lachnospiraceae bacterium 1_1_57FAA, Lachnospiraceae bacterium 1_4_56FAA, Lachnospiraceae bacterium 8_1_57FAA, *Ruminococcus lactaris*, and *Ruminococcus torques*, wherein clade_360 comprises one or more bacteria selected from the group consisting of *Dorea formicigenerans*, *Dorea longicatena*, Lachnospiraceae bacterium 2_1_46FAA, Lachnospiraceae bacterium 2_1_58FAA, Lachnospiraceae bacterium 4_1_37FAA, Lachnospiraceae bacterium 9_1_43BFAA, *Ruminococcus gnavus*, and *Ruminococcus* sp. ID8, wherein clade_396 comprises one or more bacteria selected from the group consisting of *Acetivibrio ethanolgignens*, *Anaerosporobacter mobilis*, *Bacteroides pectinophilus*, *Clostridium aminovalericum*, *Clostridium phytofermentans*, *Eubacterium hallii*, and *Eubacterium xylanophilum*, wherein clade_444 comprises one or more bacteria selected from the group consisting of *Butyrivibrio fibrisolvens*, *Eubacterium rectale*, *Eubacterium* sp. oral clone GI038, *Lachnobacterium bovis*, *Roseburia cecicola*, *Roseburia faecalis*, *Roseburia faecis*, *Roseburia hominis*, *Roseburia intestinalis*, *Roseburia inulinivorans*, *Roseburia* sp. 11SE37, *Roseburia* sp. 11SE38, *Shuttleworthia satelles*, *Shuttleworthia* sp. MSX8B, and *Shuttleworthia* sp. oral taxon G69, wherein clade_478 comprises one or more bacteria selected from the group consisting of *Faecalibacterium prausnitzii*, *Gemmiger formicilis*, and *Subdoligranulum variabile*, and wherein clade_494 comprises one or more bacteria selected from the group consisting of *Clostridium orbiscindens*, *Clostridium* sp. NML 04A032, *Flavonifractor plautii*, *Pseudoflavonifractor capillosus*, and *Ruminococcaceae bacterium* D16.

In another embodiment, clade_262 comprises one or more bacteria of *Ruminococcus torques*, wherein clade_360 comprises one or more bacteria of *Dorea longicatena*, wherein clade_396 comprises one or more bacteria of *Eubacterium hallii*, wherein clade_444 comprises one or more bacteria of *Eubacterium rectale*, wherein clade_478 comprises one or more bacteria of *Faecalibacterium prausnitzii*, and wherein clade_494 comprises one or more bacteria of *Pseudoflavonifractor capillosus*.

In one embodiment, clade_262 comprises one more bacteria selected from the group consisting of bacteria having 16S sequences having 97% or greater identity to Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_360 comprises one more bacteria selected from the group consisting of bacteria having 16S sequences having 97% or greater identity to Seq. ID No.: 1050, Seq. ID No.: 1051, Seq. ID No.: 1053, Seq. ID No.: 1058, Seq. ID No.: 1661, Seq. ID No.: 1668, Seq. ID No.: 773, and Seq. ID No.: 774, wherein clade_396 comprises one more bacteria selected from the group consisting of bacteria having 16S sequences having 97% or greater identity to Seq. ID No.: 161, Seq. ID No.: 288, Seq. ID No.: 551, Seq. ID No.: 6, Seq. ID No.: 613, Seq. ID No.: 848, and Seq. ID No.: 875, wherein clade_444 comprises one more bacteria selected from the group consisting of bacteria having 16S sequences having 97% or greater identity to Seq. ID No.: 1045, Seq. ID No.: 1634, Seq. ID No.: 1635, Seq. ID No.: 1636, Seq. ID No.: 1637, Seq. ID No.: 1638, Seq. ID No.: 1639, Seq. ID No.: 1640, Seq. ID No.: 1641, Seq. ID No.: 1728, Seq. ID No.: 1729, Seq. ID No.: 1730, Seq. ID No.: 456, Seq. ID No.: 856, and Seq. ID No.: 865, wherein clade_478 comprises one more bacteria selected from the group consisting of bacteria having 16S sequences having 97% or greater identity to Seq. ID No.: 1896, Seq. ID No.: 880, and Seq. ID No.: 932, and wherein clade_494 comprises one more bacteria selected from the group consisting of bacteria having 16S sequences having 97% or greater identity to Seq. ID No.: 1591, Seq. ID No.: 1655, Seq. ID No.: 609, Seq. ID No.: 637, and Seq. ID No.: 886.

In some embodiments, clade_262 comprises one more bacteria selected from the group consisting of bacteria having 16S sequences Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_360 comprises one more bacteria selected from the group consisting of bacteria having 16S sequences Seq. ID No.: 1050, Seq. ID No.: 1051, Seq. ID No.: 1053, Seq. ID No.: 1058, Seq. ID No.: 1661, Seq. ID No.: 1668, Seq. ID No.: 773, and Seq. ID No.: 774, wherein clade_396 comprises one more bacteria selected from the group consisting of bacteria having 16S sequences Seq. ID No.: 161, Seq. ID No.: 288, Seq. ID No.: 551, Seq. ID No.: 6, Seq. ID No.: 613, Seq. ID No.: 848, and Seq. ID No.: 875, wherein clade_444 comprises one more bacteria selected from the group consisting of bacteria having 16S sequences Seq. ID No.: 1045, Seq. ID No.: 1634, Seq. ID No.: 1635, Seq. ID No.: 1636, Seq. ID No.: 1637, Seq. ID No.: 1638, Seq. ID No.: 1639, Seq. ID No.: 1640, Seq. ID No.: 1641, Seq. ID No.: 1728, Seq. ID No.: 1729, Seq. ID No.: 1730, Seq. ID No.: 456, Seq. ID No.: 856, and Seq. ID No.: 865, wherein clade_478 comprises one more bacteria selected from the group consisting of bacteria having 16S sequences Seq. ID No.: 1896, Seq. ID No.: 880, and Seq. ID No.: 932, and wherein clade_494 comprises one more bacteria selected from the group consisting of bacteria having 16S sequences Seq. ID No.: 1591, Seq. ID No.: 1655, Seq. ID No.: 609, Seq. ID No.: 637, and Seq. ID No.: 886.

In other embodiments, clade_262 comprises one or more bacteria selected from the group consisting of bacteria having 16S sequences having 97% or greater identity to Seq. ID No.: 1670, wherein clade_360 comprises one or more bacteria selected from the group consisting of bacteria having 16S sequences having 97% or greater identity to Seq. ID No.: 774, wherein clade_396 comprises one or more bacteria selected from the group consisting of bacteria having 16S sequences having 97% or greater identity to Seq. ID No.: 848, wherein clade_444 comprises one or more bacteria selected from the group consisting of bacteria having 16S sequences having 97% or greater identity to Seq. ID No.: 856, wherein clade_478 comprises one or more bacteria selected from the group consisting of bacteria having 16S sequences having 97% or greater identity to Seq. ID No.: 880, and wherein clade_494 comprises one or more bacteria selected from the group consisting of bacteria having 16S sequences having 97% or greater identity to Seq. ID No.: 1591.

In one aspect, clade_262 comprises one or more bacteria selected from the group consisting of bacteria having 16S sequences Seq. ID No.: 1670, wherein clade_360 comprises one or more bacteria selected from the group consisting of bacteria having 16S sequences Seq. ID No.: 774, wherein clade_396 comprises one or more bacteria selected from the group consisting of bacteria having 16S sequences Seq. ID No.: 848, wherein clade_444 comprises one or more bacteria selected from the group consisting of bacteria having 16S sequences Seq. ID No.: 856, wherein clade_478 comprises one or more bacteria selected from the group consisting of bacteria having 16S sequences Seq. ID No.: 880, and wherein clade_494 comprises one or more bacteria selected from the group consisting of bacteria having 16S sequences Seq. ID No.: 1591.

In another aspect, the network ecology comprises N462.S and the therapeutic bacterial composition comprises at least one bacterium selected from each of clade_262, clade_360, and clade_478. In yet another aspect, the network ecology comprises N462.S and the therapeutic bacterial composition consists essentially of at least one bacterium selected from each of clade_262, clade_360, and clade_478.

In other aspects, clade_262 comprises one or more bacteria selected from the group consisting of *Clostridium glycyrrhizinilyticum*, *Clostridium nexile*, *Coprococcus comes*, Lachnospiraceae bacterium 1_1_57FAA, Lachnospiraceae bacterium 1_4_56FAA, Lachnospiraceae bacterium 8_1_57FAA, *Ruminococcus lactaris*, and *Ruminococcus torques*, wherein clade_360 comprises one or more bacteria selected from the group consisting of *Dorea formicigenerans*, *Dorea longicatena*, Lachnospiraceae bacterium 2_1_46FAA, Lachnospiraceae bacterium 2_1_58FAA, Lachnospiraceae bacterium 4_1_37FAA, Lachnospiraceae bacterium 9_1_43BFAA, *Ruminococcus gnavus*, and *Ruminococcus* sp. ID8, and wherein clade_478 comprises one or more bacteria selected from the group consisting of *Faecalibacterium prausnitzii*, *Gemmiger formicilis*, and *Subdoligranulum variabile*.

In another aspect, clade_262 comprises one or more bacteria of *Coprococcus comes*, wherein clade_360 comprises one or more bacteria of *Dorea longicatena*, and wherein clade_478 comprises one or more bacteria selected from the group consisting *Faecalibacterium prausnitzii* and *Subdoligranulum variabile*.

In yet another aspect, clade_262 comprises one more bacteria selected from the group consisting of bacteria having 16S sequences having 97% or greater identity to Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_360 comprises one more bacteria selected from the group consisting of bacteria having 16S sequences having 97% or greater identity to Seq. ID No.: 1050, Seq. ID No.: 1051, Seq. ID No.: 1053, Seq. ID No.: 1058, Seq. ID No.: 1661, Seq. ID No.: 1668, Seq. ID No.: 773, and Seq. ID No.: 774, and wherein clade_478 comprises one more bacteria selected from the group consisting of bacteria having 16S sequences having 97% or greater identity to Seq. ID No.: 1896, Seq. ID No.: 880, and Seq. ID No.: 932.

In certain aspects, clade_262 comprises one more bacteria selected from the group consisting of bacteria having 16S sequences Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_360 comprises one more bacteria selected from the group consisting of bacteria having 16S sequences Seq. ID No.: 1050, Seq. ID No.: 1051, Seq. ID No.: 1053, Seq. ID No.: 1058, Seq. ID No.: 1661, Seq. ID No.: 1668, Seq. ID No.: 773, and Seq. ID No.: 774, and wherein clade_478 comprises one more bacteria selected from the group consisting of bacteria having 16S sequences Seq. ID No.: 1896, Seq. ID No.: 880, and Seq. ID No.: 932.

In another aspect, clade_262 comprises one or more bacteria selected from the group consisting of bacteria having 16S sequences having 97% or greater identity to Seq. ID No.: 674, wherein clade_360 comprises one or more bacteria selected from the group consisting of bacteria having 16S sequences having 97% or greater identity to Seq. ID No.: 774, and wherein clade_478 comprises one or more bacteria selected from the group consisting of bacteria having 16S sequences having 97% or greater identity to Seq. ID No.: 1896 and Seq. ID No.: 880.

In other aspects, clade_262 comprises one or more bacteria selected from the group consisting of bacteria having 16S sequences Seq. ID No.: 674, wherein clade_360 comprises one or more bacteria selected from the group consisting of bacteria having 16S sequences Seq. ID No.: 774, and wherein clade_478 comprises one or more bacteria selected from the group consisting of bacteria having 16S sequences Seq. ID No.: 1896 and Seq. ID No.: 880.

In another embodiment, network ecology comprises N512.S and the therapeutic bacterial composition comprises at least one bacterium selected from each of clade_262, clade_360, and clade_444. In one embodiment, the network ecology comprises N512.S and the therapeutic bacterial composition consists essentially of at least one bacterium selected from each of clade_262, clade_360, and clade_444.

In other embodiments, clade_262 comprises one or more bacteria selected from the group consisting of *Clostridium glycyrrhizinilyticum, Clostridium nexile, Coprococcus comes*, Lachnospiraceae bacterium 1_1_57FAA, Lachnospiraceae bacterium 1_4_56FAA, Lachnospiraceae bacterium 8_1_57FAA, *Ruminococcus lactaris*, and *Ruminococcus torques*, wherein clade_360 comprises one or more bacteria selected from the group consisting of *Dorea formicigenerans, Dorea longicatena*, Lachnospiraceae bacterium 2_1_46FAA, Lachnospiraceae bacterium 2_1_58FAA, Lachnospiraceae bacterium 4_1_37FAA, Lachnospiraceae bacterium 9_1_43BFAA, *Ruminococcus gnavus*, and *Ruminococcus* sp. ID8, and wherein clade_444 comprises one or more bacteria selected from the group consisting of *Butyrivibrio fibrisolvens, Eubacterium rectale, Eubacterium* sp. oral clone GI038, *Lachnobacterium bovis, Roseburia cecicola, Roseburia faecalis, Roseburia faecis, Roseburia hominis, Roseburia intestinalis, Roseburia inulinivorans, Roseburia* sp. 11SE37, *Roseburia* sp. 11SE38, *Shuttleworthia satelles, Shuttleworthia* sp. MSX8B, and *Shuttleworthia* sp. oral taxon G69.

In certain embodiments, clade_262 comprises one or more bacteria selected from the group consisting of *Coprococcus comes* and *Ruminococcus torques*, wherein clade_360 comprises one or more bacteria of *Dorea longicatena*, and wherein clade_444 comprises one or more bacteria of *Eubacterium rectale*.

In one embodiment, clade_262 comprises one more bacteria selected from the group consisting of bacteria having 16S sequences having 97% or greater identity to Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_360 comprises one more bacteria selected from the group consisting of bacteria having 16S sequences having 97% or greater identity to Seq. ID No.: 1050, Seq. ID No.: 1051, Seq. ID No.: 1053, Seq. ID No.: 1058, Seq. ID No.: 1661, Seq. ID No.: 1668, Seq. ID No.: 773, and Seq. ID No.: 774, and wherein clade_444 comprises one more bacteria selected from the group consisting of bacteria having 16S sequences having 97% or greater identity to Seq. ID No.: 1045, Seq. ID No.: 1634, Seq. ID No.: 1635, Seq. ID No.: 1636, Seq. ID No.: 1637, Seq. ID No.: 1638, Seq. ID No.: 1639, Seq. ID No.: 1640, Seq. ID No.: 1641, Seq. ID No.: 1728, Seq. ID No.: 1729, Seq. ID No.: 1730, Seq. ID No.: 456, Seq. ID No.: 856, and Seq. ID No.: 865.

In another embodiment, clade_262 comprises one more bacteria selected from the group consisting of bacteria having 16S sequences Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_360 comprises one more bacteria selected from the group consisting of bacteria having 16S sequences Seq. ID No.: 1050, Seq. ID No.: 1051, Seq. ID No.: 1053, Seq. ID No.: 1058, Seq. ID No.: 1661, Seq. ID No.: 1668, Seq. ID No.: 773, and Seq. ID No.: 774, and wherein clade_444 comprises one more bacteria selected from the group consisting of bacteria having 16S sequences Seq. ID No.: 1045, Seq. ID No.: 1634, Seq. ID No.: 1635, Seq. ID No.: 1636, Seq. ID No.: 1637, Seq. ID No.: 1638, Seq. ID No.: 1639, Seq. ID No.: 1640, Seq. ID No.: 1641, Seq. ID No.: 1728, Seq. ID No.: 1729, Seq. ID No.: 1730, Seq. ID No.: 456, Seq. ID No.: 856, and Seq. ID No.: 865.

In certain embodiments, clade_262 comprises one or more bacteria selected from the group consisting of bacteria having 16S sequences having 97% or greater identity to Seq. ID No.: 1670 and Seq. ID No.: 674, wherein clade_360 comprises one or more bacteria selected from the group consisting of bacteria having 16S sequences having 97% or greater identity to Seq. ID No.: 774, and wherein clade_444 comprises one or more bacteria selected from the group consisting of bacteria having 16S sequences having 97% or greater identity to Seq. ID No.: 856.

In one aspect, clade_262 comprises one or more bacteria selected from the group consisting of bacteria having 16S sequences Seq. ID No.: 1670 and Seq. ID No.: 674, wherein clade_360 comprises one or more bacteria selected from the group consisting of bacteria having 16S sequences Seq. ID No.: 774, and wherein clade_444 comprises one or more bacteria selected from the group consisting of bacteria having 16S sequences Seq. ID No.: 856.

In another aspect, the network ecology comprises N845 and the therapeutic bacterial composition comprises at least one bacterium selected from each of clade_262, clade_360, and clade_378. In certain aspects, the network ecology comprises N845 and the therapeutic bacterial composition consists essentially of at least one bacterium selected from each of clade_262, clade_360, and clade_378.

In other aspects, clade_262 comprises one or more bacteria selected from the group consisting of *Clostridium glycyrrhizinilyticum, Clostridium nexile, Coprococcus comes*, Lachnospiraceae bacterium 1_1_57FAA, Lachnospiraceae bacterium 1_4_56FAA, Lachnospiraceae bacterium 8_1_57FAA, *Ruminococcus lactaris*, and *Ruminococcus torques*, wherein clade_360 comprises one or more bacteria selected from the group consisting of *Dorea formicigenerans, Dorea longicatena*, Lachnospiraceae bacterium 2_1_46FAA, Lachnospiraceae bacterium 2_1_58FAA, Lachnospiraceae bacterium 4_1_37FAA, Lachnospiraceae bacterium 9_1_43BFAA, *Ruminococcus gnavus*, and *Ruminococcus* sp. ID8, and wherein clade_378 comprises one or more bacteria selected from the group consisting of *Bacteroides barnesiae, Bacteroides coprocola, Bacteroides*

*coprophilus, Bacteroides dorei, Bacteroides massiliensis, Bacteroides plebeius, Bacteroides* sp. 3_1_33FAA, *Bacteroides* sp. 3_1_40A, *Bacteroides* sp. 4_3_47FAA, *Bacteroides* sp. 9_1_42FAA, *Bacteroides* sp. NB_8, and *Bacteroides vulgatus*.

In certain aspects, clade_262 comprises one or more bacteria of *Coprococcus comes*, wherein clade_360 comprises one or more bacteria of *Dorea longicatena*, and wherein clade_378 comprises one or more bacteria of *Bacteroides dorei*.

In another aspect, clade_262 comprises one more bacteria selected from the group consisting of bacteria having 16S sequences having 97% or greater identity to Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_360 comprises one more bacteria selected from the group consisting of bacteria having 16S sequences having 97% or greater identity to Seq. ID No.: 1050, Seq. ID No.: 1051, Seq. ID No.: 1053, Seq. ID No.: 1058, Seq. ID No.: 1661, Seq. ID No.: 1668, Seq. ID No.: 773, and Seq. ID No.: 774, and wherein clade_378 comprises one more bacteria selected from the group consisting of bacteria having 16S sequences having 97% or greater identity to Seq. ID No.: 267, Seq. ID No.: 272, Seq. ID No.: 273, Seq. ID No.: 274, Seq. ID No.: 284, Seq. ID No.: 289, Seq. ID No.: 309, Seq. ID No.: 310, Seq. ID No.: 313, Seq. ID No.: 314, Seq. ID No.: 323, and Seq. ID No.: 331.

In certain aspects, clade_262 comprises one more bacteria selected from the group consisting of bacteria having 16S sequences Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, wherein clade_360 comprises one more bacteria selected from the group consisting of bacteria having 16S sequences Seq. ID No.: 1050, Seq. ID No.: 1051, Seq. ID No.: 1053, Seq. ID No.: 1058, Seq. ID No.: 1661, Seq. ID No.: 1668, Seq. ID No.: 773, and Seq. ID No.: 774, and wherein clade_378 comprises one more bacteria selected from the group consisting of bacteria having 16S sequences Seq. ID No.: 267, Seq. ID No.: 272, Seq. ID No.: 273, Seq. ID No.: 274, Seq. ID No.: 284, Seq. ID No.: 289, Seq. ID No.: 309, Seq. ID No.: 310, Seq. ID No.: 313, Seq. ID No.: 314, Seq. ID No.: 323, and Seq. ID No.: 331.

In one embodiment, clade_262 comprises one or more bacteria selected from the group consisting of bacteria having 16S sequences having 97% or greater identity to Seq. ID No.: 674, wherein clade_360 comprises one or more bacteria selected from the group consisting of bacteria having 16S sequences having 97% or greater identity to Seq. ID No.: 774, and wherein clade_378 comprises one or more bacteria selected from the group consisting of bacteria having 16S sequences having 97% or greater identity to Seq. ID No.: 274.

In another embodiment, clade_262 comprises one or more bacteria selected from the group consisting of bacteria having 16S sequences Seq. ID No.: 674, wherein clade_360 comprises one or more bacteria selected from the group consisting of bacteria having 16S sequences Seq. ID No.: 774, and wherein clade_378 comprises one or more bacteria selected from the group consisting of bacteria having 16S sequences Seq. ID No.: 274.

In some embodiments, the network ecology comprises N982 and the therapeutic bacterial composition comprises at least one bacterium selected from each of clade_172, clade_262, and clade_396. In another embodiment, the network ecology comprises N982 and the therapeutic bacterial composition consists essentially of at least one bacterium selected from each of clade_172, clade_262, and clade_396.

In certain aspects, clade_172 comprises one or more bacteria selected from the group consisting of *Bifidobacteriaceae genomo* sp. C1, *Bifidobacterium adolescentis, Bifidobacterium angulatum, Bifidobacterium animalis, Bifidobacterium breve, Bifidobacterium catenulatum, Bifidobacterium dentium, Bifidobacterium gallicum, Bifidobacterium infantis, Bifidobacterium kashiwanohense, Bifidobacterium longum, Bifidobacterium pseudocatenulatum, Bifidobacterium pseudolongum, Bifidobacterium scardovii, Bifidobacterium* sp. HM2, *Bifidobacterium* sp. HMLN12, *Bifidobacterium* sp. M45, *Bifidobacterium* sp. MSX5B, *Bifidobacterium* sp. TM_7, and *Bifidobacterium thermophilum*, wherein clade_262 comprises one or more bacteria selected from the group consisting of *Clostridium glycyrrhizinilyticum, Clostridium nexile, Coprococcus comes*, Lachnospiraceae bacterium 1_1_57FAA, Lachnospiraceae bacterium 1_4_56FAA, Lachnospiraceae bacterium 8_1_57FAA, *Ruminococcus lactaris*, and *Ruminococcus torques*, and wherein clade_396 comprises one or more bacteria selected from the group consisting of *Acetivibrio ethanolgignens, Anaerosporobacter mobilis, Bacteroides pectinophilus, Clostridium aminovalericum, Clostridium phytofermentans, Eubacterium hallii*, and *Eubacterium xylanophilum*.

In another aspect, clade_172 comprises one or more bacteria of *Bifidobacterium longum*, wherein clade_262 comprises one or more bacteria of *Coprococcus comes*, and wherein clade_396 comprises one or more bacteria of *Eubacterium hallii*.

In one aspect, clade_172 comprises one more bacteria selected from the group consisting of bacteria having 16S sequences having 97% or greater identity to Seq. ID No.: 345, Seq. ID No.: 346, Seq. ID No.: 347, Seq. ID No.: 348, Seq. ID No.: 350, Seq. ID No.: 351, Seq. ID No.: 352, Seq. ID No.: 353, Seq. ID No.: 354, Seq. ID No.: 355, Seq. ID No.: 356, Seq. ID No.: 357, Seq. ID No.: 358, Seq. ID No.: 359, Seq. ID No.: 360, Seq. ID No.: 361, Seq. ID No.: 362, Seq. ID No.: 363, Seq. ID No.: 364, and Seq. ID No.: 365, wherein clade_262 comprises one more bacteria selected from the group consisting of bacteria having 16S sequences having 97% or greater identity to Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, and wherein clade_396 comprises one more bacteria selected from the group consisting of bacteria having 16S sequences having 97% or greater identity to Seq. ID No.: 161, Seq. ID No.: 288, Seq. ID No.: 551, Seq. ID No.: 6, Seq. ID No.: 613, Seq. ID No.: 848, and Seq. ID No.: 875.

In another aspect, clade_172 comprises one more bacteria selected from the group consisting of bacteria having 16S sequences Seq. ID No.: 345, Seq. ID No.: 346, Seq. ID No.: 347, Seq. ID No.: 348, Seq. ID No.: 350, Seq. ID No.: 351, Seq. ID No.: 352, Seq. ID No.: 353, Seq. ID No.: 354, Seq. ID No.: 355, Seq. ID No.: 356, Seq. ID No.: 357, Seq. ID No.: 358, Seq. ID No.: 359, Seq. ID No.: 360, Seq. ID No.: 361, Seq. ID No.: 362, Seq. ID No.: 363, Seq. ID No.: 364, and Seq. ID No.: 365, wherein clade_262 comprises one more bacteria selected from the group consisting of bacteria having 16S sequences Seq. ID No.: 1048, Seq. ID No.: 1049, Seq. ID No.: 1057, Seq. ID No.: 1663, Seq. ID No.: 1670, Seq. ID No.: 588, Seq. ID No.: 607, and Seq. ID No.: 674, and wherein clade_396 comprises one more bacteria selected from the group consisting of bacteria having 16S sequences Seq. ID No.: 161, Seq. ID No.: 288, Seq. ID No.: 551, Seq. ID No.: 6, Seq. ID No.: 613, Seq. ID No.: 848, and Seq. ID No.: 875.

In another aspect, clade_172 comprises one or more bacteria selected from the group consisting of bacteria having 16S sequences having 97% or greater identity to Seq. ID No.: 356, wherein clade_262 comprises one or more bacteria selected from the group consisting of bacteria having 16S sequences having 97% or greater identity to Seq. ID No.: 674, and wherein clade_396 comprises one or more bacteria selected from the group consisting of bacteria having 16S sequences having 97% or greater identity to Seq. ID No.: 848.

In certain aspects, clade_172 comprises one or more bacteria selected from the group consisting of bacteria having 16S sequences Seq. ID No.: 356, wherein clade_262 comprises one or more bacteria selected from the group consisting of bacteria having 16S sequences Seq. ID No.: 674, and wherein clade_396 comprises one or more bacteria selected from the group consisting of bacteria having 16S sequences Seq. ID No.: 848.

In another embodiment, the network ecology comprises N651.S and the therapeutic bacterial composition comprises at least one bacterium selected from each of clade_444, clade_516, and clade_522. In yet another embodiment, the network ecology comprises N651.S and the therapeutic bacterial composition consists essentially of at least one bacterium selected from each of clade_444, clade_516, and clade_522.

In one embodiment, clade_444 comprises one or more bacteria selected from the group consisting of *Butyrivibrio fibrisolvens, Eubacterium rectale, Eubacterium* sp. oral clone GI038, *Lachnobacterium bovis, Roseburia cecicola, Roseburia faecalis, Roseburia faecis, Roseburia hominis, Roseburia intestinalis, Roseburia inulinivorans, Roseburia* sp. 11SE37, *Roseburia* sp. 11SE38, *Shuttleworthia satelles, Shuttleworthia* sp. MSX8B, and *Shuttleworthia* sp. oral taxon G69, wherein clade_516 comprises one or more bacteria selected from the group consisting of *Anaerotruncus colihominis, Clostridium methylpentosum, Clostridium* sp. YIT 12070, *Hydrogenoanaerobacterium saccharovorans, Ruminococcus albus*, and *Ruminococcus flavefaciens*, and wherein clade_522 comprises one or more bacteria selected from the group consisting of *Bacteroides galacturonicus, Eubacterium eligens, Lachnospira multipara, Lachnospira pectinoschiza*, and *Lactobacillus rogosae*. In another embodiment, clade_444 comprises one or more bacteria of *Roseburia inulinivorans*, wherein clade_516 comprises one or more bacteria of *Anaerotruncus colihominis*, and wherein clade_522 comprises one or more bacteria of *Eubacterium eligens*. In some embodiments, clade_444 comprises one more bacteria selected from the group consisting of bacteria having 16S sequences having 97% or greater identity to Seq. ID No.: 1045, Seq. ID No.: 1634, Seq. ID No.: 1635, Seq. ID No.: 1636, Seq. ID No.: 1637, Seq. ID No.: 1638, Seq. ID No.: 1639, Seq. ID No.: 1640, Seq. ID No.: 1641, Seq. ID No.: 1728, Seq. ID No.: 1729, Seq. ID No.: 1730, Seq. ID No.: 456, Seq. ID No.: 856, and Seq. ID No.: 865, wherein clade_516 comprises one more bacteria selected from the group consisting of bacteria having 16S sequences having 97% or greater identity to Seq. ID No.: 1005, Seq. ID No.: 164, Seq. ID No.: 1656, Seq. ID No.: 1660, Seq. ID No.: 606, and Seq. ID No.: 642, and wherein clade_522 comprises one more bacteria selected from the group consisting of bacteria having 16S sequences having 97% or greater identity to Seq. ID No.: 1046, Seq. ID No.: 1047, Seq. ID No.: 1114, Seq. ID No.: 280, and Seq. ID No.: 845.

In other embodiments, clade_444 comprises one more bacteria selected from the group consisting of bacteria having 16S sequences Seq. ID No.: 1045, Seq. ID No.: 1634, Seq. ID No.: 1635, Seq. ID No.: 1636, Seq. ID No.: 1637, Seq. ID No.: 1638, Seq. ID No.: 1639, Seq. ID No.: 1640, Seq. ID No.: 1641, Seq. ID No.: 1728, Seq. ID No.: 1729, Seq. ID No.: 1730, Seq. ID No.: 456, Seq. ID No.: 856, and Seq. ID No.: 865, wherein clade_516 comprises one more bacteria selected from the group consisting of bacteria having 16S sequences Seq. ID No.: 1005, Seq. ID No.: 164, Seq. ID No.: 1656, Seq. ID No.: 1660, Seq. ID No.: 606, and Seq. ID No.: 642, and wherein clade_522 comprises one more bacteria selected from the group consisting of bacteria having 16S sequences Seq. ID No.: 1046, Seq. ID No.: 1047, Seq. ID No.: 1114, Seq. ID No.: 280, and Seq. ID No.: 845.

In one embodiment, clade_444 comprises one or more bacteria selected from the group consisting of bacteria having 16S sequences having 97% or greater identity to Seq. ID No.: 1639, wherein clade_516 comprises one or more bacteria selected from the group consisting of bacteria having 16S sequences having 97% or greater identity to Seq. ID No.: 164, and wherein clade_522 comprises one or more bacteria selected from the group consisting of bacteria having 16S sequences having 97% or greater identity to Seq. ID No.: 845.

In one aspect, clade_444 comprises one or more bacteria selected from the group consisting of bacteria having 16S sequences Seq. ID No.: 1639, wherein clade_516 comprises one or more bacteria selected from the group consisting of bacteria having 16S sequences Seq. ID No.: 164, and wherein clade_522 comprises one or more bacteria selected from the group consisting of bacteria having 16S sequences Seq. ID No.: 845.

In another aspect, the composition further comprises a pharmaceutically-acceptable excipient. In one aspect, the therapeutic bacterial composition is substantially depleted of a residual habitat product of a fecal material. In certain aspects, the composition is formulated for oral administration. In other embodiments, the composition is capable of inducing the formation of IgA, RegIII-gamma, IL-10, regulatory T cells, TGF-beta, alpha-defensin, beta-defensin, or an antimicrobial peptide in the mammalian subject. In another embodiment, the composition is comestible.

The invention provides a composition, comprising any of the compositions administered according to the methods described above. The invention also includes a dosage unit comprising predetermined ratios of the isolated bacteria present in the network ecology as described above.

The invention provides a method for producing short chain fatty acids (SCFA) within a mammalian subject, comprising: administering to said mammalian subject in need thereof an effective amount of a therapeutic bacterial composition, said therapeutic bacterial composition comprising a plurality of isolated bacteria or a purified bacterial preparation, the plurality of isolated bacteria of the purified bacterial preparation capable of forming one or a plurality of bacterial functional pathways, the one or plurality of bacterial functional pathways capable of forming a functional network ecology selected from the group consisting of N262.S, N290.S, N284.S, N271.S, N282.S, N288.S, N302.S, N279.S, N310.S, N323.S, N331.S, N332.S, N301.S, N312.S, N339.S, N325.S, N340.S, N341.S, N346.S, N338.S, N336.S, N345.S, N355.S, N356.S, N343.S, N329.S, N361.S, N353.S, N381.S, N344.S, N352.S, N357.S, N358.S, N369.S, N372.S, N375.S, N380.S, N374.S, N377.S, N368.S, N370.S, N373.S, N376.S, N389.S, N394.S, N431.S, N434.S, N390.S, N397.S, N387.S, N440.S, N396.S, N399.S, N403.S, N414.S, N430.S, N432.S, N436.S, N437.S, N457.S, N545, N386.S, N402.S, N405.S, N415.S, N421.S, N422.S, N423.S, N458.S, N459.S, N493.S, N416.S, N439.S, N447.S, N490.S, N526, N429.S, N433.S, N448.S, N488.S, N508.S, N509.S, N510.S, N511.S, N408.S, N446.S, N451.S, N474.S, N520.S, N521.S, N535.S, N516.S, N463.S, N518.S, N586, N450.S, N465.S, N519.S, N537.S, N419.S, N468.S, N477.S, N514.S, N382.S, N460.S, N462.S, N512.S, N517.S, N523.S, N547.S, N548.S, N577.S, N581.S, N585.S, N616.S, N466.S, N469.S, N480.S, N482.S, N484.S, N515.S, N533.S, N709, N730, N478.S, N572.S, N400.S, N543.S, N582.S, N621.S, N689, N769, N481.S, N525.S, N528.S, N534.S, N574.S, N580.S, N590.S, N591.S, N597.S, N664, N693, N530.S, N687, N470.S, N529.S, N539.S, N546.S, N570.S, N579.S, N602.S, N614.S, N648.S, N652.S, N655.S, N672.S, N681.S, N690.S, N692.S, N698.S, N737.S, N738.S, N785, N841, N878, N880, N881, N987, N988, N996, N1061, N479.S, N538.S, N542.S, N578.S, N609.S, N611.S, N617.S, N666.S, N675.S, N682.S, N844, N845, N846, N852, N876, N982, N1008, N649.S, N657.S, N678.S, N686.S, N710.S, N522.S, N651.S, N653.S, N654.S, N680.S, N712.S, N792, N802, N804, N807, N849, N858, N859, N875, N885, N942, N961, N972, N1051, N587.S, N589.S, N612.S, N625.S, N656.S, N714.S, N779, N781, N828, N829, N860, N894, N925, N927, N935, N947, N983, N1023, N441.S, N584.S, N794, N788, N524.S, N604.S, N610.S, N623.S, N663.S, N669.S, N676.S, N703.S, N775.S, N777.S, N780.S, N817.S, N827.S, N836.S, N871.S, N874.S, N898.S, N907.S, N998.S, N1088, N1089, N660.S, N665.S, N667.S, N733.S, N734.S, N739.S, N741.S, N782.S, N789.S, N796.S, N798.S, N800.S, N809.S, N816.S, N842.S, N843.S, N869.S, N986.S, N995.S, N1002.S, N1004.S, N1019.S, N1093, N668.S, N685.S, N835.S, N851.S, N464.S, N695.S, N776.S, N793.S, N815.S, N833.S, N891.S, N1070.S, N1092, N795.S, N797.S, N808.S, N811.S, N826.S, N830.S, N832.S, N840.S, N945.S, N960.S, N968.S, N1091, N805.S, N822.S, N928.S, N936.S, N1078.S, and N913.S.

In one embodiment, the functional network ecology is selected from the group consisting of N1008, N1023, N1051, N1061, N1070.S, N1088, N1089, N1092, N381.S, N382.S, N399.S, N400.S, N402.S, N403.S, N414.S, N429.S, N430.S, N432.S, N433.S, N436.S, N437.S, N439.S, N441.S, N447.S, N448.S, N457.S, N460.S, N462.S, N463.S, N464.S, N470.S, N474.S, N488.S, N490.S, N493.S, N508.S, N509.S, N510.S, N511.S, N512.S, N514.S, N515.S, N517.S, N518.S, N519.S, N520.S, N523.S, N524.S, N528.S, N529.S, N539.S, N543.S, N546.S, N547.S, N548.S, N570.S, N574.S, N577.S, N579.S, N580.S, N582.S, N584.S, N585.S, N589.S, N591.S, N597.S, N602.S, N604.S, N609.S, N610.S, N611.S, N612.S, N614.S, N616.S, N621.S, N623.S, N625.S, N648.S, N651.S, N652.S, N653.S, N654.S, N655.S, N660.S, N663.S, N664, N665.S, N666.S, N669.S, N672.S, N676.S, N681.S, N687, N689, N690.S, N692.S, N693, N695.S, N698.S, N703.S, N709, N712.S, N714.S, N730, N734.S, N737.S, N738.S, N769, N775.S, N777.S, N779, N780.S, N781, N785, N788, N792, N793.S, N794, N797.S, N798.S, N802, N804, N807, N817.S, N827.S, N828, N830.S, N832.S, N833.S, N836.S, N840.S, N841, N844, N845, N849, N852, N858, N859, N860, N869.S, N871.S, N874.S, N875, N878, N880, N881, N885, N894, N898.S, N907.S, N913.S, N925, N927, N942, N947, N961, N968.S, N972, N982, N983, N986.S, N987, N988, N996, and N998.S. In another embodiment, the functional network ecology is N528.S, and the plurality of bacterial functional pathways comprises the functional pathways of of KO:K00656, KO:K01069, KO:K01734, KO:K03417, KO:K03778, KO:K07246.

The invention includes a method for catalyzing secondary metabolism of bile acids within a mammalian subject, comprising: administering to said mammalian subject in need thereof an effective amount of a therapeutic bacterial composition, said therapeutic bacterial composition comprising a plurality of isolated bacteria or a purified bacterial preparation, the plurality of isolated bacteria of the purified bacterial preparation capable of forming one or a plurality of bacterial functional pathways, the one or plurality of bacterial functional pathways capable of forming a functional network ecology selected from the group consisting of N262.S, N290.S, N284.S, N271.S, N282.S, N288.S, N302.S, N279.S, N310.S, N323.S, N331.S, N332.S, N301.S, N312.S, N339.S, N325.S, N340.S, N341.S, N346.S, N338.S, N336.S, N345.S, N355.S, N356.S, N343.S, N329.S, N361.S, N353.S, N381.S, N344.S, N352.S, N357.S, N358.S, N369.S, N372.S, N375.S, N380.S, N374.S, N377.S, N368.S, N370.S, N373.S, N376.S, N389.S, N394.S, N431.S, N434.S, N390.S, N397.S, N387.S, N440.S, N396.S, N399.S, N403.S, N414.S, N430.S, N432.S, N436.S, N437.S, N457.S, N545, N386.S, N402.S, N405.S, N415.S, N421.S, N422.S, N423.S, N458.S, N459.S, N493.S, N416.S, N439.S, N447.S, N490.S, N526, N429.S, N433.S, N448.S, N488.S, N508.S, N509.S, N510.S, N511.S, N408.S, N446.S, N451.S, N474.S, N520.S, N521.S, N535.S, N516.S, N463.S, N518.S, N586, N450.S, N465.S, N519.S, N537.S, N419.S, N468.S, N477.S, N514.S, N382.S, N460.S, N462.S, N512.S, N517.S, N523.S, N547.S, N548.S, N577.S, N581.S, N585.S, N616.S, N466.S, N469.S, N480.S, N482.S, N484.S, N515.S, N533.S, N709, N730, N478.S, N572.S, N400.S, N543.S, N582.S, N621.S, N689, N769, N481.S, N525.S, N528.S, N534.S, N574.S, N580.S, N590.S, N591.S, N597.S, N664, N693, N530.S, N687, N470.S, N529.S, N539.S, N546.S, N570.S, N579.S, N602.S, N614.S, N648.S, N652.S, N655.S, N672.S, N681.S, N690.S, N692.S, N698.S, N737.S, N738.S, N785, N841, N878, N880, N881, N987, N988, N996, N1061, N479.S, N538.S, N542.S, N578.S, N609.S, N611.S, N617.S, N666.S, N675.S, N682.S, N844, N845, N846, N852, N876, N982, N1008, N649.S, N657.S, N678.S, N686.S, N710.S, N522.S, N651.S, N653.S, N654.S, N680.S, N712.S, N792, N802, N804, N807, N849, N858, N859, N875, N885, N942, N961, N972, N1051, N587.S, N589.S, N612.S, N625.S, N656.S, N714.S, N779, N781, N828, N829, N860, N894, N925, N927, N935, N947, N983, N1023, N441.S, N584.S, N794, N788, N524.S, N604.S, N610.S, N623.S, N663.S, N669.S, N676.S, N703.S, N775.S, N777.S, N780.S, N817.S, N827.S, N836.S, N871.S, N874.S, N898.S, N907.S, N998.S, N1088, N1089, N660.S, N665.S, N667.S, N733.S, N734.S, N739.S, N741.S, N782.S, N789.S, N796.S, N798.S, N800.S, N809.S, N816.S, N842.S, N843.S, N869.S, N986.S, N995.S, N1002.S, N1004.S, N1019.S, N1093, N668.S, N685.S, N835.S, N851.S, N464.S, N695.S, N776.S, N793.S, N815.S, N833.S, N891.S, N1070.S, N1092, N795.S, N797.S, N808.S, N811.S, N826.S, N830.S, N832.S, N840.S, N945.S, N960.S, N968.S, N1091, N805.S, N822. S, N928. S, N936. S, N1078. S, and N913. S.

In one embodiment, the functional network ecology is selected from the group consisting of N1008, N1023, N1051, N1061, N1070.S, N1088, N1089, N1092, N381.S, N382.S, N399.S, N400.S, N402.S, N403.S, N414.S, N429.S, N430.S, N432.S, N433.S, N436.S, N437.S, N439.S, N441.S, N447.S, N448.S, N457.S, N460.S, N462.S, N463.S, N464.S, N470.S, N474.S, N488.S, N490.S, N493.S, N508.S, N509.S, N510.S, N511.S, N512.S, N514.S, N515.S, N517.S, N518.S, N519.S, N520.S, N523.S, N524.S, N529.S, N539.S, N543.S, N546.S, N547.S, N548.S, N570.S, N574.S, N577.S, N579.S, N580.S, N582.S, N584.S, N585.S, N589.S, N591.S, N597.S, N602.S, N604.S, N609.S, N610.S, N611.S, N612.S, N614.S, N616.S, N621.S, N623.S, N625.S, N648.S, N651.S, N652.S, N653.S, N654.S, N655.S, N660.S, N663.S, N664, N665.S, N666.S, N669.S, N672.S, N676.S, N681.S, N687, N689, N690.S, N692.S, N693, N695.S, N698.S, N703.S, N709, N712.S, N714.S, N730, N734.S, N737.S, N738.S, N769, N775.S, N777.S, N779, N780.S, N781, N785, N788, N792, N793.S, N794, N797.S, N798.S, N802, N804, N807, N817.S, N827.S, N828, N830.S, N832.S, N833.S, N836.S, N840.S, N841, N844, N845, N849, N852, N858, N859, N860, N869.S, N871.S, N874.S, N875, N878, N880, N881, N885, N894, N898.S, N907.S, N913.S, N925, N927, N942, N947, N961, N968.S, N972, N982, N983, N986.S, N987, N988, N996, and N998.S. In another embodiment, the functional network ecology is N660.S and the plurality of bacterial functional pathways comprises the functional pathways of of KO:K00656, and KO:K01442.

In some embodiment, the invention includes a composition further comprising a pharmaceutically-acceptable excipient. In one embodiment, the composition is formulated for oral administration. In another embodiment, the composition is capable of inducing the formation of butyrate, propionate, acetate, 7-deoxybile acids, deoxycholate acide (DCA) and lithocholic acid (LCA) in the mammalian subject. In other embodiments, the composition is capable of inducing the depletion of glucose, pyruvate, lactate, cellulose, fructans, starch, xylans, pectins, taurocholate, glycocholate, ursocholate, cholate, glycochenodeoxycholate, taurochenodeoxycholate, ursodeoxycholate, or chenodeoxycholate; or the formation and depletion of intermediary metabolites acetyl-CoA, butyryl-CoA, propanoyl-CoA, chenodeoxycholoyl-CoA, or ursodeoxycholoyl-CoA in the mammalian subject. In another embodiment, the composition is formulated with one or more prebiotic compounds. In some embodiments, the composition is comestible.

The invention includes a composition, comprising any of the compositions administered according to the methods described above.

The invention also includes a dosage unit comprising predetermined ratios of the isolated bacteria present in the network ecology described above.

The invention comprises a pharmaceutical formulation comprising a purified bacterial population consisting essentially of a bacterial network capable of forming germinable bacterial spores, wherein the bacterial network is present in an amount effective to populate the gastrointestinal tract in a mammalian subject in need thereof to whom the formulation is administered, under conditions such that at least one type of bacteria not detectably present in the bacterial network or in the gastrointestinal tract prior to administration is augmented.

The invention also includes a pharmaceutical formulation comprising a purified bacterial population comprising a plurality of bacterial entities, wherein the bacterial entities are present in an amount effective to induce the formation of a functional bacterial network in the gastrointestinal tract in a mammalian subject in need thereof to whom the formulation is administered. In some embodiments, the functional bacterial network comprises bacterial entities present in the formulation. In other embodiments, the functional bacterial network comprises bacterial entities present in the gastrointestinal tract at the time of administration. In another embodiment, the functional bacterial network comprises bacterial entities not present in the formulation or the gastrointestinal tract at the time of administration. In one embodiment, the formulation can be provided as an oral finished pharmaceutical dosage form including at least one pharmaceutically acceptable carrier In some embodiments, the mammalian subject suffers from a dysbiosis comprising a gastrointestinal disease, disorder or condition selected from the group consisting of *Clostridium difficile* Associated Diarrhea (CDAD), Type 2 Diabetes, Type 1 Diabetes, Obesity, Irritable Bowel Syndrome (IBS), Irritable Bowel Disease (IBD), Ulcerative Colitis, Crohn's Disease, colitis, colonization with a pathogen or pathobiont, and infection with a drug-resistant pathogen or pathobiont.

In another embodiment, the bacterial network is purified from a fecal material subjected to a treatment step that comprises depleting or inactivating a pathogenic material. In one embodiment, the bacterial network is substantially depleted of a detectable level of a first pathogenic material. In some embodiments, the bacterial network is substantially depleted of a residual habitat product of the fecal material.

In one embodiment, the invention provides a method of treating or preventing a dysbiosis in a human subject, comprising administering to the human subject the formulation in an amount effective to treat or prevent a dysbiosis or to reduce the severity of at least one symptom of the dysbiosis in the human subject to whom the formulation is administered.

In another embodiment, the formulation is provided as an oral finished pharmaceutical dosage form including at least one pharmaceutically acceptable carrier, the dosage form comprising at least about $1 \times 10^4$ colony forming units of bacterial spores per dose of the composition, wherein the bacterial spores comprise at least two bacterial entities comprising 16S rRNA sequences at least 97% identical to the nucleic acid sequences selected from the group consisting of Seq. ID No.: 674, Seq. ID No.: 1670, Seq. ID No.: 774, Seq. ID No.: 848, Seq. ID No.: 856, Seq. ID No.: 1639, Seq. ID No.: 880, Seq. ID No.: 1896, Seq. ID No.: 1591, Seq. ID No.: 164, Seq. ID No.: 845, and Seq. ID No.: 659.

In yet another embodiment, the administration of the formulation results in a reduction or an elimination of at least one pathogen and/or pathobiont present in the gastrointestinal tract when the therapeutic composition is administered. In one embodiment, the administration of the formulation results in engraftment of at least one type of spore-forming bacteria present in the therapeutic composition.

In one aspect, the administration of the formulation results in augmentation in the gastrointestinal tract of the subject to whom the formulation is administered of at least one type of bacteria not present in the formulation. In another aspect, the at least one type of spore-forming bacteria are not detectably present in the gastrointestinal tract of the subject to whom the formulation is administered when the formulation is administered. In yet another aspect, the administration of the formulation results in at least two of: i) reduction or elimination of at least one pathogen and/or pathobiont present in the gastrointestinal tract when the formulation is administered; ii) engraftment of at least one type of spore-forming bacteria present in the therapeutic composition; and iii) augmentation of at least one type of spore-forming or non-spore forming bacteria not present in the therapeutic composition.

In some aspects, the administration of the therapeutic composition results in at reduction or elimination of at least one pathogen and/or pathobiont present in the gastrointestinal tract when the therapeutic composition is administered and at least one of: i) engraftment of at least one type of spore-forming bacteria present in the therapeutic composition; and ii) augmentation of at least one type of bacteria not present in the therapeutic composition.

In another aspect, the method of inducing engraftment of a bacterial population in the gastrointestinal tract of a human subject, comprising the step of administering to the human subject an orally acceptable pharmaceutical formulation comprising a purified bacterial network, under conditions such that at least i) a subset of the spore-forming bacteria sustainably engraft within the gastrointestinal tract, or ii) at least one type of bacteria not present in the therapeutic composition is augmented within the gastrointestinal tract.

The invention provides a pharmaceutical formulation comprising a purified first bacterial entity and a purified second bacterial entity, wherein the first bacterial entity comprises a first nucleic acid sequence encoding a first polypeptide capable of catalyzing a first chemical reaction, wherein the second bacterial entity comprises a second nucleic acid sequence encoding a second polypeptide capable of catalyzing a second chemical reaction, wherein the pharmaceutical formulation is formulated for oral administration to a mammalian subject in need thereof, wherein the first chemical reaction and the second chemical reaction are capable of occurring in the gastrointestinal tract of the mammalian subject under conditions such that a first product of the first chemical reaction, a substance present within said mammalian subject, or a combination of said first product with the substance is used as a substrate in the second chemical reaction to form a second product, wherein the second product induces a host cell response. In one embodiment, the substance is a mammalian subject protein or a food-derived protein. In another embodiment, the host cell response comprises production by the host cell of a biological material. In certain embodiments, the biological material comprises a cytokine, growth factor or signaling polypeptide.

In one embodiment, the host cell response comprises an immune response. In another embodiment, the host cell response comprises decreased gastric motility. In yet another embodiment, the host cell response comprises change in host gene expression, increased host metabolism, reduced gut permeability, enhanced epithelial cell junction integrity, reduced lipolysis by the action of Lipoprotein Lipase in adipose tissue, decreased hepatic gluconeogenesis, increased insulin sensitivity, increased production of FGF-19, or change in energy harvesting and/or storage.

The invention includes a pharmaceutical formulation comprising a purified first bacterial entity and a purified second bacterial entity, wherein the first bacterial entity and the second bacterial entity form a functional bacterial network in the gastrointestinal tract of a mammalian subject to whom the pharmaceutical formulation is administered, wherein the functional network modulates the level and/or activity of a biological material capable of inducing a host cell response.

The invention also includes a pharmaceutical formulation comprising a purified first bacterial entity and a purified second bacterial entity, wherein the first bacterial entity and the second bacterial entity form a functional bacterial network in the gastrointestinal tract of a mammalian subject to whom the pharmaceutical formulation is administered, wherein the functional network induces the production of a biological material capable of inducing a host cell response.

The invention comprises a therapeutic composition, comprising a network of at least two bacterial entities, wherein the network comprises at least one keystone bacterial entity and at least one non-keystone bacterial entity, wherein the at least two bacterial entities are each provided in amounts effective for the treatment or prevention of a gastrointestinal disease, disorder or condition in a mammalian subject. In one aspect, the network comprises at least three bacterial entities. In another aspect, the network comprises at least three bacterial entities including at least two keystone bacterial entities.

The invention comprises a therapeutic composition, comprising a network of at least two keystone bacterial entities capable of forming germination-competent spores, wherein the at least two keystone bacterial entities are each provided in amounts effective for the treatment or prevention of a gastrointestinal disease, disorder or condition in a mammalian subject. In one aspect, the comprision comprises a network of at least two keystone bacterial entities capable of forming germination-competent spores.

In one embodiment, the invention comprises a therapeutic composition, comprising: a first network of at least two bacterial entities, wherein the first network comprises a keystone bacterial entity and a non-keystone bacterial entity; and a second network of at least two bacterial entities, wherein the second network comprises at least one keystone bacterial entity and at least one non-keystone bacterial entity, wherein the networks are each provided in amounts effective for the treatment or prevention of a gastrointestinal disease, disorder or condition in a mammalian subject.

The invention includes a therapeutic composition, comprising a network of at least two bacterial entities, wherein the network comprises a first keystone bacterial entity and a second keystone bacterial entity, wherein the two bacterial entities are each provided in amounts effective for the treatment or prevention of a gastrointestinal disease, disorder or condition in a mammalian subject. In one aspect, the first and second keystone bacterial entities are present in the same network. In another aspect, the first and second keystone bacterial entities are present in different networks.

In some aspects, the invention comprises a diagnostic composition for the detection of a dysbiosis, comprising a first detection moiety capable of detecting a first keystone bacterial entity and a second detection moiety capable of detecting a first non-keystone bacterial entity, wherein the keystone bacterial entity and the non-keystone bacterial entity comprise a network, wherein the absence of at least one of the keystone bacterial entity and the non-keystone bacterial entity in a mammalian subject is indicative of a dysbiosis.

The invention comprises a method of altering a microbiome population present in a mammalian subject, comprising the steps of determining the presence of an incomplete network of bacterial entities in the gastrointestinal tract of the mammalian subject, and introducing to the gastrointestinal tract of the mammalian subject an effective amount of one or more supplemental bacterial entities not detectable in the gastrointestinal tract of the mammalian subject prior to such administration, under conditions such that the incomplete network is completed, thereby altering the microbiome population.

In one embodiment, the one or more supplemental bacterial entities become part of the incomplete network, thereby forming a complete network. In another embodiment, the one or more supplemental bacterial entities alter the microbiota of the mammalian subject such that one or more additional bacterial entities complete the incomplete network. In yet another embodiment, the one or more supplemental bacterial entities comprise a network.

The invention includes a method for detection and correction of a dysbiosis in a mammalian subject in need thereof, comprising the steps of: providing a fecal sample from the mammalian subject comprising a plurality of bacterial entities; contacting the fecal sample with a first detection moiety capable of detecting a first bacterial entity present in an network; detecting the absence of the first bacterial entity in the fecal sample, thereby detecting a dysbiosis in the mammalian subject; and administering to the mammalian subject a composition comprising an effective amount of the first bacterial entity. In one embodiment, the method includes confirming that the dysbiosis in the mammalian subject has been corrected.

The invention comprises a system for predicting a dysbiosis in a subject, the system comprising: a storage memory for storing a dataset associated with a sample obtained from the subject, wherein the dataset comprises content data for at least one network of bacterial entities; and a processor communicatively coupled to the storage memory for determining a score with an interpretation function wherein the score is predictive of dysbiosis in the subject.

The invention also comprises a kit for diagnosis of a state of dysbiosis in a mammalian subject in need thereof, comprising a plurality of detection means suitable for use in detecting (1) a first bacterial entity comprising a keystone bacterial entity and (2) a second bacterial entity, wherein the first and second bacterial entities comprise a functional network ecology.

BRIEF DESCRIPTION OF THE DRAWINGS

FIG. 2 highlights in bold the nucleotide sequences for each hypervariable region in the exemplary reference *E. coli* 16S sequence (SEQ ID NO: 2051) described by Brosius et al.

Subsets of networks are selected for use in defining Network Classes based on key biological criteria. Hierarchical Network clusters are defined by the presence (white) and absence (blue) of OTUs and/or Functional Metabolic Pathways and Classes are defined as branches of the hierarchical clustering tree based on the topological overlap measure.

Figure 19:
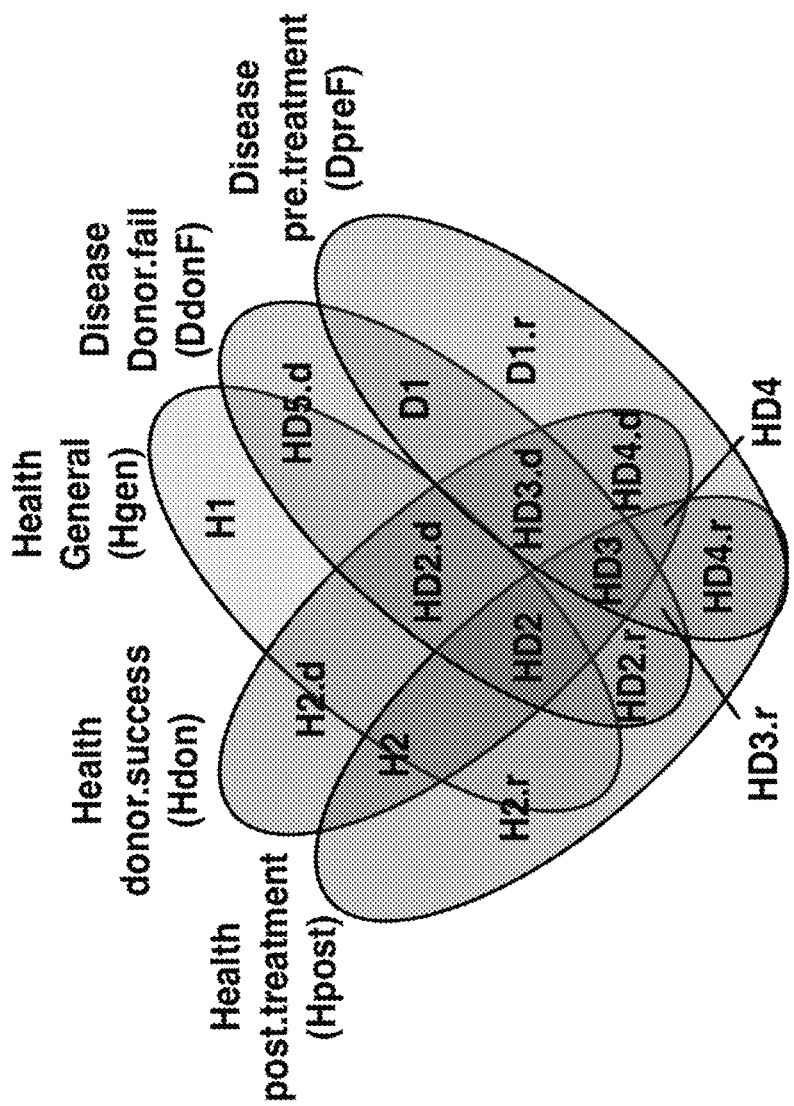

FIG. 19 shows phenotypes assigned to samples for the computational derivation of Network Ecologies that typify microbiome states of health (Hpost, Hdon, & Hgen) and states of disease (DdonF & DpreF). The composition of the microbiome of samples in different phenotypes can overlap with the intersections, defined by H, HD, D designations, having different biological meanings.

Figure 20:
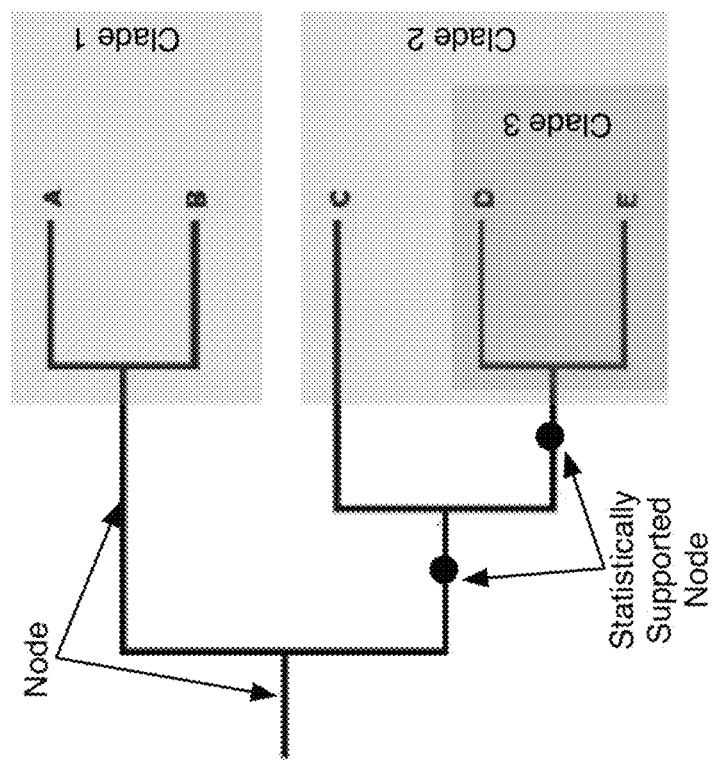

FIG. 20 shows an exemplary phylogenetic tree and the relationship of OTUs and Clades. A, B, C, D, and E represent OTUs, also known as leaves in the tree. Clade 1 comprises OTUs A and B, Clade 2 comprises OTUs C, D and E, and Clade 3 is a subset of Clade 2 comprising OTUs D and E. Nodes in a tree that define clades in the tree can be either statistically supported or not statistically supported. OTUs within a clade are more similar to each other than to OTUs in another clade and the robustness the clade assignment is denoted by the degree of statistical support for a node upstream of the OTUs in the clade.

Figure 21:
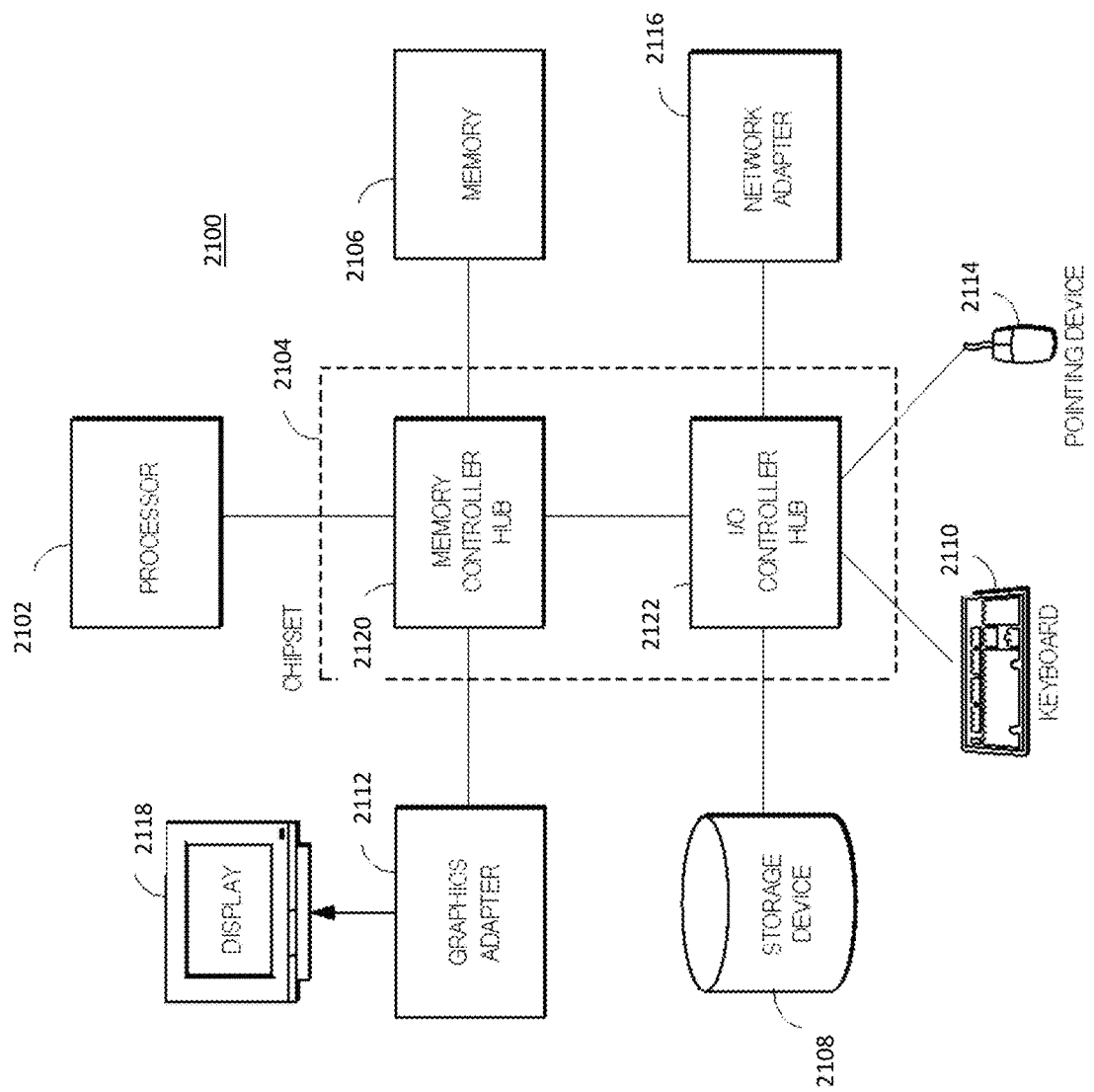

FIG. 21 is a high-level block diagram illustrating an example of a computer for use as a server or a user device, in accordance with one embodiment.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

Disclosed herein are therapeutic compositions containing combinations of bacteria for the prevention, control, and treatment of gastrointestinal diseases, and other disorders and conditions that result in or are caused by a dysbiotic microbiome in a niche of a host. Such indications include, but are not limited to *Clostridium difficile* associated diarrhea (CDAD), Type 2 Diabetes, Ulcerative colitis, as well as infection by antibiotic resistant bacteria such as Carbapenem resistant *Klebsiella pneomoniae* (CRKp) and Vancomycin Resistant *Enterococcus* (VRE). These compositions are advantageous in being suitable for safe administration to humans and other mammalian subjects and are efficacious in numerous gastrointestinal diseases, disorders and conditions and in general nutritional health. While bacterial compositions are known, these are generally single bacterial strains or combinations of bacteria that are combined without understanding the ecology formed by a consortium of bacterial organisms, resulting in poor efficacy, instability, substantial variability and lack of adequate safety.

The human body is an ecosystem in which the microbiota and the microbiome play a significant role in the basic healthy function of human systems (e.g. metabolic, immunological, and neurological). The microbiota and resulting microbiome comprise an ecology of microorganisms that co-exist within single subjects interacting with one another and their host (i.e., the mammalian subject) to form a dynamic unit with inherent biodiversity and functional characteristics. Within these networks of interacting microbes (i.e. ecologies), particular members can contribute more significantly than others; as such these members are also found in many different ecologies, and the loss of these microbes from the ecology can have a significant impact on the functional capabilities of the specific ecology. Robert Paine coined the concept "Keystone Species" in 1969 (see Paine R T. 1969. A note on trophic complexity and community stability. The American Naturalist 103: 91-93.) to describe the existence of such lynchpin species that are integral to a given ecosystem regardless of their abundance in the ecological community. Paine originally describe the role of the starfish *Pisaster ochraceus* in marine systems and since the concept has been experimentally validated in numerous ecosystems.

The present invention provides methods to define important network ecologies and functional network ecologies that occur in healthy and diseased subjects, and provides the compositional constituents of these network ecologies. The method enables the derivation of ecological modules (i.e. groups or networks of organisms and metabolic functions) within a broader ecology that can catalyze a change from a dysbiotic microbiome to one that represents a state of health. In another embodiment the methods enable the de novo construction of a network ecology based on desired biological characteristics, including functional characteristics, e.g. a functional network ecology. The methods further provide keystone species (i.e. operational taxonomic units, or OTUs) and keystone metabolic functions that are members of these microbial communities based on their ubiquitous appearance in many different networks. Importantly, this method is distinguished from previous computational approaches by being the first method to define actual network ecologies that are found in many healthy subjects. Network ecologies comprise consortia of bacterial OTUs (i.e. genera, species, or strains) that form coherent intact biological communities with defined phylogenetic and/or functional properties. In other words, the structure-function relationships contained within any Network Ecology possess an inherent biodiversity profile and resulting biological functional capabilities. The specific bacterial combinations and functional capabilities of the resulting microbiome are efficacious for the treatment or prevention of diseases, disorders and conditions of the gastrointestinal tract or for the treatment or prevention of systemic diseases, disorders and conditions that are influenced by the microbiota of the gastrointestinal tract. Further the network ecologies have a modularity to their structure and function with specific nodes (as example OTUs, phylogenetic clades, functional pathways) comprising a backbone of the network onto which different r-groups (as example OTUs, phylogenetic clades, functional pathways) can be incorporated to achieve specific biological properties of the network ecology. Network Ecologies defined in terms of functional modalities are referred to as Functional Network Ecologies.

The network ecologies provided herein are useful in settings where a microbial dysbiosis is occurring, given their capacities to achieve one or more of the following actions: i) disrupting the existing microbiota and/or microbiome; ii) establishing a new microbiota and/or microbiome; and (iii) stabilizing a functional microbiota and/or microbiome that supports health. Such network ecologies may be sustainably present upon introduction into a mammalian subject, or may be transiently present until such time as the functional microbiota and/or microbiome are re-established. In therapeutic settings, treatment with a consortium of microbial OTUs will change the microbiome of the treated host from a state of disease to a state of health. This change in the total diversity and composition can be mediated by both: (i) engraftment of OTUs that comprise the therapeutic composition into the host's ecology (Engrafted Ecology), and (ii) the establishment of OTUs that are not derived from the therapeutic composition, but for which the treatment with the therapeutic composition changes the environmental conditions such that these OTUs can establish. This Augmented Ecology is comprised of OTUs that were present at lower levels in the host pre-treatment or that were exogenously introduced from a source other than the therapeutic composition itself.

Provided herein are computational methods based at least in part on network theory (Proulx S R, Promislow D E L, Phillips P C. 2005. Network thinking in ecology and evolution. Trends in Ecology & Evolution 20: 345-353.), that delineate ecological and functional structures of a group of microorganisms based on the presence or absence of the specific OTUs (i.e. microbial orders, families, genera, species or strains) or functions inherent to those OTUs in a population of sampled mammalian subjects. Notably, these network ecologies and functional network ecologies are not simply inferred based on the clustering of OTUs according to binary co-occurrences computed from average relative abundances across a set of subject samples (See e.g. Faust K, Sathirapongsasuti J F, Izard J, Segata N, Gevers D, Raes J, and Huttenhower C. 2012. Microbial co-occurrence relationships in the human microbiome. PLoS Computational Bioliology 8: e1002606. Lozupone C, Faust K, Raes J, Faith J J, Frank D N, Zaneveld J, Gordon J I, and Knight R. 2012. Identifying genomic and metabolic features that can underlie early successional and opportunistic lifestyles of human gut symbionts. Genome Research 22: 1974-1984), but instead the ecologies represent actual communities of bacterial OTUs that are computationally derived and explicitly exist as an ecological network within one or more subjects. Further, we provide methods by which to characterize the biological significance of a given ecological network in terms of its phylogenetic diversity, functional properties, and association with health or disease. The present invention delineates ecologies suitable for the treatment or prevention of diseases, disorders, and conditions of the gastrointestinal tract or which are distal to the gastrointestinal tract but caused or perpetuated by a dysbiosis of the gut microbiota.

Definitions

As used herein, the term "purified bacterial preparation" refers to a preparation that includes bacteria that have been separated from at least one associated substance found in a source material or any material associated with the bacteria in any process used to produce the preparation.

A "bacterial entity" includes one or more bacteria. Generally, a first bacterial entity is distinguishable from a second bacterial entity As used herein, the term "formation" refers to synthesis or production.

As used herein, the term "inducing" means increasing the amount or activity of a given material as dictated by context.

As used herein, the term "depletion" refers to reduction in amount of.

As used herein, a "prebiotic" is a comestible food or beverage or ingredient thereof that allows specific changes, both in the composition and/or activity in the gastrointestinal microbiota that confers benefits upon host well-being and health. Prebiotics may include complex carbohydrates, amino acids, peptides, or other essential nutritional components for the survival of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, trans-galactooligosaccharide, and xylooligosaccharides.

As used herein, "predetermined ratios" refer to ratios determined or selected in advance.

As used herein, "germinable bacterial spores" are spores capable of forming vegetative cells under certain environmental conditions.

As used herein, "detectably present" refers to present in an amount that can be detected using assays provided herein or otherwise known in the art that exist as of the filing date.

As used herein, "augmented" refers to an increase in amount and/or localization within to a point where it becomes detectably present.

As used herein, a "fecal material" refers to a solid waste product of digested food and includes feces or bowel washes.

As used herein, a "host cell response" is a response produced by a cell comprising a host organism.

As used herein, a "mammalian subject protein" refers to a protein produced by a mammalian subject and encoded by the mammalian subject genome.

As used herein, the term "food-derived" refers to a protein found in a consumed food.

As used herein, the term "biological material" refers to a material produced by a biological organism.

As used herein, the term "detection moiety" refers to an assay component that functions to detect an analyte.

As used herein, the term "incomplete network" refers to a partial network that lacks the entire set of components needed to carry out one or more network functions.

As used herein, the term "supplemental" refers to something that is additional and non-identical.

As used herein, the term "Antioxidant" refers to, without limitation, any one or more of various substances such as beta-carotene (a vitamin A precursor), vitamin C, vitamin E, and selenium that inhibit oxidation or reactions promoted by Reactive Oxygen Species ("ROS") and other radical and non-radical species. Additionally, antioxidants are molecules capable of slowing or preventing the oxidation of other molecules. Non-limiting examples of antioxidants include astaxanthin, carotenoids, coenzyme Q10 ("CoQ10"), flavonoids, glutathione, Goji (wolfberry), hesperidin, lactowolfberry, lignan, lutein, lycopene, polyphenols, selenium, vitamin A, vitamin C, vitamin E, zeaxanthin, or combinations thereof.

"Backbone Network Ecology" or simply "Backbone Network" or "Backbone" are compositions of microbes that form a foundational composition that can be built upon or subtracted from to optimize a Network Ecology or Functional Network Ecology to have specific biological characteristics or to comprise desired functional properties, respectively. Microbiome therapeutics can be comprised of these "Backbone Networks Ecologies" in their entirety, or the "Backbone Networks" can be modified by the addition or subtraction of "R-Groups" to give the network ecology desired characteristics and properties. "R-Groups" can be defined in multiple terms including, but not limited to: individual OTUs, individual or multiple OTUs derived from a specific phylogenetic clade or a desired phenotype such as the ability to form spores, or functional bacterial compositions that comprise. "Backbone Networks" can comprise a computationally derived Network Ecology in its entirety or can be subsets of the computed network that represent key nodes in the network that contributed to efficacy such as but not limited to a composition of Keystone OTUs. The number of organisms in the human gastrointestinal tract, as well as the diversity between healthy individuals, is indicative of the functional redundancy of a healthy gut microbiome ecology. See The Human Microbiome Consortia. 2012. Structure, function and diversity of the healthy human microbiome. Nature 486: 207-214. This redundancy makes it highly likely that non-obvious subsets of OTUs or functional pathways (i.e. "Backbone Networks") are critical to maintaining states of health and or catalyzing a shift from a dysbiotic state to one of health. One way of exploiting this redundancy is through the substitution of OTUs that share a given clade (see below) or of adding members of a clade not found in the Backbone Network.

"Bacterial Composition" refers to a consortium of microbes comprising two or more OTUs. Backbone Network Ecologies, Functional Network Ecologies, Network Classes, and Core Ecologies are all types of bacterial compositions. A "Bacterial Composition" can also refer to a composition of enzymes that are derived from a microbe or multiple microbes. As used herein, Bacterial Composition includes a therapeutic microbial composition, a prophylactic microbial composition, a Spore Population, a Purified Spore Population, or ethanol treated spore population.

"Clade" refers to the OTUs or members of a phylogenetic tree that are downstream of a statistically valid node in a phylogenetic tree (FIG. 20). The clade comprises a set of terminal leaves in the phylogenetic tree (i.e. tips of the tree) that are a distinct monophyletic evolutionary unit and that share some extent of sequence similarity. Clades are hierarchical. In one embodiment, the node in a phylogenetic tree that is selected to define a clade is dependent on the level of resolution suitable for the underlying data used to compute the tree topology.

The "Colonization" of a host organism includes the non-transitory residence of a bacterium or other microscopic organism. As used herein, "reducing colonization" of a host subject's gastrointestinal tract (or any other microbiotal niche) by a pathogenic or non-pathogenic bacterium includes a reduction in the residence time of the bacterium the gastrointestinal tract as well as a reduction in the number (or concentration) of the bacterium in the gastrointestinal tract or adhered to the luminal surface of the gastrointestinal tract. The reduction in colonization can be permanent or occur during a transient period of time. Reductions of adherent pathogens can be demonstrated directly, e.g., by determining pathogenic burden in a biopsy sample, or reductions may be measured indirectly, e.g., by measuring the pathogenic burden in the stool of a mammalian host.

A "Combination" of two or more bacteria includes the physical co-existence of the two bacteria, either in the same material or product or in physically connected products, as well as the temporal co-administration or co-localization of the two bacteria.

"Cytotoxic" activity of bacterium includes the ability to kill a bacterial cell, such as a pathogenic bacterial cell. A "cytostatic" activity or bacterium includes the ability to inhibit, partially or fully, growth, metabolism, and/or proliferation of a bacterial cell, such as a pathogenic bacterial cell. Cytotoxic activity may also apply to other cell types such as but not limited to Eukaryotic cells.

"Dysbiosis" refers to a state of the microbiota or microbiome of the gut or other body area, including mucosal or skin surfaces in which the normal diversity and/or function of the ecological network is disrupted. Any disruption from the preferred (e.g., ideal) state of the microbiota can be considered a dysbiosis, even if such dysbiosis does not result in a detectable decrease in health. This state of dysbiosis may be unhealthy, it may be unhealthy under only certain conditions, or it may prevent a subject from becoming healthier. Dysbiosis may be due to a decrease in diversity, the overgrowth of one or more pathogens or pathobionts, symbiotic organisms able to cause disease only when certain genetic and/or environmental conditions are present in a patient, or the shift to an ecological network that no longer provides a beneficial function to the host and therefore no longer promotes health.

"Ecological Niche" or simply "Niche" refers to the ecological space in which an organism or group of organisms occupies. Niche describes how an organism or population or organisms responds to the distribution of resources, physical parameters (e.g., host tissue space) and competitors (e.g., by growing when resources are abundant, and when predators, parasites and pathogens are scarce) and how it in turn alters those same factors (e.g., limiting access to resources by other organisms, acting as a food source for predators and a consumer of prey).

"Germinant" is a material or composition or physical-chemical process capable of inducing vegetative growth of a bacterium that is in a dormant spore form, or group of bacteria in the spore form, either directly or indirectly in a host organism and/or in vitro.

"Inhibition" of a pathogen or non-pathogn encompasses the inhibition of any desired function or activity y the bacterial compositions of the present invention. Demonstrations of inhibition, such as decrease in the growth of a pathogenic bacterium or reduction in the level of colonization of a pathogenic bacterium are provided herein and otherwise recognized by one of ordinary skill in the art. Inhibition of a pathogenic or non-pathogenic bacterium's "growth" may include inhibiting the increase in size of the pathogenic or non-pathogenic bacterium and/or inhibiting the proliferation (or multiplication) of the pathogenic or non-pathogenic bacterium. Inhibition of colonization of a pathogenic or non-pathogenic bacterium may be demonstrated by measuring the amount or burden of a pathogen before and after a treatment. An "inhibition" or the act of "inhibiting" includes the total cessation and partial reduction of one or more activities of a pathogen, such as growth, proliferation, colonization, and function. Inhibition of function includes, for example, the inhibition of expression of pathogenic gene products such as a toxin or invasive pilus induced by the bacterial composition.

"Isolated" encompasses a bacterium or other entity or substance that has been (1) separated from at least some of the components with which it was associated when initially produced (whether in nature or in an experimental setting), and/or (2) produced, prepared, purified, and/or manufactured by the hand of man. Isolated bacteria include those bacteria that are cultured, even if such cultures are not monocultures. Isolated bacteria may be separated from at least about 10%, about 20%, about 30%, about 40%, about 50%, about 60%, about 70%, about 80%, about 90%, or more of the other components with which they were initially associated. In some embodiments, isolated bacteria are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. The terms "purify," "purifying" and "purified" refer to a bacterium or other material that has been separated from at least some of the components with which it was associated either when initially produced or generated (e.g., whether in nature or in an experimental setting), or during any time after its initial production. A bacterium or a bacterial population may be considered purified if it is isolated at or after production, such as from a material or environment containing the bacterium or bacterial population, or by passage through culture, and a purified bacterium or bacterial population may contain other materials up to about 10%, about 20%, about 30%, about 40%, about 50%, about 60%, about 70%, about 80%, about 90%, or above about 90% and still be considered "isolated." In some embodiments, purified bacteria and bacterial populations are more than about 80%, about 85%, about 90%, about 91%, about 92%, about 93%, about 94%, about 95%, about 96%, about 97%, about 98%, about 99%, or more than about 99% pure. In the instance of bacterial compositions provided herein, the one or more bacterial types present in the composition can be independently purified from one or more other bacteria produced and/or present in the material or environment containing the bacterial type. Bacterial compositions and the bacterial components thereof are generally purified from residual habitat products.

"Keystone OTU" or "Keystone Function" refers to one or more OTUs or Functional Pathways (e.g. KEGG or COG pathways) that are common to many network ecologies or functional network ecologies and are members of networks that occur in many subjects (i.e. are pervasive). Due to the ubiquitous nature of Keystone OTUs and their associated Functions Pathways, they are central to the function of network ecologies in healthy subjects and are often missing or at reduced levels in subjects with disease. Keystone OTUs and their associated functions may exist in low, moderate, or high abundance in subjects. "Non-Keystone OTU" or "non-Keystone Function" refers to an OTU or Function that is observed in a Network Ecology or a Functional Network Ecology and is not a keystone OTU or Function.

"Microbiota" refers to the community of microorganisms that occur (sustainably or transiently) in and on an animal subject, typically a mammal such as a human, including eukaryotes, archaea, bacteria, and viruses (including bacterial viruses i.e., phage).

"Microbiome" refers to the genetic content of the communities of microbes that live in and on the human body, both sustainably and transiently, including eukaryotes, archaea, bacteria, and viruses (including bacterial viruses (i.e., phage)), wherein "genetic content" includes genomic DNA, RNA such as ribosomal RNA, the epigenome, plasmids, and all other types of genetic information.

"Microbial Carriage" or simply "Carriage" refers to the population of microbes inhabiting a niche within or on humans. Carriage is often defined in terms of relative abundance. For example, OTU1 comprises 60% of the total microbial carriage, meaning that OTU1 has a relative abundance of 60% compared to the other OTUs in the sample from which the measurement was made. Carriage is most often based on genomic sequencing data where the relative abundance or carriage of a single OTU or group of OTUs is defined by the number of sequencing reads that are assigned to that OTU/s relative to the total number of sequencing reads for the sample. Alternatively, Carriage may be measured using microbiological assays.

"Microbial Augmentation" or simply "augmentation" refers to the establishment or significant increase of a population of microbes that are (i) absent or undetectable (as determined by the use of standard genomic and microbiological techniques) from the administered therapeutic microbial composition, (ii) absent, undetectable, or present at low frequencies in the host niche (for example: gastrointestinal tract, skin, anterior-nares, or vagina) before the delivery of the microbial composition, and (iii) are found after the administration of the microbial composition or significantly increased, for instance 2-fold, 5-fold, $1 \times 10^2$, $1 \times 10^3$, $1 \times 10^4$, $1 \times 10^5$, $1 \times 10^6$, $1 \times 10^7$, or greater than $1 \times 10^8$, in cases where they were present at low frequencies. The microbes that comprise an augmented ecology can be derived from exogenous sources such as food and the environment, or grow out from micro-niches within the host where they reside at low frequency. The administration of a bacterial microbial composition induces an environmental shift in the target niche that promotes favorable conditions for the growth of these commensal microbes. In the absence of treatment with a bacterial composition, the host can be constantly exposed to these microbes; however, sustained growth and the positive health effects associated with the stable population of increased levels of the microbes comprising the augmented ecology are not observed.

"Microbial Engraftment" or simply "engraftment" refers to the establishment of OTUs present in the bacterial composition in a target niche that are absent in the treated host prior to treatment. The microbes that comprise the engrafted ecology are found in the therapeutic microbial composition and establish as constituents of the host microbial ecology upon treatment. Engrafted OTUs can establish for a transient period of time, or demonstrate long-term stability in the microbial ecology that populates the host post treatment with a bacterial composition. The engrafted ecology can induce an environmental shift in the target niche that promotes favorable conditions for the growth of commensal microbes capable of catalyzing a shift from a dysbiotic ecology to one representative of a health state.

As used herein, the term "Minerals" is understood to include boron, calcium, chromium, copper, iodine, iron, magnesium, manganese, molybdenum, nickel, phosphorus, potassium, selenium, silicon, tin, vanadium, zinc, or combinations thereof.

"Network Ecology" refers to a consortium of clades or OTUs that co-occur in some number of subjects. As used herein, a "network" is defined mathematically by a graph delineating how specific nodes (i.e. clades or OTUs) and edges (connections between specific clades or OTUs) relate to one another to define the structural ecology of a consortium of clades or OTUs. Any given Network Ecology will possess inherent phylogenetic diversity and functional properties. A Network Ecology can also be defined in terms of its functional capabilities where for example the nodes would be comprised of elements such as, but not limited to, enzymes, clusters of orthologous groups (COGS; ncbi.nlm.nih.gov/books/NBK21090/), or KEGG Orthology Pathways (genome.jp/kegg/); these networks are referred to as a "Functional Network Ecology". Functional Network Ecologies can be reduced to practice by defining the group of OTUs that together comprise the functions defined by the Functional Network Ecology.

"Network Class" and "Network Class Ecology" refer to a group of network ecologies that in general are computationally determined to comprise ecologies with similar phylogenetic and/or functional characteristics. A Network Class therefore contains important biological features, defined either phylogenetically or functionally, of a group (i.e., a cluster) of related network ecologies. One representation of a Network Class Ecology is a designed consortium of microbes, typically non-pathogenic bacteria, that represents core features of a set of phylogenetically or functionally related network ecologies seen in many different subjects. In many occurrences, a Network Class, while designed as described herein, exists as a Network Ecology observed in one or more subjects. Network Class ecologies are useful for reversing or reducing a dysbiosis in subjects where the underlying, related Network Ecology has been disrupted. Exemplary Network Classes are provided in Table 12 and examples of phylogenetic signature by family of Network Classes are given in Table 13.

To be free of "non-comestible products" means that a bacterial composition or other material provided herein does not have a substantial amount of a non-comestible product, e.g., a product or material that is inedible, harmful or otherwise undesired in a product suitable for administration, e.g., oral administration, to a human subject. Non-comestible products are often found in preparations of bacteria from the prior art.

"Operational taxonomic units" and "OTU" (or plural, "OTUs") refer to a terminal leaf in a phylogenetic tree and is defined by a nucleic acid sequence, e.g., the entire genome, or a specific genetic sequence, and all sequences that share sequence identity to this nucleic acid sequence at the level of species. In some embodiments the specific genetic sequence may be the 16S sequence or a portion of the 16S sequence. In other embodiments, the entire genomes of two entities are sequenced and compared. In another embodiment, select regions such as multilocus sequence tags (MLST), specific genes, or sets of genes may be genetically compared. In 16S embodiments, OTUs that share ≥97% average nucleotide identity across the entire 16S or some variable region of the 16S are considered the same OTU. See e.g. Claesson M J, Wang Q, O'Sullivan O, Greene-Diniz R, Cole J R, Ross R P, and O'Toole P W. 2010. Comparison of two next-generation sequencing technologies for resolving highly complex microbiota composition using tandem variable 16S rRNA gene regions. Nucleic Acids Res 38: e200. Konstantinidis K T, Ramette A, and Tiedje J M. 2006. The bacterial species definition in the genomic era. Philos Trans R Soc Lond B Biol Sci 361: 1929-1940. In embodiments involving the complete genome, MLSTs, specific genes, other than 16S, or sets of genes OTUs that share ≥95% average nucleotide identity are considered the same OTU. See e.g., Achtman M, and Wagner M. 2008. Microbial diversity and the genetic nature of microbial species. Nat. Rev. Microbiol. 6: 431-440. Konstantinidis K T, Ramette A, and Tiedje J M. 2006. The bacterial species definition in the genomic era. Philos Trans R Soc Lond B Biol Sci 361: 1929-1940. OTUs are frequently defined by comparing sequences between organisms. Generally, sequences with less than 95% sequence identity are not considered to form part of the same OTU. OTUs may also be characterized by any combination of nucleotide markers or genes, in particular highly conserved genes (e.g., "house-keeping" genes), or a combination thereof. Such characterization employs, e.g., WGS data or a whole genome sequence.

Table 1 below shows a List of Operational Taxonomic Units (OTU) with taxonomic assignments made to Genus, Species, and Phylogenetic Clade. Clade membership of bacterial OTUs is based on 16S sequence data. Clades are defined based on the topology of a phylogenetic tree that is constructed from full-length 16S sequences using maximum likelihood methods familiar to individuals with ordinary skill in the art of phylogenetics. Clades are constructed to ensure that all OTUs in a given clade are: (i) within a specified number of bootstrap supported nodes from one another, and (ii) within 5% genetic similarity. OTUs that are within the same clade can be distinguished as genetically and phylogenetically distinct from OTUs in a different clade based on 16S-V4 sequence data, while OTUs falling within the same clade are closely related. OTUs falling within the same clade are evolutionarily closely related and may or may not be distinguishable from one another using 16S-V4 sequence data. Members of the same clade, due to their evolutionary relatedness, play similar functional roles in a microbial ecology such as that found in the human gut. Compositions substituting one species with another from the same clade are likely to have conserved ecological function and therefore are useful in the present invention. All OTUs are denoted as to their putative capacity to form spores and whether they are a Pathogen or Pathobiont (see Definitions for description of "Pathobiont"). NIAID Priority Pathogens are denoted as 'Category-A', 'Category-B', or 'Category-C', and Opportunistic Pathogens are denoted as 'OP'. OTUs that are not pathogenic or for which their ability to exist as a pathogen is unknown are denoted as 'N'. The 'SEQ ID Number' denotes the identifier of the OTU in the Sequence Listing File and 'Public DB Accession' denotes the identifier of the OTU in a public sequence repository.

"Pathobiont" refer to specific bacterial species found in healthy hosts that may trigger immune-mediated pathology and/or disease in response to certain genetic or environmental factors (Chow et al. 2011. Curr Op Immunol. Pathobionts of the intestinal microbiota and inflammatory disease. 23: 473-80). Thus, a pathobiont is an opportunistic microbe that is mechanistically distinct from an acquired infectious organism. Thus, the term "pathogen" includes both acquired infectious organisms and pathobionts.

"Pathogen", "pathobiont" and "pathogenic" in reference to a bacterium or any other organism or entity that includes any such organism or entity that is capable of causing or affecting a disease, disorder or condition of a host organism containing the organism or entity, including but not limited to pre-diabetes, type 1 diabetes or type 2 diabetes.

"Phenotype" refers to a set of observable characteristics of an individual entity. As example an individual subject may have a phenotype of "health" or "disease". Phenotypes describe the state of an entity and all entities within a phenotype share the same set of characteristics that describe the phenotype. The phenotype of an individual results in part, or in whole, from the interaction of the entity's genome and/or microbiome with the environment, especially including diet.

"Phylogenetic Diversity" is a biological characteristic that refers to the biodiversity present in a given Network Ecology or Network Class Ecology based on the OTUs that comprise the network. Phylogenetic diversity is a relative term, meaning that a Network Ecology or Network Class that is comparatively more phylogenetically diverse than another network contains a greater number of unique species, genera, and taxonomic families. Uniqueness of a species, genera, or taxonomic family is generally defined using a phylogenetic tree that represents the genetic diversity all species, genera, or taxonomic families relative to one another. In another embodiment phylogenetic diversity may be measured using the total branch length or average branch length of a phylogenetic tree. Phylogenetic Diversity may be optimized in a bacterial composition by including a wide range of biodiversity.

"Phylogenetic tree" refers to a graphical representation of the evolutionary relationships of one genetic sequence to another that is generated using a defined set of phylogenetic reconstruction algorithms (e.g. parsimony, maximum likelihood, or Bayesian). Nodes in the tree represent distinct ancestral sequences and the confidence of any node is provided by a bootstrap or Bayesian posterior probability, which measures branch uncertainty.

"Prediabetes" refers a condition in which blood glucose levels are higher than normal, but not high enough to be classified as diabetes. Individuals with pre-diabetes are at increased risk of developing type 2 diabetes within a decade. According to CDC, prediabetes can be diagnosed by fasting glucose levels between 100-125 mg/dL, 2 hour post-glucose load plasma glucose in oral glucose tolerance test (OGTT) between 140 and 199 mg/dL, or hemoglobin A1c test between 5.7%-6.4%.

"rDNA", "rRNA", "16S-rDNA", "16S-rRNA", "16S", "16S sequencing", "16S-NGS", "18S", "18S-rRNA", "18S-rDNA", "18S sequencing", and "18S-NGS" refer to the nucleic acids that encode for the RNA subunits of the ribosome. rDNA refers to the gene that encodes the rRNA that comprises the RNA subunits. There are two RNA subunits in the ribosome termed the small subunit (SSU) and large subunit (LSU); the RNA genetic sequences (rRNA) of these subunits is related to the gene that encodes them (rDNA) by the genetic code. rDNA genes and their complementary RNA sequences are widely used for determination of the evolutionary relationships amount organisms as they are variable, yet sufficiently conserved to allow cross organism molecular comparisons. Typically 16S rDNA sequence (approximately 1542 nucleotides in length) of the 30S SSU is used for molecular-based taxonomic assignments of Prokaryotes and the 18S rDNA sequence (approximately 1869 nucleotides in length) of 40S SSU is used for Eukaryotes. 16S sequences are used for phylogenetic reconstruction as they are in general highly conserved, but contain specific hypervariable regions that harbor sufficient nucleotide diversity to differentiate genera and species of most bacteria.

"Residual habitat products" refers to material derived from the habitat for microbiota within or on a human or animal. For example, microbiota live in feces in the gastrointestinal tract, on the skin itself, in saliva, mucus of the respiratory tract, or secretions of the genitourinary tract (i.e., biological matter associated with the microbial community). Substantially free of residual habitat products means that the bacterial composition no longer contains the biological matter associated with the microbial environment on or in the human or animal subject and is 100% free, 99% free, 98% free, 97% free, 96% free, or 95% free of any contaminating biological matter associated with the microbial community. Residual habitat products can include abiotic materials (including undigested food) or it can include unwanted microorganisms. Substantially free of residual habitat products may also mean that the bacterial composition contains no detectable cells from a human or animal and that only microbial cells are detectable. In one embodiment, substantially free of residual habitat products may also mean that the bacterial composition contains no detectable viral (including bacterial viruses (i.e., phage)), fungal, mycoplasmal contaminants. In another embodiment, it means that fewer than $1 \times 10^{-2}\%$, $1 \times 10^{-3}\%$, $1 \times 10^{-4}\%$, $1 \times 10^{-5}\%$, $1 \times 10^{-6}\%$, $1 \times 10^{-7}\%$, $1 \times 10^{-8}$ of the viable cells in the bacterial composition are human or animal, as compared to microbial cells. There are multiple ways to accomplish this degree of purity, none of which are limiting. Thus, contamination may be reduced by isolating desired constituents through multiple steps of streaking to single colonies on solid media until replicate (such as, but not limited to, two) streaks from serial single colonies have shown only a single colony morphology. Alternatively, reduction of contamination can be accomplished by multiple rounds of serial dilutions to single desired cells (e.g., a dilution of $10^{-8}$ or $10^{-9}$), such as through multiple 10-fold serial dilutions. This can further be confirmed by showing that multiple isolated colonies have similar cell shapes and Gram staining behavior. Other methods for confirming adequate purity include genetic analysis (e.g. PCR, DNA sequencing), serology and antigen analysis, enzymatic and metabolic analysis, and methods using instrumentation such as flow cytometry with reagents that distinguish desired constituents from contaminants.

"Spore" or a population of "spores" includes bacteria (or other single-celled organisms) that are generally viable, more resistant to environmental influences such as heat and bacteriocidal agents than vegetative forms of the same bacteria, and typically capable of germination and outgrowth. Spores are characterized by the absence of active metabolism until they respond to specific environmental signals, causing them to germinate. "Spore-formers" or bacteria "capable of forming spores" are those bacteria containing the genes and other necessary abilities to produce spores under suitable environmental conditions. A Table of preferred spore-forming bacterial compositions is provided in Table 11.

"Spore population" refers to a plurality of spores present in a composition. Synonymous terms used herein include spore composition, spore preparation, ethanol-treated spore fraction and spore ecology. A spore population may be purified from a fecal donation, e.g. via ethanol or heat treatment, or a density gradient separation or any combination of methods described herein to increase the purity, potency and/or concentration of spores in a sample. Alternatively, a spore population may be derived through culture methods starting from isolated spore former species or spore former OTUs or from a mixture of such species, either in vegetative or spore form.

In one embodiment, the spore preparation comprises spore forming species wherein residual non-spore forming species have been inactivated by chemical or physical treatments including ethanol, detergent, heat, sonication, and the like; or wherein the non-spore forming species have been removed from the spore preparation by various separations steps including density gradients, centrifugation, filtration and/or chromatography; or wherein inactivation and separation methods are combined to make the spore preparation. In yet another embodiment, the spore preparation comprises spore forming species that are enriched over viable non-spore formers or vegetative forms of spore formers. In this embodiment, spores are enriched by 2-fold, 5-fold, 10-fold, 50-fold, 100-fold, 1000-fold, 10,000-fold or greater than 10,000-fold compared to all vegetative forms of bacteria. In yet another embodiment, the spores in the spore preparation undergo partial germination during processing and formulation such that the final composition comprises spores and vegetative bacteria derived from spore forming species.

"Sporulation induction agent" is a material or physical-chemical process that is capable of inducing sporulation in a bacterium, either directly or indirectly, in a host organism and/or in vitro.

To "increase production of bacterial spores" includes an activity or a sporulation induction agent. "Production" includes conversion of vegetative bacterial cells into spores and augmentation of the rate of such conversion, as well as decreasing the germination of bacteria in spore form, decreasing the rate of spore decay in vivo, or ex vivo, or to increasing the total output of spores (e.g. via an increase in volumetric output of fecal material).

"Subject" refers to any animal subject including humans, laboratory animals (e.g., primates, rats, mice), livestock (e.g., cows, sheep, goats, pigs, turkeys, and chickens), and household pets (e.g., dogs, cats, and rodents). The subject may be suffering from a dysbiosis, that contributes to or causes a condition classified as diabetes or pre-diabetes, including but not limited to mechanisms such as metabolic endotoxemia, altered metabolism of primary bile acids, immune system activation, or an imbalance or reduced production of short chain fatty acids including butyrate, propionate, acetate, and branched chain fatty acids.

As used herein the term "Vitamin" is understood to include any of various fat-soluble or water-soluble organic substances (non-limiting examples include Vitamin A, Vitamin B1 (thiamine), Vitamin B2 (riboflavin), Vitamin B3 (niacin or niacinamide), Vitamin B5 (pantothenic acid), Vitamin B6 (pyridoxine, pyridoxal, or pyridoxamine, or pyridoxine hydrochloride), Vitamin B7 (biotin), Vitamin B9 (folic acid), and Vitamin B12 (various cobalamins; commonly cyanocobalamin in vitamin supplements), Vitamin C, Vitamin D, Vitamin E, Vitamin K, K1 and K2 (i.e., MK-4, MK-7), folic acid and biotin) essential in minute amounts for normal growth and activity of the body and obtained naturally from plant and animal foods or synthetically made, pro-vitamins, derivatives, analogs.

"V1-V9 regions" or "16S V1-V9 regions" refers to the 16S rRNA refers to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. Brosius et al., Complete nucleotide sequence of a 16S ribosomal RNA gene from *Escherichia coli*, PNAS 75(10):4801-4805 (1978). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rRNA by comparing the candidate sequence in question to a reference sequence and identifying the hypervariable regions based on similarity to the reference hypervariable regions, or alternatively, one can employ Whole Genome Shotgun (WGS) sequence characterization of microbes or a microbial community.

Interactions Between Microbiome and Host

Interactions between the human microbiome and the host shape host health and disease via multiple mechanisms, including the provision of essential functions by the microbiota. Examples of these mechanisms include but are not limited to the function of the microbiota in ensuring a healthy level of bile acid metabolism, energy harvesting and storage, and regulation of immune responses, and reducing deleterious and unhealthy levels of gut permeability or metabolic endotoxemia.

Importance of Bile Acids to Human Health and Role of Microbiota

Primary bile acids, cholic acid (CA) and chenodeoxycholic acid (CDCA) are synthesized from cholesterol in the liver in humans. The synthesized primary bile acids are conjugated to glycine, taurine, or sulfate before secretion into the bile by specific transporters located in the basolateral membrane of the hepatocyte. The ingestion of a meal triggers the release of bile from the gallbladder into the intestinal lumen, where bile acids form micelles with dietary lipids and lipid-soluble vitamins, facilitating their absorption. ~95% of bile acids are reabsorbed via specific transporters expressed in the distal ileum, and the remaining 5% escapes the enterohepatic cycle and travels towards the large intestine to be excreted in the feces. In the colon, the bile acids may undergo deconjugation and dehydroxylation by the gut microflora. The resulting secondary bile acids are mainly deoxycholic acid (DCA) and lithocholic acid (LCA). The bile acid pool undergoes this enterohepatic cycle around 12x/day in humans. Although the bile acid pool size is constant, the flux of bile acids varies during the day; bile acid flux and plasma bile acid concentrations are highest postprandially (See reviews Prawitt, J et al. 2011 Curr Diab Rep Bile acid metabolism and the pathogenesis of type 2 diabetes 11: 160-166; Nieuwdorp et al. 2014 Gastroenterology. Role of the Microbiome in Energy Regulation and Metabolism. pii: S0016-5085(14)00219-4. doi: 10.1053/j.gastro.2014.02.008).

Commensal bacteria are involved in processing primary bile acids to secondary bile acids in the colon. Known biotransformations of bile acids by commensal GI bacteria include deconjugation of the conjugated bile salts to liberate free bile acids and amino acid moieties, removal of hydroxyl groups principally the C-7 hydroxyl group of the cholic acid moiety, oxidative and reductive reactions of the existing hydroxyl groups, and epimerization of bile acids.

The canonical first step in bile acid metabolism is deconjugation of the taurine or glycine group through enzymes termed bile salt hydrolases, to yield CA and CDCA. These bile acids are then substrates for a series of enzymatic steps that remove the 7-alphahydroxy group to form deoxycholic acid (DCA) and lithocholic acid (LCA). LCA has particularly low solubility due to the loss of hydrophilic side chains compared to any of the other bile acids. It is also feasible for microbes to dehydroxylate the conjugated primary bile acids, giving rise to gluco-DCA; gluco-LCA; tauro-DCA; and tauro-LCA. Further modifications are possible, including the microbial conversion of CDCA to a 7-betahydroxy epimer, ursodeoxycholic acid (UDCA). Many other secondary bile acids are made in smaller amounts by the gut microbiota, for example, alpha-, beta-, gamma-, and omega-muricholic acids and many others (see Swann J R et al., 2011 PNAS Systemic gut microbial modulation of bile acid metabolism in host tissue compartments 108: 4523-30).

Intestinal microbiota play a key role in bile acid metabolism. Germ-free mice have altered metabolism of bile acids, including increased levels of conjugated bile acids throughout the intestine, with no deconjugation, and strongly decreased fecal excretion. Provision of ampicillin to mice increases biliary bile acid output 3-fold and decreases fecal output by 70%.

Dysbiosis of the gut microbiome affecting bile acid metabolism may affect adiposity, glucose regulation, and inflammation, among other effects. Bile acids are essential solubilizers of lipids, fats, and lipid soluble vitamins to enhance absorption of nutrients in the small intestine, and are also signaling molecules that regulate metabolism, including glucose homeostasis and basal metabolic rate. See Houten, S M et al. 2006 EMBO J. Endocrine function of bile acids. 25: 1419-25; Prawitt, J et al. 2011 Curr Diab Rep. Bile acid metabolism and the pathogenesis of type 2 diabetes. 11: 160-166. For example, bile acid sequestrants (non-absorbable polymers that complex bile acids in the intestinal lumen and divert them from the enterohepatic cycle) can improve glycemic control in Type 2 diabetes patients. Prawitt, J et al. 2011 Curr Diab Rep Bile acid metabolism and the pathogenesis of type 2 diabetes 11: 160-166.

The most prominent targets of action by bile acids and their metabolites include FXR (farnesoid X receptor), an orphan nuclear receptor within the liver and intestine, and TGR5, a G-protein coupled receptor found on gallbladder, ileum, colon, brown and white adipose tissue. FXR is preferentially activated by CDCA, and in turn upregulates the expression of gene products including FGF-19 (fibroblast growth factor 19) in humans. FGF-15 (the murine analogue of FGF-19) increases basal metabolic rate and reverses weight gain in mice given a high fat diet. FXR activation also down-regulates hepatic gluconeogenesis. Although both conjugated and unconjugated bile acids can bind to FXR, the conjugated forms must be actively transported into the cell to initiate signaling whereas the unconjugated bile acids can diffuse through the membrane owing to their lower molecular weight, higher pKa and tendency to exist in the protonated form.

TGR5 is preferentially activated by the secondary bile acid LCA and tauro-LCA with downstream effects, among others, on expression of incretin hormones such as GLP-1 that modulate insulin production and help maintain glucose homeostasis.

Bile acids are therefore important metabolic regulators. Additional insight into the importance of the interplay between the gut microbiome, bile acid metabolism, and glucose homeostasis is provided by the observation that treating obese male patients with a 7-day course of vancomycin decreases total microbiota diversity, specifically depleting species in the diverse *Clostridium* IV and XIVa clusters. Among the *Clostridia* are various organisms that metabolize bile acids as well as others that produce short chain fatty acids, including butyrate and propionate. In contrast, treatment with a 7-day course of amoxicillin produces a trend toward increased microbiota diversity. Moreover, fecal bile acid composition is markedly changed following vancomycin treatment; secondary bile acids DCA, LCA and iso-LCA decrease whereas primary bile acids CA and CDCA increase. Amoxicillin treatment does not alter the ratio of bile acids in fecal samples. FGF-19 levels in serum are also decreased following vancomycin treatment, but not amoxicillin treatment. Peripheral insulin sensitivity changes following vancomycin but not amoxicillin treatment. Vrieze, A et al., 2013 J Hepatol Impact of oral vancomycin on gut microbiota, bile acid metabolism, and insulin sensistivity dx.doi.org/10.1016/j.jhep.2013.11.034.

While the study by Vrieze et al. points out the potential for microbes to improve insulin homeostasis through enhanced secondary bile acid metabolism, the authors point out several limitations of their work. Most importantly, while the HIT-Chip analysis used to generate fecal microbial profiles provides valuable information regarding classes of organisms, it does not provide mechanistic information or identify specific species or functional enzymatic pathways responsible for the observed effects. Moreover, the HIT-Chip is a hybridization based assay and the similarity of sequences among the organisms in the Clostridial clusters may lead to mis-assignments. As a result, others have failed to define specific compositions that can be used to modulate insulin sensitivity via bile acid metabolism.

In addition to the role for bile acids as metabolic regulators, bile acids are also linked to inflammatory disease. Crohn's Disease patients in the Metagenomics of the Human Intestinal Tract (MetaHIT) cohort show reduced bile salt hydrolase (BSH) gene abundance compared to patients without disease, and increased primary bile acids in inflammatory bowel syndrome patients is correlated with stool frequency and consistency (Duboc et al. 2012 Neurogastroenterol Motil. Increase in fecal primary bile acids and dysbiosis in patients with diarrhea-predominant irritable bowel syndrome. doi: 10.1111/j.1365-2982.2012.01893.x). Furthermore, TGR5 is expressed on immune monocytes and macrophages in addition to GI and liver tissues, and FXR and TGR5 are known to be involved in regulation of inflammation in enterohepatic tissues (Jones et al., 2014 Expert Opin Biol Ther The human microbiome and bile acid metabolism: dysbiosis, dysmetabolism, disease and intervention doi:10.1517/14712598.2014.880420)

Multiple methods are available for determination of bile acids in serum, bile and faces of individuals. As reviewed by Sharma (Sharma, K R, Review on bile acid analysis, Int J Pharm Biomed Sci 2012, 3(2), 28-34), a variety of methods can be used, such as chemical (Carey J B, et al, 1958, The bile acids in normal human serum with comparative observations in patients with jaundice. J Lab Clin Med 1958, 46, 860-865), thin layer chromatography (Fausa O, and Shalhegg B A. 1976 Quantitative determination of bile acids and their conjugates using thin-layer chromatography and a purified 3-α hydroxysteroid dehydrogenase. Scand J Gastroenterol 9, 249-254.), high performance liquid chromatography (Islam S, et al Fasting serum bile acid level in cirrhosis "A semi quantitative index of hepatic function". J Hepatol 1985, 1, 609-617; Paauw J D, at al. Assay for taurine conjugates of bile acids in serum by reversed phase high performance liquid chromatography. J Chromatograph B Biomed Appl 1996, 685, 171-175), radioimmunoassay (Wildgrube J, Stockhausan H, Peter M, Mauritz G, Mandawi R. Radioimmunoassay of bile acids in tissues, bile and urine. Clin Chem 1983, 29, 494-498), enzyme linked colorimetric and radioimmunoassay (Guo W, et al. A study on detection of serum fasting total bile acid and chologlycin in neonates for cholestasis. Chin Med Sci J 1996, 11, 244-247.), mass spectrometry (Sjovell J, et al. Mass spectrometry of bile acids. Method in enzymology. Vol. III, Academic Press, New York 1985.), tandem mass spectrometry (Griffiths W J. Tandem mass spectrometry in study of fatty acids, bile acids and steroids. Mass Spectrum Rev 2003, 22, 81-152.), gas chromatography using high resolution glass capillary columns and mass spectrometry (Setchell K D R, Matsui A. Serum bile acid analysis. Clin Chim Acta 1983, 127, 1-17.), gas chromatography (Fischer S, et al. Hepatic levels of bile acids in end stage chronic cholestatic liver disease. Clin Chim Acta 1996, 251, 173-186.), gas liquid chromatography (Van Berge Hengouwen G P et al., Quantitative anaylsis of bile acids in serum and bile, using gas liquid chromatography. Clin Chim Acta 1974, 54, 249-261; Batta A K, et al. Characterization of serum and urinary bile acids in patients with primary biliary cirrhosis by gas-liquid chromatography-mass spectrometry: effect of ursodeoxycholic acid treatment. J Lipid Res 1989, 30, 1953-1962), luminometric method (Styrellius I, Thore A, Bjorkhem I. Luminometric method. In: Methods of enzymatic analysis. (Ed. III). Bergmeyer, Hans Ulirch [Hrsg]. 8: 274-281, 1985.), UV method for bile assay (Stayer E, et al. Fluorimetric method for serum. In: Methods of enzymatic analysis. (Ed.III). Bergmeyer, Hans Ulrich; [Hrsg]. 8, 288-290, 1985; Stayer E, et al. UV method for bile, gastric juice and duodenai aspirates. In: Methods of enzymatic analysis, (e.d.III). Bergmeyer, Hans Ulrich [Hrsg]. 8: 285-287, 1985), enzymatic colorimetric method (Collins B J, et al. Measurement of total bile acids in gastric juice. J Clin Pathol 1984, 37, 313-316) and enzymatic fluorimetric method can be used (Murphy G M, et al. A fluorometric and enzymatic method for the estimation of serum total bile acids. J Clin Path 1970, 23, 594-598; Hanson N Q, Freier E F. Enzymic measurement of total bile acid adapted to the Cobas Fara Centrifugal analyzer. Clin Chem. 1985, 35, 1538-1539).

Importance of Short Chain Fatty Acids (SCFA) to Human Health and Role of Microbiota Short chain fatty acids (SCFAs) are a principal product of bacterial fermentation in the colon. SCFAs, particularly acetate, propionate and butyrate, are thought to have many potential benefits to the mammalian host. SCFAs are organic acids with fewer than 6 carbons and include acetate, propionate, butyrate, valerate, isovalerate, and 2-methyl butyrate. While longer chain fatty acids are derived primarily from dietary sources, SCFAs are derived from the breakdown of non-digestible plant fiber. Butyrate is a primary energy source for colonocytes, whereas propionate is thought to be metabolized mostly by the liver via portal vein circulation from the colon. Acetate is derived from the microbiota is thought to be more generally available to tissues.

In addition to acting as metabolic substrates, SCFAs have multiple benefits, including that SCFAs produced by the microbiota are essential for immune homeostasis and particularly for immune modulation by regulatory T cells. Direct ingestion of acetate, propionate or butyrate, or a mixture of all three by mice, stimulates the proliferation and maturation of regulatory T cells (Tregs) that reside in the colon. Mice given SCFAs in drinking water have significantly higher levels of colonic CD4+ FoxP3+ T cells (Tregs) than germ free and SPFA controls, and these Treg cells are functionally more potent as measured by the expression of IL-10 mRNA and protein, and by their ability to inhibit CD8+ effector T cells in vitro (Smith P M et al. 2013 Science The microbial metabolites, short-chain fatty acid regulate colonic Treg cell homeostasis 341: 569-73). This effect of SCFAs is mediated via signaling through GPR43 (FFAR2), a G protein coupled receptor expressed on a variety of cells but with high frequency on colonic Treg cells. GPR43 signaling is upstream of modification of histone deacetylase activity (particularly HDAC9 and HDCA3), which is known to alter gene expression via reconfiguration of chromatin. Furthermore, the effects of experimental colitis induced by adoptive T cell transfer are reduced by SCFAs including propionate alone and a mixture of acetate, propionate or butyrate in a GPR43 dependent fashion.

Beyond the direct effects of SCFA administered orally to animals, microbes can produce SCFA in situ in the colon and improve outcomes in several disease models. Daily administration of $10^9$ cfu of Butyricicoccus pullicaecorum, a butyrate forming organism first isolated from chickens, for 1 week ameliorates TNBS-induced colitis in a rat model (Eeckhaut V et al., 2013 Gut Progress towards butyrate-producing pharmabiotics: Butyricicoccus pullicaecorum capsule and efficacy in TNBS models in comparison with therapeutics doi:10.1136/gutjnl-2013-305293). In humans, topical administration of butyrate or sodium butyrate via a rectal enema may be beneficial to ulcerative colitis patients (Scheppach W et al. 1992 Gastroenterol Effect of butyrate enemas on the colonic mucosa in distal ulcerative colitis 103: 51-56; Vernia P et al. 2003 Eur. J. Clin. Investig Topical butyrate improves efficacy of 5-ASA in refractory distal ulcerative colitis: results of a multicentre trial. 33: 244-48). Butyrate has effects at multiple levels including signaling via GPR109A, which is expressed on the apical surface of intestinal epithelial cells (IECs). GPR109A lowers NFKB-mediated gene expression, including reduced expression of the inflammatory cytokines TNF-alpha, IL-6 and IL-1beta.

Oral administration of SCFAs in mice also has direct effects on metabolism. SCFAs are a significant energy source and thus fermentation by the microbiota can contribute up 5-10% of the basal energy requirements of a human. SCFAs upregulate production of glucagon-like peptide 1 (GLP-1), peptide (P)YY and insulin. GLP-1 and PYY are noted to play a role in enhancing satiety and reducing food intake. Furthermore, fecal transplantation from lean human donors to obese recipients with metabolic syndrome results in a significant increase in insulin sensitivity after 6 weeks. This change is most correlated with the transfer of *Eubacterium hallii*, a gram-positive, butyrate-fermenting microbe (Vrieze, A., et al., 2012 Gastroenterol Transfer of intestinal microbiota from lean donors increases insulin sensitivity 143: 913-6).

A common factor underlying both diabetes and obesity is the phenomenon of low-level inflammation termed metabolic endotoxemia (see below). Metabolic endotoxemia refers to increased permeability of the gut ("leaky gut syndrome") coupled with increased translocation of lipopolysaccharide (LPS), mediating an inflammatory response that triggers insulin resistance, changes in lipid metabolism, and liver inflammation responsible for non-alcoholic fatty liver disease (NAFLD). Low level bacteremia may also lead to the translocation of viable gram-negative organisms into distal tissues, such as adipocytes, and further drive inflammation. SCFAs provide a benefit here as well, both by providing an energy source to enhance colonic epithelial cell integrity and by stimulating the expression of tight junction proteins to reduce translocation of gram-negative LPS, bacterial cells and their fragments (Wang H B et al, 2012 Dig Dis Sci Butyrate enhances intestinal epithelial barrier function via up-regulation of tight junction protein Claudin-1 transcription 57: 3126-35).

For all of these reasons, it would be useful to have microbial communities with an enhanced ability to produce SCFAs for the treatment of diseases such as diabetes, obesity, inflammation, ulcerative colitis and NAFLD.

Acetate, propionate and butyrate are formed as end-products in anaerobic fermentation. SCFA producing bacteria in the gut gain energy by substrate-level phosphorylation during oxidative breakdown of carbon precursors. However, the resulting reducing equivalents, captured in the form of NADH, must be removed to maintain redox balance, and hence the energetic driving force to produce large amounts of reduced end-products such as butyrate and propionate, in order to regenerates NAD+. Acetate, propionate and butyrate are not the only end products of fermentation: microbes in the gut also produce lactate, formate, hydrogen and carbon dioxide depending on the conditions. As discussed below, lactate and acetate can also drive the formation of butyrate and propionate through cross-feeding by one microorganism to another.

The rate of SCFA production in the colon is highly dependent on many factors including the availability of polysaccharide carbon sources (such as, but not limited to, fructans, starches, cellulose, galactomannans, xylans, arabinoxylans, pectins, inulin, fructooligosaccharides, and the like), the presence of alternative electron sinks such as sulfate and nitrate, the redox potential, hydrogen ($H_2$) partial pressure and pH. As described above, cross-feeding among organisms can also play a role, for instance when a lactate forming organism provides lactate as a substrate for a butyrate or propionate producer, or when a saccharolytic organism breaks down a complex carbohydrate to provide a mono- or disaccharide for fermentation. Acetate, which can be as high as 30 mM in the gut, is also a key building block of butyrate through the action of the enzyme butyryl-CoA: acetate CoA transferase, the final step in the production of butyrate. Importantly, this enzyme can also function as a propionyl-CoA: acetate CoA transferase, resulting in the production of propionate.

Since diet is a principal determinant of the variety of carbon sources and other nutrients available in the colon, it is clear that a functional ecology for SCFA production will comprise multiple organisms capable of adapting to diet-driven changes in in the gut environment. Thus, there exists a need for a bacterial composition that can ferment sufficient quantities of SCFA products in spite of the varying environmental conditions imposed by a changing diet. Such bacterial compositions will comprise organisms capable of fermenting a variety of carbon sources into SCFA.

Role of Microbiota in Metabolic Endotoxemia/Bacteremia

Chronic, low-grade inflammation is characteristic of obesity and is recognized to play an underlying pathogenic role in the metabolic complications and negative health outcomes of the disease. Notably, obesity is associated with elevated plasma levels of bacterial lipopolysaccharide (LPS). Energy intake, in particular a high fat diet (HFD), increases gut permeability and increases plasma LPS levels 2- to 3-fold. LPS in the circulatory system reflects passage of bacterial fragments across the gut into systemic circulation (termed "metabolic endotoxemia"), either through increases in diffusion due to intestinal paracellular permeability or through absorption by enterocytes during chylomicron secretion. Subcutaneous infusion of LPS into wild type mice maintained on a normal chow diet for 4 weeks leads to increased whole body, liver and adipose tissue weights, adipose and liver inflammation as well as fasted hyperglycemia and insulinemia, effects that are comparable to those induced by HFD (Cani et al., 2007 Diabetes. Metabolic endotoxemia initiates obesity and insulin resistance doi:10.2337/db06-1491). In addition to bacterial fragments, the translocation of live bacteria to host tissues may also be a feature of obesity (termed "metabolic bacteremia") (Shen et al., 2013 Mol Aspects Med. The gut microbiota, obesity and insulin resistance doi: 10.1016/j.mam.2012.11.001).

Host-microbiota interactions at the gut mucosal interface are involved in intestinal barrier functionality and bacterial surveillance/detection. Dysbiosis can promote bacterial translocation and obesity-associated inflammation. In one instance, metabolic endotoxemia of HFD-induced obesity in mice is associated with reductions in *Bifidobacterium*, and both may be ameliorated through treatment with inulin (oligofructose) (Cani et al. Diabetologia Selective increases of bifidobacteria in gut microflora improve high-fat-diet-induced diabetes in mice through a mechanism associated with endotoxaemia doi: 10.1007/s00125-007-0791-0). The beneficial effects of inulin and *Bifidobacterium* are associated with enhanced production of intestinotrophic proglucagon-derived peptide 2 (GLP-2), a peptide produced by L cells of the intestine that promotes intestinal growth (Cani et al. Gut. Changes in gut microbiota control inflammation in obese mice through a mechanism involving GLP-2-driven improvement of gut permeability. doi: 10.1136/gut.2008.165886). Alternative pathways involving host-microbiota interactions and intestinal barrier integrity and metabolic endotoxemia/bacteremia include but are not limited to those involving intestinotrophic proglucagon-derived peptide (GLP)-2, endocannabinoid (eCB) signaling, and pattern recognition receptors including nucleotide-binding oligomerization domain (NOD)-like receptors (NLR) such as NOD1/NLRC1 and NOD2/NLRC2 as well as Toll like receptors (TLR) such as TLR-2, TLR-4, TLR-5 and TLR adapter protein myeloid differentiation primary-response protein 88 (MyD88) (see review Shen et al., 2013 Mol Aspects Med. The gut microbiota, obesity and insulin resistance doi: 10.1016/j.mam.2012.11.001).

Role of Microbiota in Energy Harvesting and Storage

The gut microbiota is involved in host energy harvesting. Germ free (GF) mice consume more energy but are significantly leaner than wild type counterparts. Conventionalization of GF mice given a low-fat, polysaccharide-rich diet with the microbiota of conventionally-raised mice leads to 60% more adiposity and insulin resistance despite reduced food intake (Backhed et al., 2004 PNAS The gut microbiota as an environmental factor that regulates fat storage doi: 10.1073/pnas.0407076101). GF mice conventionalized with microbiota from obese mice show significantly greater increase in total body fat than GF mice conventionalized with microbiota from lean mice. Obese (ob/ob) mice have significantly less energy remaining in their feces relative to their lean littermates as measured by bomb calorimetry (Turnbaugh et al. 2006 Nature. An obesity-associated gut microbiome with increased capacity for energy harvest doi: 10.1038/nature05414). In humans, "overnutrition" (defined as energy consumption as a percentage of weight-maintaining energy needs) is associated with proportionally more Firmicutes and fewer Bacteroidetes and energy loss (stool calories as a percentage of ingested calories) in lean subjects is negatively associated with the proportional change in Firmicutes and positively associated with the proportional change in Bacteroidetes, suggesting impact of the gut microbiota on host energy harvest (Jumpertz et al., 2011 Am J Clin Nutr. Energy-balance studies reveal associations between gut microbes, caloric load, and nutrient absorption in humans. doi: 10.3945/ajcn.110.010132).

In addition to affecting host energy harvesting, gut microbiota is also implicated in energy storage. The increase in body fat observed upon conventionalization of GF mice is associated with a decrease in Fasting-induced adipose factor (Fiaf) expression in the ileum and a 122% increase in Lipoprotein Lipase (LPL) activity in epididymal adipose tissue (Backhed et al., 2004 PNAS The gut microbiota as an environmental factor that regulates fat storage doi/10.1073/pnas.0407076101). Fiaf (also known as angiopoietin-like 4) is a protein secreted by adipose tissues, liver and intestine that inhibits the activity of LPL, a key enzyme in the hydrolysis of lipoprotein-associated triglycerides and the release of fatty acids for transport into cells. In adipocytes, fatty acids released by LPL are re-esterified into triglyceride and stored as fat (Shen et al., 2013 Mol Aspects Med. The gut microbiota, obesity and insulin resistance doi: 10.1016/j.mam.2012.11.001).

Other Functional Pathways

The pathways and mechanisms discussed above on the functional pathways and mechanisms by which the microbiota shape host health and disease is not meant to be exhaustive. Alternative functional pathways and mechanisms exist, including but not limited to pathways involving AMP-activated protein kinase (AMPK), TLR-5, and SREBP-1c and ChREBP.

Emergence of Antibiotic Resistance in Bacteria

Antibiotic resistance is an emerging public health issue (Carlet J, Collignon P, Goldmann D, Goossens H, Gyssens I C, Harbarth S, Jarlier V, Levy S B, N'Doye B, Pittet D, et al. 2011. Society's failure to protect a precious resource: antibiotics. Lancet 378: 369-371.). Numerous genera of bacteria harbor species that are developing resistance to antibiotics. These include but are not limited to Vancomycin Resistant *Enterococcus* (VRE) and Carbapenem resistant *Klebsiella* (CRKp). *Klebsiella pneumoniae* and *Escherichia coli* strains are becoming resistant to carbapenems and require the use of old antibiotics characterized by high toxicity, such as colistin (Canton R, Akóva M, Carmeli Y, Giske C G, Glupczynski Y, Gniadkowski M, Livermore D M, Miriagou V, Naas T, Rossolini G M, et al. 2012. Rapid evolution and spread of carbapenemases among Enterobacteriaceae in Europe. Clin Microbiol Infect 18: 413-431.). Further multiply drug resistant strains of multiple species, including *Pseudomonas aeruginosa, Enterobacter* spp, and *Acinetobacter* spp are observed clinically including isolates that are highly resistant to ceftazidime, carbapenems, and quinolones (European Centre for Disease Prevention and Control: EARSS net database. ecdc.europa.eu). The Centers for Disease Control and Prevention in 2013 released a Threat Report (cdc.gov/drugresistance/threat_report 2013) citing numerous bacterial infection threats that included *Clostridium difficile*, Carbapenem-resistant Enterobacteriaceae (CRE), Multidrug-resistant *Acinetobacter*, Drug-resistant *Campylobacter*, Extended spectrum β-lactamase producing Enterobacteriaceae (ESBLs), Vancomycin-resistant *Enterococcus* (VRE), Multidrug-resistant *Pseudomonas aeruginosa*, Drug-resistant Non-typhoidal *Salmonella*, Drug-resistant *Salmonella Typhi*, Drug-resistant *Shigella*, Methicillin-resistant *Staphylococcus aureus* (MRSA), Drug-resistant *Streptococcus pneumoniae*, Vancomycin-resistant *Staphylococcus aureus* (VRSA), Erythromycin-resistant Group A *Streptococcus*, and Clindamycin-resistant Group B *Streptococcus*. The increasing failure of antibiotics due the rise of resistant microbes demands new therapeutics to treat bacterial infections. Administration of a microbiome therapeutic bacterial composition offers potential for such therapies. Applicants have discovered that patients suffering from recurrent *C. difficile* associated diarrhea (CDAD) often harbor antibiotic resistant Gram-negative bacteria, in particular Enterobacteriaceae and that treatment with a bacterial composition effectively treats CDAD and reduces the antibiotic resistant Gram-negative bacteria. The gastrointestinal tract is implicated as a reservoir for many of these organisms including VRE, MRSA, *Pseudomonas aeruginosa, Acinetobacter* and the yeast *Candida* (Donskey, Clinical Infectious Diseases 2004 39:214,The Role of the Intestinal Tract as a Reservoir and Source for Transmission of Nosocomial Pathogens), and thus as a source of nosocomial infections. Antibiotic treatment and other decontamination procedures are among the tools in use to reduce colonization of these organisms in susceptible patients including those who are immunosuppressed. Bacterial-based therapeutics would provide a new tool for decolonization, with a key benefit of not promoting antibiotic resistance as antibiotic therapies do.

Compositions of the Invention

Network Ecologies

As described above, the Network Ecology and Functional Network Ecology refer to a consortium of OTUs or Functional modalities respectively that co-occur in a group of subjects. The network is defined mathematically by a graph delineating how specific nodes (i.e., OTUs or functional modalities) and edges (connections between specific OTUs or functional modalities) relate to one another to define the structural ecology of a consortium of OTUs or functions. Any given Network Ecology or Functional Network Ecology will possess inherent phylogenetic diversity and functional properties.

A Network Class or Core Network refers to a group of Network Ecologies or Functional Network ecologies that are computationally determined to comprise ecologies with similar phylogenetic and/or functional characteristics. A Network Class or Core Network therefore contains important biological features, defined either phylogenetically or functionally, of a group (i.e., a cluster) of related network ecologies.

Keystone OTUs or Functions are one or more OTUs or Functions that are common to many network Ecologies or Functional Netwok Ecologies and are members of Networks Ecologies or Functional Network Ecologies that occur in many subjects (i.e., are pervasive). Due to the ubiquitous nature of Keystone OTUs and Functions, they are central to the function of network ecologies in healthy subjects and are often missing or at reduced levels in subjects with disease. Keystone OTUs and Functions may exist in low, moderate, or high abundance in subjects.

Bacteria that are members of the keystone OTUs, core network or network ecology are provided herein.

Bacterial Compositions

Provided are bacteria and combinations of bacteria that comprise network ecologies and functional network ecologies of the human gut microbiota. The bacteria and combinations of bacteria that comprise network ecologies have a capacity to meaningfully provide functions of a healthy microbiota when administered to mammalian hosts. Without being limited to a specific mechanism, it is believed that the members of network ecologies can inhibit the growth, proliferation, germination and/or colonization of one or a plurality of pathogenic bacteria in the dysbiotic microbiotal niche, and may also augment the growth, proliferation, germination and/or colonization of desired bacteria so that a healthy, diverse and protective microbiota colonizes and populates the intestinal lumen to establish or reestablish ecological control over pathogens or potential pathogens (e.g., some bacteria are pathogenic bacteria only when present in a dysbiotic environment). The term pathogens refers to a bacterium or a group of bacteria or any other organism or entity that is capable of causing or affecting a disease, disorder or condition of a host containing the bacterium, organism or entity, including but not limited to metabolic diseases such as prediabetes, type 1 diabetes, and type 2 diabetes.

As used herein, a "type" or more than one "types" of bacteria may be differentiated at the genus level, the species, level, the sub-species level, the strain level or by any other taxonomic method, as described herein and otherwise known in the art.

Bacterial compositions can comprise two types of bacteria (termed "binary combinations" or "binary pairs"), and typically a large number of bacteria types. For instance, a bacterial composition can comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, or at least 21, 22, 23, 24, 25, 26, 27, 28, 29 30, 31, 32, 33, 34, 35, 36, 37, 38, 39, or at least 40, at least 50 or greater than 50 types of bacteria, as defined by species or operational taxonomic unit (OTU), or otherwise as provided herein. In some embodiments, the bacterial composition includes at least 60, 70, 80, 90, 100, 150, 200, 250, 300, 350, 400, 450, 500, 550, 600, or greater numbers of bacteria types.

In another embodiment, the number of types of bacteria present in a bacterial composition is at or below a known value. For example, in such embodiments the network ecology comprises 1000, 900, 800, 700, 600, 500, 400, 300, 200, 100, 50 or fewer types of bacteria, such as 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 or fewer, or 9 or fewer types of bacteria, 8 or fewer types of bacteria, 7 or fewer types of bacteria, 6 or fewer types of bacteria, 5 or fewer types of bacteria, 4 or fewer types of bacteria, or 3 or fewer types of bacteria.

Bacterial Compositions Described by Species

Bacterial compositions that comprise network ecologies may be prepared comprising at least two types of isolated bacteria, chosen from the species in Table 1.

In one embodiment, the bacterial composition that comprises at least one and preferably more than one of the following: *Enterococcus faecalis* (previously known as *Streptococcus faecalis*), *Clostridium innocuum*, *Clostridium ramosum*, *Bacteroides ovatus*, *Bacteroides vulgatus*, *Bacteroides thetaoiotaomicron*, *Escherichia coli* (1109 and 1108-1), *Clostridum bifermentans*, and *Blautia producta* (previously known as *Peptostreptococcus productus*). In an alternative embodiment, at least one of the preceding species is not substantially present in the bacterial composition.

In one embodiment, the bacterial composition comprises at least one and preferably more than one of the following: *Enterococcus faecalis* (previously known as *Streptococcus faecalis*), *Clostridium innocuum*, *Clostridium ramosum*, *Bacteroides ovatus*, *Bacteroides vulgatus*, *Bacteroides thetaoiotaomicron*, *Escherichia coli* (1109 and 1108-1), *Clostridium bifermentans*, and *Blautia producta* (previously known as *Peptostreptococcus productus*). In an alternative embodiment, at least one of the preceding species is not substantially present in the bacterial composition.

In another embodiment, the bacterial composition comprises at least one and preferably more than one of the following: *Acidaminococcus intestinalis*, *Bacteroides ovatus*, two strains of *Bifidobacterium adolescentis*, two strains of *Bifidobacterium longum*, *Blautia producta*, *Clostridium cocleatum*, *Collinsella aerofaciens*, two strains of *Dorea longicatena*, *Escherichia coli*, *Eubacterium desmolans*, *Eubacterium eligens*, *Eubacterium limosum*, four strains of *Eubacterium rectale*, *Eubacterium ventriosumi*, *Faecalibacterium prausnitzii*, *Lachnospira pectinoshiza*, *Lactobacillus casei*, *Lactobacillus casei/paracasei*, *Paracateroides distasonis*, *Raoultella* sp., one strain of *Roseburia* (chosen from *Roseburia faecalis* or *Roseburia faecis*), *Roseburia intestinalis*, two strains of *Ruminococcus torques*, two strains of *Ruminococcus obeum*, and *Streptococcus mitis*. In an alternative embodiment, at least one of the preceding species is not substantially present in the bacterial composition.

In yet another embodiment, the bacterial composition comprises at least one and preferably more than one of the following: *Barnesiella intestinihominis*; *Lactobacillus reuteri*; a species characterized as one of *Enterococcus hirae*, *Enterococus faecium*, or *Enterococcus durans*; a species characterized as one of *Anaerostipes caccae* or *Clostridium indolis*; a species characterized as one of *Staphylococcus warneri* or *Staphylococcus pasteuri*; and *Adlercreutzia equolifaciens*. In an alternative embodiment, at least one of the preceding species is not substantially present in the bacterial composition.

In other embodiments, the bacterial composition comprises at least one and preferably more than one of the following: *Clostridium absonum*, *Clostridium argentinense*, *Clostridium baratii*, *Clostridium bartlettii*, *Clostridium bifermentans*, *Clostridium botulinum*, *Clostridium butyricum*, *Clostridium cadaveris*, *Clostridium camis*, *Clostridium celatum*, *Clostridium chauvoei*, *Clostridium clostridioforme*, *Clostridium cochlearium*, *Clostridium difficile*, *Clostridium fallax*, *Clostridium felsineum*, *Clostridium ghonii*, *Clostridium glycolicum*, *Clostridium haemolyticum*, *Clostridium hastiforme*, *Clostridium histolyticum*, *Clostridium indolis*, *Clostridium innocuum*, *Clostridium irregulare*, *Clostridium limosum*, *Clostridium malenominatum*, *Clostridium novyi*, *Clostridium oroticum*, *Clostridium paraputrificum*, *Clostridium perfringens*, *Clostridium piliforme*, *Clostridium putrefaciens*, *Clostridium putrificum*, *Clostridium ramosum*, *Clostridium sardiniense*, *Clostridium sartagoforme*, *Clostridium scindens*, *Clostridium septicum*, *Clostridium sordellii*, *Clostridium sphenoides*, *Clostridium spiroforme*, *Clostridium sporogenes*, *Clostridium subterminale*, *Clostridium symbiosum*, *Clostridium tertium*, *Clostridium tetani*, *Clostridium welchii*, and *Clostridium villosum*. In an alternative embodiment, at least one of the preceding species is not substantially present in the bacterial composition.

In one embodiment, the bacterial composition that comprises a network ecology comprises at least one and preferably more than one of the following: *Clostridium innocuum*, *Clostridum bifermentans*, *Clostridium butyricum*, *Bacteroides fragilis*, *Bacteroides thetaiotaomicron*, *Bacteroides uniformis*, three strains of *Escherichia coli*, and *Lactobacillus* sp. In an alternative embodiment, at least one of the preceding species is not substantially present in the bacterial composition.

In one embodiment, the bacterial composition that comprises a network ecology comprises at least one and preferably more than one of the following: *Clostridium bifermentans*, *Clostridium innocuum*, *Clostridium butyricum*, three strains of *Escherichia coli*, three strains of *Bacteroides*, and *Blautia producta*. In an alternative embodiment, at least one of the preceding species is not substantially present in the bacterial composition.

In one embodiment, the bacterial composition that comprises a network ecology comprises at least one and preferably more than one of the following: *Bacteroides* sp., *Escherichia coli*, and non pathogenic *Clostridia*, including *Clostridium innocuum*, *Clostridium bifermentans* and *Clostridium ramosum*. In an alternative embodiment, at least one of the preceding species is not substantially present in the bacterial composition.

In one embodiment, the bacterial composition that comprises a network ecology comprises at least one and preferably more than one of the following: *Bacteroides* species, *Escherichia coli* and non-pathogenic *Clostridia*, such as *Clostridium butyricum*, *Clostridium bifermentans* and *Clostridium innocuum*. In an alternative embodiment, at least one of the preceding species is not substantially present in the bacterial composition.

In one embodiment, the bacterial composition that comprises a network ecology comprises at least one and preferably more than one of the following: *Bacteroides caccae*, *Bacteroides capillosus*, *Bacteroides coagulans*, *Bacteroides distasonis*, *Bacteroides eggerthii*, *Bacteroides forsythus*, *Bacteroides fragilis*, *Bacteroides fragilis-ryhm*, *Bacteroides gracilis*, *Bacteroides levii*, *Bacteroides macacae*, *Bacteroides merdae*, *Bacteroides ovatus*, *Bacteroides pneumosintes*, *Bacteroides putredinis*, *Bacteroides pyogenes*, *Bacteroides splanchnicus*, *Bacteroides stercoris*, *Bacteroides tectum*, *Bacteroides thetaiotaomicron*, *Bacteroides uniformis*, *Bacteroides ureolyticus*, and *Bacteroides vulgatus*. In an alternative embodiment, at least one of the preceding species is not substantially present in the bacterial composition.

In one embodiment, the bacterial composition that comprises a network ecology comprises at least one and preferably more than one of the following: *Bacteroides*, *Eubacteria*, *Fusobacteria*, *Propionibacteria*, *Lactobacilli*, anaerobic cocci, *Ruminococcus*, *Escherichia coli*, *Gemmiger*, *Desulfomonas*, and *Peptostreptococcus*. In an alternative embodiment, at least one of the preceding species is not substantially present in the bacterial composition.

In one embodiment, the bacterial composition that comprises a network ecology comprises at least one and preferably more than one of the following: *Bacteroides fragilis* ss. *Vulgatus, Eubacterium aerofaciens, Bacteroides fragilis* ss. *Thetaiotaomicron, Blautia producta* (previously known as *Peptostreptococcus productus* II), *Bacteroides fragilis* ss. *Distasonis, Fusobacterium prausnitzii, Coprococcus eutactus, Eubacterium aerofaciens* III, *Blautia producta* (previously known as *Peptostreptococcus productus* I), *Ruminococcus bronii, Bifidobacterium adolescentis, Gemmiger formicilis, Bifidobacterium longum, Eubacterium siraeum, Ruminococcus torques, Eubacterium rectale Eubacterium rectale* IV, *Eubacterium eligens, Bacteroides eggerthii, Clostridium leptum, Bacteroides fragilis* ss. *A, Eubacterium biforme, Bifidobacterium infantis, Eubacterium rectale* III-F, *Coprococcus comes, Bacteroides capillosus, Ruminococcus albus, Eubacterium formicigenerans, Eubacterium hallii, Eubacterium ventriosum* I, *Fusobacterium russii, Ruminococcus obeum, Eubacterium rectale* II, *Clostridium ramosum* I, *Lactobacillus leichmanii, Ruminococcus cailidus, Butyrivibrio crossotus, Acidaminococcus fermentans, Eubacterium ventriosum, Bacteroides fragilis* ss. *fragilis, Bacteroides AR, Coprococcus catus, Eubacterium hadrum, Eubacterium cylindroides, Eubacterium ruminantium, Eubacterium CH-1, Staphylococcus epidermidis, Peptostreptococcus BL, Eubacterium limosum, Bacteroides praeacutus, Bacteroides L, Fusobacterium mortiferum Fusobacterium naviforme, Clostridium innocuum, Clostridium ramosum, Propionibacterium acnes, Ruminococcus flavefaciens, Ruminococcus AT, Peptococcus AU-1, Eubacterium AG, -AK, -AL, -AL-1, -AN; Bacteroides fragilis* ss. *ovatus, -ss. d, -ss. f; Bacteroides L-1, L-5; Fusobacterium nucleatum, Fusobacterium mortiferum, Escherichia coli, Streptococcus morbiliorum, Peptococcus magnus, Peptococcus G, AU-2; Streptococcus intermedius, Ruminococcus lactaris, Ruminococcus CO Gemmiger X, Coprococcus BH, —CC; Eubacterium tenue, Eubacterium ramulus, Eubacterium AE, -AG-H, -AG-M, AJ, -BN-1; Bacteroides clostridiiformis* ss. *clostridliformis, Bacteroides coagulans, Bacteroides orails, Bacteroides ruminicola* ss. *brevis, -ss. ruminicola, Bacteroides splanchnicus, Desuifomonas pigra, Bacteroides L-4, -N-i; Fusobacterium H, Lactobacillus G,* and *Succinivibrio A*. In an alternative embodiment, at least one of the preceding species is not substantially present in the bacterial composition.

Bacterial Compositions Described by Operational Taxonomic Unit (OTUs)

Bacterial compositions may be prepared comprising at least two types of isolated bacteria, chosen from the SEQ ID Numbers (OTUs) in Table 1.

OTUs can be defined either by full 16S sequencing of the rRNA gene (Table 1), by sequencing of a specific hypervariable region of this gene (i.e. V1, V2, V3, V4, V5, V6, V7, V8, or V9), or by sequencing of any combination of hypervariable regions from this gene (e.g. V1-3 or V3-5). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes.

Using well known techniques, in order to determine the full 16S sequence or the sequence of any hypervariable region of the 16S sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing can be, but is not limited to being, performed using the Sanger method or using a next-generation sequencing method, such as an Illumina (sequencing by synthesis) method using barcoded primers allowing for multiplex reactions.

OTUs can be defined by a combination of nucleotide markers or genes, in particular highly conserved genes (e.g., "house-keeping" genes), or a combination thereof, full-genome sequence, or partial genome sequence generated using amplified genetic products, or whole genome sequence (WGS). Using well defined methods familiar to one with ordinary skill in the art, DNA extracted from a bacterial sample will have specific genomic regions amplified using PCR and sequenced to determine the nucleotide sequence of the amplified products. In the whole genome shotgun (WGS) method, extracted DNA will be directly sequenced without amplification. Sequence data can be generated using any sequencing technology including, but not limited to Sanger, Illumina, 454 Life Sciences, Ion Torrent, ABI, Pacific Biosciences, and/or Oxford Nanopore.

In one embodiment, the OTUs can be characterized by one or more of the variable regions of the 16S sequence (V1-V9). These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. (See, e.g., Brosius et al., Complete nucleotide sequence of a 16S ribosomal RNA gene from *Escherichia coli*, PNAS 75(10):4801-4805 (1978)). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU.

Bacterial Compositions Exclusive of Certain Bacterial Species Or Strains

In one embodiment, the bacterial composition does not comprise at least one of *Enterococcus faecalis* (previously known as *Streptococcus faecalis*), *Clostridium innocuum, Clostridium ramosum, Bacteroides ovatus, Bacteroides vulgatus, Bacteroides thetaoiotaomicron, Escherichia coli* (1109 and 1108-1), *Clostridum bifermentans,* and *Blautia producta* (previously known as *Peptostreptococcus productus*).

In another embodiment, the bacterial composition does not comprise at least one of *Acidaminococcus intestinalis, Bacteroides ovatus,* two species of *Bifidobacterium adolescentis,* two species of *Bifidobacterium longum, Collinsella aerofaciens,* two species of *Dorea longicatena, Escherichia coli, Eubacterium eligens, Eubacterium limosum,* four species of *Eubacterium rectale, Eubacterium ventriosumi, Faecalibacterium prausnitzii, Lactobacillus casei, Lactobacillus paracasei, Paracateroides distasonis, Raoultella* sp., one species of *Roseburia* (chosen from *Roseburia faecalis* or *Roseburia faecis*), *Roseburia intestinalis,* two species of *Ruminococcus torques,* and *Streptococcus mitis.*

In yet another embodiment, the bacterial composition does not comprise at least one of *Barnesiella intestinihomi-* nis; *Lactobacillus reuteri*; a species characterized as one of *Enterococcus hirae, Enterococus faecium,* or *Enterococcus durans*; a species characterized as one of *Anaerostipes caccae* or *Clostridium indolis*; a species characterized as one of *Staphylococcus warneri* or *Staphylococcus pasteuri*; and *Adlercreutzia equolifaciens*.

In other embodiments, the bacterial composition does not comprise at least one of *Clostridium absonum, Clostridium argentinense, Clostridium baratii, Clostridium bifermentans, Clostridium botulinum, Clostridium butyricum, Clostridium cadaveris, Clostridium camis, Clostridium celatum, Clostridium chauvoei, Clostridium clostridioforme, Clostridium cochlearium, Clostridium difficile, Clostridium fallax, Clostridium felsineum, Clostridium ghonii, Clostridium glycolicum, Clostridium haemolyticum, Clostridium hastiforme, Clostridium histolyticum, Clostridium indolis, Clostridium innocuum, Clostridium irregulare, Clostridium limosum, Clostridium malenominatum, Clostridium novyi, Clostridium oroticum, Clostridium paraputrificum, Clostridium perfringens, Clostridium piliforme, Clostridium putrefaciens, Clostridium putrificum, Clostridium ramosum, Clostridium sardiniense, Clostridium sartagoforme, Clostridium scindens, Clostridium septicum, Clostridium sordellii, Clostridium sphenoides, Clostridium spiroforme, Clostridium sporogenes, Clostridium subterminale, Clostridium symbiosum, Clostridium tertium, Clostridium tetani, Clostridium welchii,* and *Clostridium villosum*.

In another embodiment, the bacterial composition does not comprise at least one of *Clostridium innocuum, Clostridum bifermentans, Clostridium butyricum, Bacteroides Bacteroides thetaiotaomicron, Bacteroides uniformis,* three strains of *Escherichia coli,* and *Lactobacillus* sp.

In another embodiment, the bacterial composition does not comprise at least one of *Clostridium bifermentans, Clostridium innocuum, Clostridium butyricum,* three strains of *Escherichia coli,* three strains of *Bacteroides,* and *Blautia producta* (previously known as *Peptostreptococcus productus*).

In another embodiment, the bacterial composition does not comprise at least one of *Bacteroides* sp., *Escherichia coli,* and non pathogenic *Clostridia,* including *Clostridium innocuum, Clostridium bifermentans* and *Clostridium ramosum*.

In another embodiment, the bacterial composition does not comprise at least one of more than one *Bacteroides* species, *Escherichia coli* and non-pathogenic *Clostridia,* such as *Clostridium butyricum, Clostridium bifermentans* and *Clostridium innocuum*.

In another embodiment, the bacterial composition does not comprise at least one of *Bacteroides caccae, Bacteroides capillosus, Bacteroides coagulans, Bacteroides distasonis, Bacteroides eggerthii, Bacteroides forsythus, Bacteroides fragilis, Bacteroides fragilis-ryhm, Bacteroides gracilis, Bacteroides levii, Bacteroides macacae, Bacteroides merdae, Bacteroides ovatus, Bacteroides pneumosintes, Bacteroides putredinis, Bacteroides pyogenes, Bacteroides splanchnicus, Bacteroides stercoris, Bacteroides tectum, Bacteroides thetaiotaomicron, Bacteroides uniformis, Bacteroides ureolyticus,* and *Bacteroides vulgatus*.

In another embodiment, the bacterial composition does not comprise at least one of *Bacteroides, Eubacteria, Fusobacteria, Propionibacteria, Lactobacilli,* anaerobic cocci, *Ruminococcus, Escherichia coli, Gemmiger, Desulfomonas,* and *Peptostreptococcus*.

In another embodiment, the bacterial composition does not comprise at least one of *Bacteroides fragilis* ss. *Vulgatus, Eubacterium aerofaciens, Bacteroides fragilis* ss. *Thetaiotaomicron, Blautia producta* (previously known as *Peptostreptococcus* productus II), *Bacteroides fragilis* ss. *Distasonis, Fusobacterium prausnitzii, Coprococcus eutactus, Eubacterium aerofaciens* III, *Blautia producta* (previously known as *Peptostreptococcus productus* I), *Ruminococcus bromii, Bifidobacterium adolescentis, Gemmiger formicilis, Bifidobacterium longum, Eubacterium siraeum, Ruminococcus torques, Eubacterium rectale* III-H, *Eubacterium rectale* IV *Eubacterium eligens, Bacteroides eggerthii, Clostridium leptum, Bacteroides fragilis* ss. A, *Eubacterium biforme, Bifidobacterium infantis, Eubacterium rectale* III-F; *Coprococcus comes, Bacteroides capillosus, Ruminococcus albus, Eubacterium formicigenerans, Eubacterium hallii, Eubacterium ventriosum* I, *Fusobacterium russii, Ruminococcus obeum, Eubacterium rectale* II, *Clostridium ramosum* I, *Lactobacillus leichmanii, Ruminococcus cailidus, Butyrivibrio crossotus, Acidaminococcus fermentans, Eubacterium ventriosum, Bacteroides fragilis* ss. *fragilis, Bacteroides* AR, *Coprococcus catus, Eubacterium hadrum, Eubacterium cylindroides, Eubacterium ruminantium, Eubacterium* CH-1, *Staphylococcus epidermidis, Peptostreptococcus* BL, *Eubacterium limosum, Bacteroides praeacutus, Bacteroides* L, *Fusobacterium mortiferum* I, *Fusobacterium naviforme, Clostridium innocuum, Clostridium ramosum, Propionibacterium acnes, Ruminococcus flavefaciens, Ruminococcus* AT, *Peptococcus* AU-1, *Eubacterium* AG, -AK, -AL, -AL-1, AN; *Bacteroides fragilis* ss. *ovatus,* -ss. d, -ss. f; *Bacteroides* L-1, L-5; *Fusobacterium nucleatum, Fusobacterium mortiferum, Escherichia coli, Streptococcus morbiliorum, Peptococcus magnus, Peptococcus* G, AU-2; *Streptococcus intermedius, Ruminococcus lactaris, Ruminococcus* CO *Gemmiger* X, *Coprococcus* BH, —CC; *Eubacterium tenue, Eubacterium ramulus, Eubacterium* AE, -AG-H, -AG-M, AJ, -BN-1; *Bacteroides clostridiiformis* ss. *clostridliformis, Bacteroides coagulans, Bacteroides orails, Bacteroides ruminicola* ss. *brevis,* -ss. *ruminicola, Bacteroides splanchnicus, Desuifomonas pigra, Bacteroides* L-4, -N-i; *Fusobacterium* H, *Lactobacillus* G, and *Succinivibrio* A.

Inhibition of Bacterial Pathogens

In some embodiments, the bacterial composition provides a protective or therapeutic effect against infection by one or more GI pathogens of interest. Table 1 provides a list of OTUs that are either pathogens, pathobionts, or opportunistic pathogens.

In some embodiments, the pathogenic bacterium is selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium, Bacillus,* multi-drug resistant bacteria, extended spectrum beta-lactam resistant Enterococci (ESBL), Carbapenem-resistent Enterobacteriaceae (CRE), and vancomycin-resistant Enterococci (VRE).

In some embodiments, these pathogens include, but are not limited to, *Aeromonas hydrophila, Campylobacter fetus, Plesiomonas shigelloides, Bacillus cereus, Campylobacter jejuni, Clostridium botulinum, Clostridium difficile, Clostridium perfringens,* enteroaggregative *Escherichia coli,* enterohemorrhagic *Escherichia coli,* enteroinvasive *Escherichia coli,* enterotoxigenic *Escherichia coli* (such as, but not limited to, LT and/or ST), *Escherichia coli* 0157:H7,

*Helicobacter pylori, Klebsiellia pneumonia, Lysteria monocytogenes, Plesiomonas shigelloides, Salmonella* spp., *Salmonella typhi, Salmonella paratyphi, Shigella* spp., *Staphylococcus aureus, Staphylococcus aureus,* vancomycin-resistant *enterococcus* spp., *Vibrio* spp., *Vibrio cholerae, Vibrio parahaemolyticus, Vibrio vulnificus,* and *Yersinia enterocolitica.*

In one embodiment, the pathogen of interest is at least one pathogen chosen from *Clostridium difficile, Salmonella* spp., pathogenic *Escherichia coli,* vancomycin-resistant *Enterococcus* spp., and extended spectrum beta-lactam resistant Enterococci (ESBL).

Purified Spore Populations

In some embodiments, the bacterial compositions comprise purified spore populations or a combination of a purified spore population with a non-spore population. Purified spore populations contain combinations of commensal bacteria of the human gut microbiota with the capacity to meaningfully provide functions of a healthy microbiota when administered to a mammalian subject. Without being limited to a specific mechanism, it is thought that such compositions inhibit the growth of a pathogen such as *C. difficile, Salmonella* spp., enteropathogenic *E. coli,* and vancomycin-resistant *Enterococcus* spp., so that a healthy, diverse and protective microbiota can be maintained or, in the case of pathogenic bacterial infections such as *C. difficile* infection, repopulate the intestinal lumen to reestablish ecological control over potential pathogens. In some embodiments, yeast spores and other fungal spores are also purified and selected for therapeutic use.

Disclosed herein are therapeutic and prophylactic compositions containing non-pathogenic, germination-competent bacterial spores, spore forming organisms and non-spore forming organisms, for the prevention, control, and treatment of gastrointestinal diseases, disorders and conditions and for general nutritional health. These compositions are advantageous in being suitable for safe administration to humans and other mammalian subjects and are efficacious in numerous gastrointestinal diseases, disorders and conditions and in general nutritional health. While spore-based compositions are known, these are generally prepared according to various techniques such as lyophilization or spray-drying of liquid bacterial cultures, resulting in poor efficacy, instability, substantial variability and lack of adequate safety.

It has now been found that populations of bacterial spores can be obtained from biological materials obtained from mammalian subjects, including humans. These populations are formulated into compositions as provided herein, and administered to mammalian subjects using the methods as provided herein.

Provided herein are therapeutic bacterial compositions containing a purified population of bacterial spores, spore forming organisms and non-spore forming organisms.

As used herein, the terms "purify", "purified" and "purifying" refer to the state of a population (e.g., a plurality of known or unknown amount and/or concentration) of desired bacterial spores or bacteria, that have undergone one or more processes of purification, e.g., a selection or an enrichment of the desired bacterial spore, or alternatively a removal or reduction of residual habitat products as described herein. In some embodiments, a purified population has no detectable undesired activity or, alternatively, the level or amount of the undesired activity is at or below an acceptable level or amount. In other embodiments, a purified population has an amount and/or concentration of desired bacterial spores or bacteria at or above an acceptable amount and/or concentration. In other embodiments, the purified population of bacterial spores or bacteria is enriched as compared to the starting material (e.g., a fecal material liquid culture) from which the population is obtained. This enrichment may be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material.

In certain embodiments, the purified populations of bacterial spores have reduced or undetectable levels of one or more pathogenic activities, such as toxicity, an infection of the mammalian recipient subject, an immunomodulatory activity, an autoimmune response, a metabolic response, or an inflammatory response or a neurological response. Such a reduction in a pathogenic activity may be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In other embodiments, the purified populations of bacterial spores have reduced sensory components as compared to fecal material, such as reduced odor, taste, appearance, and umami.

Provided are purified populations of bacterial spores or bacteria that are substantially free of residual habitat products. In certain embodiments, this means that the bacterial spore or bacterial composition no longer contains a substantial amount of the biological matter associated with the microbial community while living on or in the human or animal subject, and the purified population of spores may be 100% free, 99% free, 98% free, 97% free, 96% free, or 95% free of any contamination of the biological matter associated with the microbial community. Substantially free of residual habitat products may also mean that the bacterial spore composition contains no detectable cells from a human or animal, and that only microbial cells are detectable, in particular, only desired microbial cells are detectable. In another embodiment, it means that fewer than $1\times10^{1}\%$, $1\times10^{-3}\%$, $1\times10^{-4}\%$, $1\times10^{-5}\%$, $1\times10^{-6}\%$, $1\times10^{-7}\%$, $1\times10^{-8}\%$ of the cells in the bacterial composition are human or animal, as compared to microbial cells. In another embodiment, the residual habitat product present in the purified population is reduced at least a certain level from the fecal material obtained from the mammalian donor subject, e.g., reduced by at least about 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999%.

In one embodiment, substantially free of residual habitat products or substantially free of a detectable level of a pathogenic material means that the bacterial composition contains no detectable viral (including bacterial viruses (i.e., phage)), fungal, or mycoplasmal or toxoplasmal contaminants, or a eukaryotic parasite such as a helminth. Alternatively, the purified spore populations are substantially free of an acellular material, e.g., DNA, viral coat material, or non-viable bacterial material.

As described herein, purified spore populations can be demonstrated by genetic analysis (e.g., PCR, DNA sequencing), serology and antigen analysis, and methods using instrumentation such as flow cytometry with reagents that distinguish desired bacterial spores from non-desired, contaminating materials.

Exemplary biological materials include fecal materials such as feces or materials isolated from the various segments of the small and large intestines. Fecal materials are obtained from a mammalian donor subject, or can be obtained from more than one donor subject, e.g., 2, 3, 4, 5, 6, 7, 8, 9, 10, 15, 20, 25, 30, 35, 40, 45, 50, 75, 100, 200, 300, 400, 500, 750, 1000 or from greater than 1000 donors, where such materials are then pooled prior to purification of the desired bacterial spores.

In alternative embodiments, the desired bacterial spores or bacteria are purified from a single fecal material sample obtained from a single donor, and after such purification are combined with purified spore populations or bacteria from other purifications, either from the same donor at a different time, or from one or more different donors, or both.

Preferred bacterial genera include *Acetonema, Alkaliphilus, Alicyclobacillus, Amphibacillus, Ammonifex, Anaerobacter, Anaerofustis, Anaerostipes, Anaerotruncus, Anoxybacillus, Bacillus, Blautia, Brevibacillus, Bryantella, Caldicellulosiruptor, Caloramator, Candidatus, Carboxydibrachium, Carboxydothermus, Clostridium, Cohnella, Coprococcus, Dendrosporobacter Desulfitobacterium, Desulfosporosinus, Desulfotomaculum, Dorea, Eubacterium, Faecalibacterium, Filifactor, Geobacillus, Halobacteroides, Heliobacillus, Heliobacterium, Heliophilum, Heliorestis, Lachnoanaerobaculum, Lysinibacillus, Moorella, Oceanobacillus, Orenia* (S.), *Oxalophagus, Oxobacter, Paenibacillus, Pelospora, Pelotomaculum, Propionispora, Roseburia, Ruminococcus, Sarcina, Sporobacterium, Sporohalobacter, Sporolactobacillus, Sporomusa, Sporosarcina, Sporotomaculum, Subdoligranulum, Symbiobacterium, Syntrophobotulus, Syntrophospora, Terribacillus, Thermoanaerobacter*, and *Thermosinus*.

In some embodiments, spore-forming bacteria are identified by the presence of nucleic acid sequences that modulate sporulation. In particular, signature sporulation genes are highly conserved across members of distantly related genera including *Clostridium* and *Bacillus*. Traditional approaches of forward genetics have identified many, if not all, genes that are essential for sporulation (spo). The developmental program of sporulation is governed in part by the successive action of four compartment-specific sigma factors (appearing in the order σF, σE, σG and σK), whose activities are confined to the forespore (σF and σG) or the mother cell (σE and σK).

Provided are spore populations containing more than one type of bacterium. As used herein, a "type" or more than one "types" of bacteria may be differentiated at the genus level, the species, level, the sub-species level, the strain level or by any other taxonomic method, as described herein and otherwise known in the art.

In some embodiments, all or essentially all of the bacterial spores or bacterial species present in a purified population are originally isolated obtained from a fecal material treated as described herein or otherwise known in the art. In alternative embodiments, one or more than one bacterial spores, bacteria, or types of bacterial spores are generated in culture and combined to form a purified bacterial composition, including a purified spore population. In other alternative embodiments, one or more of these culture-generated populations are combined with a fecal material-derived populations to generate a hybrid population. Bacterial compositions may contain at least two types of these preferred bacteria, including strains of the same species. For instance, a bacterial composition may comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 or more than 20 types of bacteria, as defined by species or operational taxonomic unit (OTU) encompassing such species.

Thus, provided herein are methods for production of a bacterial composition containing a population of bacterial spores suitable and/or non-sporulating bacteria for therapeutic administration to a mammalian subject in need thereof. And the composition is produced by generally following the steps of: (a) providing a fecal material obtained from a mammalian donor subject; and (b) subjecting the fecal material to at least one purification treatment or step under conditions such that a population of bacterial spores is produced from the fecal material. The composition is formulated such that a single oral dose contains at least about $1\times10^4$ colony forming units of the bacterial spores, and a single oral dose will typically contain about $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, or greater than $1\times10^{15}$ CFUs of the bacterial spores. The presence and/or concentration of a given type of bacteria or bacterial spore may be known or unknown in a given purified spore population. If known, for example the concentration of bacteria or spores of a given strain, or the aggregate of all strains, is e.g., $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, or greater than $1\times10^{15}$ viable bacteria or bacterial spores per gram of composition or per administered dose.

In some formulations, the composition contains at least about 10%, 20%, 30%, 40%, 50%, 60%, 70%, 80%, 90% or greater than 90% spores on a mass basis. In some formulations, the administered dose does not exceed 200, 300, 400, 500, 600, 700, 800, 900 milligrams or 1, 1.1, 1.2, 1.3, 1.4, 1.5, 1.6, 1.7, 1.8, or 1.9 grams in mass.

The bacterial compositions are generally formulated for oral or gastric administration, typically to a mammalian subject. In particular embodiments, the composition is formulated for oral administration as a solid, semi-solid, gel, or liquid form, such as in the form of a pill, tablet, capsule, or lozenge. In some embodiments, such formulations contain or are coated by an enteric coating to protect the bacteria through the stomach and small intestine, although spores are generally resistant to the stomach and small intestines.

The bacterial compositions may be formulated to be effective in a given mammalian subject in a single administration or over multiple administrations. For example, a single administration is substantially effective to reduce *Cl. difficile* and/or *Cl. difficile* toxin content in a mammalian subject to whom the composition is administered. Substantially effective means that *Cl. difficile* and/or *Cl. difficile* toxin content in the subject is reduced by at least 10%, 20%, 30%, 40%, 50%, 60%, 70%, 80%, 90%, 95%, 98%, 99% or greater than 99% following administration of the composition.

Kits For Diagnosis of a State of Dysbiosis in a Subject

In some embodiments, the invention includes kits for carrying out methods of the invention described herein and in the claims. In some embodiments, the invention includes a kit for diagnosis of a state of dysbiosis in a mammalian subject in need thereof. In one embodiment, the kit includes a plurality of detection means suitable for use in detecting (1) a first bacterial entity comprising a keystone bacterial entity and (2) a second bacterial entity, wherein the first and second bacterial entities comprise a Network Ecology, as described herein. The kit can include instructions for use of the kit.

In other embodiments, the kit provides detection means, reagents, and instructions for detecting a first bacterial entity and a second bacterial entity that comprise a Network Ecology by: obtaining a fecal sample from a mammalian subject comprising a plurality of bacterial entities, contacting the fecal sample with a first detection moiety (and in some cases, a second detection moiety) capable of detecting the first bacterial entity and the second bacterial entity present in the network, detecting the absence of the first and/or second bacterial entities in the fecal sample, and thereby detecting a dysbiosis in the mammailian subject. In some embodiments, the kit provides reagents and steps for administering to the mammailian subject a composition comprising an effect amount of the first and/or second bacterial species.

In some embodiments, the kit includes detection means and instructions for obtaining a fecal sample from the mammalian subject comprising a plurality of bacterial entities; contacting the fecal sample with a first detection moiety capable of detecting a first bacterial entity present in an network; detecting the absence of the first bacterial entity in the fecal sample, thereby detecting a dysbiosis in the mammalian subject; and administering to the mammalian subject a composition comprising an effective amount of the first bacterial entity.

In other embodiments, the kit includes reagents and instructions for a method for treating, preventing, or reducing the severity of a disorder selected from the group consisting of *Clostridium difficile* Associated Diarrhea (CDAD), Type 2 Diabetes, Obesity, Irritable Bowel Disease (IBD), colonization with a pathogen or pathobiont, and infection with a drug-resistant pathogen or pathobiont, comprising: administering to a mammalian subject in need thereof an effective amount of a therapeutic bacterial composition, said therapeutic bacterial composition comprising a plurality of isolated bacteria or a purified bacterial preparation, the plurality of isolated bacteria or the purified bacterial preparation capable of forming a network ecology selected from the group consisting of those described throughout the specification.

In another embodiment, the kit includes reagents and instructions for a method for producing short chain fatty acids (SCFA) within a mammalian subject, comprising: administering to said mammalian subject in need thereof an effective amount of a therapeutic bacterial composition, said therapeutic bacterial composition comprising a plurality of isolated bacteria or a purified bacterial preparation, the plurality of isolated bacteria of the purified bacterial preparation capable of forming one or a plurality of bacterial functional pathways, the one or plurality of bacterial functional pathways capable of forming a functional network ecology selected from the group consisting of those described throughout the specification.

In another embodiment, the kit includes reagents and instructions for a method for catalyzing secondary metabolism of bile acids within a mammalian subject, comprising: administering to said mammalian subject in need thereof an effective amount of a therapeutic bacterial composition, said therapeutic bacterial composition comprising a plurality of isolated bacteria or a purified bacterial preparation, the plurality of isolated bacteria of the purified bacterial preparation capable of forming one or a plurality of bacterial functional pathways, the one or plurality of bacterial functional pathways capable of forming a functional network ecology selected from the group consisting of those described throughout the specification.

Systems for Predicting a Dysbiosis in a Subject

The invention provides systems for predicting a dysbiosis in a subject, the system comprising: a storage memory for storing a dataset associated with a sample obtained from the subject, wherein the dataset comprises content data for at least one network of bacterial entities described herein, and a processor communicatively coupled to the storage memory for determining a score with an interpretation function wherein the score is predictive of dysbiosis in the subject.

In some embodiments, the invention provides systems for detecting a dysbiosis in a subject comprising: a storage memory for storing a dataset associated with a sample obtained from the subject, wherein the dataset comprises content data for at least one network of bacterial entities described herein, and a processor communicatively coupled to the storage memory for determining a score with an interpretation function, wherein the score is predictive of dysbiosis in the subject.

An example of a computer system and its components that can be used to perform methods of the invention are described below in FIG. 21.

Computer Overview

FIG. 21 is a high-level block diagram illustrating an example of a computer 2100 for use as a server or a user device, in accordance with one embodiment. Illustrated are at least one processor 2102 coupled to a chipset 2104. The chipset 2104 includes a memory controller hub 2120 and an input/output (I/O) controller hub 2122. A memory 2106 and a graphics adapter 2112 are coupled to the memory controller hub 2120, and a display device 2118 is coupled to the graphics adapter 2112. A storage device 2108, keyboard 2110, pointing device 2114, and network adapter 2116 are coupled to the I/O controller hub 2122. Other embodiments of the computer 2100 have different architectures. For example, the memory 2106 is directly coupled to the processor 2102 in some embodiments.

The storage device 2108 is a non-transitory computer-readable storage medium such as a hard drive, compact disk read-only memory (CD-ROM), DVD, or a solid-state memory device. The memory 2106 holds instructions and data used by the processor 2102. The pointing device 2114 is used in combination with the keyboard 2110 to input data into the computer system 200. The graphics adapter 2112 displays images and other information on the display device 2118. In some embodiments, the display device 2118 includes a touch screen capability for receiving user input and selections. The network adapter 2116 couples the computer system 2100 to the network. Some embodiments of the computer 2100 have different and/or other components than those shown in FIG. 21. For example, the server can be formed of multiple blade servers and lack a display device, keyboard, and other components.

The computer 2100 is adapted to execute computer program modules for providing functionality described herein. As used herein, the term "module" refers to computer program instructions and other logic used to provide the specified functionality. Thus, a module can be implemented in hardware, firmware, and/or software. In one embodiment, program modules formed of executable computer program instructions are stored on the storage device 2108, loaded into the memory 2106, and executed by the processor 2102.

Methods of the Invention

Method of Determining Network Ecologies

Figure 16:
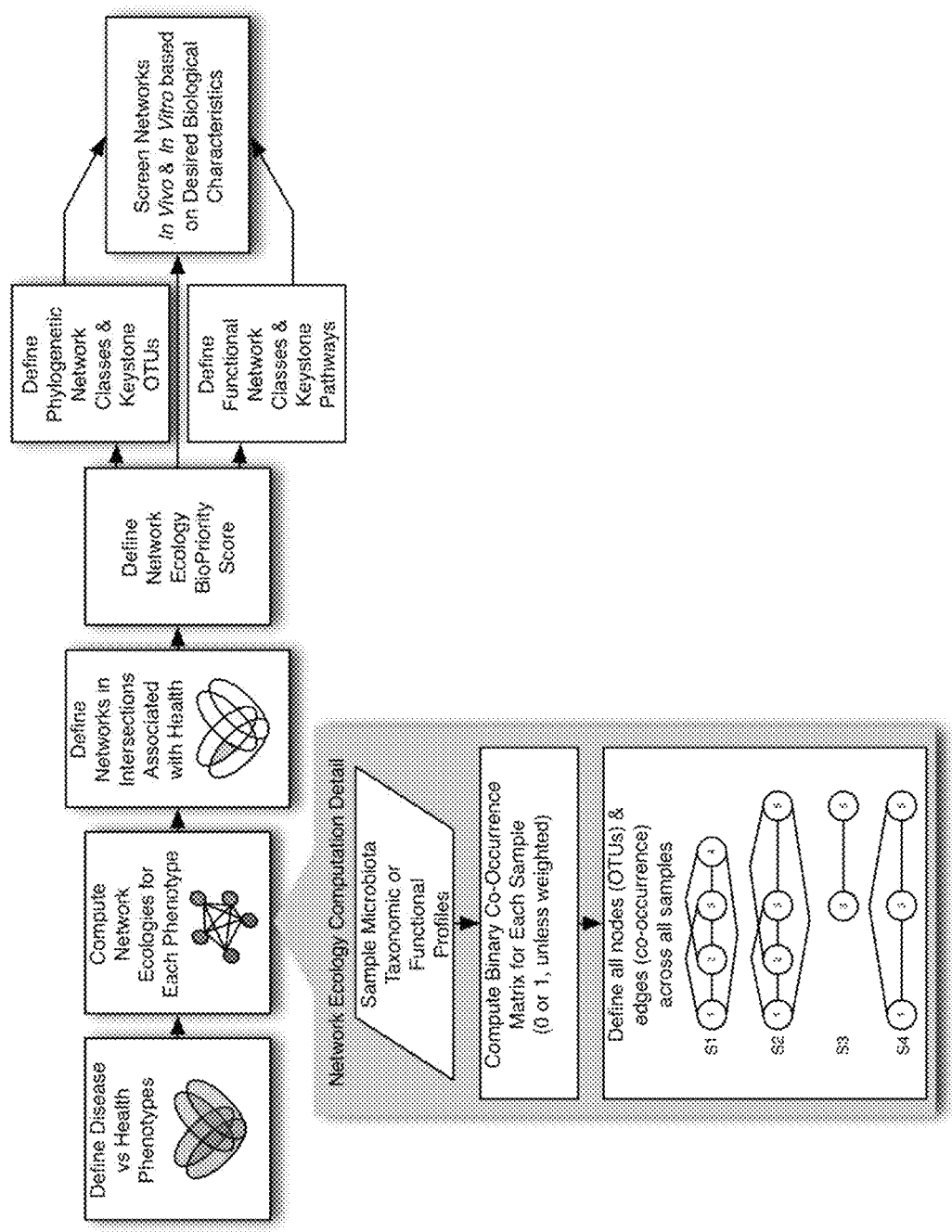
FIG. 16 is an overview of a method to computationally derive network ecologies, according to an embodiment of the invention.

Methods are provided for a computational approach based in part on network theory to construct the ecology of a group of microorganisms based on the presence or absence of specific OTUs (i.e., microbial genera, species or strains) in a given set of sampled subjects. See FIG. 16. See e.g., Cormen T H, Leiserson C E, Rivest R L, and Stein C. 2009. Introduction to Algorithms. Third edition. The MIT Press. Garey M R, and Johnson D S. 1979. Computers and Intractability: A Guide to the Theory of NP-Completeness. First Edition. W. H. Freeman. The approach includes the following: (i) identifying the microbial network ecologies that are present in both healthy and diseased subjects, (ii) identifying the keystone OTUs and/or functions (FIG. 17), and phylogenetic clades that characterize a given ecology, and (iii) providing specific metrics with which to prioritize the various network ecologies with respect to their capacity to be useful in restoring the microbiome from a state of dysbiosis to a state of health. In general the method first defines all low and high order networks within given sets of subjects, and then utilizes a comparative approach to define biologically significant networks.

This method comprises computing a co-occurrence matrix of OTUs (i.e., presence or absence) for each subject across a defined subject population (populations are defined by a specific phenotype such as but not limited to "subjects who are healthy", or "subjects with disease"). The method comprises computing all nodes (OTUs, or species, or strains) and edges (co-occurrence between OTUs, or species, or strains) that define the Network Ecology in a given subject's sample. Each co-occurrence is scored using a discrete binary variable denoting presence or absence. While the algorithm allows co-occurrences to be weighted based on the relative abundance of OTUs in the samples, in general, this is undesirable since low abundance OTUs may be important ecologically. Furthermore, a discretized measure of presence or absence of nodes eliminates bias and errors in the computed network ecologies that will arise from bias in methods used to generate relative abundance measures. A discreet method measuring presence or absence enables the detection of low frequency OTUs and the elucidation of networks that are often missed by methods based on relative abundance measures. Following derivation of all low and high order networks in a given subject, one can define all the network ecologies in a given phenotype (i.e., collections of data sets from subjects with a unifying characteristic, for example, all data sets from healthy subjects) by defining the node and edge combinations that are maximally observed across all subjects. Without being bound by theory, it is understood that such network ecologies are present in a mammalian subject. The algorithm iterates the construction of network ecologies to rank all ecologies (i.e. nodes and edges) within each sample based on co-occurrence, [maximum co-occurrence; maximum co-occurrence less 1; maximum co-occurrence less 2; etc.] until the networks with minimum co-occurrence are defined (i.e., a minimum edge score is achieved). This method can be computationally intensive for data sets containing a large number of subjects. For data sets containing a large number of subjects the algorithm uses a strategy whereby first seed network ecologies are constructed using the method defined above in a subset of subjects and then combinations of these seed networks are used to search for higher order networks across the entire data set.

Biological significance can be assigned to the observed network ecologies and members of a given Network Ecology based on multiple computed metrics including, but not limited to: (i) the frequency that a given OTU or Network Ecology is observed; (ii) the number of OTUs in the network; the frequency of occurrence of the network across subjects (i.e., pervasiveness); (iii) the phylogenetic breadth of the network, (iv) specific functional properties, and (v) whether the network occurs preferentially in individuals that are healthy versus those harboring disease (i.e., the various phenotypes). All network ecologies or OTUs that occur in one phenotype (e.g., health) are compared to those that occur in other phenotypes (e.g., one or more specific disease states) to core Network ecologies or OTUs that are found in one, two, or any multiple of phenotypes. Network ecologies are considered to be related if at least 70%, 80%, or 90% of their OTUs are in common. All network ecologies or OTUs are assigned a score for their biological significance based on but not limited to: (i) the intersections of phenotypes in which they occur or do not occur (e.g. present in health but not disease), and (ii) the various metrics above defined. The final output of all of these steps defines a set of Network Ecologies that are of high biological significance and a set of Keystone OTUs and/or metabolic functions that are integral components of these derived ecologies.

Figure 18:
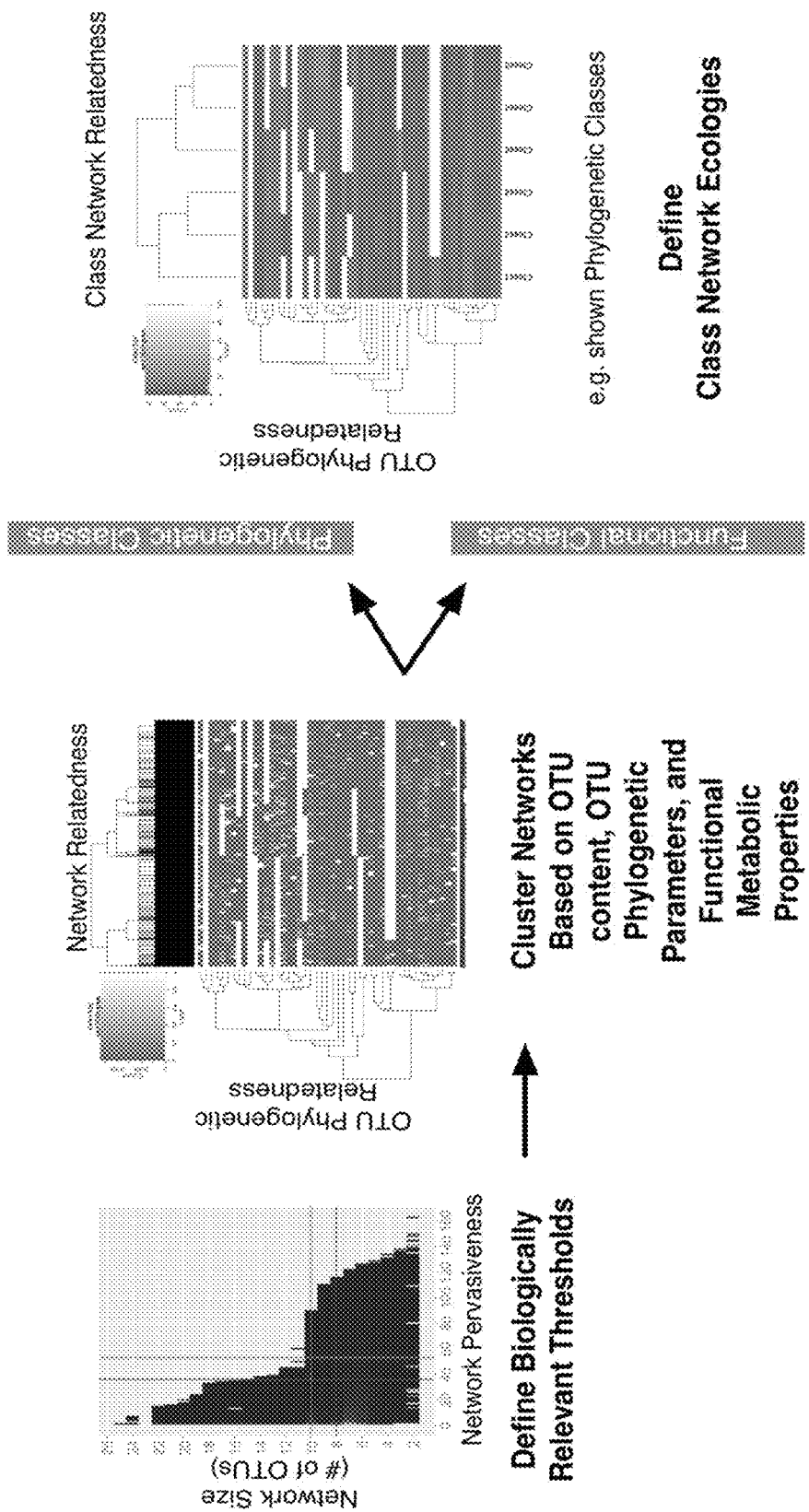
FIG. 18 exemplifies a Derivation of Network Ecology Classes, according to an embodiment of the invention.

From these Network Ecologies, the method includes defining "Network Classes" that represent network groups or clusters with specific, related compositional characteristics with respect to OTU content, phylogenetic diversity, and metabolic functional capacity (FIG. 18). Network Classes can be first defined by setting an inclusion threshold for networks to include in the analysis that is based on biological characteristics of the networks such as but not limited to the size (number of OTUs) and pervasiveness (i.e., how frequently a given network is observed in a population of individuals). Selected network ecologies are then clustered using two vectors: one vector is phylogenetic relatedness of individual OTUs as defined by a computed phylogenetic tree, and the second vector is network relatedness based on the OTUs content in the individual networks. In another embodiment, clustering vectors are related based on metabolic functional pathways harbored by individual OTUs, and network relatedness is based on the functional pathways present in each individual network. Network Classes are defined by specific nodes in the dendrogram representing the computed network relatedness, and each class is characterized by a specific combination of OTUs. In one embodiment, these nodes are defined as branches of the hierarchical clustering tree based on the topological overlap measure; this measure is a highly robust measure of network interconnectedness. See Langfelder P, Zhang B, Horvath S. 2008. Defining clusters from a hierarchical cluster tree: the Dynamic Tree Cut package for R. Bioinformatics 24: 719-720.

From these Networks Classes, a target microbial composition's usefulness, e.g., as a therapeutic, is selected using desired phylogenetic and functional properties for subsequent testing in in vitro and in vivo models. Exemplary Network Classes are delineated in Table 12, and Table 13 defines taxonomic families that are characteristic of Network Classes.

As described herein, provided are compositions (Table 8) containing keystone OTUs for states of health, including one or more of the OTUs provided below in Table 9.

As described herein, provided are compositions containing keystone OTUs, keystone metabolic functions and, optionally, non-keystone OTUs, including one or more of the OTUs provided below in Table 10.

In some therapeutic compositions, keystone OTUs are provided from members of a genera or family selected from Table 9.

Exemplary network ecologies are provided in Table 8, Table 11, Table 12, Table 14a 14b, and 14c, and Table 17.

Exemlary functional network ecologies are provided in Table 18 and Table 21.

Thus, provided herein are methods for production of a composition containing a population of bacteria as either vegetative cells or spores or both, suitable for therapeutic administration to a mammalian subject in need thereof. The composition is produced by generally following the steps of: (a) defining a target composition by selecting a Network Ecology, Functional Network Ecology, a Network Class, or a set of Keystone OTUs or Keystone Metabolic Functions that comprise the Network Ecology or Functional Network Ecology of interest (a) providing bacterial OTUs obtained from one or more bacterial cultures, biological or environmental sources, or a mammalian donor subject; and (b) combining the bacterial OTUs in a ratio and an amount sufficient to form a Network Ecology or Functional Network Ecology. The composition is formulated such that a single oral dose contains at least about $1 \times 10^4$ colony forming units of the bacteria, and a single oral dose will typically contain about $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, or greater than $1 \times 10^{15}$ CFUs of the bacteria. The concentration of bacterial of a given species or strain, or the aggregate of all species or strains, is e.g., $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, $1 \times 10^{13}$, $1 \times 10^{14}$, $1 \times 10^{15}$, or greater than $1 \times 10^{15}$ viable bacteria per gram of composition or per administered dose.

The bacterial compositions are generally formulated for oral or gastric administration, typically to a mammalian subject. In particular embodiments, the composition is formulated for oral administration as a solid, semi-solid, gel, or liquid form, such as in the form of a pill, tablet, capsule, or lozenge. In some embodiments, such formulations contain or are coated by an enteric coating to protect the bacteria through the stomach and small intestine, although compositions containing spores are generally resistant to the environment of the stomach and small intestine. Alternatively, the bacterial composition may be formulated for nasogastric or rectal administration.

The bacterial compositions may be formulated to be effective in a given mammalian subject in a single administration or over multiple administrations. For example, a single administration is substantially effective to reduce *Clostridium difficile* (i.e., *C. difficile*) and/or *C. difficile* toxin content and/or toxin activity, in a mammalian subject to whom the composition is administered. Substantially effective means that *Cl. difficile* and/or *C. difficile* toxin content in the subject is reduced by at least 10%, 20%, 30%, 40%, 50%, 60%, 70%, 80%, 90%, 95%, 98%, 99% or greater than 99% following administration of the composition.

Methods for Determining 16S Sequences

OTUs can be defined either by full 16S sequencing of the rRNA gene, by sequencing of a specific hypervariable region of this gene (i.e. V1, V2, V3, V4, V5, V6, V7, V8, or V9), or by sequencing of any combination of hypervariable regions from this gene (e.g. V1-3 or V3-5). The bacterial 16S rDNA is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes.

Using well known techniques, in order to determine the full 16S sequence or the sequence of any hypervariable region of the 16S sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing can be, but is not limited to being, performed using the Sanger method or using a next-generation sequencing method, such as an Illumina (sequencing by synthesis) method using barcoded primers allowing for multiplex reactions.

OTUs can be defined by a combination of nucleotide markers or genes, in particular highly conserved genes (e.g., "house-keeping" genes), or a combination thereof, full-genome sequence, or partial genome sequence generated using amplified genetic products, or whole genome sequence (WGS). Using well defined methods DNA extracted from a bacterial sample will have specific genomic regions amplified using PCR and sequenced to determine the nucleotide sequence of the amplified products. In the whole genome shotgun (WGS) method, extracted DNA will be directly sequenced without amplification. Sequence data can be generated using any sequencing technology including, but not limited to Sanger, Illumina, 454 Life Sciences, Ion Torrent, ABI, Pacific Biosciences, and/or Oxford Nanopore.

Methods for Preparing a Bacterial Composition for Administration to a Subject

Methods for producing bacterial compositions can include three main processing steps, combined with one or more mixing steps. The steps include organism banking, organism production, and preservation.

For banking, the strains included in the bacterial composition may be (1) isolated directly from a specimen or taken from a banked stock, (2) optionally cultured on a nutrient agar or broth that supports growth to generate viable biomass, and (3) the biomass optionally preserved in multiple aliquots in long-term storage.

In embodiments that use a culturing step, the agar or broth can contain nutrients that provide essential elements and specific factors that enable growth. An example would be a medium composed of 20 g/L glucose, 10 g/L yeast extract, 10 g/L soy peptone, 2 g/L citric acid, 1.5 g/L sodium phosphate monobasic, 100 mg/L ferric ammonium citrate, 80 mg/L magnesium sulfate, 10 mg/L hemin chloride, 2 mg/L calcium chloride, 1 mg/L menadione. A variety of microbiological media and variations are well known in the art (e.g. R. M. Atlas, Handbook of Microbiological Media (2010) CRC Press). Medium can be added to the culture at the start, may be added during the culture, or may be intermittently/continuously flowed through the culture. The strains in the bacterial composition may be cultivated alone, as a subset of the bacterial composition, or as an entire collection comprising the bacterial composition. As an example, a first strain may be cultivated together with a second strain in a mixed continuous culture, at a dilution rate lower than the maximum growth rate of either cell to prevent the culture from washing out of the cultivation.

The inoculated culture is incubated under favorable conditions for a time sufficient to build biomass. For bacterial compositions for human use, this is often at 37° C. temperature, pH, and other parameter with values similar to the normal human niche. The environment can be actively controlled, passively controlled (e.g., via buffers), or allowed to drift. For example, for anaerobic bacterial compositions (e.g., gut microbiota), an anoxic/reducing environment can be employed. This can be accomplished by addition of reducing agents such as cysteine to the broth, and/or stripping it of oxygen. As an example, a culture of a bacterial composition can be grown at 37° C., pH 7, in the medium above, pre-reduced with 1 g/L cysteine ☐HCl.

When the culture has generated sufficient biomass, it can be preserved for banking. The organisms can be placed into a chemical milieu that protects from freezing (adding 'cryoprotectants'), drying ('lyoprotectants'), and/or osmotic shock ('osmoprotectants'), dispensing into multiple (optionally identical) containers to create a uniform bank, and then treating the culture for preservation. Containers are generally impermeable and have closures that assure isolation from the environment. Cryopreservation treatment is accomplished by freezing a liquid at ultra-low temperatures (e.g., at or below −80° C.). Dried preservation removes water from the culture by evaporation (in the case of spray drying or 'cool drying') or by sublimation (e.g., for freeze drying, spray freeze drying). Removal of water improves long-term bacterial composition storage stability at temperatures elevated above cryogenic. If the bacterial composition comprises spore forming species and results in the production of spores, the final composition can be purified by additional means, such as density gradient centrifugation preserved using the techniques described above. Bacterial composition banking can be done by culturing and preserving the strains individually, or by mixing the strains together to create a combined bank. As an example of cryopreservation, a bacterial composition culture can be harvested by centrifugation to pellet the cells from the culture medium, the supernate decanted and replaced with fresh culture broth containing 15% glycerol. The culture can then be aliquoted into 1 mL cryotubes, sealed, and placed at −80° C. for long-term viability retention. This procedure achieves acceptable viability upon recovery from frozen storage.

Organism production can be conducted using similar culture steps to banking, including medium composition and culture conditions. It can be conducted at larger scales of operation, especially for clinical development or commercial production. At larger scales, there can be several subcultivations of the bacterial composition prior to the final cultivation. At the end of cultivation, the culture is harvested to enable further formulation into a dosage form for administration. This can involve concentration, removal of undesirable medium components, and/or introduction into a chemical milieu that preserves the bacterial composition and renders it acceptable for administration via the chosen route. For example, a bacterial composition can be cultivated to a concentration of $10^{10}$ CFU/mL, then concentrated 20-fold by tangential flow microfiltration; the spent medium can be exchanged by diafiltering with a preservative medium consisting of 2% gelatin, 100 mM trehalose, and 10 mM sodium phosphate buffer. The suspension can then be freeze-dried to a powder and titrated.

After drying, the powder can be blended to an appropriate potency, and mixed with other cultures and/or a filler such as microcrystalline cellulose for consistency and ease of handling, and the bacterial composition formulated as provided herein.

Methods of Treating a Subject

In some embodiments, the compositions disclosed herein are administered to a patient or a user (sometimes collectively referred to as a "subject"). As used herein "administer" and "administration" encompasses embodiments in which one person directs another to consume a bacterial composition in a certain manner and/or for a certain purpose, and also situations in which a user uses a bacteria composition in a certain manner and/or for a certain purpose independently of or in variance to any instructions received from a second person. Non-limiting examples of embodiments in which one person directs another to consume a bacterial composition in a certain manner and/or for a certain purpose include when a physician prescribes a course of conduct and/or treatment to a patient, when a parent commands a minor user (such as a child) to consume a bacterial composition, when a trainer advises a user (such as an athlete) to follow a particular course of conduct and/or treatment, and when a manufacturer, distributer, or marketer recommends conditions of use to an end user, for example through advertisements or labeling on packaging or on other materials provided in association with the sale or marketing of a product.

The bacterial compositions offer a protective and/or therapeutic effect against diseases, disorders or conditions associated with dysbiosis of the gut microbiota, including but not limited to metabolic disorders such as pre-diabetes, type 1 diabetes, type 2 diabetes, obesity and non-alcoholic fatty liver disease (NAFLD), gastrointestinal disorders such as inflammatory bowel disease (IBD, such as ulcerative colitis and Crohns' disease), pouchitis and irritable bowel syndrome (IBS), and infectious diseases as described herein.

In some embodiments, the bacterial compositions offer a protective and/or therapeutic effect against diseases, disorders or conditions associated with dysbiosis of the gut microbiota, including but not limited to, metabolic diseases (e.g., Type 1 diabetes, Type 2 diabetes, Gestational diabetes, Diabetes complications, Prediabetes, NAFLD/NASH, Obesity, Weight Loss), GI diseases (Inflammatory bowel disease (IBD), Irritable bowel syndrome (IBS), Ulcerative Colitis, Crohn's Disease). Infectious diseases (*Clostridium difficile* Associated Diarrhea (CDAD), Carbapenem-resistant Enterobacteriaceae (CRE), Multidrug-resistant *Acinetobacter*, Drug-resistant *Campylobacter*, Extended spectrum β-lactamase producing Enterobacteriaceae (ESBLs), Vancomycin-resistant *Enterococcus* (VRE), Multidrug-resistant *Pseudomonas aeruginosa*, Drug-resistant Non-typhoidal *Salmonella*, Drug-resistant *Salmonella Typhi*, Drug-resistant *Shigella*, Methicillin-resistant *Staphylococcus aureus* (MRSA), Drug-resistant *Streptococcus pneumonia*, Vancomycin-resistant *Staphylococcus aureus* (VRSA), Erythromycin-resistant Group A *Streptococcus*, Clindamycin-resistant Group B *Streptococcus*, Pathogenic fungus, or *Candida* infection).

The present bacterial compositions can be administered to animals, including humans, laboratory animals (e.g., primates, rats, mice), livestock (e.g., cows, sheep, goats, pigs, turkeys, chickens), and household pets (e.g., dogs, cats, rodents).

In the present method, the bacterial composition can be administered enterically, in other words, by a route of access to the gastrointestinal tract. This includes oral administration, rectal administration (including enema, suppository, or colonoscopy), by an oral or nasal tube (nasogastric, nasojejunal, oral gastric, or oral jejunal), as detailed more fully herein.

Pretreatment Protocols

Prior to administration of the bacterial composition, the patient can optionally have a pretreatment protocol to prepare the gastrointestinal tract to receive the bacterial composition.

As one way of preparing the patient for administration of the microbial ecosystem, at least one antibiotic can be administered to alter the bacteria in the patient. As another way of preparing the patient for administration of the microbial ecosystem, a standard colon-cleansing preparation can be administered to the patient to substantially empty the contents of the colon, such as used to prepare a patient for a colonoscopy. By "substantially emptying the contents of the colon," this application means removing at least 75%, at least 80%, at least 90%, at least 95%, or about 100% of the contents of the ordinary volume of colon contents. Antibiotic treatment can precede the colon-cleansing protocol.

If a patient has received an antibiotic for treatment of an infection, or if a patient has received an antibiotic as part of a specific pretreatment protocol, in one embodiment, the antibiotic can be stopped in sufficient time to allow the antibiotic to be substantially reduced in concentration in the gut before the bacterial composition is administered. In one embodiment, the antibiotic can be discontinued 1, 2, or 3 days before the administration of the bacterial composition. In another embodiment, the antibiotic can be discontinued 3, 4, 5, 6, or 7 antibiotic half-lives before administration of the bacterial composition. In another embodiment, the antibiotic can be chosen so the constituents in the bacterial composition have an MIC50 that is higher than the concentration of the antibiotic in the gut.

MIC50 of a bacterial composition or the elements in the composition can be determined by methods well known in the art. Reller et al., Antimicrobial Susceptibility Testing: A Review of General Principles and Contemporary Practices, Clinical Infectious Diseases 49(11):1749-1755 (2009). In such an embodiment, the additional time between antibiotic administration and administration of the bacterial composition is not necessary. If the pretreatment protocol is part of treatment of an acute infection, the antibiotic can be chosen so that the infection is sensitive to the antibiotic, but the constituents in the bacterial composition are not sensitive to the antibiotic.

Administration of Bacterial Compositions

The bacterial compositions of the invention are suitable for administration to mammals and non-mammalian animals in need thereof. In certain embodiments, the mammalian subject is a human subject who has one or more symptoms of a dysbiosis.

When the mammalian subject is suffering from a disease, disorder or condition characterized by an aberrant microbiota, the bacterial compositions described herein are suitable for treatment thereof. In some embodiments, the mammalian subject has not received antibiotics in advance of treatment with the bacterial compositions. For example, the mammalian subject has not been administered at least two doses of vancomycin, metronidazole and/or or similar antibiotic compound within one week prior to administration of the therapeutic composition. In other embodiments, the mammalian subject has not previously received an antibiotic compound in the one month prior to administration of the therapeutic composition. In other embodiments, the mammalian subject has received one or more treatments with one or more different antibiotic compounds and such treatment(s) resulted in no improvement or a worsening of symptoms.

In some embodiments, the gastrointestinal disease, disorder or condition is diarrhea caused by C. difficile including recurrent C. difficile infection, ulcerative colitis, colitis, Crohn's disease, or irritable bowel disease. Beneficially, the therapeutic composition is administered only once prior to improvement of the disease, disorder or condition. In some embodiments the therapeutic composition is administered at intervals greater than two days, such as once every three, four, five or six days, or every week or less frequently than every week. Or the preparation may be administered intermittently according to a set schedule, e.g., once a day, once weekly, or once monthly, or when the subject relapses from the primary illness. In another embodiment, the preparation may be administered on a long-term basis to subjects who are at risk for infection with or who may be carriers of these pathogens, including subjects who will have an invasive medical procedure (such as surgery), who will be hospitalized, who live in a long-term care or rehabilitation facility, who are exposed to pathogens by virtue of their profession (livestock and animal processing workers), or who could be carriers of pathogens (including hospital workers such as physicians, nurses, and other health care professionals).

In embodiments, the bacterial composition is administered enterically. This preferentially includes oral administration, or by an oral or nasal tube (including nasogastric, nasojejunal, oral gastric, or oral jejunal). In other embodiments, administration includes rectal administration (including enema, suppository, or colonoscopy). The bacterial composition may be administered to at least one region of the gastrointestinal tract, including the mouth, esophagus, stomach, small intestine, large intestine, and rectum. In some embodiments it is administered to all regions of the gastrointestinal tract. The bacterial compositions may be administered orally in the form of medicaments such as powders, capsules, tablets, gels or liquids. The bacterial compositions may also be administered in gel or liquid form by the oral route or through a nasogastric tube, or by the rectal route in a gel or liquid form, by enema or instillation through a colonoscope or by a suppository.

If the composition is administered colonoscopically and, optionally, if the bacterial composition is administered by other rectal routes (such as an enema or suppository) or even if the subject has an oral administration, the subject may have a colon cleansing preparation. The colon-cleansing preparation can facilitate proper use of the colonoscope or other administration devices, but even when it does not serve a mechanical purpose it can also maximize the proportion of the bacterial composition relative to the other organisms previously residing in the gastrointestinal tract of the subject. Any ordinarily acceptable colon cleansing preparation may be used such as those typically provided when a subject undergoes a colonoscopy.

Dosages and Schedule for Administration

In some embodiments, the bacteria and bacterial compositions are provided in a dosage form. In certain embodiments, the dosage form is designed for administration of at least one OTU or combination thereof disclosed herein, wherein the total amount of bacterial composition administered is selected from 0.1 ng to 10 g, 10 ng to 1 g, 100 ng to 0.1 g, 0.1 mg to 500 mg, 1 mg to 100 mg, or from 10-15 mg. In other embodiments, the bacterial composition is consumed at a rate of from 0.1 ng to 10 g a day, 10 ng to 1 g a day, 100 ng to 0.1 g a day, 0.1 mg to 500 mg a day, 1 mg to 100 mg a day, or from 10-15 mg a day, or more.

In certain embodiments, the treatment period is at least 1 day, at least 2 days, at least 3 days, at least 4 days, at least 5 days, at least 6 days, at least 1 week, at least 2 weeks, at least 3 weeks, at least 4 weeks, at least 1 month, at least 2 months, at least 3 months, at least 4 months, at least 5 months, at least 6 months, or at least 1 year. In some embodiments the treatment period is from 1 day to 1 week, from 1 week to 4 weeks, from 1 month, to 3 months, from 3 months to 6 months, from 6 months to 1 year, or for over a year.

In one embodiment, $10^5$ and $10^{12}$ microorganisms total can be administered to the patient in a given dosage form. In another embodiment, an effective amount can be provided in from 1 to 500 ml or from 1 to 500 grams of the bacterial composition having from $10^7$ to $10^{11}$ bacteria per ml or per gram, or a capsule, tablet or suppository having from 1 mg to 1000 mg lyophilized powder having from $10^7$ to $10^{11}$ bacteria. Those receiving acute treatment can receive higher doses than those who are receiving chronic administration.

Any of the preparations described herein can be administered once on a single occasion or on multiple occasions, such as once a day for several days or more than once a day on the day of administration (including twice daily, three times daily, or up to five times daily). In another embodiment, the preparation can be administered intermittently according to a set schedule, e.g., once weekly, once monthly, or when the patient relapses from the primary illness. In one embodiment, the preparation can be administered on a long-term basis to individuals who are at risk for infection with or who may be carriers of these pathogens.

Patient Selection

Particular bacterial compositions can be selected for individual patients or for patients with particular profiles. For example, 16S sequencing can be performed for a given patient to identify the bacteria present in his or her microbiota. The sequencing can either profile the patient's entire microbiome using 16S sequencing (to the family, genera, or species level), a portion of the patient's microbiome using 16S sequencing, or it can be used to detect the presence or absence of specific candidate bacteria that are biomarkers for health or a particular disease state. Based on the biomarker data, a particular composition can be selected for administration to a patient to supplement or complement a patient's microbiota in order to restore health or treat or prevent disease. In another embodiment, patients can be screened to determine the composition of their microbiota to determine the likelihood of successful treatment.

Combination Therapy

The bacterial compositions can be administered with other agents in a combination therapy mode, including anti-microbial agents and prebiotics. Administration can be sequential, over a period of hours or days, or simultaneous.

In one embodiment, the bacterial compositions are included in combination therapy with one or more anti-microbial agents, which include anti-bacterial agents, anti-fungal agents, anti-viral agents and anti-parasitic agents.

Anti-bacterial agents can include cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); and carbapenem antibiotics (ertapenem, doripenem, imipenem/cilastatin, and meropenem).

Anti-viral agents can include Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, Foscarnet, Fomivirsen, Ganciclovir, Indinavir, Idoxuridine, Lamivudine, Lopinavir Maraviroc, MK-2048, Nelfinavir, Nevirapine, Penciclovir, Raltegravir, Rilpivirine, Ritonavir, Saquinavir, Stavudine, Tenofovir Trifluridine, Valaciclovir, Valganciclovir, Vidarabine, Ibacitabine, Amantadine, Oseltamivir, Rimantidine, Tipranavir, Zalcitabine, Zanamivir and Zidovudine.

Examples of antifungal compounds include, but are not limited to polyene antifungals such as natamycin, rimocidin, filipin, nystatin, amphotericin B, candicin, and hamycin; imidazole antifungals such as miconazole, ketoconazole, clotrimazole, econazole, omoconazole, bifonazole, butoconazole, fenticonazole, isoconazole, oxiconazole, sertaconazole, sulconazole, and tioconazole; triazole antifungals such as fluconazole, itraconazole, isavuconazole, ravuconazole, posaconazole, voriconazole, terconazole, and albaconazole; thiazole antifungals such as abafungin; allylamine antifungals such as terbinafine, naftifine, and butenafine; and echinocandin antifungals such as anidulafungin, caspofungin, and micafungin. Other compounds that have antifungal properties include, but are not limited to polygodial, benzoic acid, ciclopirox, tolnaftate, undecylenic acid, flucytosine or 5-fluorocytosine, griseofulvin, and haloprogin.

In one embodiment, the bacterial compositions are included in combination therapy with one or more corticosteroids, mesalazine, mesalamine, sulfasalazine, sulfasalazine derivatives, immunosuppressive drugs, cyclosporin A, mercaptopurine, azathiopurine, prednisone, methotrexate, antihistamines, glucocorticoids, epinephrine, theophylline, cromolyn sodium, anti-leukotrienes, anti-cholinergic drugs for rhinitis, anti-cholinergic decongestants, mast-cell stabilizers, monoclonal anti-IgE antibodies, vaccines, and combinations thereof.

A prebiotic is a selectively fermented ingredient that allows specific changes, both in the composition and/or activity in the gastrointestinal microbiota that confers benefits upon host well-being and health. Prebiotics can include complex carbohydrates, amino acids, peptides, or other essential nutritional components for the survival of the bacterial composition. Prebiotics include, but are not limited to, amino acids, biotin, fructooligosaccharide, galactooligosaccharides, inulin, lactulose, mannan oligosaccharides, oligofructose-enriched inulin, oligofructose, oligodextrose, tagatose, trans-galactooligosaccharide, and xylooligosaccharides.

Methods for Testing Bacterial Compositions for Populating Effect

In Vivo Assay for Determining Whether a Bacterial Composition Populates a Subject's Gastrointestinal Tract In order to determine that the bacterial composition populates the gastrointestinal tract of a subject, an animal model, such as a mouse model, can be used. The model can begin by evaluating the microbiota of the mice. Qualitative assessments can be accomplished using 16S profiling of the microbial community in the feces of normal mice. It can also be accomplished by full genome sequencing, whole genome shotgun sequencing (WGS), or traditional microbiological techniques. Quantitative assessments can be conducted using quantitative PCR (qPCR), described below, or by using traditional microbiological techniques and counting colony formation.

Optionally, the mice can receive an antibiotic treatment to mimic the condition of dysbiosis. Antibiotic treatment can decrease the taxonomic richness, diversity, and evenness of the community, including a reduction of abundance of a significant number of bacterial taxa. Dethlefsen et al., The pervasive effects of an antibiotic on the human gut microbiota, as revealed by deep 16S rRNA sequencing, PLoS Biology 6(11):3280 (2008). At least one antibiotic can be used, and antibiotics are well known. Antibiotics can include aminoglycoside antibiotic (amikacin, arbekacin, gentamicin, kanamycin, neomycin, netilmicin, paromomycin, rhodostreptomycin, streptomycin, tobramycin, and apramycin), amoxicillin, ampicillin, Augmentin (an amoxicillin/clavulanate potassium combination), cephalosporin (cefaclor, defadroxil, cefazolin, cefixime, fefoxitin, cefprozil, ceftazimdime, cefuroxime, cephalexin), clavulanate potassium, clindamycin, colistin, gentamycin, kanamycin, metronidazole, or vancomycin. As an individual, nonlimiting specific example, the mice can be provided with drinking water containing a mixture of the antibiotics kanamycin, colistin, gentamycin, metronidazole and vancomycin at 40 mg/kg, 4.2 mg/kg, 3.5 mg/kg, 21.5 mg/kg, and 4.5 mg/kg (mg per average mouse body weight), respectively, for 7 days. Alternatively, mice can be administered ciprofloxacin at a dose of 15-20 mg/kg (mg per average mouse body weight), for 7 days. If the mice are provided with an antibiotic, a wash out period of from one day to three days may be provided with no antibiotic treatment and no bacterial composition treatment.

Subsequently, the bacterial composition is administered to the mice by oral gavage. The bacterial composition may be administered in a volume of 0.2 ml containing $10^4$ CFUs of each type of bacteria in the bacterial composition. Dose-response may be assessed by using a range of doses, including, but not limited to $10^2$, $10^3$, $10^4$, $10^5$, $10^6$, $10^7$, $10^8$, $10^9$, and/or $10^{10}$.

The mice can be evaluated using 16S sequencing, full genome sequencing, whole genome shotgun sequencing (WGS), or traditional microbiological techniques to determine whether the bacterial composition has populated the gastrointestinal tract of the mice. For example only, one day, three days, one week, two weeks, and one month after administration of the bacterial composition to the mice, 16S profiling is conducted to determine whether the test bacterial composition has populated the gastrointestinal tract of the mice. Quantitative assessments, including qPCR and traditional microbiological techniques such as colony counting, can additionally or alternatively be performed, at the same time intervals.

Furthermore, the number of sequence counts that correspond exactly to those in the bacterial composition over time can be assessed to determine specifically which components of the bacterial composition reside in the gastrointestinal tract over a particular period of time. In one embodiment, the strains of the bacterial composition persist for a desired period of time. In another embodiment, the components of the bacterial composition persist for a desired period of time, while also increasing the ability of other microbes (such as those present in the environment, food, etc.) to populate the gastrointestinal tract, further increasing overall diversity, as discussed below.

Ability of Bacterial compositions to Populate Different Regions of the Gastrointestinal Tract The present bacterial compositions can also be assessed for their ability to populate different regions of the gastrointestinal tract. In one embodiment, a bacterial composition can be chosen for its ability to populate one or more than one region of the gastrointestinal tract, including, but not limited to the stomach, the small intestine (duodenum, jejunum, and ileum), the large intestine (the cecum, the colon (the ascending, transverse, descending, and sigmoid colon), and the rectum).

An in vivo study can be conducted to determine which regions of the gastrointestinal tract a given bacterial composition will populate. A mouse model similar to the one described above can be conducted, except instead of assessing the feces produced by the mice, particular regions of the gastrointestinal tract can be removed and studied individually. For example, at least one particular region of the gastrointestinal tract can be removed and a qualitative or quantitative determination can be performed on the contents of that region of the gastrointestinal tract. In another embodiment, the contents can optionally be removed and the qualitative or quantitative determination may be conducted on the tissue removed from the mouse.

qPCR

As one quantitative method for determining whether a bacterial composition populates the gastrointestinal tract, quantitative PCR (qPCR) can be performed. Standard techniques can be followed to generate a standard curve for the bacterial composition of interest, either for all of the components of the bacterial composition collectively, individually, or in subsets (if applicable). Genomic DNA can be extracted from samples using commercially-available kits, such as the Mo Bio Powersoil®-htp 96 Well Soil DNA Isolation Kit (Mo Bio Laboratories, Carlsbad, Calif.), the Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions.

In some embodiments, qPCR can be conducted using HotMasterMix (5PRIME, Gaithersburg, Md.) and primers specific for the bacterial composition of interest, and may be conducted on a MicroAmpx Fast Optical 96-well Reaction Plate with Barcode (0.1 mL) (Life Technologies, Grand Island, N.Y.) and performed on a BioRad C1000™ Thermal Cycler equipped with a CFX96™ Real-Time System (Bio-Rad, Hercules, Calif.), with fluorescent readings of the FAM and ROX channels. The Cq value for each well on the FAM channel is determined by the CFX Manager™ software version 2.1. The $\log_{10}$(cfu/ml) of each experimental sample is calculated by inputting a given sample's Cq value into linear regression model generated from the standard curve comparing the Cq values of the standard curve wells to the known $\log_{10}$(cfu/ml) of those samples. The skilled artisan may employ alternative qPCR modes.

Methods for Characterization of Bacterial Compositions

In certain embodiments, provided are methods for testing certain characteristics of bacterial compositions. For example, the sensitivity of bacterial compositions to certain environmental variables is determined, e.g., in order to select for particular desirable characteristics in a given composition, formulation and/or use. For example, the constituents in the bacterial composition can be tested for pH resistance, bile acid resistance, and/or antibiotic sensitivity, either individually on a constituent-by-constituent basis or collectively as a bacterial composition comprised of multiple bacterial constituents (collectively referred to in this section as bacterial composition).

pH Sensitivity Testing

If a bacterial composition will be administered other than to the colon or rectum (i.e., for example, an oral route), optionally testing for pH resistance enhances the selection of bacterial compositions that will survive at the highest yield possible through the varying pH environments of the distinct regions of the GI tract. Understanding how the bacterial compositions react to the pH of the GI tract also assists in formulation, so that the number of bacteria in a dosage form can be increased if beneficial and/or so that the composition may be administered in an enteric-coated capsule or tablet or with a buffering or protective composition. As the pH of the stomach can drop to a pH of 1 to 2 after a high-protein meal for a short time before physiological mechanisms adjust it to a pH of 3 to 4 and often resides at a resting pH of 4 to 5, and as the pH of the small intestine can range from a pH of 6 to 7.4, bacterial compositions can be prepared that survive these varying pH ranges (specifically wherein at least 1%, 5%, 10%, 15%, 20%, 25%, 30%, 40%, 50%, 60%, 70%, 80%, 90%, or as much as 100% of the bacteria can survive gut transit times through various pH ranges). This can be tested by exposing the bacterial composition to varying pH ranges for the expected gut transit times through those pH ranges. Therefore, as a nonlimiting example only, 18-hour cultures of bacterial compositions can be grown in standard media, such as gut microbiota medium ("GMM", see Goodman et al., Extensive personal human gut microbiota culture collections characterized and manipulated in gnotobiotic mice, PNAS 108(15):6252-6257 (2011)) or another animal-products-free medium, with the addition of pH adjusting agents for a pH of 1 to 2 for 30 minutes, a pH of 3 to 4 for 1 hour, a pH of 4 to 5 for 1 to 2 hours, and a pH of 6 to 7.4 for 2.5 to 3 hours. An alternative method for testing stability to acid is described in U.S. Pat. No. 4,839,281. Survival of bacteria may be determined by culturing the bacteria and counting colonies on appropriate selective or non-selective media.

Bile Acid Sensitivity Testing

Additionally, in some embodiments, testing for bile-acid resistance enhances the selection of bacterial compositions that will survive exposures to bile acid during transit through the GI tract. Bile acids are secreted into the small intestine and can, like pH, affect the survival of bacterial compositions. This can be tested by exposing the bacterial compositions to bile acids for the expected gut exposure time to bile acids. For example, bile acid solutions can be prepared at desired concentrations using 0.05 mM Tris at pH 9 as the solvent. After the bile acid is dissolved, the pH of the solution may be adjusted to 7.2 with 10% HCl. Bacterial compositions can be cultured in 2.2 ml of a bile acid composition mimicking the concentration and type of bile acids in the patient, 1.0 ml of 10% sterile-filtered feces media and 0.1 ml of an 18-hour culture of the given strain of bacteria. Incubations may be conducted for from 2.5 to 3 hours or longer. An alternative method for testing stability to bile acid is described in U.S. Pat. No. 4,839,281. Survival of bacteria can be determined by culturing the bacteria and counting colonies on appropriate selective or non-selective media.

Antibiotic Sensitivity Testing

As a further optional sensitivity test, bacterial compositions can be tested for sensitivity to antibiotics. In one embodiment, bacterial compositions can be chosen so that the bacterial constituents are sensitive to antibiotics such that if necessary they can be eliminated or substantially reduced from the patient's gastrointestinal tract by at least one antibiotic targeting the bacterial composition.

Adherence to Gastrointestinal Cells

The bacterial compositions may optionally be tested for the ability to adhere to gastrointestinal cells. A method for testing adherence to gastrointestinal cells is described in U.S. Pat. No. 4,839,281.

Methods for Purifying Spores

Solvent Treatments

To purify the bacterial spores, the fecal material is subjected to one or more solvent treatments. A solvent treatment is a miscible solvent treatment (either partially miscible or fully miscible) or an immiscible solvent treatment. Miscibility is the ability of two liquids to mix with each to form a homogeneous solution. Water and ethanol, for example, are fully miscible such that a mixture containing water and ethanol in any ratio will show only one phase. Miscibility is provided as a wt/wt %, or weight of one solvent in 100 g of final solution. If two solvents are fully miscible in all proportions, their miscibility is 100%. Provided as fully miscible solutions with water are alcohols, e.g., methanol, ethanol, isopropanol, butanol, etc. The alcohols can be provided already combined with water; e.g., a solution containing 10%, 20%, 25%, 30%, 35%, 40%, 45%, 50%, 55%, 60%, 65%, 70%, 75%, 89%, 85%, 90%, 95% or greater than 95% Other solvents are only partially miscible, meaning that only some portion will dissolve in water. Diethyl ether, for example, is partially miscible with water. Up to 7 grams of diethyl ether will dissolve in 93 g of water to give a 7% (wt/wt %) solution. If more diethyl ether is added, a two phase solution will result with a distinct diethyl ether layer above the water. Other miscible materials include ethers, dimethoxyethane, or tetrahydrofuran In contrast, an oil such as an alkane and water are immiscible and form two phases. Further, immiscible treatments are optionally combined with a detergent, either an ionic detergent or a non-ionic detergent. Exemplary detergents include Triton X-100, Tween 20, Tween 80, Nonidet P40, a pluronic, or a polyol.

Chromatography Treatments

To purify spore populations, the fecal materials are subjected to one or more chromatographic treatments, either sequentially or in parallel. In a chromatographic treatment, a solution containing the fecal material is contacted with a solid medium containing a hydrophobic interaction chromatographic (HIC) medium or an affinity chromatographic medium. In an alternative embodiment, a solid medium capable of absorbing a residual habitat product present in the fecal material is contacted with a solid medium that adsorbs a residual habitat product. In certain embodiments, the HIC medium contains sepharose or a derivatized sepharose such as butyl sepharose, octyl sepharose, phenyl sepharose, or butyl-s sepharose. In other embodiments, the affinity chromatographic medium contains material derivatized with mucin type I, II, III, IV, V, or VI, or oligosaccharides derived from or similar to those of mucins type I, II, III, IV, V, or VI. Alternatively, the affinity chromatographic medium contains material derivatized with antibodies that recognize spore-forming bacteria.

Mechanical Treatments

Provided herein is the physical disruption of the fecal material, particularly by one or more mechanical treatment such as blending, mixing, shaking, vortexing, impact pulverization, and sonication. As provided herein, the mechanical disrupting treatment substantially disrupts a non-spore material present in the fecal material and does not substantially disrupt a spore present in the fecal material. Mechanical treatments optionally include filtration treatments, where the desired spore populations are retained on a filter while the undesirable (non-spore) fecal components to pass through, and the spore fraction is then recovered from the filter medium. Alternatively, undesirable particulates and eukaryotic cells may be retained on a filter while bacterial cells including spores pass through. In some embodiments the spore fraction retained on the filter medium is subjected to a diafiltration step, wherein the retained spores are contacted with a wash liquid, typically a sterile saline-containing solution or other diluent, in order to further reduce or remove the undesirable fecal components.

Thermal Treatments

Provided herein is the thermal disruption of the fecal material. Generally, the fecal material is mixed in a saline-containing solution such as phosphate-buffered saline (PBS) and subjected to a heated environment, such as a warm room, incubator, water-bath, or the like, such that efficient heat transfer occurs between the heated environment and the fecal material. Preferably the fecal material solution is mixed during the incubation to enhance thermal conductivity and disrupt particulate aggregates. Thermal treatments can be modulated by the temperature of the environment and/or the duration of the thermal treatment. For example, the fecal material or a liquid comprising the fecal material is subjected to a heated environment, e.g., a hot water bath of at least about 20, 25, 30, 35, 40, 45, 50, 55, 60, 65, 70, 75, 80, 85, 90, 95, 100 or greater than 100 degrees Celsius, for at least about 1, 5, 10, 15, 20, 30, 45 seconds, or 1, 2, 3, 4, 5, 6, 7, 8, 9, 10, 15, 20, 25, 30, 40, or 50 minutes, or 1, 2, 3, 4, 5, 6, 7, 8, 9, 10 or more than 10 hours. In certain embodiments the thermal treatment occurs at two different temperatures, such as 30 seconds in a 100 degree Celsius environment followed by 10 minutes in a 50 degree Celsius environment. In preferred embodiments the temperature and duration of the thermal treatment are sufficient to kill or remove pathogenic materials while not substantially damaging or reducing the germination-competency of the spores.

Irradiation Treatments

Provided are methods of treating the fecal material or separated contents of the fecal material with ionizing radiation, typically gamma irradiation, ultraviolet irradiation or electron beam irradiation provided at an energy level sufficient to kill pathogenic materials while not substantially damaging the desired spore populations. For example, ultraviolet radiation at 254 nm provided at an energy level below about 22,000 microwatt seconds per $cm^2$ will not generally destroy desired spores.

Centrifugation and Density Separation Treatments

Provided are methods of separating desired spore populations from the other components of the fecal material by centrifugation. A solution containing the fecal material is subjected to one or more centrifugation treatments, e.g., at about 1000×g, 2000×g, 3000×g, 4000×g, 5000×g, 6000×g, 7000×g, 8000×g or greater than 8000×g. Differential centrifugation separates desired spores from undesired non-spore material; at low forces the spores are retained in solution, while at higher forces the spores are pelleted while smaller impurities (e.g., virus particles, phage) are retained in solution. For example, a first low force centrifugation pellets fibrous materials; a second, higher force centrifugation pellets undesired eukaryotic cells, and a third, still higher force centrifugation pellets the desired spores while small contaminants remain in suspension. In some embodiments density or mobility gradients or cushions (e.g., step cushions), such as Percoll, Ficoll, Nycodenz, Histodenz or sucrose gradients, are used to separate desired spore populations from other materials in the fecal material.

Also provided herein are methods of producing spore populations that combine two or more of the treatments described herein in order to synergistically purify the desired spores while killing or removing undesired materials and/or activities from the spore population. It is generally desirable to retain the spore populations under non-germinating and non-growth promoting conditions and media, in order to minimize the growth of pathogenic bacteria present in the spore populations and to minimize the germination of spores into vegetative bacterial cells.

Pharmaceutical Compositions and Formulations of the Invention

Formulations

Provided are formulations for administration to humans and other subjects in need thereof. Generally the bacterial compositions are combined with additional active and/or inactive materials in order to produce a final product, which may be in single dosage unit or in a multi-dose format.

In some embodiments, the composition comprises at least one carbohydrate. A "carbohydrate" refers to a sugar or polymer of sugars. The terms "saccharide," "polysaccharide," "carbohydrate," and "oligosaccharide" may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate can be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates can contain modified saccharide units, such as 2'-deoxyribose wherein a hydroxyl group is removed, 2'-fluororibose wherein a hydroxyl group is replace with a fluorine, or N-acetylglucosamine, a nitrogen-containing form of glucose (e.g., 2'-fluororibose, deoxyribose, and hexose). Carbohydrates can exist in many different forms, for example, conformers, cyclic forms, acyclic forms, stereoisomers, tautomers, anomers, and isomers.

In some embodiments, the composition comprises at least one lipid. As used herein, a "lipid" includes fats, oils, triglycerides, cholesterol, phospholipids, fatty acids in any form including free fatty acids. Fats, oils and fatty acids can be saturated, unsaturated (cis or trans) or partially unsaturated (cis or trans). In some embodiments, the lipid comprises at least one fatty acid selected from lauric acid (12:0), myristic acid (14:0), palmitic acid (16:0), palmitoleic acid (16:1), margaric acid (17:0), heptadecenoic acid (17:1), stearic acid (18:0), oleic acid (18:1), linoleic acid (18:2), linolenic acid (18:3), octadecatetraenoic acid (18:4), arachidic acid (20:0), eicosenoic acid (20:1), eicosadienoic acid (20:2), eicosatetraenoic acid (20:4), eicosapentaenoic acid (20:5) (EPA), docosanoic acid (22:0), docosenoic acid (22:1), docosapentaenoic acid (22:5), docosahexaenoic acid (22:6) (DHA), and tetracosanoic acid (24:0). In other embodiments, the composition comprises at least one modified lipid, for example, a lipid that has been modified by cooking.

In some embodiments, the composition comprises at least one supplemental mineral or mineral source. Examples of minerals include, without limitation: chloride, sodium, calcium, iron, chromium, copper, iodine, zinc, magnesium, manganese, molybdenum, phosphorus, potassium, and selenium. Suitable forms of any of the foregoing minerals include soluble mineral salts, slightly soluble mineral salts, insoluble mineral salts, chelated minerals, mineral complexes, non-reactive minerals such as carbonyl minerals, and reduced minerals, and combinations thereof.

In certain embodiments, the composition comprises at least one supplemental vitamin. The at least one vitamin can be fat-soluble or water soluble vitamins. Suitable vitamins include but are not limited to vitamin C, vitamin A, vitamin E, vitamin B12, vitamin K, riboflavin, niacin, vitamin D, vitamin B6, folic acid, pyridoxine, thiamine, pantothenic acid, and biotin. Suitable forms of any of the foregoing are salts of the vitamin, derivatives of the vitamin, compounds having the same or similar activity of the vitamin, and metabolites of the vitamin.

In other embodiments, the composition comprises an excipient. Non-limiting examples of suitable excipients include a buffering agent, a preservative, a stabilizer, a binder, a compaction agent, a lubricant, a dispersion enhancer, a disintegration agent, a flavoring agent, a sweetener, and a coloring agent.

In another embodiment, the excipient is a buffering agent. Non-limiting examples of suitable buffering agents include sodium citrate, magnesium carbonate, magnesium bicarbonate, calcium carbonate, and calcium bicarbonate.

In some embodiments, the excipient comprises a preservative. Non-limiting examples of suitable preservatives include antioxidants, such as alpha-tocopherol and ascorbate, and antimicrobials, such as parabens, chlorobutanol, and phenol.

In other embodiments, the composition comprises a binder as an excipient. Non-limiting examples of suitable binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, and combinations thereof.

In another embodiment, the composition comprises a lubricant as an excipient. Non-limiting examples of suitable lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

In other embodiments, the composition comprises a dispersion enhancer as an excipient. Non-limiting examples of suitable dispersants include starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

In some embodiments, the composition comprises a disintegrant as an excipient. In other embodiments, the disintegrant is a non-effervescent disintegrant. Non-limiting examples of suitable non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. In another embodiment, the disintegrant is an effervescent disintegrant. Non-limiting examples of suitable effervescent disintegrants include sodium bicarbonate in combination with citric acid, and sodium bicarbonate in combination with tartaric acid.

In another embodiment, the excipient comprises a flavoring agent. Flavoring agents can be chosen from synthetic flavor oils and flavoring aromatics; natural oils; extracts from plants, leaves, flowers, and fruits; and combinations thereof. In some embodiments the flavoring agent is selected from cinnamon oils; oil of wintergreen; peppermint oils; clover oil; hay oil; anise oil; eucalyptus; vanilla; citrus oil such as lemon oil, orange oil, grape and grapefruit oil; and fruit essences including apple, peach, pear, strawberry, raspberry, cherry, plum, pineapple, and apricot.

In other embodiments, the excipient comprises a sweetener. Non-limiting examples of suitable sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevia Rebaudiana* (Stevioside); chloro derivatives of sucrose such as sucralose; and sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In yet other embodiments, the composition comprises a coloring agent. Non-limiting examples of suitable color agents include food, drug and cosmetic colors (FD&C), drug and cosmetic colors (D&C), and external drug and cosmetic colors (Ext. D&C). The coloring agents can be used as dyes or their corresponding lakes.

The weight fraction of the excipient or combination of excipients in the formulation is usually about 99% or less, such as about 95% or less, about 90% or less, about 85% or less, about 80% or less, about 75% or less, about 70% or less, about 65% or less, about 60% or less, about 55% or less, 50% or less, about 45% or less, about 40% or less, about 35% or less, about 30% or less, about 25% or less, about 20% or less, about 15% or less, about 10% or less, about 5% or less, about 2% or less, or about 1% or less of the total weight of the composition.

The bacterial compositions disclosed herein can be formulated into a variety of forms and administered by a number of different means. The compositions can be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. In an exemplary embodiment, the bacterial composition is administered orally.

Solid dosage forms for oral administration include capsules, tablets, caplets, pills, troches, lozenges, powders, and granules. A capsule typically comprises a core material comprising a bacterial composition and a shell wall that encapsulates the core material. In some embodiments, the core material comprises at least one of a solid, a liquid, and an emulsion. In other embodiments, the shell wall material comprises at least one of a soft gelatin, a hard gelatin, and a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In yet other embodiments, at least one polymer functions as taste-masking agents.

Tablets, pills, and the like can be compressed, multiply compressed, multiply layered, and/or coated. The coating can be single or multiple. In one embodiment, the coating material comprises at least one of a saccharide, a polysaccharide, and glycoproteins extracted from at least one of a plant, a fungus, and a microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments the coating material comprises a protein. In another embodiment, the coating material comprises at least one of a fat and an oil. In other embodiments, the at least one of a fat and an oil is high temperature melting. In yet another embodiment, the at least one of a fat and an oil is hydrogenated or partially hydrogenated. In one embodiment, the at least one of a fat and an oil is derived from a plant. In other embodiments, the at least one of a fat and an oil comprises at least one of glycerides, free fatty acids, and fatty acid esters. In some embodiments, the coating material comprises at least one edible wax. The edible wax can be derived from animals, insects, or plants. Non-limiting examples include beeswax, lanolin, bayberry wax, carnauba wax, and rice bran wax. Tablets and pills can additionally be prepared with enteric coatings.

Alternatively, powders or granules embodying the bacterial compositions disclosed herein can be incorporated into a food product. In some embodiments, the food product is a drink for oral administration. Non-limiting examples of a suitable drink include fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. Other suitable means for oral administration include aqueous and nonaqueous solutions, emulsions, suspensions and solutions and/or suspensions reconstituted from non-effervescent granules, containing at least one of suitable solvents, preservatives, emulsifying agents, suspending agents, diluents, sweeteners, coloring agents, and flavoring agents.

In some embodiments, the food product can be a solid foodstuff. Suitable examples of a solid foodstuff include without limitation a food bar, a snack bar, a cookie, a brownie, a muffin, a cracker, an ice cream bar, a frozen yogurt bar, and the like.

In other embodiments, the compositions disclosed herein are incorporated into a therapeutic food. In some embodiments, the therapeutic food is a ready-to-use food that optionally contains some or all essential macronutrients and micronutrients. In another embodiment, the compositions disclosed herein are incorporated into a supplementary food that is designed to be blended into an existing meal. In one embodiment, the supplemental food contains some or all essential macronutrients and micronutrients. In another embodiment, the bacterial compositions disclosed herein are blended with or added to an existing food to fortify the food's protein nutrition. Examples include food staples (grain, salt, sugar, cooking oil, margarine), beverages (coffee, tea, soda, beer, liquor, sports drinks), snacks, sweets and other foods.

In one embodiment, the formulations are filled into gelatin capsules for oral administration. An example of an appropriate capsule is a 250 mg gelatin capsule containing from 10 (up to 100 mg) of lyophilized powder ($10^8$ to $10^{11}$ bacteria), 160 mg microcrystalline cellulose, 77.5 mg gelatin, and 2.5 mg magnesium stearate. In an alternative embodiment, from $10^5$ to $10^{12}$ bacteria may be used, $10^5$ to $10^7$, $10^6$ to $10^7$, or $10^8$ to $10^{10}$, with attendant adjustments of the excipients if necessary. In an alternative embodiment, an enteric-coated capsule or tablet or with a buffering or protective composition can be used.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, Biochemistry (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B(1992).

Example 1: Sequence-based Genomic Characterization of Operational Taxonomic Units (OTU) and Functional Genes Method for Determining 16S rDNA Gene Sequence As described above, OTUs are defined either by full 16S sequencing of the rRNA gene, by sequencing of a specific hypervariable region of this gene (i.e. V1, V2, V3, V4, V5, V6, V7, V8, or V9), or by sequencing of any combination of hypervariable regions from this gene (e.g. V1-3 or V3-5). The bacterial 16S rRNA gene is approximately 1500 nucleotides in length and is used in reconstructing the evolutionary relationships and sequence similarity of one bacterial isolate to another using phylogenetic approaches. 16S sequences are used for phylogenetic reconstruction as they are in general highly conserved, but contain specific hypervariable regions that harbor sufficient nucleotide diversity to differentiate genera and species of most microbes. rRNA gene sequencing methods are applicable to both the analysis of non-enriched samples, but also for identification of microbes after enrichment steps that either enrich the microbes of interest from the microbial composition and/or the nucleic acids that harbor the appropriate rDNA gene sequences as described below. For example, enrichment treatments prior to 16S rDNA gene characterization will increase the sensitivity of 16S as well as other molecular-based characterization nucleic acid purified from the microbes.

Using well known techniques, in order to determine the full 16S sequence or the sequence of any hypervariable region of the 16S rRNA sequence, genomic DNA is extracted from a bacterial sample, the 16S rDNA (full region or specific hypervariable regions) amplified using polymerase chain reaction (PCR), the PCR products cleaned, and nucleotide sequences delineated to determine the genetic composition of 16S gene or subdomain of the gene. If full 16S sequencing is performed, the sequencing method used may be, but is not limited to, Sanger sequencing. If one or more hypervariable regions are used, such as the V4 region, the sequencing may be, but is not limited to being, performed using the Sanger method or using a next-generation sequencing method, such as an Illumina (sequencing by synthesis) method using barcoded primers allowing for multiplex reactions.

Method for Determining 18S rDNA and ITS Gene Sequence

Methods to assign and identify fungal OTUs by genetic means can be accomplished by analyzing 18S sequences and the internal transcribed spacer (ITS). The rRNA of fungi that forms the core of the ribosome is transcribed as a signal gene and consists of the 8S, 5.8S and 28S regions with ITS4 and 5 between the 8S and 5.8S and 5.8S and 28S regions, respectively. These two intercistronic segments between the 18S and 5.8S and 5.8S and 28S regions are removed by splicing and contain significant variation between species for barcoding purposes as previously described (Schoch et al Nuclear ribosomal internal transcribed spacer (ITS) region as a universal DNA barcode marker for Fungi. PNAS 109:6241-6246. 2012). 18S rDNA is traditionally used for phylogenetic reconstruction however the ITS can serve this function as it is generally highly conserved but contains hypervariable regions that harbor sufficient nucleotide diversity to differentiate genera and species of most fungus.

Using well known techniques, in order to determine the full 18S and ITS sequences or a smaller hypervariable section of these sequences, genomic DNA is extracted from a microbial sample, the rDNA amplified using polymerase chain reaction (PCR), the PCR products cleaned, and nucleotide sequences delineated to determine the genetic composition rDNA gene or subdomain of the gene. The sequencing method used may be, but is not limited to, Sanger sequencing or using a next-generation sequencing method, such as an Illumina (sequencing by synthesis) method using barcoded primers allowing for multiplex reactions.

Method for Determining Other Marker Gene Sequences

In addition to the 16S and 18S rRNA gene, one may define an OTU by sequencing a selected set of genes that are known to be marker genes for a given species or taxonomic group of OTUs. These genes may alternatively be assayed using a PCR-based screening strategy. As example, various strains of pathogenic *Escherichia coli* can be distinguished using DNAs from the genes that encode heat-labile (LTI, LTIIa, and LTIIb) and heat-stable (STI and STII) toxins, verotoxin types 1, 2, and 2e (VT1, VT2, and VT2e, respectively), cytotoxic necrotizing factors (CNF1 and CNF2), attaching and effacing mechanisms (eaeA), enteroaggregative mechanisms (Eagg), and enteroinvasive mechanisms (Einv). The optimal genes to utilize for taxonomic assignment of OTUs by use of marker genes will be familiar to one with ordinary skill of the art of sequence based taxonomic identification.

Genomic DNA Extraction

Genomic DNA is extracted from pure microbial cultures using a hot alkaline lysis method. 1 μl of microbial culture is added to 9 μl of Lysis Buffer (25 mM NaOH, 0.2 mM EDTA) and the mixture is incubated at 95° C. for 30 minutes. Subsequently, the samples are cooled to 4° C. and neutralized by the addition of 10 μl of Neutralization Buffer (40 mM Tris-HCl) and then diluted 10-fold in Elution Buffer (10 mM Tris-HCl). Alternatively, genomic DNA is extracted from pure microbial cultures using commercially available kits such as the Mo Bio Ultraclean® Microbial DNA Isolation Kit (Mo Bio Laboratories, Carlsbad, Calif.) or by standard methods known to those skilled in the art. For fungal samples, DNA extraction can be performed by methods described previously (US20120135127) for producing lysates from fungal fruiting bodies by mechanical grinding methods.

Amplification of 16S Sequences for Downstream Sanger Sequencing

To amplify bacterial 16S rDNA (e.g, in FIG. 1), 2 μl of extracted gDNA is added to a 20 μl final volume PCR reaction. For full-length 16 sequencing the PCR reaction also contains 1× HotMasterMix (5PRIME, Gaithersburg, Md.), 250 nM of 27f (AGRGTTTGATCMTGGCTCAG (SEQ ID NO: 2033), IDT, Coralville, Iowa), and 250 nM of 1492r (TACGGYTACCTTGTTAYGACTT (SEQ ID NO: 2034), IDT, Coralville, Iowa), with PCR Water (Mo Bio Laboratories, Carlsbad, Calif.) for the balance of the volume.

Figure 1:
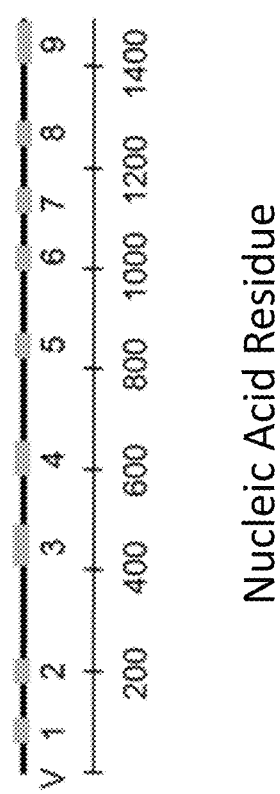
FIG. 1 provides a schematic of 16S rRNA gene and denotes the coordinates of hypervariable regions 1-9 (V1-V9), according to an embodiment of the invention. Coordinates of V1-V9 are 69-99, 137-242, 433-497, 576-682, 822-879, 986-1043, 1117-1173, 1243-1294, and 1435-1465 respectively, based on numbering using *E. coli* system of nomenclature defined by Brosius et al., Complete nucleotide sequence of a 16S ribosomal RNA gene (16S rRNA) from *Escherichia coli*, PNAS 75(10):4801-4805 (1978).

FIG. 1 shows the hypervariable regions mapped onto a 16s sequence and the sequence regions corresponding to these sequences on a sequence map. A schematic is shown of a 16S rRNA gene and the figure denotes the coordinates of hypervariable regions 1-9 (V1-V9), according to an embodiment of the invention. Coordinates of V1-V9 are 69-99, 137-242, 433-497, 576-682, 822-879, 986-1043, 1117-1173, 1243-1294, and 1435-1465 respectively, based on numbering using *E. coli* system of nomenclature defined by Brosius et al., Complete nucleotide sequence of a 16S ribosomal RNA gene (16S rRNA) from *Escherichia coli*, PNAS 75(10):4801-4805 (1978).

Alternatively, other universal bacterial primers or thermostable polymerases known to those skilled in the art are used. For example, primers are available to those skilled in the art for the sequencing of the the "V1-V9 regions" of the 16S rRNA (e.g., FIG. 1). These regions refer to the first through ninth hypervariable regions of the 16S rRNA gene that are used for genetic typing of bacterial samples. These regions in bacteria are defined by nucleotides 69-99, 137-242, 433-497, 576-682, 822-879, 986-1043, 1117-1173, 1243-1294 and 1435-1465 respectively using numbering based on the *E. coli* system of nomenclature. See Brosius et al., Complete nucleotide sequence of a 16S ribosomal RNA gene from *Escherichia coli*, PNAS 75(10):4801-4805 (1978). In some embodiments, at least one of the V1, V2, V3, V4, V5, V6, V7, V8, and V9 regions are used to characterize an OTU. In one embodiment, the V1, V2, and V3 regions are used to characterize an OTU. In another embodiment, the V3, V4, and V5 regions are used to characterize an OTU. In another embodiment, the V4 region is used to characterize an OTU. A person of ordinary skill in the art can identify the specific hypervariable regions of a candidate 16S rRNA (e.g., FIG. 1) by comparing the candidate sequence in question to the reference sequence (as in FIG. 2) and identifying the hypervariable regions based on similarity to the reference hypervariable regions. FIG. 2 highlights in bold the nucleotide sequences for each hypervariable region in the exemplary reference *E. coli* 16S sequence described by Brosius et al.

The PCR is performed on commercially available thermocyclers such as a BioRad MyCycler™ Thermal Cycler (BioRad, Hercules, Calif.). The reactions are run at 94° C. for 2 minutes followed by 30 cycles of 94° C. for 30 seconds, 51° C. for 30 seconds, and 68° C. for 1 minute 30 seconds, followed by a 7 minute extension at 72° C. and an indefinite hold at 4° C. Following PCR, gel electrophoresis of a portion of the reaction products is used to confirm successful amplification of a ~1.5 kb product.

To remove nucleotides and oligonucleotides from the PCR products, 2 μl of HT ExoSap-IT (Affymetrix, Santa Clara, Calif.) is added to 5 μl of PCR product followed by a 15 minute incubation at 37° C. and then a 15 minute inactivation at 80° C.

Amplification of 16S Sequences for Downstream Characterization By Massively Parallel Sequencing Technologies Amplification performed for downstream sequencing by short read technologies such as Illumina require amplification using primers known to those skilled in the art that additionally include a sequence-based barcoded tag. As example, to amplify the 16s hypervariable region V4 region of bacterial 16S rDNA, 2 μl of extracted gDNA is added to a 20 μl final volume PCR reaction. The PCR reaction also contains 1× HotMasterMix (5PRIME, Gaithersburg, Md.), 200 nM of V4_515f_adapt (AATGATACGGCGAC-CACCGAGATCTACACTATGGTAAT-TGTGTGCCAGCMGCCGCGG TAA (SEQ ID NO: 2035), IDT, Coralville, Iowa), and 200 nM of barcoded 806rbc (CAAGCAGAAGACGGCATACGAGAT_12bpGolay Barcode_AGTCAGTCAGCCGGACTAC HVGGGTWTCTAAT (SEQ ID NOs: 2036-2037, respectively, in order of appearance), IDT, Coralville, Iowa), with PCR Water (Mo Bio Laboratories, Carlsbad, Calif.) for the balance of the volume. These primers incorporate barcoded adapters for Illumina sequencing by synthesis. Optionally, identical replicate, triplicate, or quadruplicate reactions may be performed. Alternatively other universal bacterial primers or thermostable polymerases known to those skilled in the art are used to obtain different amplification and sequencing error rates as well as results on alternative sequencing technologies.

The PCR amplification is performed on commercially available thermocyclers such as a BioRad MyCycler™ Thermal Cycler (BioRad, Hercules, Calif.). The reactions are run at 94° C. for 3 minutes followed by 25 cycles of 94° C. for 45 seconds, 50° C. for 1 minute, and 72° C. for 1 minute 30 seconds, followed by a 10 minute extension at 72° C. and a indefinite hold at 4° C. Following PCR, gel electrophoresis of a portion of the reaction products is used to confirm successful amplification of a ~1.5 kb product. PCR cleanup is performed as described above.

Sanger Sequencing of Target Amplicons from Pure Homogeneous Samples

To detect nucleic acids for each sample, two sequencing reactions are performed to generate a forward and reverse sequencing read. For full-length 16s sequencing primers 27f and 1492r are used. 40 ng of ExoSap-IT-cleaned PCR products are mixed with 25 pmol of sequencing primer and Mo Bio Molecular Biology Grade Water (Mo Bio Laboratories, Carlsbad, Calif.) to 15 µl total volume. This reaction is submitted to a commercial sequencing organization such as Genewiz (South Plainfield, N.J.) for Sanger sequencing.

Amplification of 18S and ITS regions for Downstream Sequencing

To amplify the 18S or ITS regions, 2 µL fungal DNA were amplified in a final volume of 30 µL with 15 µL AmpliTaq Gold 360 Mastermix, PCR primers, and water. The forward and reverse primers for PCR of the ITS region are 5'-TCCTCCGCTTATTGATATGC-3' (SEQ ID NO: 2038) and 5'-GGAAGTAAAAGTCGTAACAAGG-3' (SEQ ID NO: 2039) and are added at 0.2 uM concentration each. The forward and reverse primers for the 18s region are 5'-GTAGTCATATGCTTGTCTC-3' (SEQ ID NO: 2040) and 5'-CTTCCGTCAATTCCTTTAAG-3' (SEQ ID NO: 2041) and are added at 0.4 uM concentration each. PCR is performed with the following protocol: 95 C for 10 min, 35 cycles of 95 C for 15 seconds, 52 C for 30 seconds, 72 C for 1.5 s; and finally 72 C for 7 minutes followed by storage at 4 C. All forward primers contained the M13F-20 sequencing primer, and reverse primers included the M13R-27 sequencing primer. PCR products (3 µL) were enzymatically cleaned before cycle sequencing with 1 µL ExoSap-IT and 1 µL Tris EDTA and incubated at 37° C. for 20 min followed by 80° C. for 15 min. Cycle sequencing reactions contained 5 µL cleaned PCR product, 2 µL BigDye Terminator v3.1 Ready Reaction Mix, 1 µL 5× Sequencing Buffer, 1.6 pmol of appropriate sequencing primers designed by one skilled in the art, and water in a final volume of 10 µL. The standard cycle sequencing protocol is 27 cycles of 10 s at 96° C., 5 s at 50° C., 4 min at 60° C., and hold at 4° C. Sequencing cleaning is performed with the BigDye XTerminator Purification Kit as recommended by the manufacturer for 10-µL volumes. The genetic sequence of the resulting 18S and ITS sequences is performed using methods familiar to one with ordinary skill in the art using either Sanger sequencing technology or next-generation sequencing technologies such as but not limited to Illumina.

Preparation of Extracted Nucleic Acids for Metagenomic Characterization by Massively Parallel Sequencing Technologies Extracted nucleic acids (DNA or RNA) are purified and prepared by downstream sequencing using standard methods familiar to one with ordinary skill in the art and as described by the sequencing technology's manufactures instructions for library preparation. In short, RNA or DNA are purified using standard purification kits such as but not limited to Qiagen's RNeasy Kit or Promega's Genomic DNA purification kit. For RNA, the RNA is converted to cDNA prior to sequence library construction. Following purification of nucleic acids, RNA is converted to cDNA using reverse transcription technology such as but not limited to Nugen Ovation RNA-Seq System or Illumina Truseq as per the manufacturer's instructions. Extracted DNA or transcribed cDNA are sheared using physical (e.g., Hydroshear), acoustic (e.g., Covaris), or molecular (e.g., Nextera) technologies and then size selected as per the sequencing technologies manufacturer's recommendations. Following size selection, nucleic acids are prepared for sequencing as per the manufacturer's instructions for sample indexing and sequencing adapter ligation using methods familiar to one with ordinary skill in the art of genomic sequencing.

Massively Parallel Sequencing of Target Amplicons from Heterogeneous Samples DNA Quantification & Library Construction The cleaned PCR amplification products are quantified using the Quant-iT™ PicoGreen® dsDNA Assay Kit (Life Technologies, Grand Island, N.Y.) according to the manufacturer's instructions. Following quantification, the barcoded cleaned PCR products are combined such that each distinct PCR product is at an equimolar ratio to create a prepared Illumina library.

Nucleic Acid Detection

The prepared library is sequenced on Illumina HiSeq or MiSeq sequencers (Illumina, San Diego, Calif.) with cluster generation, template hybridization, isothermal amplification, linearization, blocking and denaturation and hybridization of the sequencing primers performed according to the manufacturer's instructions. 16SV4SeqFw (TATGGTAAT-TGTGTGCCAGCMGCCGCGGTAA (SEQ ID NO: 2042)), 16SV4SeqRev (AGTCAGTCAGCCGGAC-TACHVGGGTWTCTAAT (SEQ ID NO. 2037)), and 16SV4Index (ATT-AGAWACCCBDGTAGTCCGGCTGACTGACT (SEQ ID NO: 2043) (IDT, Coralville, Iowa) are used for sequencing. Other sequencing technologies can be used such as but not limited to 454, Pacific Biosciences, Helicos, Ion Torrent, and Nanopore using protocols that are standard to someone skilled in the art of genomic sequencing.

Example 2. Sequence Read Annotation

Primary Read Annotation

Nucleic acid sequences are analyzed and annotated to define taxonomic assignments using sequence similarity and phylogenetic placement methods or a combination of the two strategies. A similar approach can be used to annotate protein names, protein function, transcription factor names, and any other classification schema for nucleic acid sequences. Sequence similarity based methods include those familiar to individuals skilled in the art including, but not limited to BLAST, BLASTx, tBLASTn, tBLASTx, RDP-classifier, DNAclust, and various implementations of these algorithms such as Qiime or Mothur. These methods rely on mapping a sequence read to a reference database and selecting the match with the best score and e-value. Common databases include, but are not limited to the Human Microbiome Project, NCBI non-redundant database, Greengenes, RDP, and Silva for taxonomic assignments. For functional assignments reads are mapped to various functional databases such as but not limited to COG, KEGG, BioCyc, and MetaCyc. Further functional annotations can be derived from 16S taxonomic annotations using programs such as PICRUST (M. Langille, et al 2013. Nature Biotechnology 31, 814-821). Phylogenetic methods can be used in combination with sequence similarity methods to improve the calling accuracy of an annotation or taxonomic assignment. Here tree topologies and nodal structure are used to refine the resolution of the analysis. In this approach we analyze nucleic acid sequences using one of numerous sequence similarity approaches and leverage phylogenetic methods that are well known to those skilled in the art, including but not limited to maximum likelihood phylogenetic reconstruction (see e.g. Liu K, Linder C R, and Warnow T. 2011. RAxML and FastTree: Comparing Two Methods for Large-Scale Maximum Likelihood Phylogeny Estimation. PLoS ONE 6: e27731. McGuire G, Denham M C, and Balding D J. 2001. Models of sequence evolution for DNA sequences containing gaps. Mol. Biol. Evol 18: 481-490. Wróbel B. 2008. Statistical measures of uncertainty for branches in phylogenetic trees inferred from molecular sequences by using model-based methods. J. Appl. Genet. 49: 49-67.) Sequence reads (e.g. 16S, 18S, or ITS) are placed into a reference phylogeny comprised of appropriate reference sequences. Annotations are made based on the placement of the read in the phylogenetic tree. The certainty or significance of the OTU annotation is defined based on the OTU's sequence similarity to a reference nucleic acid sequence and the proximity of the OTU sequence relative to one or more reference sequences in the phylogeny. As an example, the specificity of a taxonomic assignment is defined with confidence at the the level of Family, Genus, Species, or Strain with the confidence determined based on the position of bootstrap supported branches in the reference phylogenetic tree relative to the placement of the OTU sequence being interrogated. Nucleic acid sequences can be assigned functional annotations using the methods described above.

Clade Assignments

The ability of 16S-V4 OTU identification to assign an OTU as a specific species depends in part on the resolving power of the 16S-V4 region of the 16S gene for a particular species or group of species. Both the density of available reference 16S sequences for different regions of the tree as well as the inherent variability in the 16S gene between different species will determine the definitiveness of a taxonomic annotation. Given the topological nature of a phylogenetic tree and the fact that tree represents hierarchical relationships of OTUs to one another based on their sequence similarity and an underlying evolutionary model, taxonomic annotations of a read can be rolled up to a higher level using a clade-based assignment procedure. Using this approach, clades are defined based on the topology of a phylogenetic tree that is constructed from full-length 16S sequences using maximum likelihood or other phylogenetic models familiar to individuals with ordinary skill in the art of phylogenetics. Clades are constructed to ensure that all OTUs in a given clade are: (i) within a specified number of bootstrap supported nodes from one another (generally, 1-5 bootstraps), and (ii) share a defined percent similarity (for 16S molecular data typically set to 95%-97% sequence similarity). OTUs that are within the same clade can be distinguished as genetically and phylogenetically distinct from OTUs in a different clade based on 16S-V4 sequence data. OTUs falling within the same clade are evolutionarily closely related and may or may not be distinguishable from one another using 16S-V4 sequence data. The power of clade based analysis is that members of the same clade, due to their evolutionary relatedness, are likely to play similar functional roles in a microbial ecology such as that found in the human gut. Compositions substituting one species with another from the same clade are likely to have conserved ecological function and therefore are useful in the present invention. Notably in addition to 16S-V4 sequences, clade-based analysis can be used to analyze 18S, ITS, and other genetic sequences.

Notably, 16S sequences of isolates of a given OTU are phylogenetically placed within their respective clades, sometimes in conflict with the microbiological-based assignment of species and genus that may have preceded 16S-based assignment. Discrepancies between taxonomic assignment based on microbiological characteristics versus genetic sequencing are known to exist from the literature.

For a given network ecology or functional network ecology one can define a set of OTUs from the network's representative clades. As example, if a network was comprised of clade_100 and clade_102 it can be said to be comprised of at least one OTU from the group consisting of *Corynebacterium coyleae*, *Corynebacterium mucifaciens*, and *Corynebacterium ureicelerivorans*, and at least one OTU from the group consisting of *Corynebacterium appendicis*, *Corynebacterium genitalium*, *Corynebacterium glaucum*, *Corynebacterium imitans*, *Corynebacterium riegelii*, *Corynebacterium* sp. L_2012475, *Corynebacterium* sp. NML 93_0481, *Corynebacterium sundsvallense*, and *Corynebacterium tuscaniae* (see Table 1). Conversely as example, if a network was said to consist of *Corynebacterium coyleae* and/or *Corynebacterium mucifaciens* and/or *Corynebacterium ureicelerivorans*, and also consisted of *Corynebacterium appendicis* and/or *Corynebacterium genitalium* and/or *Corynebacterium glaucum* and/or *Corynebacterium imitans* and/or *Corynebacterium riegelii* and/or *Corynebacterium* sp. L_2012475 and/or *Corynebacterium* sp. NML 93_0481 and/or *Corynebacterium sundsvallense* and/or *Corynebacterium tuscaniae* it can be said to be comprised of clade_100 and clade_102.

The applicants made clade assignments to all OTUs reported in the application using the above described method and these assignments are reported in Table 1. In some embodiments, the network analysis permits substitutions of clade_172 by clade_172i. In another embodiment, the network analysis permits substitutions of clade_198 by clade_198i. In another embodiment, the network analysis permits substitutions of clade_260 by clade_260c, clade_260g or clade_260h. In another embodiment, the network analysis permits substitutions of clade_262 by clade_262i. In another embodiment, the network analysis permits substitutions of clade_309 by clade_309c, clade_309e, clade_309g, clade_309h or clade_309i. In another embodiment, the network analysis permits substitutions of clade_313 by clade_313f. In another embodiment, the network analysis permits substitutions of clade_325 by clade_325f. In another embodiment, the network analysis permits substitutions of clade_335 by clade_335i. In another embodiment, the network analysis permits substitutions of clade_351 by clade_351e. In another embodiment, the network analysis permits substitutions of clade_354 by clade_354e. In another embodiment, the network analysis permits substitutions of clade_360 by clade_360c, clade_360g, clade_360h, or clade_360i. In another embodiment, the network analysis permits substitutions of clade_378 by clade_378e. In another embodiment, the network analysis permits substitutions of clade_38 by clade_38e or clade_38i. In another embodiment, the network analysis permits substitutions of clade_408 by clade_408b, clade_408d, clade_408f, clade_408g or clade_408h. In another embodiment, the network analysis permits substitutions of clade_420 by clade_420f. In another embodiment, the network analysis permits substitutions of clade_444 by clade_444i. In another embodiment, the network analysis permits substitutions of clade_478 by clade_478i. In another embodiment, the network analysis permits substitutions of clade_479 by clade_479c, by clade_479g or by clade_479h. In another embodiment, the network analysis permits substitutions of clade_481 by clade_481a, clade_481b, clade_481e, clade_481g, clade_481h or by clade_481i. In another embodiment, the network analysis permits the network analysis permits substitutions of clade_497 by clade_497e or by clade_497f. In another embodiment, the network analysis permits the network analysis permits substitutions of clade_512 by clade_512i. In another embodiment, the network analysis permits the network analysis permits substitutions of clade_516 by clade_516c, by clade_516g or by clade_516h. In another embodiment, the network analysis permits the network analysis permits substitutions of clade_522 by clade_522i. In another embodiment, the network analysis permits the network analysis permits substitutions of clade_553 by clade_553i. In another embodiment, the network analysis permits the network analysis permits substitutions of clade_566 by clade_566f. In another embodiment, the network analysis permits the network analysis permits substitutions of clade_572 by clade_572i. In another embodiment, the network analysis permits the network analysis permits substitutions of clade_65 by clade_65e. In another embodiment, the network analysis permits the network analysis permits substitutions of clade_92 by clade_92e or by clade_92i. In another embodiment, the network analysis permits the network analysis permits substitutions of clade_96 by clade_96g or by clade_96h. In another embodiment, the network analysis permits the network analysis permits substitutions of clade_98 by clade_98i. These permitted clade substitutions are described in Table 22.

Metagenomic Read Annotation

Metagenomic or whole genome shotgun sequence data is annotated as described above, with the additional step that sequences are either clustered or assembled prior to annotation. Following sequence characterization as described above, sequence reads are demultiplexed using the indexing (i.e. barcodes). Following demultiplexing sequence reads are either: (i) clustered using a rapid clustering algorithm such as but not limited to UCLUST (http://drive5.com/usearch/manual/uclust algo.html) or hash methods such VICUNA (Xiao Yang, Patrick Charlebois, Sante Gnerre, Matthew G Coole, Niall J. Lennon, Joshua Z. Levin, James Qu, Elizabeth M. Ryan, Michael C. Zody, and Matthew R. Henn. 2012. De novo assembly of highly diverse viral populations. BMC Genomics 13:475). Following clustering a representative read for each cluster is identified based and analyzed as described above in "Primary Read Annotation". The result of the primary annotation is then applied to all reads in a given cluster. (ii) A second strategy for metagenomic sequence analysis is genome assembly followed by annotation of genomic assemblies using a platform such as but not limited to MetAMOS (T J. Treangen et al. 2013 Geneome Biology 14:R2), HUMAaN (Abubucker S, Segata N, Goll J, Schubert A M, Izard J, Cantarel B L, Rodriguez-Mueller B, Zucker J, Thiagaraj an M, Henrissat B, et al. 2012. Metabolic Reconstruction for Metagenomic Data and Its Application to the Human Microbiome ed. J. A. Eisen. PLoS Computational Biology 8: e1002358) and other methods familiar to one with ordinary skill in the art.

Example 3. OTU Identification Using Microbial Culturing Techniques

The identity of the bacterial species which grow up from a complex fraction can be determined in multiple ways. First, individual colonies are picked into liquid media in a 96 well format, grown up and saved as 15% glycerol stocks at −80° C. Aliquots of the cultures are placed into cell lysis buffer and colony PCR methods can be used to amplify and sequence the 16S rDNA gene (Example 1). Alternatively, colonies are streaked to purity in several passages on solid media. Well separated colonies are streaked onto the fresh plates of the same kind and incubated for 48-72 hours at 37° C. The process is repeated multiple times in order to ensure purity. Pure cultures are analyzed by phenotypic- or sequence-based methods, including 16S rDNA amplification and sequencing as described in Example 1. Sequence characterization of pure isolates or mixed communities e.g. plate scrapes and spore fractions can also include whole genome shotgun sequencing. The latter is valuable to determine the presence of genes associated with sporulation, antibiotic resistance, pathogenicity, and virulence. Colonies are also scraped from plates en masse and sequenced using a massively parallel sequencing method as described in Example 1, such that individual 16S signatures can be identified in a complex mixture. Optionally, the sample can be sequenced prior to germination (if appropriate DNA isolation procedures are used to lsye and release the DNA from spores) in order to compare the diversity of germinable species with the total number of species in a spore sample. As an alternative or complementary approach to 16S analysis, MALDI-TOF-mass spec is used for species identification (Barreau M, Pagnier I, La Scola B. 2013. Improving the identification of anaerobes in the clinical microbiology laboratory through MALDI-TOF mass spectrometry. Anaerobe 22: 123-125).

Example 4. Microbiological Strain Identification Approaches

Pure bacterial isolates are identified using microbiological methods as described in Wadsworth-KTL Anaerobic Microbiology Manual (Jouseimies-Somer H, Summanen P H, Citron D, Baron E, Wexler H M, Finegold S M. 2002. Wadsworth-KTL Anaerobic Bacteriology Manual), and The Manual of Clinical Microbiology (ASM Press, 10th Edition). These methods rely on phenotypes of strains and include Gram-staining to confirm Gram positive or negative staining behavior of the cell envelope, observance of colony morphologies on solid media, motility, cell morphology observed microscopically at 60× or 100× magnification including the presence of bacterial endospores and flagella. Biochemical tests that discriminate between genera and species are performed using appropriate selective and differential agars and/or commercially available kits for identification of Gram negative and Gram positive bacteria and yeast, for example, RapID tests (Remel) or API tests (bioMerieux). Similar identification tests can also be performed using instrumentation such as the Vitek 2 system (bioMerieux). Phenotypic tests that discriminate between genera and species and strains (for example the ability to use various carbon and nitrogen sources) can also be performed using growth and metabolic activity detection methods, for example the Biolog Microbial identification microplates. The profile of short chain fatty acid production during fermentation of particular carbon sources can also be used as a way to discriminate between species (Wadsworth-KTL Anaerobic Microbiology Manual, Jousimies-Somer, et al 2002). MALDI-TOF-mass spectrometry can also be used for species identification (as reviewed in Anaerobe 22:123).

Example 5. Computational Prediction of Network Ecologies

Source data comprising a genomic-based characterization of a microbiome of individual samples were used as input to computationally delineate network ecologies that would have biological properties that are characteristic of a state of health and could catalzye a shift from a state of microbial dysbiosis to a state of health. Applicants obtained 16S and metagenomic sequence datasets from public data repositories (see e.g. The Human Microbiome Project Consortium. 2012. Structure, function and diversity of the healthy human microbiome. Nature 486: 207-214. Data accessible at URL: hmpdacc.org) and MetaHit Project (Arumugam M, Raes J, Pelletier E, Paslier D L, Yamada T, Mende D R, Fernandes G R, Tap J, Bruls T, Batto J-M, et al. 2011. Enterotypes of the human gut microbiome. Nature 473: 174-180. Data accessible at URL: metahit.eu) for relevant microbiome studies in multiple disease indications including CDAD, Type 2 Diabetes, Ulcerative Colitis, and Irritable Bowel Disease, or generated data sets from samples directly using the methods described in Examples 1 & 2 and further described in the literature (see e.g. Aagaard K, Riehle K, Ma J, Segata N, Mistretta T-A, Coarfa C, Raza S, Rosenbaum S, Van den Veyver I, Milosavljevic A, et al. 2012. A Metagenomic Approach to Characterization of the Vaginal Microbiome Signature in Pregnancy ed. A. J. Ratner. PLoS ONE 7: e36466. Jumpstart Consortium Human Microbiome Project Data Generation Working Group. 2012. Evaluation of 16S rDNA-Based Community Profiling for Human Microbiome Research ed. J. Ravel. PLoS ONE 7: e39315. The Human Microbiome Project Consortium. 2012. Structure, function and diversity of the healthy human microbiome. Nature 486: 207-214.). Nucleic acid sequences were analyzed and taxonomic and phylogenetic assignments of specific OTUs were made using sequence similarity and phylogenetic methods that are well known to those skilled in the art, including but not limited to maximum likelihood phylogenetic reconstruction (see e.g. Liu K, Linder C R, and Warnow T. 2011. RAxML and FastTree: Comparing Two Methods for Large-Scale Maximum Likelihood Phylogeny Estimation. PLoS ONE 6: e27731. McGuire G, Denham M C, and Balding D J. 2001. Models of sequence evolution for DNA sequences containing gaps. Mol. Biol. Evol 18: 481-490. Wróbel B. 2008. Statistical measures of uncertainty for branches in phylogenetic trees inferred from molecular sequences by using model-based methods. J. Appl. Genet. 49: 49-67.) From these taxonomic assignments OTUs and clades in the dataset were defined using the method described in Examples 1 and 2. The certainty of the OTU call was defined based on the OTU's sequence similarity to a reference nucleic acid sequence and the proximity of the OTU sequence relative to one or more reference sequences in the phylogeny. The specificity of an OTU's taxonomic and phlylogenetic assignment determines whether the match is assigned at the level of Family, Genus, Species, or Strain, and the confidence of this assignment is determined based on the position of bootstrap supported branches in the reference phylogenetic tree relative to the placement of the OTU sequence being interrogated. In addition, microbial OTU assignments may be obtained from assignments made in peer-reviewed publications.

Applicants designated individual subject samples to biologically relevant sample phenotypes such as but not limited to "healthy state," "recurrent *Clostridium difficile* infection," "Crohn's disease," "Insulin Resistance," "Obesity," "Type 2 diabetes," "Ulcerative Colitis". In one embodiment samples are assigned to "health" and "disease" phenotypes. In another embodiment, samples are assigned higher resolution phenotype such as but not limited to: "health:human", "health:mouse", "health:human microbiome project", "health:microbiota donor", "health:microbiota recipient", "disease:microbiota recipient", or "disease:no treatment", "disease:human", or "disease:mouse". In another embodiment, samples where assigned to higher resolution phenotypes, such as but not limited to those defined in FIG. 19 that characterize phenotypes specific to samples from fecal donors and patients who received a fecal microbial transplant from these donors. FIG. 19 shows phenotypes assigned to samples for the computational derivation of Network Ecologies that typify microbiome states of health (Hpost, Hdon, & Hgen) and states of disease (DdonF & DpreF).

In another embodiment, other phenotypes that define a category of disease or health that represents the underlying state of the population under study can be used. Applicants then computationally determined the microbial network ecologies for each phenotype using the OTU and clade assignments that comprise the microbial profile for each sample and the algorithms described above in the Section entitled "Method of Determining Network Ecologies."

Tables 8, 11, and 14a below provide exemplary network ecologies that define states of health as compared to states of dysbiosis or disease for multiple disease indications. The disease indications for which the network ecologies represent a health state are denoted in Table 8, and Keystone and Non-Keystone OTUs (see Example 6) are delineated in Tables 9-10. Importantly, Network Ecologies that represent a state of health in one disease indication can represent states of health in additional disease states. Additionally, Keystone OTUs found in a network associated with health for different disease indications can overlap. Applicants found that a large number of network ecologies overlapped particularly between those associated with health in the cases of CDAD and Type 2 Diabetes despite the analysis of substantially different genomic data sets for the two diseases.

Example 6. Identification of Network Classes, Keystone OTUs, Clades, and Functional Modalities Identification of Keystone OTUs, Clades and Functions The human body is an ecosystem in which the microbiota and the microbiome play a significant role in the basic healthy function of human systems (e.g. metabolic, immunological, and neurological). The microbiota and resulting microbiome comprise an ecology of microorganisms that co-exist within single subjects interacting with one another and their host (i.e., the mammalian subject) to form a dynamic unit with inherent biodiversity and functional characteristics. Within these networks of interacting microbes (i.e. ecologies), particular members can contribute more significantly than others; as such these members are also found in many different ecologies, and the loss of these microbes from the ecology can have a significant impact on the functional capabilities of the specific ecology. Robert Paine coined the concept "Keystone Species" in 1969 (see Paine R T. 1969. A note on trophic complexity and community stability. The American Naturalist 103: 91-93) to describe the existence of such lynchpin species that are integral to a given ecosystem regardless of their abundance in the ecological community. Paine originally describe the role of the starfish *Pisaster ochraceus* in marine systems and since the concept has been experimentally validated in numerous ecosystems.

Keystone OTUs (as shown in Table 9), Phylogenetic Clades (a.k.a. Clades), and/or Functions (for example, but not limited to, KEGG Orthology Pathways) are computationally-derived by analysis of network ecologies elucidated from a defined set of samples that share a specific phenotype. Keystone OTUs, Clades and/or Functions are defined as all Nodes within a defined set of networks that meet two or more of the following criteria. Using Criterion 1, the node is frequently observed in networks, and the networks in which the node is observed are found in a large number of individual subjects; the frequency of occurrence of these Nodes in networks and the pervasiveness of the networks in individuals indicates these Nodes perform an important biological function in many individuals. Using Criterion 2, the node is frequently observed in networks, and the Node is observed contains a large number of edges connecting it to other nodes in the network. These Nodes are thus "superconnectors", meaning that they form a nucleus of a majority of networks (See FIG. 17) and as such have high biological significance with respect to their functional contributions to a given ecology.

Figure 17:
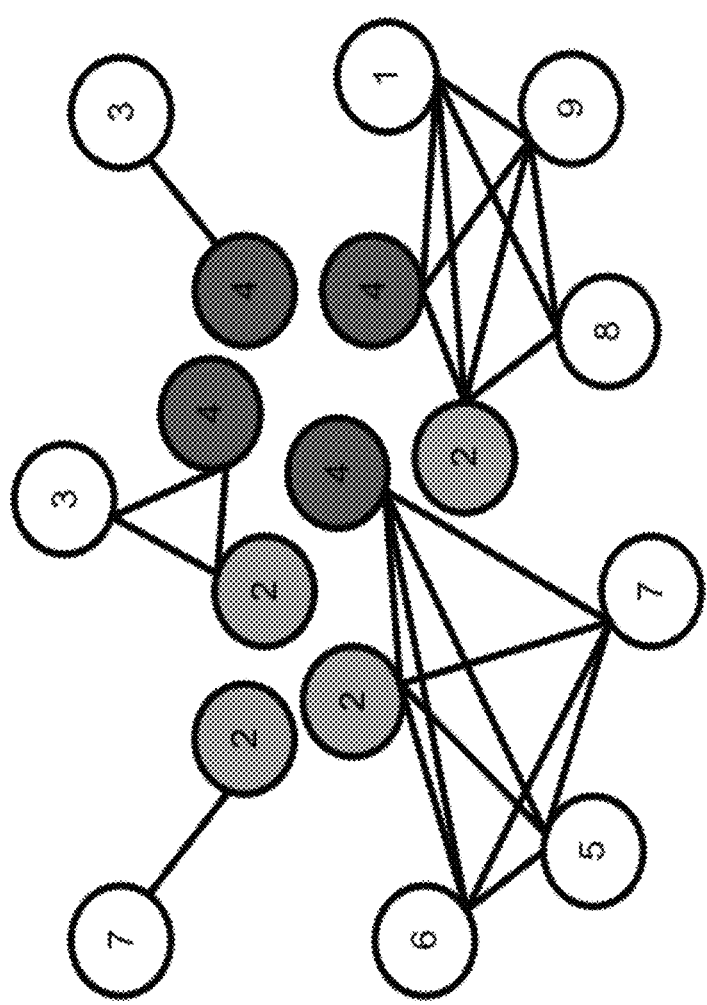
FIG. 17 is a schematic representation of how Keystone OTUs (nodes 2 and 4, shaded circles) are central members of many network ecologies that contain non-Keystone OTUs (nodes 1, 3, and 5-9). Distinct network ecologies include [node 2--node 7], [node--3--node 2--node--4], [node 2--node 4--node 5--node 6--node 7], [node 1--node 2--node 8--node 9], and [node--node 3].

FIG. 17 is a schematic representation of how Keystone OTUs (nodes 2 and 4, shaded circles) are central members of many network ecologies that contain non-Keystone OTUs (nodes 1, 3, and 5-9). Distinct network ecologies include [node 2--node 7], [node--3--node 2--node--4], [node 2--node 4--node 5--node 6--node 7], [node 1--node 2--node 8--node 9], and [node--node 3].

Using Criterion 3, the Node is found in networks containing a large number of Nodes (i.e., they are large networks), and the networks in which the Node is found occur in a large number of subjects; these networks are potentially of high interest as it is unlikely that large networks occurring in many individuals would occur by chance alone strongly suggesting biological relevance. Optionally, the required thresholds for the frequency at which a Node is observed in network ecologies, the frequency at which a given network is observed across subject samples, and the size of a given network to be considered a Keystone Node are defined by the 50th, 70th, 80th, or 90th percentiles of the distribution of these variables. Optionally, the required thresholds are defined by the value for a given variable that is significantly different from the mean or median value for a given variable using standard parametric or non-parametric measures of statistical significance. In another embodiment a Keystone Node is defined as one that occurs in a sample phenotype of interest such as but not limited to "health" and simultaneously does not occur in a sample phenotype that is not of interest such as but not limited to "disease." Optionally, a Keystone Node is defined as one that is shown to be significantly different from what is observed using permuted test datasets to measure significance. In another embodiment of Criterion 2 Keystone OTUs, Clades, or Functions can be defined using a hierarchical clustering method that clusters Networks based on their OTU, Clade, or functional pathways. Statistically significant branch points in the hierarchy are defined based on the topological overlap measure; this measure is a highly robust measure of network interconnectedness (Langfelder P, Zhang B, Horvath S. 2008. Defining clusters from a hierarchical cluster tree: the Dynamic Tree Cut package for R. Bioinformatics 24: 719-720.). Once these branch points are defined the Keystones are delineated as OTUs, clades or functional pathways that are found consistently across all networks in all or a subset of the network clusters.

Applicants defined the Keystone OTUs and Clades characteristic of health states for the computationally determined networks reported in Table 8 for the various disease indications analyzed using the three criterion defined above. Keystone Clades were defined from the Keystone OTUs using clade definitions as outlined in Example 1. Keystone OTUs are reported in Table 9. Importantly, we identified the absence of Keystone OTUs in multiple particular disease states, indicating that bacterial compositions comprised of specific sets of Keystone OTUs are likely to have utility in multiple disease indications.

Demonstration that Keystone OTUs inhibit *C. difficile* Growth in a Competitive In Vitro Simulation Assay To screen the ability of binary combinations comprising at least one Keystone OTU (binary pairs) to inhibit the growth of *Clostridium difficile* in vitro, vials of −80° C. glycerol stock banks of each OTU were thawed and diluted to 1e8 CFU/mL. Each strain was then diluted 10× (to a final concentration of 1e7 CFU/mL of each strain) into 200 uL of PBS+15% glycerol in the wells of a 96-well plate. Plates were then frozen at −80° C. When needed for the assay, plates were removed from −80° C. and thawed at room temperature under anaerobic conditions prior to use.

An overnight culture of *Clostridium difficile* was grown under anaerobic conditions in SweetB-FosIn or other suitable media for the growth of *C. difficile*. SweetB-FosIn is a complex media composed of brain heart infusion, yeast extract, cysteine, cellobiose, maltose, soluble starch, and fructooligosaccharides/inulin, and hemin, and is buffered with morpholino-propane sulphonic acid (MOPS). After 24 hr of growth the culture was diluted 100,000 fold into SweetB-FosIn. The diluted *C. difficile* mixture was then aliquoted to wells of a 96-well plate (180 uL to each well). 20 uL of a unique binary pair of Keystone OTUs was then added to each well at a final concentration of 1e6 CFU/mL of each species. Alternatively the assay can be tested with binary pairs at different initial concentrations (1e9 CFU/mL, 1e8 CFU/mL, 1e7 CFU/mL, 1e5 CFU/mL, 1e4 CFU/mL, 1e3 CFU/mL, 1e2 CFU/mL). Control wells only inoculated with *C. difficile* were included for a comparison to the growth of *C. difficile* without inhibition. Additional wells were used for controls that either inhibit or do not inhibit the growth of *C. difficile*. Plates were wrapped with parafilm and incubated for 24 hr at 37° C. under anaerobic conditions. After 24 hr the wells containing *C. difficile* alone were serially diluted and plated to determine titer on selective media such as CCFA (Anaerobe Systems) or CDSA (Becton Dickinson). The 96-well plate was then frozen at −80° C. before quantifying *C. difficile* by qPCR.

*C. difficile* in each well was quantified by qPCR. A standard curve was generated from a well on each assay plate containing only pathogenic *C. difficile* grown in SweetB+FosIn media as provided herein and compare to the microbiological titer determined above. Genomic DNA was extracted from the standard curve samples along with the other wells. Genomic DNA was extracted from 5 μl of each sample using a dilution, freeze/thaw, and heat lysis protocol. 5 μL of thawed samples were added to 45 μL of UltraPure water (Life Technologies, Carlsbad, Calif.) and mixed by pipetting. The plates with diluted samples were frozen at −20° C. until use for qPCR which includes a heated lysis step prior to amplification. Alternatively the genomic DNA could be isolated using the Mo Bio Powersoil®-htp 96 Well Soil DNA Isolation Kit (Mo Bio Laboratories, Carlsbad, Calif.), Mo Bio Powersoil® DNA Isolation Kit (Mo Bio Laboratories, Carlsbad, Calif.), or the QIAamp DNA Stool Mini Kit (QIAGEN, Valencia, Calif.) according to the manufacturer's instructions.

The qPCR reaction mixture contained 1× SsoAdvanced Universal Probes Supermix, 900 nM of Wr-tcdB-F primer (AGCAGTTGAATATAGTGGTTTAGTTAGAGTTG (SEQ ID NO: 2044), IDT, Coralville, Iowa), 900 nM of Wr-tcdB-R primer (CATGCTTTTTTAGTTTCTGGATTGAA (SEQ ID NO: 2045), IDT, Coralville, Iowa), 250 nM of Wr-tcdB-P probe (6FAM-CATCCAGTCTCAAT-TGTATATGTTTCTCCA-MGB (SEQ ID NO. 2046), Life Technologies, Grand Island, N.Y.), and Molecular Biology Grade Water (Mo Bio Laboratories, Carlsbad, Calif.) to 18 µl (Primers adapted from: Wroblewski, D. et al., Rapid Molecular Characterization of *Clostridium difficile* and Assessment of Populations of *C. difficile* in Stool Specimens, Journal of Clinical Microbiology 47:2142-2148 (2009)). This reaction mixture was aliquoted to wells of a Hard-shell Low-Profile Thin Wall 96-well Skirted PCR Plate (BioRad, Hercules, Calif.). To this reaction mixture, 2 µl of diluted, frozen, and thawed samples were added and the plate sealed with a Microseal 'B' Adhesive Seal (BioRad, Hercules, Calif.). The qPCR was performed on a BioRad C1000™ Thermal Cycler equipped with a CFX96™ Real-Time System (BioRad, Hercules, Calif.). The thermocycling conditions were 95° C. for 15 minutes followed by 45 cycles of 95° C. for 5 seconds, 60° C. for 30 seconds, and fluorescent readings of the FAM channel. Alternatively, the qPCR could be performed with other standard methods known to those skilled in the art.

The Cq value for each well on the FAM channel was determined by the CFX Manager™ 3.0 software. The log 10(cfu/mL) of *C. difficile* each experimental sample was calculated by inputting a given sample's Cq value into a linear regression model generated from the standard curve comparing the Cq values of the standard curve wells to the known log 10(cfu/mL) of those samples. The log inhibition was calculated for each sample by subtracting the log 10(cfu/mL) of *C. difficile* in the sample from the log 10(cfu/mL) of *C. difficile* in the sample on each assay plate used for the generation of the standard curve that has no additional bacteria added. The mean log inhibition was calculated for all replicates for each composition.

A histogram of the range and standard deviation of each composition was plotted. Ranges or standard deviations of the log inhibitions that were distinct from the overall distribution were examined as possible outliers. If the removal of a single log inhibition datum from one of the binary pairs that were identified in the histograms would bring the range or standard deviation in line with those from the majority of the samples, that datum was removed as an outlier, and the mean log inhibition was recalculated.

The pooled variance of all samples evaluated in the assay was estimated as the average of the sample variances weighted by the sample's degrees of freedom. The pooled standard error was then calculated as the square root of the pooled variance divided by the square root of the number of samples. Confidence intervals for the null hypothesis were determined by multiplying the pooled standard error to the z score corresponding to a given percentage threshold. Mean log inhibitions outside the confidence interval were considered to be inhibitory if positive or stimulatory if negative with the percent confidence corresponding to the interval used. Samples with mean log inhibition greater than the 99% confidence interval (C.I) of the null hypothesis are reported as ++++, those with a 95%<C.I.<99% as +++, those with a 90%<C.I.<95% as ++, those with a 80%<C.I.<90% as + while samples with mean log inhibition less than than the 99% confidence interval (C.I) of the null hypothesis are reported as −−−−, those with a 95%<C.I.<99% as −−−, those with a 90%<C.I.<95% as −−, those with a 80%<C.I.<90% as −. Many binary pairs comprising Keystone OTUs inhibit *C. difficile* as delineated in Table 20.

Assignment of a Network Classes Based on Phylogenetic Diversity and Functional Modalities "Network Classes" can be delineated by clustering computationally determined network ecologies into groupings based on the OTUs observed in a given network. In one example, OTUs are treated individualistically with each OTU representing a unique entity within the network. In other examples, the OTUs are clustered according to their phylogenetic relationships defined by a phylogenetic tree, e.g., into clades. In yet another embodiment, functional modules such as but not limited to KEGG Orthology Pathways can be used to cluster the networks, OTUs and Clades according to the biological or biochemical functions they comprise. A set of ecological networks from which a Network Class is defined, is selected using one or a combination of the following criteria: (i) networks that are derived from a biological phenotype, (ii) the frequency at which a given network is observed across samples, or (iii) the size of the network. In one embodiment, the required thresholds for the frequency at which a given network is observed across subject samples, and the size of a given network to be considered for further analysis are defined by the $50^{th}$, $70^{th}$, $80^{th}$, or $90^{th}$ percentiles of the distribution of these variables. In another embodiment, the required thresholds are defined by the value for a given variable that is significantly different from the mean or median value for a given variable using standard parametric or non-parametric measures of statistical significance. In yet another embodiment, ecological networks derived from Network Classes are selected that contain 5 or fewer, 10 or fewer, 15 or fewer, 20 or fewer, 25 or fewer, or 50 or fewer OTUs, Clades, or Functional modalities.

Network Class ecologies are defined using a heatmap analytical strategy whereby the OTU content of a given network is mapped relative to the networks in which it exists (See, e.g., FIG. 18). FIG. 18 is a Derivation of Network Ecology Classes, according to an embodiment of the invention. Subsets of networks are selected for use in defining Network Classes based on key biological criteria. Hierarchical Network clusters are defined by the presence (white) and absence (blue (or dark color)) of OTUs and/or Functional Metabolic Pathways and Classes are defined as branches of the hierarchical clustering tree based on the topological overlap measure.

Both OTUs comprising the network ecologies and the network ecologies themselves are ordered using a dendrogram that represents the relatedness of each OTU to every other OTU, or each Network Ecology to every other Network Ecology. The dendrogram for OTUs can be constructed using various clustering algorithms including but not limited to phylogenetic maximum likelihood, hierarchical clustering, or k-means clustering. In one embodiment, each row in the heatmap represents a single OTU, each column represents a Network Ecology and the color in the heatmap at a given row/column intersection represents whether the given OTU is present or absent in the given network. In another embodiment, the color in the heatmap represents the summed number of occurrences of the OTU in a set of related networks, represented as a cluster in the dendrogram of network ecologies. In another embodiment, the row and column intersections represent a summary variable calculated from the collapse of multiple rows and/or columns at selected nodes in the dendrograms. Network Classes are defined finding significant branch points in the hierarchical dendrogram. In one embodiment these branch points are defined as branches of the hierarchical clustering tree based on the topological overlap measure; this measure is a highly robust measure of network interconnectedness (Langfelder P, Zhang B, Horvath S. 2008. Defining clusters from a hierarchical cluster tree: the Dynamic Tree Cut package for R. Bioinformatics 24: 719-720.). Network Classes are defined based on OTU presence/absence or presence/absence and frequency patterns in network clusters; these patterns can be defined using specific OTUs, taxonomic groupings, or phylogenetic clades defined by the phylogenetically derived dendrogram (i.e. phylogenetic tree). Network Classes can be defined with the intent of maximizing the phylogenetic diversity of the class, and/or representing specific regions of functional relevance on the phylogenetic tree.

We defined a set of Network Classes for the Network Ecologies reported in Table 8 that were computationally inferred from health and disease datasets tied to CDAD studies using the method described above. We defined six Network Classes for these network ecologies (FIG. 18 and Tables 12-13).

Example 7. Biologically-Informed Optimization of Network Ecologies Based on Biological Properties Network Ecologies can be optimized to have specific biological properties including but not limited to being of specific size (as example a specific number or OTUs); having a frequency of being observed in a population of healthy individuals (i.e. pervasiveness); having a certain percentage of spore forming OTUs as constituents; having a certain percentage of Keystone OTUs, clades or functions; having a defined phylogenetic breadth (as example defined by the total evolutionary distance spanned on a tree by the constituent members, or by the total number of genera or other taxonomic unit); or comprising specific functional capabilities such as but not limited to the ability metabolize secondary bile acids, or produce short chain fatty acids (SCFAs), or the biological intersection in which network ecology falls in a comparative phenotype map (see FIG. 19). The constituents of a network ecology can be optimized using both computational means as well as experimental means.

In one embodiment, we developed a biopriority score for networks that was computationally derived. This algorithm took the form of $[F1*W1]+[F2*W2]+[F3*W3]+[F4*W4]$ where F is a biological criteria of interest and W is a weighting for that factor based on its importance to the derivation of the target network ecology. As example, if having a network with phylogenetic breadth was important one would weight this factor greater than the other factors. We developed a biopriority score that took into consideration the biological intersection of the network (FIG. 19), phylogenetic breadth, the pervasiveness or prevalence of the network in populations of healthy individuals, and the percentage of OTUs in the network that were Keystone OTUs. Network Ecologies reported in Table 8 were ranked based on this scoring and networks with a high score were preferentially screened and in vivo mouse model of C. difficile infection (Table 16).

Figure 3:
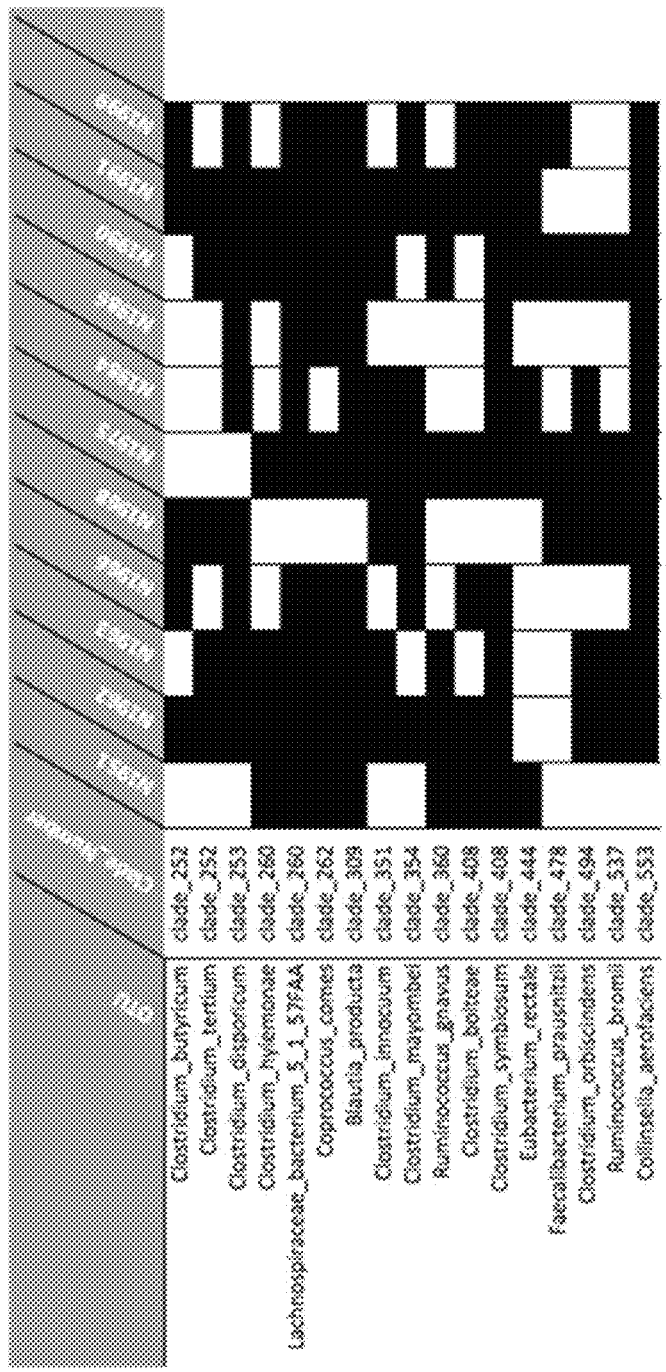
FIG. 3 provides the OTU and clade composition of networks tested in experiment SP-376, according to an embodiment of the invention.

In another embodiment we used a phylogenetic method paired with empirical testing to optimize the network ecologies for efficacy for the treatment of CDAD. Based on computational insights from our network analysis (Table 8), applicants defined Keystone Clades that represent specific phylogenetic clusters of OTUs. Applicants constructed various bacterial compositions using the methods described in Example 9 below, whereby applicants varied the phylogenetic breadth of the network ecologies based on the inclusion or exclusion of OTUs from specific clades. To test the effect of these variations on efficacy, 11 networks that feature clade substitutions, additions, or subtractions were tested at the same target dose of 1e7 CFU per OTU per animal in the mouse model of C. difficile infection experiment SP-376 (see Example 13 and Table 16). FIG. 3 provides an overview of the various clade substitutions or removals The removal of clades 494 & 537 and the addition of clade_444 from network N1962, which was highly efficacious in protecting from symptoms of C. difficile infection with no mortality, yields network N1991, which was still largely protective of weight loss, but had increased mean maximum clinical scores relative to N1962.

N1990 adds clades 444 & 478 to N1962, and resulted in decreased mean minimum relative weight and increased mean maximum clinical scores relative to N1962 while remaining efficacious relative to the experiment's vehicle control.

Removal of clades 252 & 253 and the addition of clades 444 & 478 from N1962 produces N1975, which has increased mortality, decreased mean minimum relative weight and increased mean maximum clinical scores relative to N1962, which is only slightly less efficacious than the vehicle control.

The optimization of network ecologies to design microbiome therapeutics (as example a composition comprised of bacterial OTUs) with particular biological properties and features is executed using the strategy of having a core Backbone Network Ecology onto which R-Groups are added or subtracted to design toward particular characteristics. The Backbone forms a foundational composition of organisms or functions that are core to efficacy and need be present to observe efficacy. On this backbone one can make various compositional modifications using R-groups. R-Groups can be defined in multiple terms including but not limited to: individual OTUs, individual or multiple OTUs derived from a specific phylogenetic clade, and functional modalities comprised of multiple functional pathways and/or specific metabolic pathways. In other embodiments, R-groups could be considered prebiotics and other co-factors that are design into, or administered with a network ecology to promote specific biological properties.

Example 8. Network Analysis Across Multiple Data Sets and Selection of Target Network Ecologies with Capacity to Sporulate One can select Network Ecologies and/or Network Class Ecologies as lead targets by defining networks with a specific biological function or activity such as sporulation. Networks Ecologies or Network Class Ecologies are first selected as described above and in Example 5 and 6. In one example, all Network Ecologies or Network Class Ecologies that contain at least one OTU that is capable of forming spores are targeted. In another example, all Network Ecologies or Network Class Ecologies that contain at least one OTU that is capable of forming spores, and that are comprised of at least 50%, 75%, or 100% Keystone OTUs are targeted. Keystone OTUs are selected as described above and in Example 6. OTUs are defined as spore formers using either phenotypic assays (see e.g. Stackebrandt and Hippe. Taxonomy and Systematics. In *Clostridia*. Biotechnology and Medical Applications.) or genetic assays (see e.g. Abecasis A B, Serrano M, Alves R, Quintais L, Pereira-Leal J B, and Henriques A O. 2013. A genomic signature and the identification of new sporulation genes. J. Bacteriol.; Paredes-Sabja D, Setlow P, and Sarker M R. 2011. Germination of spores of Bacillales and Clostridiales species: mechanisms and proteins involved. Trends Microbiol. 19: 85-94). Exemplary network ecologies that are comprised of spore formers are illustrated in Table11.

Example 9. Construction of Defined Ecobiotic Compositions

Source of Microbial Cultures. Pure cultures of organisms are isolated from the stool, oral cavity or other niche of the body of clinically qualified donors (as in Example 10) that contains microorganisms of interest using microbiological methods including those described below, and as are known to those skilled in the art. Alternatively, pure cultures are sourced from repositories such as the ATCC (atcc.org) or the DSMZ (dsmz.de/) which preserve and distribute cultures of bacteria, yeasts, phages, cell lines and other biological materials.

Enrichment and Purification of Bacteria. To purify individual bacterial strains, dilution plates were selected in which the density enables distinct separation of single colonies. Colonies were picked with a sterile implement (either a sterile loop or toothpick) and re-streaked to BBA or other solid media. Plates were incubated at 37° C. for 3-7 days. One or more well-isolated single colonies of the major morphology type were re-streaked. This process was repeated at least three times until a single, stable colony morphology is observed. The isolated microbe was then cultured anaerobically in liquid media for 24 hours or longer to obtain a pure culture of 106-1010 cfu/ml. Liquid growth medium might include Brain Heart Infusion-based medium (Atlas, Handbook of Microbiological Media, 4th ed, ASM Press, 2010) supplemented with yeast extract, hemin, cysteine, and carbohydrates (for example, maltose, cellobiose, soluble starch) or other media described previously. The culture was centrifuged at 10,000×g for 5 min to pellet the bacteria, the spent culture media was removed, and the bacteria were resuspended in sterile PBS. Sterile 75% glycerol was added to a final concentration of 20%. An aliquot of glycerol stock was titered by serial dilution and plating. The remainder of the stock was frozen on dry ice for 10-15 min and then placed at −80° C. for long term storage.

Cell Bank Preparation

Cell banks (RCBs) of bacterial strains were prepared as follows. Bacterial strains were struck from −80° C. frozen glycerol stocks to *Brucella* blood agar with Hemin or Vitamin K (Atlas, Handbook of Microbiological Media, 4th ed, ASM Press, 2010), M2GSC (Atlas, Handbook of Microbiological Media, 4th ed, ASM Press, 2010) or other solid growth media and incubated for 24 to 48 h at 37° C. in an anaerobic chamber with a gas mixture of H2:CO2:N2 of 10:10:80. Single colonies were then picked and used to inoculate 250 ml to 1 L of Wilkins-Chalgren broth, Brain-Heart Infusion broth, M2GSC broth or other growth media, and grown to mid to late exponential phase or into the stationary phase of growth. Alternatively, the single colonies may be used to inoculate a pilot culture of 10 ml, which were then used to inoculate a large volume culture. The growth media and the growth phase at harvest were selected to enhance cell titer, sporulation (if desired) and phenotypes that might be associated desired in vitro or in vivo. Optionally, cultures were grown static or shaking, depending which yielded maximal cell titer. The cultures were then concentrated 10 fold or more by centrifugation at 5000 rpm for 20 min, and resuspended in sterile phosphate buffered saline (PBS) plus 15% glycerol. 1 ml aliquots were transferred into 1.8 ml cryovials which were then frozen on dry ice and stored at −80° C. The identity of a given cell bank was confirmed by PCR amplification of the 16S rDNA gene, followed by Sanger direct cycle sequencing. See Examples 1, 2. Each bank was confirmed to yield colonies of a single morphology upon streaking to *Brucella* blood agar or M2GSC agar. When more than one morphology was observed, colonies were confirmed to be the expected species by PCR and sequencing analysis of the 16S rDNA gene. Variant colony morphologies can be observed within pure cultures, and in a variety of bacteria the mechanisms of varying colony morphologies have been well described (van der Woude, Clinical Microbiology Reviews, 17:518, 2004), including in *Clostridium* species (Wadsworth-KTL Anaerobic Bacteriology Manual, 6th Ed, Jousimie-Somer, et al 2002). For obligate anaerobes, RCBs were confirmed to lack aerobic colony forming units at a limit of detection of 10 cfu/ml.

Titer Determination

The number of viable cells per ml was determined on the freshly harvested, washed and concentrated culture by plating serial dilutions of the RCB to *Brucella* blood agar or other solid media, and varied from 106 to 1010 cfu/ml. The impact of freezing on viability was determined by titering the banks after one or two freeze-thaw cycles on dry ice or at −80° C., followed by thawing in an anaerobic chamber at room temperature. Some strains displayed a 1-3 log drop in viable cfu/ml after the 1st and/or 2nd freeze thaw, while the viability of others were unaffected.

Preparation of Bacterial Compositions

Individual strains were typically thawed on ice and combined in an anaerobic chamber to create mixtures, followed by a second freeze at −80° C. to preserve the mixed samples. When making combinations of strains for in vitro or in vivo assays, the cfu in the final mixture was estimated based on the second freeze-thaw titer of the individual strains. For experiments in rodents, strains may be combined at equal counts in order to deliver between 1e4 and 1e10 per strain. Additionally, some bacteria may not grow to sufficient titer to yield cell banks that allowed the production of compositions where all bacteria were present at 1e10.

Selection of Media for Growth

Provided are appropriate media to support growth, including preferred carbon sources. For example, some organisms prefer complex sugars such as cellobiose over simple sugars. Examples of media used in the isolation of sporulating organisms include EYA, BHI, BHIS, and GAM (see below for complete names and references). Multiple dilutions are plated out to ensure that some plates will have well isolated colonies on them for analysis, or alternatively plates with dense colonies may scraped and suspended in PBS to generate a mixed diverse community.

Plates are incubated anaerobically or aerobically at 37° C. for 48-72 or more hours, targeting anaerobic or aerobic spore formers, respectively.

Solid plate media include:

Gifu Anaerobic Medium (GAM, Nissui) without dextrose supplemented with fructooligosaccharides/inulin (0.4%), mannitol (0.4%), inulin (0.4%), or fructose (0.4%), or a combination thereof Sweet GAM [Gifu Anaerobic Medium (GAM, Nissui)] modified, supplemented with glucose, cellobiose, maltose, L-arabinose, fructose, fructooligosaccharides/inulin, mannitol and sodium lactate)

*Brucella* Blood Agar (BBA, Atlas, Handbook of Microbiological Media, 4th ed, ASM Press, 2010)

PEA sheep blood (Anaerobe Systems; 5% Sheep Blood Agar with Phenylethyl Alcohol)

Egg Yolk Agar (EYA) (Atlas, Handbook of Microbiological Media, 4th ed, ASM Press, 2010)

Sulfite polymyxin milk agar (Mevissen-Verhage et al., J. Clin. Microbiol. 25:285-289 (1987))

Mucin agar (Derrien et al., IJSEM 54: 1469-1476 (2004))

Polygalacturonate agar (Jensen & Canale-Parola, Appl. Environ. Microbiol. 52:880-997 (1986))

M2GSC (Atlas, Handbook of Microbiological Media, 4th ed, ASM Press, 2010)

M2 agar (Atlas, Handbook of Microbiological Media, 4th ed, ASM Press, 2010) supplemented with starch (1%), mannitol (0.4%), lactate (1.5 g/L) or lactose (0.4%)

Sweet B—Brain Heart Infusion agar (Atlas, Handbook of Microbiological Media, 4th ed, ASM Press, 2010) supplemented with yeast extract (0.5%), hemin, cysteine (0.1%), maltose (0.1%), cellobiose (0.1%), soluble starch (sigma, 1%), MOPS (50 mM, pH 7).

PY-salicin (peptone-yeast extract agar supplemented with salicin) (Atlas, Handbook of Microbiological Media, 4th ed, ASM Press, 2010).

Modified Brain Heart Infusion (M-BHI) [[sweet and sour]] contains the following per L: 37.5 g Brain Heart Infusion powder (Remel), 5 g yeast extract, 2.2 g meat extract, 1.2 g liver extract, 1 g cystein HCl, 0.3 g sodium thioglycolate, 10 mg hemin, 2 g soluble starch, 2 g FOS/Inulin, 1 g cellobiose, 1 g L-arabinose, 1 g mannitol, 1 Na-lactate, 1 mL Tween 80, 0.6 g $MgSO_4 \times 7H_2O$, 0.6 g $CaCl_2$, 6 g $(NH_4)_2SO_4$, 3 g $KH_2PO_4$, 0.5 g $K_2HPO_4$, 33 mM Acetic acid, 9 mM propionic acid, 1 mM Isobutyric acid, 1 mM isovaleric acid, 15 g agar, and after autoclaving add 50 mL of 8% $NaHCO_3$ solution and 50 mL 1M MOPS-KOH (pH 7).

Noack-Blaut *Eubacterium* agar (See Noack et al. J. Nutr. (1998) 128:1385-1391)

BHIS az1/ge2—BHIS az/ge agar (Reeves et. al. Infect. Immun. 80:3786-3794 (2012)) [Brain Heart Infusion agar (Atlas, Handbook of Microbiological Media, 4th ed, ASM Press, 2010) supplemented with yeast extract 0.5%, cysteine 0.1%, 0.1% cellobiose, 0.1% inulin, 0.1% maltose, aztreonam 1 mg/L, gentamycin 2 mg/L]

BHIS ClnM az1/ge2—BHIS ClnM [Brain Heart Infusion agar (Atlas, Handbook of Microbiological Media, 4th ed, ASM Press, 2010) supplemented with yeast extract 0.5%, cysteine 0.1%, 0.1% cellobiose, 0.1% inulin, 0.1% maltose, aztreonam 1 mg/L, gentamycin 2 mg/L].

Method of Preparing the Bacterial Composition for Administration to a Patient

Two strains for the bacterial composition are independently cultured and mixed together before administration. Both strains are independently be grown at 37° C., pH 7, in a GMM or other animal-products-free medium, pre-reduced with 1 g/L cysteine YHCl. After each strain reaches a sufficient biomass, it is preserved for banking by adding 15% glycerol and then frozen at −80° C. in 1 ml cryotubes.

Each strain is then be cultivated to a concentration of $10^{10}$ CFU/mL, then concentrated 20-fold by tangential flow microfiltration; the spent medium is exchanged by diafiltering with a preservative medium consisting of 2% gelatin, 100 mM trehalose, and 10 mM sodium phosphate buffer, or other suitable preservative medium. The suspension is freeze-dried to a powder and titrated.

After drying, the powder is blended with microcrystalline cellulose and magnesium stearate and formulated into a 250 mg gelatin capsule containing 10 mg of lyophilized powder ($10^8$ to $10^{11}$ bacteria), 160 mg microcrystalline cellulose, 77.5 mg gelatin, and 2.5 mg magnesium stearate.

Example 10. Construction and Administration of an Ethanol-Treated Spore Preparation Provision of fecal material. Fresh fecal samples were obtained from healthy human donors who have been screened for general good health and for the absence of infectious diseases, and meet inclusion and exclusion criteria, inclusion criteria include being in good general health, without significant medical history, physical examination findings, or clinical laboratory abnormalities, regular bowel movements with stool appearance typically Type 2, 3, 4, 5 or 6 on the Bristol Stool Scale, and having a BMI≥18 kg/m2 and ≤25 kg/m2. Exclusion criteria generally included significant chronic or acute medical conditions including renal, hepatic, pulmonary, gastrointestinal, cardiovascular, genitourinary, endocrine, immunologic, metabolic, neurologic or hematological disease, a family history of, inflammatory bowel disease including Crohn's disease and ulcerative colitis, Irritable bowel syndrome, colon, stomach or other gastrointestinal malignancies, or gastrointestinal polyposis syndromes, or recent use of yogurt or commercial probiotic materials in which an organism(s) is a primary component. Non-related donors were screened for general health history for absence of chronic medical conditions (including inflammatory bowel disease; irritable bowel syndrome; Celiac disease; or any history of gastrointestinal malignancy or polyposis), absence of risk factors for transmissible infections, antibiotic non-use in the previous 6 months, and negative results in laboratory assays for blood-borne pathogens (HIV, HTLV, HCV, HBV, CMV, HAV and *Treponema pallidum*) and fecal bacterial pathogens (*Salmonella, Shigella, Yersinia, Campylobacter, E. coli* O157), ova and parasites, and other infectious agents (Giardia, *Cryptosporidium, Cyclospora, Isospora*) prior to stool donation. Samples were collected directly using a commode specimen collection system, which contains a plastic support placed on the toilet seat and a collection container that rests on the support. Feces were deposited into the container, and the lid was then placed on the container and sealed tightly. The sample was then delivered on ice within 1-4 hours for processing. Samples were mixed with a sterile disposable tool, and 2-4 g aliquots were weighed and placed into tubes and flash frozen in a dry ice/ethanol bath. Aliquots are frozen at −80 degrees Celsius until use.

Optionally, the fecal material was suspended in a solution, and/or fibrous and/or particulate materials were removed using either filtration or centrifugation. A frozen aliquot containing a known weight of feces was removed from storage at −80° C. and allowed to thaw at room temperature. Sterile 1×PBS was added to create a 10% w/v suspension, and vigorous vortexing was performed to suspend the fecal material until the material appeared homogeneous. The material was then left to sit for 10 minutes at room temperature to sediment fibrous and particulate matter. The suspension above the sediment was then carefully removed into a new tube and contains a purified spore population. Optionally, the suspension was then centrifuged at a low speed, e.g., 1000×g, for 5 minutes to pellet particulate matter including fibers. The pellet was discarded and the supernatant, which contained vegetative organisms and spores, was removed into a new tube. The supernatant was then centrifuged at 6000×g for 10 minutes to pellet the vegetative organisms and spores. The pellet was then resuspended in 1×PBS with vigorous vortexing until the material appears homogenous.

Generation of a Spore Preparation from Alcohol Treatment of Fecal Material

A 10% w/v suspension of human fecal material in PBS was filtered, centrifuged at low speed, and the supernate containing spores was mixed with absolute ethanol in a 1:1 ratio and vortexed to mix. The suspension was incubated at room temperature for 1 hour. After incubation the suspension was centrifuged at high speed to concentrate spores into a pellet containing a purified spore-containing preparation. The supernate was discarded and the pellet resuspended in an equal mass of glycerol, and the purified spore preparation was placed into capsules and stored at −80 degrees Celsius.

Characterization of Spores Content in Purified Spore Populations

In one embodiment, counts of viable spores are determined by performing 10 fold serial dilutions in PBS and plating to *Brucella* Blood Agar Petri plates or applicable solid media. Plates are incubated at 37 degrees Celsius for 2 days. Colonies are counted from a dilution plate with 50-400 colonies and used to back-calculate the number of viable spores in the population. The ability to germinate into vegetative bacteria is also demonstrated. Visual counts are determined by phase contrast microscopy. A spore preparation is either diluted in PBS or concentrated by centrifugation, and a 5 microliter aliquot is placed into a Petroff Hauser counting chamber for visualization at 400× magnification. Spores are counted within ten 0.05 mm×0.05 mm grids and an average spore count per grid is determined and used to calculate a spore count per ml of preparation. Lipopolysaccharide (LPS) reduction in purified spore populations is measured using a Limulus amebocyte lysate (LAL) assay such as the commercially available ToxinSensor™ Chromogenic LAL Endotoxin Assay Kit (GenScript, Piscataway, N.J.) or other standard methods known to those skilled in the art.

In a second embodiment, counts of spores are determined using a spore germination assay. Germinating a spore fraction increases the number of viable spores that will grow on various media types. To germinate a population of spores, the sample is moved to the anaerobic chamber, resuspended in prereduced PBS, mixed and incubated for 1 hour at 37° C. to allow for germination. Germinants can include aminoacids (e.g., alanine, glycine), sugars (e.g., fructose), nucleosides (e.g., inosine), bile salts (e.g., cholate and taurocholate), metal cations (e.g., Mg2+, Ca2+), fatty acids, and long-chain alkyl amines (e.g., dodecylamine, Germination of bacterial spores with alkyl primary amines" J. Bacteriology, 1961.). Mixtures of these or more complex natural mixtures, such as rumen fluid or Oxgall, can be used to induce germination. Oxgall is dehydrated bovine bile composed of fatty acids, bile acids, inorganic salts, sulfates, bile pigments, cholesterol, mucin, lecithin, glycuronic acids, porphyrins, and urea. The germination can also be performed in a growth medium like prereduced BHIS/oxgall germination medium, in which BHIS (Brain heart infusion powder (37 g/L), yeast extract (5 g/L), L-cysteine HCl (1 g/L)) provides peptides, amino acids, inorganic ions and sugars in the complex BHI and yeast extract mixtures and Oxgall provides additional bile acid germinants.

In addition, pressure may be used to germinate spores. The selection of germinants can vary with the microbe being sought. Different species require different germinants and different isolates of the same species can require different germinants for optimal germination. Finally, it is important to dilute the mixture prior to plating because some germinants are inhibitory to growth of the vegetative-state microorganisms. For instance, it has been shown that alkyl amines must be neutralized with anionic lipophiles in order to promote optimal growth. Bile acids can also inhibit growth of some organisms despite promoting their germination, and must be diluted away prior to plating for viable cells.

For example, BHIS/oxgall solution is used as a germinant and contains 0.5×BHIS medium with 0.25% oxgall (dehydrated bovine bile) where 1×BHIS medium contains the following per L of solution: 6 g Brain Heart Infusion from solids, 7 g peptic digest of animal tissue, 14.5 g of pancreatic digest of casein, 5 g of yeast extract, 5 g sodium chloride, 2 g glucose, 2.5 g disodium phosphate, and 1 g cysteine. Additionally, Ca-DPA is a germinant and contains 40 mM $CaCl_2$, and 40 mM dipicolinic acid (DPA). Rumen fluid (Bar Diamond, Inc.) is also a germinant. Simulated gastric fluid (Ricca Chemical) is a germinant and is 0.2% (w/v) Sodium Chloride in 0.7% (v/v) Hydrochloric Acid. Mucin medium is a germinant and prepared by adding the following items to 1 L of distilled sterile water: 0.4 g $KH_2PO_4$, 0.53 g $Na_2HPO_4$, 0.3 g $NH_4Cl$, 0.3 g NaCl, 0.1 g $MgCl_2\times 6H_2O$, 0.11 g $CaCl_2$, 1 ml alkaline trace element solution, 1 ml acid trace element solution, 1 ml vitamin solution, 0.5 mg resazurin, 4 g $NaHCO_3$, 0.25 g $Na_2S\times 9\ H_2O$. The trace element and vitamin solutions prepared as described previously (Stams et al., 1993). All compounds were autoclaved, except the vitamins, which were filter-sterilized. The basal medium was supplemented with 0.7% (v/v) clarified, sterile rumen fluid and 0.25% (v/v) commercial hog gastric mucin (Type III; Sigma), purified by ethanol precipitation as described previously (Miller & Hoskins, 1981). This medium is referred herein as mucin medium.

Fetal Bovine Serum (Gibco) can be used as a germinant and contains 5% FBS heat inactivated, in Phosphate Buffered Saline (PBS, Fisher Scientific) containing 0.137M Sodium Chloride, 0.0027M Potassium Chloride, 0.0119M Phosphate Buffer. Thioglycollate is a germinant as described previously (Kamiya et al Journal of Medical Microbiology 1989) and contains 0.25M (pH10) sodium thioglycollate. Dodecylamine solution containing 1 mM dodecylamine in PBS is a germinant. A sugar solution can be used as a germinant and contains 0.2% fructose, 0.2% glucose, and 0.2% mannitol. Amino acid solution can also be used as a germinant and contains 5 mM alanine, 1 mM arginine, 1 mM histidine, 1 mM lysine, 1 mM proline, 1 mM asparagine, 1 mM aspartic acid, 1 mM phenylalanine. A germinant mixture referred to herein as Germix 3 can be a germinant and contains 5 mM alanine, 1 mM arginine, 1 mM histidine, 1 mM lysine, 1 mM proline, 1 mM asparagine, 1 mM aspartic acid, 1 mM phenylalanine, 0.2% taurocholate, 0.2% fructose, 0.2% mannitol, 0.2% glucose, 1 mM inosine, 2.5 mM Ca-DPA, and 5 mM KCl. BHIS medium+DPA is a germinant mixture and contains BHIS medium and 2 mM Ca-DPA. *Escherichia coli* spent medium supernatant referred to herein as EcSN is a germinant and is prepared by growing *E. coli* MG1655 in SweetB/Fos inulin medium anaerobically for 48 hr, spinning down cells at 20,000 rcf for 20 minutes, collecting the supernatant and heating to 60 C for 40 min. Finally, the solution is filter sterilized and used as a germinant solution.

Determination of Bacterial Pathogens In Purified Spore Populations

Bacterial pathogens present in a purified spore population are determined by qPCR using specific oligonucleotide primers as follows.

Standard Curve Preparation

The standard curve is generated from wells containing the pathogen of interest at a known concentration or simultaneously quantified by selective spot plating. Serial dilutions of duplicate cultures are performed in sterile phosphate-buffered saline. Genomic DNA is then extracted from the standard curve samples along with the other samples.

Genomic DNA Extraction

Genomic DNA may be extracted from 100 µl of fecal samples, fecal-derived samples, or purified spore preparations using the Mo Bio Powersoil®-htp 96 Well Soil DNA Isolation Kit (Mo Bio Laboratories, Carlsbad, Calif.) according to the manufacturer's instructions with two exceptions: the beadbeating is performed for 2×4:40 minutes using a BioSpec Mini-Beadbeater-96 (BioSpec Products, Bartlesville, Okla.) and the DNA is eluted in 50 µl of Solution C6. Alternatively the genomic DNA could be isolated using the Mo Bio Powersoil® DNA Isolation Kit (Mo Bio Laboratories, Carlsbad, Calif.), the Sigma-Aldrich Extract-N-Amp™ Plant PCR Kit, the QIAamp DNA Stool Mini Kit (QIAGEN, Valencia, Calif.) according to the manufacturer's instructions.

qPCR Composition and Conditions

The qPCR reaction to detect *C. difficile* contains 1× HotMasterMix (5PRIME, Gaithersburg, Md.), 900 nM of Wr-tcdB-F (AGCAGTTGAATATAGTGGTTTAGT-TAGAGTTG (SEQ ID NO. 2044), IDT, Coralville, Iowa), 900 nM of Wr-tcdB-R (CATGCTTTTTTAGTTTCTGGAT-TGAA (SEQ ID NO. 2045), IDT, Coralville, Iowa), 250 nM of We-tcdB-P (6FAM-CATCCAGTCTCAAT-TGTATATGTTTCTCCA-MGB (SEQ ID NO. 2046), Life Technologies, Grand Island, N.Y.), and PCR Water (Mo Bio Laboratories, Carlsbad, Calif.) to 18 µl (Primers adaped from: Wroblewski, D. et al. Rapid Molecular Characterization of *Clostridium difficile* and Assessment of Populations of *C. difficile* in Stool Specimens. Journal of Clinical Microbiology 47:2142-2148 (2009)). This reaction mixture is aliquoted to wells of a MicroAmp® Fast Optical 96-well Reaction Plate with Barcode (0.1 mL) (Life Technologies, Grand Island, N.Y.). To this reaction mixture, 2 µl of extracted genomic DNA is added. The qPCR is performed on a BioRad C1000™ Thermal Cycler equipped with a CFX96™ Real-Time System (BioRad, Hercules, Calif.). The thermocycling conditions are 95° C. for 2 minutes followed by 45 cycles of 95° C. for 3 seconds, 60° C. for 30 seconds, and fluorescent readings of the FAM and ROX channels. Other bacterial pathogens can be detected by using primers and a probe specific for the pathogen of interest.

Data Analysis

The Cq value for each well on the FAM channel is determined by the CFX Manager™ Software Version 2.1. The log 10(cfu/ml) of each experimental sample is calculated by inputting a given sample's Cq value into linear regression model generated from the standard curve comparing the Cq values of the standard curve wells to the known log 10(cfu/ml) of those samples. Viral pathogens present in a purified spore population are determined by qPCR as described herein and otherwise known in the art.

Example 11. Characterization of Microbiome in Ethanol-Treated Spore Population and Patients Post-Treatment Microbial Population Engraftment, Augmentation, and Reduction of Pathogen Carriage in Patients Treated with Spore Compositions Complementary genomic and microbiological methods were used to characterize the composition of the microbiota from Patient 1, 2, 3, 4, and 5, 6, 7, 8, 9, and 10 at pretreatment (pretreatment) and up to 4 weeks post-treatment.

Table 3 shows bacterial OTUs associated with engraftment and ecological augmentation and establishment of a more diverse microbial ecology in patients treated with an ethanol-treated spore preparation. OTUs that comprise an augmented ecology are below the limit of detection in the patient prior to treatment and/or exist at extremely low frequencies such that they do not comprise a significant fraction of the total microbial carriage and are not detectable by genomic and/or microbiological assay methods in the bacterial composition. OTUs that are members of the engrafting and augmented ecologies were identified by characterizing the OTUs that increase in their relative abundance post treatment and that respectively are: (i) present in the ethanol-treated spore preparation and not detectable in the patient pretreatment (engrafting OTUs), or (ii) absent in the ethanol-treated spore preparation, but increase in their relative abundance in the patient through time post treatment with the preparation due to the formation of favorable growth conditions by the treatment (augmenting OTUs). Notably, the latter OTUs can grow from low frequency reservoirs in the patient, or be introduced from exogenous sources such as diet. OTUs that comprise a "core" augmented or engrafted ecology can be defined by the percentage of total patients in which they are observed to engraft and/or augment; the greater this percentage the more likely they are to be part of a core ecology responsible for catalyzing a shift away from a dysbiotic ecology. The dominant OTUs in an ecology can be identified using several methods including but not limited to defining the OTUs that have the greatest relative abundance in either the augmented or engrafted ecologies and defining a total relative abundance threshold. As example, the dominant OTUs in the augmented ecology of Patient-1 were identified by defining the OTUs with the greatest relative abundance, which together comprise 60% of the microbial carriage in this patient's augmented ecology by day 25 post-treatment.

Figure 5:
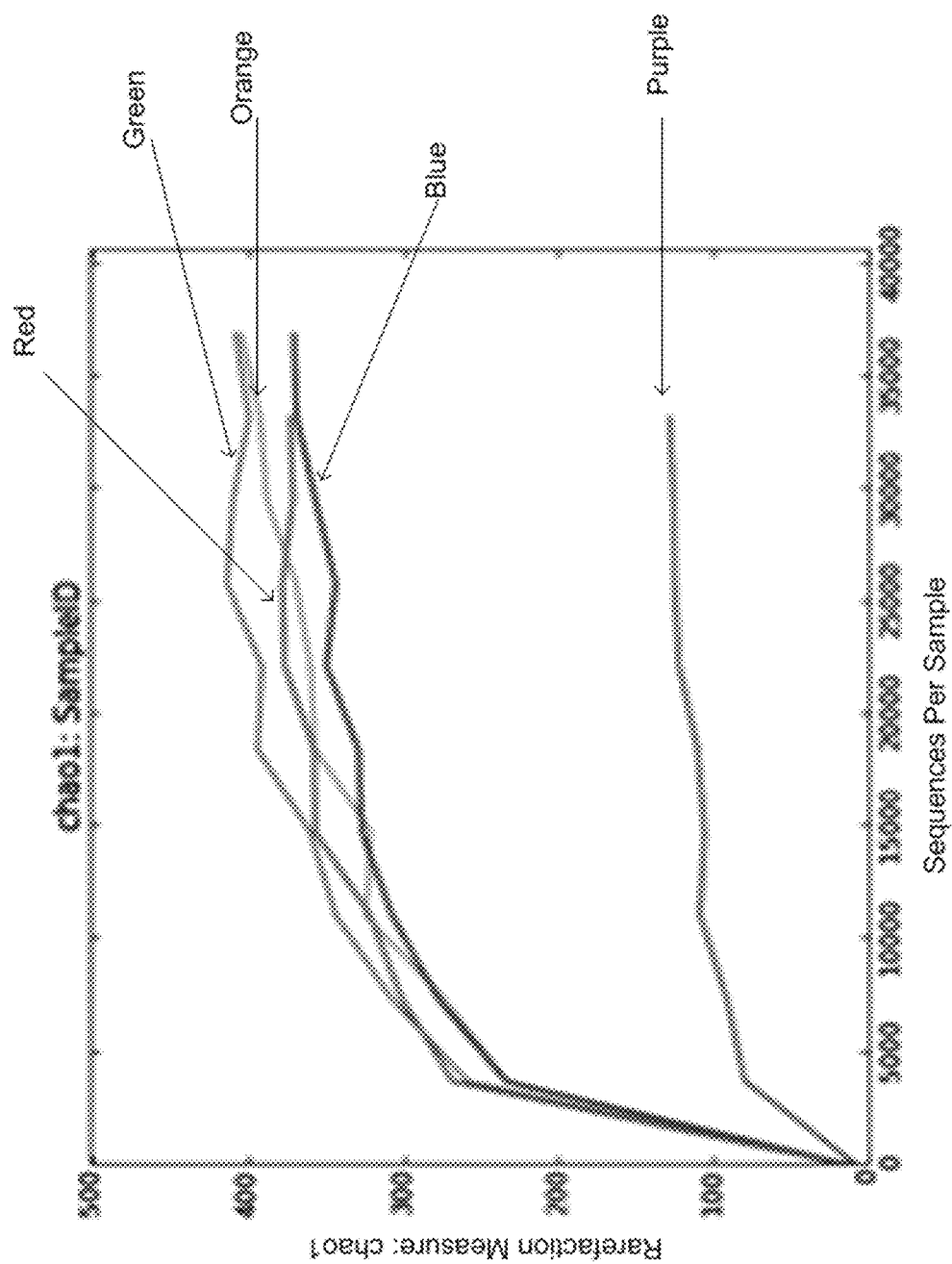
FIG. 5 demonstrates the microbial diversity measured in the ethanol-treated spore treatment sample and patient pre- and post-treatment samples, according to an embodiment of the invention. Total microbial diversity is defined using the Chao1 Alpha-Diversity Index and is measured at the same genomic sampling depths to confirm adequate and comparable sequence coverage of the target samples. The patient pretreatment (purple) harbored a microbiome that was significantly reduced in total diversity as compared to the ethanol-treated spore treatment (red) and patient post treatment at days 5 (blue), 14 (orange), and 25 (green).
Figure 6:
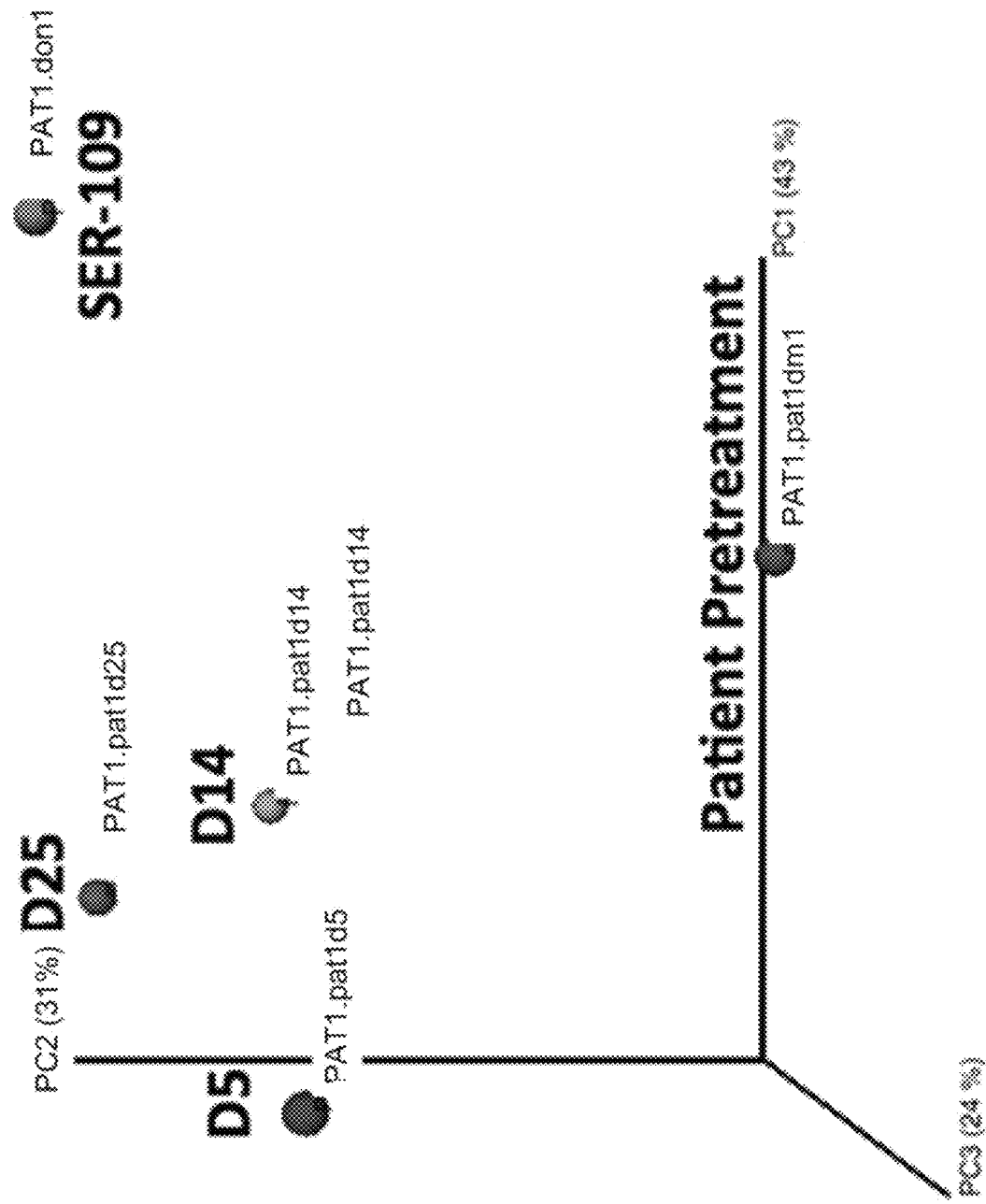
FIG. 6 demonstrates how patient microbial ecology is shifted by treatment with an ethanol-treated spore treatment from a dysbiotic state to a state of health. Principal coordinates analysis based on the total diversity and structure of the microbiome (Bray Curtis Beta Diversity) of the patient pre- and post-treatment delineates that the combination of engraftment of the OTUs from the spore treatment and the augmentation of the patient microbial ecology leads to a microbial ecology that is distinct from both the pretreatment microbiome and the ecology of the ethanol-treated spore treatment.

Patient treatment with the ethanol-treated spore preparation leads to the population of a microbial ecology that has greater diversity than prior to treatment (See FIGS. 5 & 6). Genomic-based microbiome characterization confirmed engraftment of a range of OTUs that were not detectable in the patient pretreatment (Table 3). These OTUs comprised both bacterial species that were capable and not capable of forming spores, and OTUs that represent multiple phylogenetic clades. Organisms not detectable in Patient 1 pretreatment either engraft directly from the ethanol-treated spore fraction or are augmented by the creation of a gut environment favoring a healthy, diverse microbiota. Microbiological analysis shows that *Bacteroides fragilis* group species were increased by 4 and 6 logs in patients 1 and 2 (FIG. 7).

FIG. 5 shows the microbial diversity measured in the ethanol-treated spore treatment sample and patient pre- and post-treatment samples. Total microbial diversity is defined using the Chaol Alpha-Diversity Index and is measured at different genomic sampling depths to confirm adequate sequence coverage to assay the microbiome in the target samples. The patient pretreatment (purple) harbored a microbiome that was significantly reduced in total diversity as compared to the ethanol-treated spore product (red) and patient post treatment at days 5 (blue), 14 (orange), and 25 (green).

FIG. 6 shows patient microbial ecology is shifted by treatment with an ethanol-treated spore treatment from a dysbiotic state to a state of health. Principal Coordinates Analysis based on the total diversity and structure of the microbiome (Bray-Curtis Beta-Diversity) of the patient pre- and post-treatment delineates that the engraftment of OTUs from the spore treatment and the augmentation of the patient microbial ecology leads to a microbial ecology that is distinct from both the pretreatment microbiome and the ecology of the ethanol-treated spore treatment (Table 3).

Figure 7:
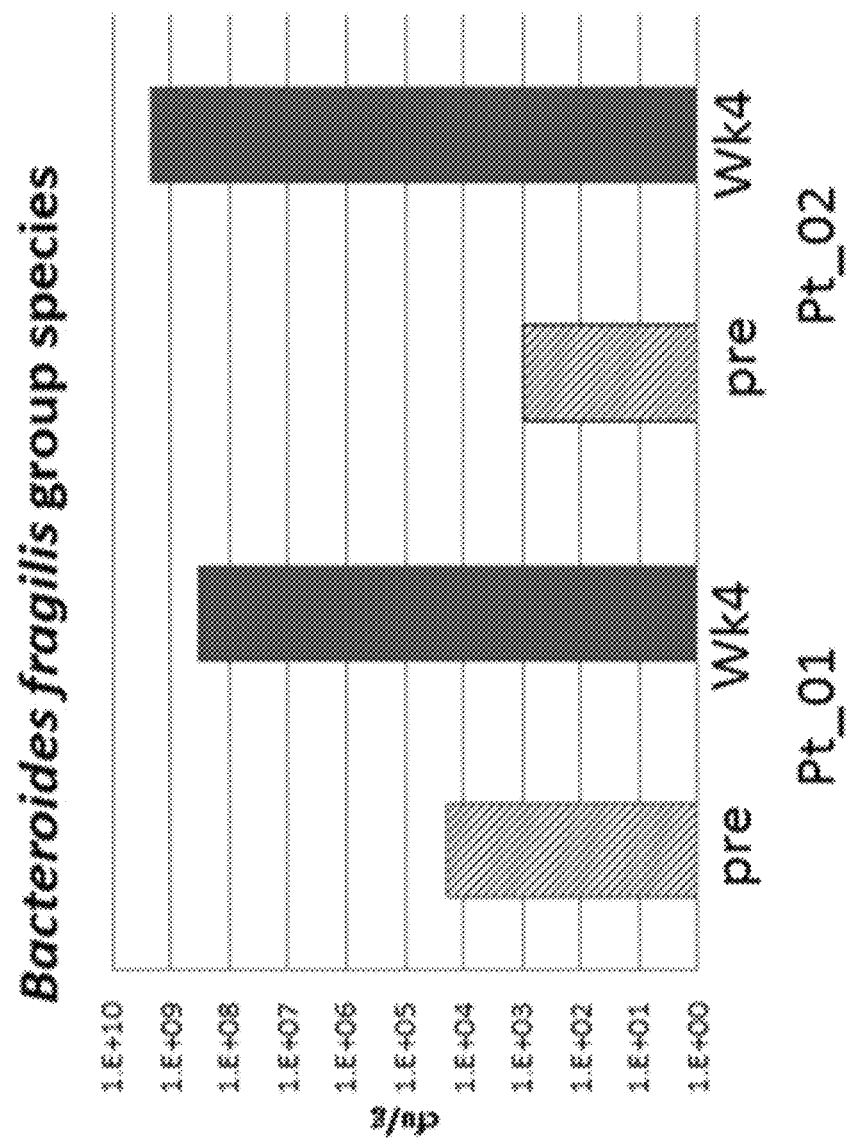
FIG. 7 demonstrates the augmentation of *Bacteroides* species in patients treated with the spore population, according to an embodiment of the invention.

FIG. 7 shows the augmentation of *Bacteroides* species in patients. Comparing the number of *Bacteroides fragilis* groups species in feces (cfu/g) pre-treatment and in week 4 post treatment reveals an increase of 4 logs or greater. The ability of 16S-V4 OTU identification to assign an OTU as a specific species depends in part on the resolution of the 16S-V4 region of the 16S gene for a particular species or group of species. Both the density of available reference 16S sequences for different regions of the tree as well as the inherent variability in the 16S gene between different species will determine the definitiveness of a taxonomic annotation to a given sequence read. Given the topological nature of a phylogenetic tree and that the tree represents hierarchical relationships of OTUs to one another based on their sequence similarity and an underlying evolutionary model, taxonomic annotations of a read can be rolled up to a higher level using a clade-based assignment procedure (Table 1). Using this approach, clades are defined based on the topology of a phylogenetic tree that is constructed from full-length 16S sequences using maximum likelihood or other phylogenetic models familiar to individuals with ordinary skill in the art of phylogenetics. Clades are constructed to ensure that all OTUs in a given clade are: (i) within a specified number of bootstrap supported nodes from one another (generally, 1-5 bootstraps), and (ii) within a 5% genetic similarity. OTUs that are within the same clade can be distinguished as genetically and phylogenetically distinct from OTUs in a different clade based on 16S-V4 sequence data. OTUs falling within the same clade are evolutionarily closely related and may or may not be distinguishable from one another using 16S-V4 sequence data. The power of clade based analysis is that members of the same clade, due to their evolutionary relatedness, play similar functional roles in a microbial ecology such as that found in the human gut. Compositions substituting one species with another from the same clade are likely to have conserved ecological function and therefore are useful in the present invention.

Stool samples were aliquoted and resuspended 10× vol/wt in either 100% ethanol (for genomic characterization) or PBS containing 15% glycerol (for isolation of microbes) and then stored at −80° C. until needed for use. For genomic 16S sequence analysis colonies picked from plate isolates had their full-length 16S sequence characterized as described in Examples 2 and 3, and primary stool samples were prepared targeting the 16S-V4 region using the method for heterogeneous samples described herein.

Notably, 16S sequences of isolates of a given OTU are phylogenetically placed within their respective clades despite that the actual taxonomic assignment of species and genus may suggest they are taxonomically distinct from other members of the clades in which they fall. Discrepancies between taxonomic names given to an OTU is based on microbiological characteristics versus genetic sequencing are known to exist from the literature. The OTUs footnoted in this table are known to be discrepant between the different methods for assigning a taxonomic name.

Engraftment of OTUs from the ethanol-treated spore preparation treatment into the patient as well as the resulting augmentation of the resident microbiome led to a significant decrease in and elimination of the carriage of pathogenic species other than *C. difficile* in the patient. 16S-V4 sequencing of primary stool samples demonstrated that at pretreatment, 20% of reads were from the genus *Klebsiella* and an additional 19% were assigned to the genus *Fusobacterium*. These striking data are evidence of a profoundly dysbiotic microbiota associated with recurrent *C. difficile* infection and chronic antibiotic use. In healthy individuals, *Klebsiella* is a resident of the human microbiome in only about 2% of subjects based on an analysis of HMP database (hmpdacc.org), and the mean relative abundance of *Klebsiella* is only about 0.09% in the stool of these people. Its surprising presence at 20% relative abundance in Patient 1 before treatment is an indicator of a proinflammatory gut environment enabling a "pathobiont" to overgrow and outcompete the commensal organisms normally found in the gut. Similarly, the dramatic overgrowth of *Fusobacterium* indicates a profoundly dysbiotic gut microbiota. One species of *Fusobacterium*, *F. nucleatum* (an OTU phylogenetically indistinguishable from *Fusobacterium* sp. 3_1_33 based on 16S-V4), has been termed "an emerging gut pathogen" based on its association with IBD, Crohn's disease, and colorectal cancer in humans and its demonstrated causative role in the development of colorectal cancer in animal models [Allen-Vercoe, Gut Microbes (2011) 2:294-8]. Importantly, neither *Klebsiella* nor *Fusobacterium* was detected in the 16S-V4 reads by Day 25 (Table 4).

To further characterize the colonization of the gut by *Klebsiella* and other Enterobacteriaceae and to speciate these organisms, pretreatment and Day 25 fecal samples stored at −80 C as PBS-glycerol suspensions were plated on a variety of selective media including MacConkey lactose media (selective for gram negative enterobacteria) and Simmons Citrate Inositol media (selective for *Klebsiella* spp) [Van Cregten et al, J. Clin. Microbiol. (1984) 20: 936-41]. Enterobacteria identified in the patient samples included *K. pneumoniae*, *Klebsiella* sp. Co_9935 and *E. coli*. Strikingly, each *Klebsiella* species was reduced by 2-4 logs whereas *E. coli*, a normal commensal organism present in a healthy microbiota, was reduced by less than 1 log (Table 14 below). This decrease in *Klebsiella* spp. carriage is consistent across multiple patients. Four separate patients were evaluated for the presence of *Klebsiella* spp. pre treatment and 4 weeks post treatment. *Klebsiella* spp. were detected by growth on selective Simmons Citrate Inositol media as previously described. Serial dilution and plating, followed by determining cfu/mL titers of morphologically distinct species and 16S full length sequence identification of representatives of those distinct morphological classes, allowed calculation of titers of specific species.

The genus *Bacteroides* is an important member of the gastrointestinal microbiota; 100% of stool samples from the Human Microbiome Project contain at least one species of *Bacteroides* with total relative abundance in these samples ranging from 0.96% to 93.92% with a median relative abundance of 52.67% (hmpdacc.org reference data set HMSMCP). *Bacteroides* in the gut has been associated with amino acid fermentation and degradation of complex polysaccharides. Its presence in the gut is enhanced by diets rich in animal-derived products as found in the typical western diet [David, L. A. et al, Nature (2013) doi:10.1038/nature12820]. Strikingly, prior to treatment, fewer than 0.008% of the 16S-V4 reads from Patient 1 mapped to the genus *Bacteroides* strongly suggesting that *Bacteroides* species were absent or that viable *Bacteroides* were reduced to an extremely minor component of the patient's gut microbiome. Post treatment, ≥42% of the 16S-V4 reads could be assigned to the genus *Bacteroides* within 5 days of treatment and by Day 25 post treatment 59.48% of the patients gut microbiome was comprised of *Bacteroides*. These results were confirmed microbiologically by the absence of detectable *Bacteroides* in the pretreatment sample plated on two different *Bacteroides* selective media: *Bacteroides* Bile Esculin (BBE) agar which is selective for *Bacteroides fragilis* group species [Livingston, S. J. et al J. Clin. Microbiol (1978). 7: 448-453] and Polyamine Free Arabinose (PFA) agar [Noack et al. J. Nutr. (1998) 128: 1385-1391; modified by replacing glucose with arabinose]. The highly selective BBE agar had a limit of detection of $<2 \times 10^3$ cfu/g, while the limit of detection for *Bacteroides* on PFA agar was approximately $2 \times 10^7$ cfu/g due to the growth of multiple non-*Bacteroides* species in the pretreatment sample on that medium. Colony counts of *Bacteroides* species on Day 25 were up to $2 \times 10^{10}$ cfu/g, consistent with the 16S-V4 sequencing, demonstrating a profound reconstitution of the gut microbiota in Patient 1 (Table 5 below).

The significant abundance of *Bacteroides* in Patient 1 on Day 25 (and as early as Day 5 as shown by 16S-V4 sequencing) is remarkable. Viable *Bacteroides fragilis* group species were not present in the ethanol-treated spore population based on microbiological plating (limit of detection of 10 cfu/ml). Thus, administration of the ethanol-treated spore population to Patient 1 resulted in microbial population of the patient's GI tract, not only due to the engraftment of bacterial species such as but not limited to spore forming species, but also the restoration of high levels of non-spore forming species commonly found in healthy individuals through the creation of a niche that allowed for the repopulation of *Bacteroides* species. These organisms were most likely either present at extremely low abundance in the GI tract of Patient 1, or present in a reservoir in the GI tract from which they could rebound to high titer. Those species may also be reinoculated via oral uptake from food following treatment. We term this healthy repopulation of the gut with OTUs that are not present in the bacterial composition such as but not limited to a spore population or ethanol-treated spore population, "Augmentation." Augmentation is an important phenomenon in that it shows the ability to use an ethanol-treated spore ecology or other bacterial composition to restore a healthy microbiota by seeding a diverse array or commensal organisms beyond the actual component organisms in the bacterial composition such as but not limited to an ethanol-treated spore population itself; specifically the spore composition treatment itself and the engraftment of OTUs from the spore composition create a niche that enables the outgrowth of OTUs required to shift a dysbiotic microbiome to a microbial ecology that is associated with health. The diversity of *Bacteroides* species and their approximate relative abundance in the gut of Patient 1 is shown in Table 16, comprising at least 8 different species.

Figure 8:
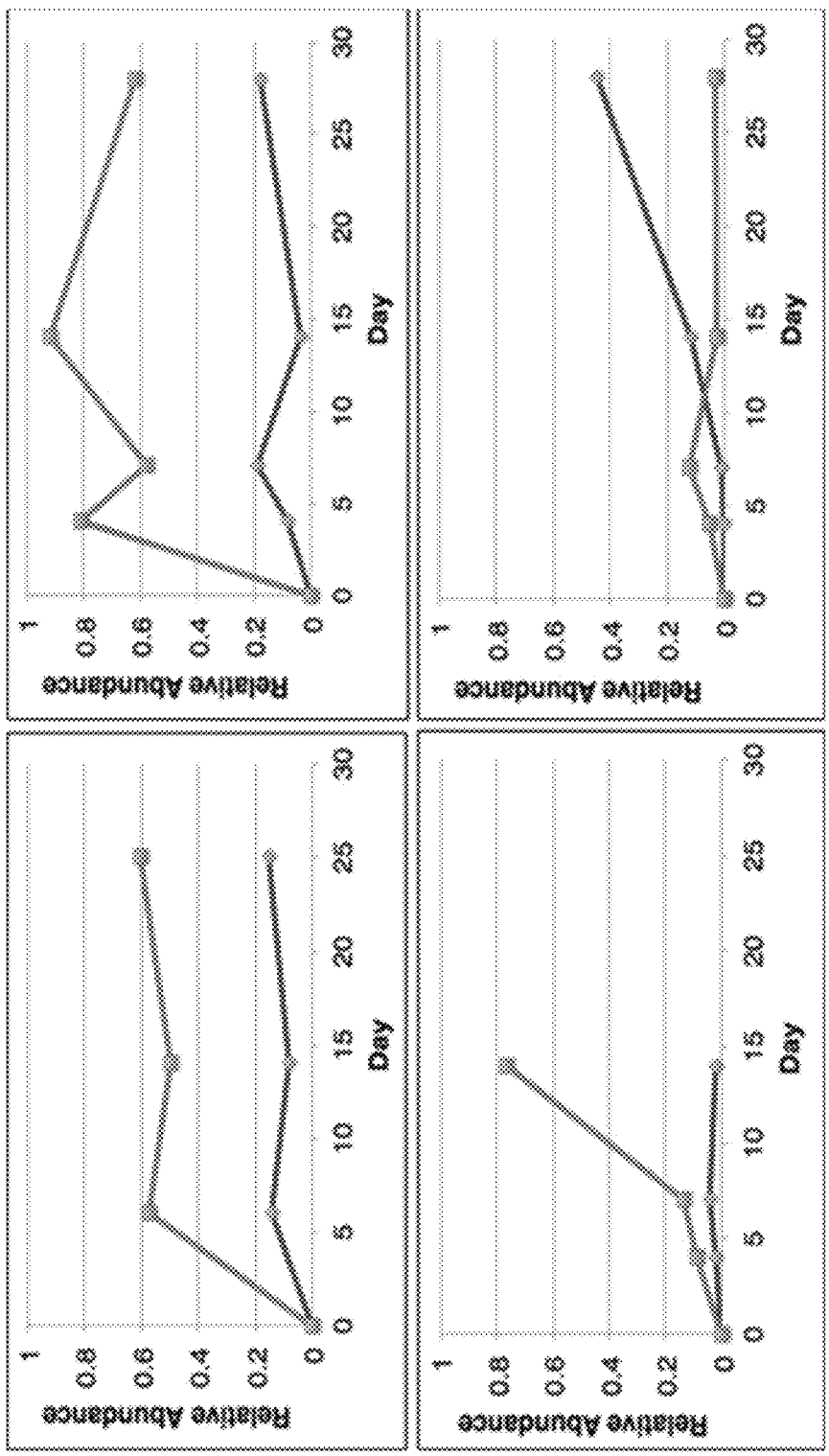
FIG. 8 shows species engrafting versus species augmenting in patients microbiomes after treatment with a bacterial composition such as but not limited to an ethanol-treated spore population, according to an embodiment of the invention. Relative abundance of species that engrafted or augmented as described were determined based on the number of 16S sequence reads. Each plot is from a different patient treated with the bacterial composition such as but not limited to an ethanol-treated spore population for recurrent *C. difficile*.

FIG. 8 shows species engrafting versus species augmenting in patients microbiomes after treatment with a bacterial composition such as but not limited to an ethanol-treated spore population. Relative abundance of species that engrafted or augmented as described were determined based on the number of 16S sequence reads. Each plot is from a different patient treated with the bacterial composition such as but not limited to an ethanol-treated spore population for recurrent *C. difficile*.

The impact of the bacterial composition such as but not limited to an ethanol-treated spore population treatment on carriage of imipenem resistant Enterobacteriaceae was assessed by plating pretreatment and Day 28 clinical samples from Patients 2, 4 and 5 on MacConkey lactose plus 1 ug/mL of imipenem. Resistant organisms were scored by morphology, enumerated and DNA was submitted for full length 16S rDNA sequencing as described above. Isolates were identified as *Morganella morganii*, *Providencia rettgeri* and *Proteus penneri*. Each of these are gut commensal organisms; overgrowth can lead to bacteremia and/or urinary tract infections requiring aggressive antibiotic treatment and, in some cases, hospitalization [Kim, B-N, et al Scan J. Inf Dis (2003) 35: 98-103; Lee, I—K and Liu, J-W J. Microbiol Immunol Infect (2006) 39: 328-334; O'Hara et al, Clin Microbiol Rev (2000) 13: 534]. The titer of organisms at pretreatment and Day 28 by patient is shown in Table 17. Importantly, administration of the bacterial composition such as but not limited to an ethanol-treated spore preparation resulted in greater than 100-fold reduction in 4 of 5 cases of Enterobacteriaceae carriage with multiple imipenem resistant organisms (See Table 17 which shows titers (in cfu/g) of imipenem-resistant *M. morganii*, *P. rettgeri* and *P. penneri* from Patients 2, 4 & 5).

In addition to speciation and enumeration, multiple isolates of each organism from Patient 4 were grown overnight in 96-well trays containing a 2-fold dilution series of imipenem in order to quantitatively determine the minimum inhibitory concentration (MIC) of antibiotic. Growth of organisms was detected by light scattering at 600 nm on a SpectraMax M5e plate reader. In the clinical setting, these species are considered resistant to imipenem if they have an MIC of 1 ug/mL or greater. *M. morganii* isolates from pretreatment samples from Patient 4 had MICs of 2-4 ug/mL and *P. penneri* isolates had MICs of 4-8 ug/mL. Thus, the bacterial composition, such as but not limited to, an ethanol-treated spores administered to Patient 4 caused the clearance of 2 imipenem resistant organisms (Table 4). While this example specifically uses a spore preparation, the methods herein describe how one skilled in the art would use a more general bacterial composition to achieve the same effects. The specific example should not be viewed as a limitation of the scope of this disclosure.

Identifying the Core Ecology From the Bacterial Combination

Ten different bacterial compositions were made by the ethanol-treated spore preparation methods from 6 different donors (as described above). The spore preparations were used to treat 10 patients, each suffering from recurrent *C. difficile* infection. Donors were identified using the inclusion/exclusion criteria described above under provision of fecal material. None of the patients experienced a relapse of *C. difficile* in the 4 weeks of follow up after treatment, whereas the literature would predict that 70-80% of subjects would experience a relapse following cessation of antibiotic [Van Nood, et al, NEJM (2013)]. Thus, the ethanol-treated spore preparations derived from multiple different donors and donations showed remarkable clinical efficacy. These ethanol-treated spore preparations are a subset of the bacterial compositions described herein and the results should not be viewed as a limitation on the scope of the broader set of bacterial compositions.

To define the Core Ecology underlying the remarkable clinical efficacy of the bacterial compositions e.g. ethanol-treated spore preparations, the following analysis was carried out. The OTU composition of the spore preparation was determined by 16S-V4 rDNA sequencing and computational assignment of OTUs per Example 2. A requirement to detect at least ten sequence reads in the ethanol-treated spore preparation was set as a conservative threshold to define only OTUs that were highly unlikely to arise from errors during amplification or sequencing. Methods routinely employed by those familiar to the art of genomic-based microbiome characterization use a read relative abundance threshold of 0.005% (see e.g. Bokulich, A. et al. 2013. Quality-filtering vastly improves diversity estimates from Illumina amplicon sequencing. Nature Methods 10: 57-59), which would equate to ≥2 reads given the sequencing depth obtained for the samples analyzed in this example, as cut-off which is substantially lower than the ≥10 reads used in this analysis. All taxonomic and clade assignments were made for each OTU as described in Example 2. The resulting list of OTUs, clade assignments, and frequency of detection in the spore preparations are shown in Table 18. Table 18 shows OTUs detected by a minimum of ten 16S-V4 sequence reads in at least one ethanol-treated spore preparatio. OTUs that engraft in a treated patients and the percentage of patients in which they engraft are denoted, as are the clades, spore forming status, and Keystone OTU status. Starred OTUs occur in ≥80% of the ethanol preps and engraft in ≥50% of the treated patients.

Next, it was reasoned that for an OTU to be considered a member of the Core Ecology of the bacterial composition, that OTU must be shown to engraft in a patient. Engraftment is important for two reasons. First, engraftment is a sine qua non of the mechanism to reshape the microbiome and eliminate *C. difficile* colonization. OTUs that engraft with higher frequency are highly likely to be a component of the Core Ecology of the spore preparation or broadly speaking a set bacterial composition. Second, OTUs detected by sequencing a bacterial composition (as in Table 6 may include non-viable cells or other contaminant DNA molecules not associated with the composition. The requirement that an OTU must be shown to engraft in the patient eliminates OTUs that represent non-viable cells or contaminating sequences. Table 6 also identifies all OTUs detected in the bacterial composition that also were shown to engraft in at least one patient post-treatment. OTUs that are present in a large percentage of the bacterial composition e.g. ethanol spore preparations analyzed and that engraft in a large number of patients represent a subset of the Core Ecology that are highly likely to catalyze the shift from a dysbiotic disease ecology to a healthy microbiome.

A third lens was applied to further refine insights into the Core Ecology of the bacterial composition (e.g. spore preparation). Computational-based, network analysis has enabled the description of microbial ecologies that are present in the microbiota of a broad population of healthy individuals (see Example 5). These network ecologies are comprised of multiple OTUs, some of which are defined as Keystone OTUs. Keystone OTUs are computationally defined as described in Example 6. Keystone OTUs form a foundation to the microbially ecologies in that they are found and as such are central to the function of network ecologies in healthy subjects. Keystone OTUs associated with microbial ecologies associated with healthy subjects are often are missing or exist at reduced levels in subjects with disease. Keystone OTUs may exist in low, moderate, or high abundance in subjects. Table 6 further notes which of the OTUs in the bacterial composition e.g. spore preparation are Keystone OTUs exclusively associated with individuals that are healthy and do not harbor disease. The presence of computationally derived Keystone OTUs in the Core Ecology of the doses validates the predictive capacity of computationally derived network ecologies.

There are several important findings from this data. A relatively small number of species, 16 in total, are detected in all of the spore preparations from 6 donors and 10 donations. This is surprising because the HMP database (hmpdacc.org) describes the enormous variability of commensal species across healthy individuals. The presence of a small number of consistent OTUs lends support to the concept of a Core Ecology and Backbone Networks. The engraftment data further supports this conclusion. A regression analysis shows a significant correlation between frequency of detection in a spore preparation and frequency of engraftment in a donor: R=0.43 (p<0.001). While this may seem obvious, there is no a priori requirement that an OTU detected frequently in the bacterial composition e.g. spore preparation will or should engraft. For instance, *Lutispora thermophila*, a spore former found in all ten spore preparations, did not engraft in any of the patients. *Bilophila wadsworthia*, a gram negative anaerobe, is present in 9 of 10 donations, yet it does not engraft in any patient, indicating that it is likely a non-viable contaminant in the ethanol-treated spore preparation. Finally, it is worth noting the high preponderance of previously defined Keystone OTUs among the most frequent OTUs in the spore preparations.

These three factors—prevalence in the bacterial composition such as but not limited to a spore preparation, frequency of engraftment, and designation as a Keystone OTUs—enabled the creation of a "Core Ecology Score" (CES) to rank individual OTUs. CES was defined as follows:

40% weighting for presence of OTU in spore preparation
multiplier of 1 for presence in 1-3 spore preparations
multiplier of 2.5 for presence in 4-8 spore preparations
multiplier of 5 for presences in ≥9 spore preparations
40% weighting for engraftment in a patient
multiplier of 1 for engraftment in 1-4 patients
multiplier of 2.5 for engraftment in 5-6 patients
multiplier of 5 for engraftment in ≥7 patients
20% weighting to Keystone OTUs
multiplier of 1 for a Keystone OTU
multiplier of 0 for a non-Keystone OTU Using this guide, the CES has a maximum possible score of 5 and a minimum possible score of 0.8. As an example, an OTU found in 8 of the 10 bacterial composition such as but not limited to a spore preparations that engrafted in 3 patients and was a Keystone OTU would be assigned the follow CES:

$$CES=(0.4\times2.5)+(0.4\times1)+(0.2\times1)=1.6$$

Table 7 ranks the top 20 OTUs by CES with the further requirement that an OTU must be shown to engraft to be a considered an element of a core ecology.

Defining Efficacious Subsets of the Core Ecology

The number of organisms in the human gastrointestinal tract, as well as the diversity between healthy individuals, is indicative of the functional redundancy of a healthy gut microbiome ecology (see The Human Microbiome Consortia. 2012. Structure, function and diversity of the healthy human microbiome. Nature 486: 207-214). This redundancy makes it highly likely that subsets of the Core Ecology describe therapeutically beneficial components of the bacterial composition such as but not limited to an ethanol-treated spore preparation and that such subsets may themselves be useful compositions for populating the GI tract and for the treatment of C. difficile infection given the ecologies functional characteristics. Using the CES, individual OTUs can be prioritized for evaluation as an efficacious subset of the Core Ecology.

Another aspect of functional redundancy is that evolutionarily related organisms (i.e. those close to one another on the phylogenetic tree, e.g. those grouped into a single clade) will also be effective substitutes in the Core Ecology or a subset thereof for treating C. difficile.

To one skilled in the art, the selection of appropriate OTU subsets for testing in vitro (see Example 20 below) or in vivo (see Examples 13 or 14) is straightforward. Subsets may be selected by picking any 2, 3, 4, 5, 6, 7, 8, 9, 10, or more than 10 OTUs from Table 6, with a particular emphasis on those with higher CES, such as the OTUs described Table 7. In addition, using the clade relationships defined in Example 2 above and Table 1, related OTUs can be selected as substitutes for OTUs with acceptable CES values. These organisms can be cultured anaerobically in vitro using the appropriate media (selected from those described in Example 5 above), and then combined in a desired ratio. A typical experiment in the mouse C. difficile model utilizes at least $10^4$ and preferably at least $10^5$, $10^6$, $10^7$, $10^8$, $10^9$ or more than $10^9$ colony forming units of a each microbe in the composition. Variations in the culture yields may sometimes mean that organisms are combined in unequal ratios, e.g. 1:10, 1:100, 1:1,000, 1:10,000, 1:100,000, or greater than 1:100,000. What is important in these compositions is that each strain be provided in a minimum amount so that the strain's contribution to the efficacy of the Core Ecology subset can be measured. Using the principles and instructions described here, it is straightforward for one of skill in the art to make clade-based substitutions to test the efficacy of subsets of the Core Ecology. Table 18 describes the clades for each OTU detected in a spore preparation, and Table 1 describes the OTUs that can be used for substitutions based on clade relationships. Examples of network ecologies empirically screened in vivo are presented in Example 13 below.

Example 12. Presence of Network Ecologies and Keystone OTUs in Clinically Prepped Ethanol-Treated Spore Preparation and CDAD Patients Post Treatment Network ecologies computationally determined as described in Example 5 and reported in Table 8 as being networks or subsets of networks characteristic of health states in the context of CDAD or other disease indications (Table 14a-b) are observed in the ethanol-treated spore preparation (a.k.a. the bacterial composition) and the microbiome of patients post treatment (see Example 11) indicating that they play an important role in treatment of CDAD and other indications. For each computationally determined network ecology (Table 8), we determined whether the full network or a subset of the network was observed in the microbiome of (i) each of the 10 ethanol-treated spore preparations used to treat patients with recurrent Clostridium difficile associated diarrhea; (ii) the engrafted ecology of each of the 10 patients (see Example 11); (iii) the augmented ecology of each of the 10 patients (see Example 11); or (iv) of each of the 10 patient's microbiome pretreatment. If the computationally determined networks are indeed representative of a state of health and not a disease state, one would expect that these networks would be responsible for catalyzing a shift from a disease state to a health state. This can happen either by the network ecology changing the gut environment to favor the growth of OTUs that are required to establish a health state (i.e. promoting augmentation) or by the engraftment of OTUs in the bacterial composition or both. Applicants observed that numerous computationally determined networks and/or subsets of these networks were in fact observed both in the bacterial composition used to treat the patients and the microbiota that expanded post-treatment (Table 14b). These same networks or sub-sets of networks were significantly under-represented in the patients pre-treatment. To demonstrate this, we computed the percentage of network OTUs that are found in (i) the treatment bacterial composition, (ii) the post-treatment augmented ecology, (iii) the post-treatment engrafted ecology, and (iv) the pretreatment ecology (i.e. patient microbiome prior to administration of the bacterial composition). Applicants observed across all doses of bacterial composition and patient samples that on average 46%±19%, 28%±14%, 11%±8%, and 7%±4% of the computed networks OTUs were present in the various microbiome ecologies, respectively (reported here as average±standard deviation). There was a significant difference ($p<0.0001$, ANOVA) between all of these percentages indicating that prior to treatment, the OTUs found in CDAD patients are significantly under-represented in the networks, and that the network OTUs are significantly over-represented in the bacterial compositions and post-treatment patient samples, affirming the predictive utility of the computational network analysis. These results in combination with those reported in Table 14b demonstrate that, prior to treatment, the patients harbored a significantly lower number of OTUs that comprised network ecologies. In contrast, the ecology of the bacterial composition, as well as the augmenting ecologies whose appearance was catalyzed by the spore population, were significantly overrepresented in patients whose CDAD resolved due to treatment.

We observed both large and small computationally determined network ecologies characteristic of states of health in the ethanol-treated spore population and the patients post treatment (Table 14a). These observed networks ranged in size from 2-15 OTUs and were comprised of OTUs that represented from 29% to 100% of the OTUs in the computationally determined network ecology. Notably, on average the network ecologies found in the ethanol-treated spore population or the patient ecologies post treatment comprised 72%±15% (average±SD) of the computationally determined network ecology again strongly indicating an important role of the computed network ecologies in catalyzing a shift in a dysbiotic disease ecology to a state of health in these patients with recurrent CDAD. Further, Keystone OTUs in the computationally determined network ecologies were frequently observed in the ethanol-treated spore preparations and in the patients' post-treatment gut ecologies. Clades representing Keystone OTUs where typically more common in the bacterial composition and post-treatment patient ecologies than in the pre-treatment dysbiotic patient ecology (Table 15).

The computed network ecologies and their respective subsets that are observed in the ethanol-treated spore preparation and the various patient ecologies post-treatment represent both complete and foundational networks (e.g., Backbone Network Ecology). Microbial therapeutics can be comprised of these network ecologies in their entirety, or they can be modified by the addition or subtraction of other OTUs or functional modalities as described in Example 7 and Example 22 to design particular phylogenetic and/or functional characteristics, including metabolic functions such as SCFA production or bile acid metabolism, into the microbial therapeutic.

Example 13. In Vivo Validation of Network Ecology Bacterial Compositions Efficacy in *Clostridium Difficile* Infection Prevention Mouse Model To test the therapeutic potential of the bacterial composition such as but not limited to a spore population, a prophylactic mouse model of *C. difficile* infection was used (model based on Chen X, Katchar K, Goldsmith J D, Nanthakumar N, Cheknis A, Gerding D N, Kelly C P. 2008. A mouse model of *Clostridium difficile*-associated disease. Gastroenterology 135: 1984-1992.). Two cages of five mice each were tested for each arm of the experiment. All mice received an antibiotic cocktail consisting of 10% glucose, kanamycin (0.5 mg/ml), gentamicin (0.044 mg/ml), colistin (1062.5 U/ml), metronidazole (0.269 mg/ml), ciprofloxacin (0.156 mg/ml), ampicillin (0.1 mg/ml) and Vancomycin (0.056 mg/ml) in their drinking water on days −14 through −5 and a dose of 10 mg/kg Clindamycin by oral gavage on day −3. On day −1, test articles are spun for 5 minutes at 12,100 rcf, their supernatants' removed, and the remaining pellets are resuspended in sterile PBS, prereduced if bacterial composition is not in spore form, and delivered via oral gavage. On day 0 they were challenged by administration of approximately 4.5 log 10 cfu of *C. difficile* (ATCC 43255) or sterile PBS (for the Naive arm) via oral gavage. Optionally a positive control group received vancomycin from day −1 through day 3 in addition to the antibiotic protocol and *C. difficile* challenge specified above. Feces were collected from the cages for analysis of bacterial carriage. Mortality, weight and clinical scoring of *C. difficile* symptoms based upon a 0-4 scale by combining scores for Appearance (0-2 pts based on normal, hunched, piloerection, or lethargic), and Clinical Signs (0-2 points based on normal, wet tail, cold-to-the-touch, or isolation from other animals) are assessed every day from day −2 through day 6. Mean minimum weight relative to day −1 and mean maximum clinical score where a death is assigned a clinical score of 4 as well as average cumulative mortality are calculated. Reduced mortality, increased mean minimum weight relative to day −1, and reduced mean maximum clinical score with death assigned to a score of 4 relative to the vehicle control are used to assess the success of the test article.

Table 16 reports results for 15 experiments of the prophylactic mouse model of *C. difficile* infection. In the 15 experiments, 157 of the arms tested network ecologies, with 86 distinct networks ecologies tested (Table 17). Of those 157 arms, 136 of the arms and 73 of the networks performed better than the respective experiment's vehicle control arm by at least one of the following metrics: cumulative mortality, mean minimum relative weight, and mean maximum clinical score. Examples of efficacious networks include but are not limited to networks N1979 as tested in SP-361 which had 0% cumulative mortality, 0.97 mean minimum relative weight, and 0 mean maximum clinical score or N2007 which had 10% cumulative mortality, 0.91 mean minimum relative weight, and 0.9 mean maximum clinical score with both networks compared to the vehicle control in SP-361 which had 30% cumulative mortality, 0.88 mean minimum relative weight, and 2.4 mean maximum clinical score. In SP-376, N1962 had no cumulative mortality, mean maximum clinical scores of 0 at both target doses tested with mean minimum relative weights of 0.98 and 0.95 for target doses of 1e8 and 1e7 CFU/OTU/mouse respectively. These results confirm that bacterial compositions comprising bacteria identified from computationally determined networks or subsets of these determined networks have utility and efficacy in the mouse model.

Example 14. In Vivo Validation of Network Ecology Bacterial Composition Efficacy in Prophylactic and Relapse Prevention Hamster Model Previous studies with hamsters using toxigenic and non-toxigenic strains of *C. difficile* demonstrated the utility of the hamster model in examining relapse post antibiotic treatment and the effects of prophylaxis treatments with cecal flora in *C. difficile* infection (Wilson et al. 1981, Wilson et al. 1983, Borriello et al. 1985) and more broadly in gastrointestinal infectious disease. To demonstrate prophylactic use of ethanol-treated spores and ethanol treated, gradient-purified spores to ameliorate *C. difficile* infection, the following hamster model was used. In the prophylactic model, Clindamycin (10 mg/kg s.c.) was given on day −5, the test article or control was administered on day −3, and *C. difficile* challenge occurred on day 0. In the positive control arm, vancomycin was then administered on day 1-5 (and vehicle control was delivered on day −3). Feces were collected on day −5, −4, −1, 1, 3, 5, 7, 9 and fecal samples were assessed for pathogen carriage and reduction by microbiological methods. 16S sequencing approaches or other methods could also be utilized by one skilled in the art. Mortality was assessed multiple times per day through 21 days post *C. difficile* challenge. The percentage survival curves showed that ethanol-treated spores and ethanol treated, gradient-purified spores better protected the hamsters compared to the Vancomycin control, and vehicle control.

Figure 9:
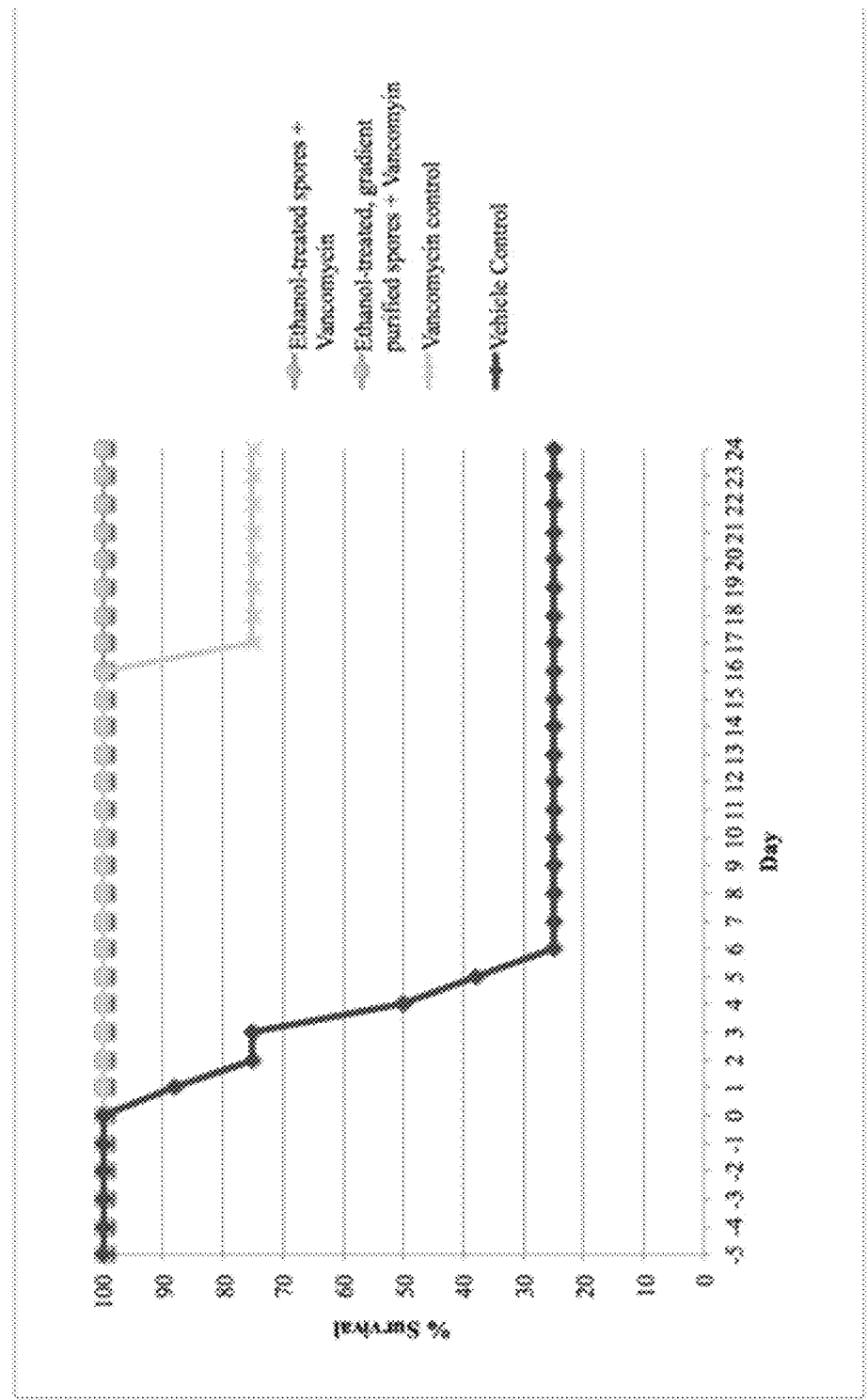
FIG. 9 shows a set of survival curves demonstrating efficacy of the ethanol enriched spore population in a mouse prophylaxis model of *C. difficile*, according to an embodiment of the invention.

FIG. 9 shows a prophylaxis model with the ethanol-treated spore preparation and the ethanol treated, gradient-purified spore preparation. In the relapse prevention model, hamsters were challenged with toxigenic *C. difficile* strains on day 0, and treated with clindamycin by oral gavage on day 1, and vancomycin was dosed on days 2-6. Test or control treatment was then administered on day 7, 8, and 9. The groups of hamsters for each arm consisted of 8 hamsters per group. Fecal material was collected on day −1, 1, 3, 5, 7, 10 and 13 and hamster mortality was assessed throughout. Survival curves were used to assess the efficacy of the test articles, e.g., ethanol treated or ethanol treated, gradient purified spores versus the control treatment in preventing hamster death. The survival curves demonstrated maximum efficacy for the ethanol treated, gradient-purified spores followed by the ethanol-treated spores. Both treatments improved survival percentage over vancomycin treatment.

Also in the relapse prevention model, the efficacy of a bacterial community of pure cultures, N1962, was tested. The survival curves demonstrate protection against relapse by N1962 relative to the vancomycin control treatment.

Figure 10:
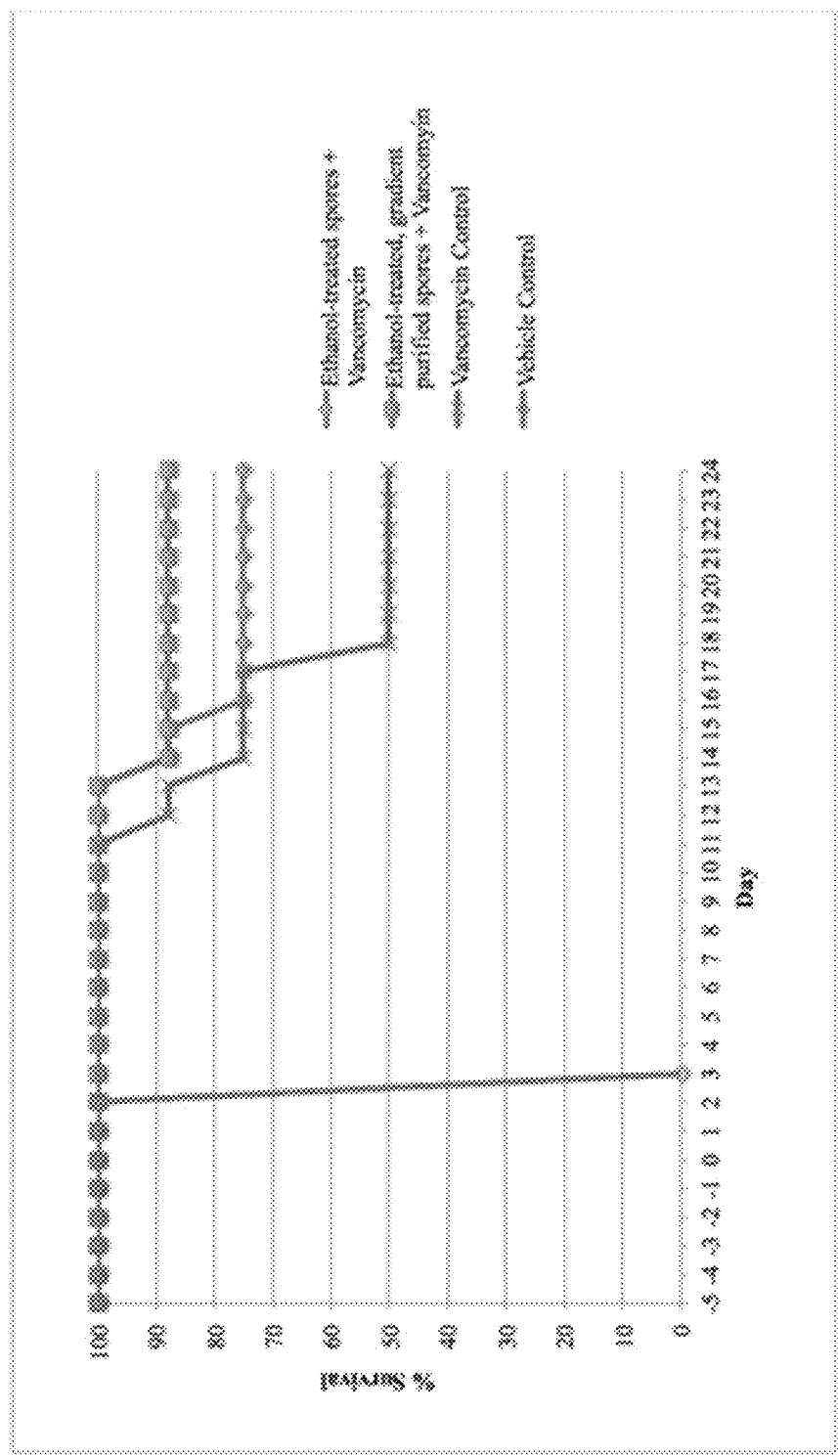
FIG. 10 illustrates an in vivo hamster *Clostridium difficile* relapse prevention model to validate efficacy of ethanol-treated spores and ethanol treated, gradient purified spores, according to an embodiment of the invention.

FIG. 10 shows a relapse prevention model with ethanol-treated spores and ethanol treated, gradient purified spores. In particular, it shows an in vivo hamster *Clostridium difficile* relapse prevention model to validate efficacy of ethanol-treated spores and ethanol treated, gradient purified spores.

Figure 11:
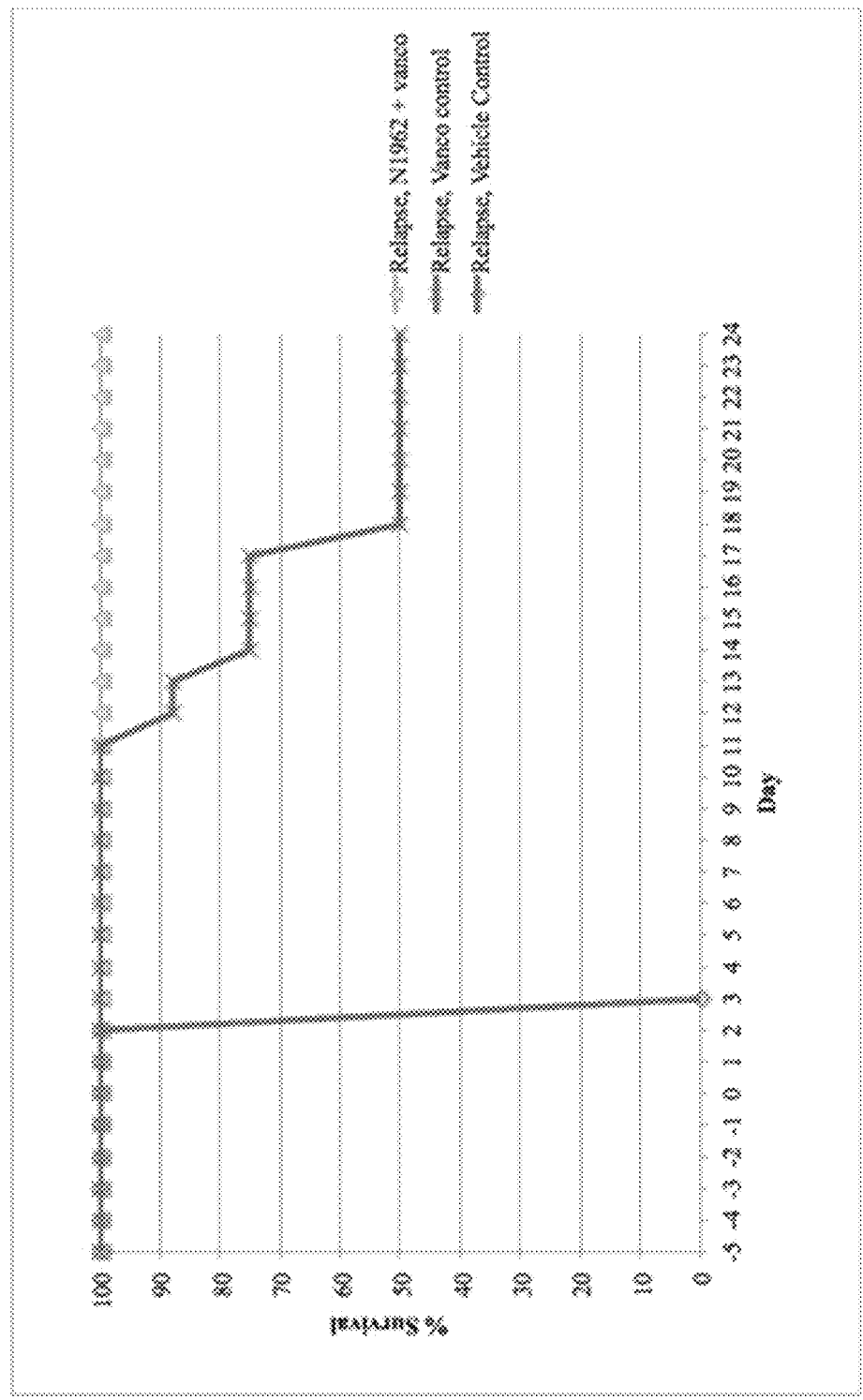
FIG. 11 shows an in vivo hamster *Clostridium difficile* relapse prevention model to validate efficacy of network ecology bacterial composition, according to an embodiment of the invention.

FIG. 11 shows a relapse prevention model with a bacterial community. In particular, it shows an in vivo hamster

*Clostridium difficile* relapse prevention model to validate efficacy of network ecology bacterial composition.

Example 15. Derivation of Functional Profile of Individual Microbial OTUs or Consortia of OTUs Representing Specific Network Ecologies To generate a functional profile of an OTU, or consortium of OTUs one can leverage multiple-omic data types. These include, but are not limited to functional prediction based on 16S rRNA sequence, functional annotation of metagenomic or full-genome sequences, transcriptomics, and metabolomics. A consortium of OTUs of interest can be defined using numerous criteria including but not limited to: (i) a computationally derived network of OTUs based on the analysis of samples that represent states of health and disease such as those delineated in Example 5 and reported in Table 8, (ii) a consortia of OTUs that are identified in an individual sample or group of samples using either a 16S-based, metagenomic-based, or microbiological-based methods such as delineated in Examples 3, 4 and 16, and (iii) a list of OTUs derived from the assessment of literature.

For 16S rRNA sequences, phylogenetic investigation of communities by reconstruction of unobserved states, also known as PICRUSt (Langille M G I, Zaneveld J, Caporaso J G, McDonald D, Knights D, Reyes J A, Clemente J C, Burkepile D E, Vega Thurber R L, Knight R, et al. 2013. Predictive functional profiling of microbial communities using 16S rRNA marker gene sequences. Nat Biotechnol.), enables the prediction of a functional metabolic pathway of an OTU or a consortium of OTUs based on the KEGG database of reference functional pathways and functional ontologies (Kyoto Encyclopedia of Genes and Genomes; genome.jp/kegg/). PICRUSt matches the taxonomic annotation of a single 16S sequence read with a reference functional annotation of a genome sequence for a given OTU or set of OTUs. From these reference genome annotations, a functional annotation is assigned to each OTU. PICRUSt is composed of two high-level workflows: gene content inference and metagenome inference. The gene content inference produces gene content predictions for a set of reference OTUs as well as copy number predictions. The metagenome inference then uses these inputs and an OTU table that defines the OTUs in a sample and their relative abundances to then infer the functional metabolic profile of the OTUs in the OTU table. In an alternative, but related method, one can lookup for all of the OTUs in a consortia the OTU taxonomic identifications in a functional reference database such as IMG (http://img.jgi.doe.gov) and then derive a functional annotation of the network by concatenating the database's metabolic pathway maps (e.g. KEGG Pathway Orthology in case of IMG) for each of the OTUs in the consortia (see below for specific example).

To generate functional annotation from metagenomic or whole genome shotgun sequence data, reads are first clustered and then representative reads are annotated. Sequence annotation is then performed as described in Example 1, with the additional step that sequences are either clustered or assembled prior to annotation. Following sequence characterization as described above using a technology such as but not limited to Illumina, sequence reads are demultiplexed using the indexing barcodes. Following demultiplexing sequence reads are clustered using a rapid clustering algorithm such as but not limited to UCLUST (drive5.com/usearch/manual/uclust algo.html) or hash-based methods such VICUNA (Xiao Yang, Patrick Charlebois, Sante Gnerre, Matthew G Coole, Niall J. Lennon, Joshua Z. Levin, James Qu, Elizabeth M. Ryan, Michael C. Zody, and Matthew R. Henn. 2012. De novo assembly of highly diverse viral populations. BMC Genomics 13:475). Following clustering a representative read for each cluster is identified and analyzed as described above in Example 2 "Primary Read Annotation". The result of the primary annotation is then applied to all reads in a given cluster. In another embodiment, metagenomic sequences are first assembled into contigs and then these assembled contigs are annotated using methods familiar to one with ordinary skill in the art of genome assembly and annotation. Platforms such as but not limited to MetAMOS (TJ. Treangen et al. 2013 Geneome Biology 14:R2), and HUMAaN (Abubucker S, Segata N, Goll J, Schubert A M, Izard J, Cantarel B L, Rodriguez-Mueller B, Zucker J, Thiagaraj an M, Henrissat B, et al. 2012. Metabolic Reconstruction for Metagenomic Data and Its Application to the Human Microbiome ed. J. A. Eisen. PLoS Computational Biology 8: e1002358) are suitable for analysis of metagenomic data sets using the methods described above. Tools such as MetAMOS are also suitable for the generation of a functional annotation of complete genome sequence assembled from the sample or obtained from a reference genome database such as but not limited to NCBI's genome database (ncbi.nlm.nih.gov/genome). In all cases, functional pathways are derived from the sequence read annotations based on the mapping of the sequence annotations to a functional database, such as but not limited to KEGG (genome.jp/kegg), Biocyc (biocyc.org), IMG (img.jgi.doe.gov), MetaCyc (metacyc.org), or Reactome (reactome.org). Various tools are available for this task that are familiar to one with ordinary skill in the art including, but not limited to, The HMP Unified Metabolic Analysis Network (HUMAnN) (Abubucker S, Segata N, Goll J, Schubert A M, Izard J, Cantarel B L, Rodriguez-Mueller B, Zucker J, Thiagarajan M, Henrissat B, et al. 2012. Metabolic Reconstruction for Metagenomic Data and Its Application to the Human Microbiome ed. J.A. Eisen. PLoS Computational Biology 8: e1002358). The HUMAnN software recovers the presence, absence, and abundance of microbial gene families and pathways from metagenomic data. Cleaned short DNA reads are aligned to the KEGG Orthology (or any other characterized sequence database with functional annotation assigned to genetic sequences) using accelerated translated BLAST. Gene family abundances are calculated as weighted sums of the alignments from each read, normalized by gene length and alignment quality. Pathway reconstruction is performed using a maximum parsimony approach followed by taxonomic limitation (to remove false positive pathway identifications) and gap filling (to account for rare genes in abundant pathways). The resulting output is a set of matrices of pathway coverages (presence/absence) and abundances, as analyzed here for the seven primary body sites of the Human Microbiome Project.

Transcriptomic or RNA-Seq data are also a means to generate a functional profile of a sample (Wang Z, Gerstein M, Snyder M. 2009. RNA-Seq: a revolutionary tool for transcriptomics. Nat Rev Genet 10: 57-63). Briefly, long RNAs are first converted into a library of cDNA fragments through either RNA fragmentation or DNA fragmentation. Sequencing adaptors appropriate to the sequencing technology being used for downstream sequencing are subsequently added to each cDNA fragment and a short sequence is obtained from each cDNA using high-throughput sequencing technology. The resulting sequence reads are aligned with the reference genome or transcriptome and annotated and mapped to functional pathways as described above. Reads are categorized as three types: exonic reads, junction reads and poly(A) end-reads. These three types of reads in combination with the gene annotation are used to generate a base-resolution expression profile for each gene.

In yet another method to generate a metabolic profile of a microbial ecology, characterization of metabolites produced by the ecology are analyzed in tissues or fluids. Samples can include, without limitation, blood, urine, serum, feces, ileal fluid, gastric fluid, pulmonary aspirates, tissue culture fluid, or bacterial culture supernatants. Both targeted and untargeted methods can be utilized for metabolomics analysis (Patti G J, Yanes O, Siuzdak G. 2012. Innovation: Metabolomics: the apogee of the omics trilogy. Nat Rev Mol Cell Biol 13: 263-269.). Metabolomic methods utilize LC/MS-based technologies to generate a metabolite profile of sample. In the triple quadrupole (QqQ)-based targeted metabolomic workflow, standard compounds for the metabolites of interest are first used to set up selected reaction monitoring methods. Here, optimal instrument voltages are determined and response curves are generated using reference standards for absolute quantification. After the targeted methods have been established on the basis of standard metabolites, metabolites are extracted from the sample using methods familiar to one with ordinary skill in the art. Extraction methods can include liquid:liquid extraction using organic solvents or two-phase aqueous methods, solid phase extraction using hydrophobic or ion exchange resins, filtrations to remove solid contaminants, centrifugation or other means of clarification, and counter-current techniques. The data output provides quantification only of those metabolites for which standards are available. In the untargeted metabolomic workflow, extracted metabolites are first iseparated by liquid chromatography followed by mass spectrometry (LC/MS). After data acquisition, the results are processed by using bioinformatic software such as XCMS to perform nonlinear retention time alignment and identify peaks that are changing between the groups of related samples. The m/z values for the peaks of interest are searched in a metabolite databases to obtain putative identifications. Putative identifications are then confirmed by comparing tandem mass spectrometry (MS/MS) data and retention time data to that of standard compounds. The untargeted workflow is global in scope and outputs data related to comprehensive cellular metabolism.

Applicants generated a functional profile for all of the computationally determined network ecologies delineated in Table 8 and Table 14a that were derived using the methods outlined in Example 5. Table 18 and Table 21 provide written description of the corresponding functional network ecologies respectively. For each network, applicants generated a functional metabolic profile by concatenating the KEGG Orthology Pathways for each OTU available in the IMG functional database (img.jgi.doe.gov). The taxonomic annotations of each OTU in the network were mapped to the taxon_display_names in the IMG database. For each taxon_display_name the taxon_iod with the best 16S sequence match to the 16S sequence of the OTU in the computed network ecology was selected (best match based on expectation value and an alignment score). The functional annotation for each OTU in the network was then derived from IMG's KEGG Orthology Pathway (i.e. ko_id) for the given taxon_iod. KEGG Orthology Pathways (KO) for all the OTUs in the network were concatenated and then the list was made unique to generate a non-redundant functional profile of the network. In another embodiment, the ko_id list is not made unique and the functional profile of the network is defined based on the relative abundances of the ko_ids not just their presence or absence. It is with the level of ordinary skill using the aforementioned disclosure to construct functional network ecologies that substitute the exemplified OTUs with equivalent OTUs that harbor the orthologous KEGG Orthology Pathways. Such substitiutions are contemplated to be within the scope of the present invention, either literally or as an equivalent to the claimed invention as determined by determined by a court of competent jurisdiction.

Each functional network ecology was scored for its ability to metabolize bile acids and to produce short chain fatty acids (SCFAs). As described above, both bile acid metabolism and the production of SCFAs by bacterial ecologies plays an important role in human health. Specifically, applicants subsetted the KEGG Orthology Pathways computed for each network ecology to those described to be involved in secondary bile acid biosynthesis, butryrate (a.k.a. butanoate) metabolism, propionate (a.k.a. propanoate) metabolism, or pyruvate metabolism (leads to production of acetate). We identified and ranked network ecologies for their capacity to metabolize bile acid and produce SCFAs by defining a bile acid and SCFA functional score (F-Score) that defines a network ecologies' capacity to perform these two important metabolic roles. The F-score is defined by the total number of KEGG Orthology Pathways in a given network that mapped to secondary bile acid biosynthesis, a butyrate metabolism, a propionate metabolism, or a pyruvate metabolism (Table 18). A functional translation of the KEGG Orthology Pathways (i.e., KO numbers) and their respective metabolic ontology classification is provided in Table 19 as reference. Significantly, as shown in Table 18, there are only two computed network ecologies that did not harbor at least one pathway related to secondary bile acid biosynthesis, butyrate metabolism, propionate metabolism, or a pyruvate metabolism, suggesting both likely importance of these pathways to the metabolism of a large number of gastrointestinal ecologies, and the importance of these pathways to catalyzing a shift from a disease to a health state in the example cases of CDAD and Type 2 Diabetes.

Example 16. Use of Biolog Assay to Generate a Nutrient Utilization Functional Profile of an OTU or Consortium of OTU Metabolic capabilities of individual organisms or a consortia of organisms can be determined using Biolog technology in which metabolic activity is detected by measurement of NADH production using a redox sensitive dye. Carbon source or other metabolic capabilities of a single species can be determined, as described below. Carbon source utilization of an ecology or network can also be assessed using the same methods.

A screen was performed to test the ability of *Clostridium difficile* and potential competitor species to utilize a panel of 190 different carbon sources. The screen was carried out using PM1 and PM2 MicroPlates (Biolog #12111, #12112), IF-0a base media (Biolog #72268) and Biolog Redox Dye Mix D (Biolog #74224). For each strain, a 1 uL aliquot from −80° C. glycerol stock was streaked out for single colonies to solid *Brucella* Blood Agar plates (BBA) (Anaerobe Systems #AS-111) and incubated anaerobically at 37° C. for 24 hr. A single colony was then re-streaked to a BBA plate and incubated anaerobically at 37° C. for 24 hr. The MicroPlates were pre-reduced by incubating for at least 24 hr in a hydrogen free anaerobic environment before use. All liquid media and supplements used were pre-reduced by placing them in an anaerobic chamber with loose lids for at least 24 hr before use. Alternatively, combinations of bacteria can also be tested.

The base media for inoculation was prepared by adding 0.029 mL of 1M potassium ferricyanide to 0.240 mL of Dye Mix D followed by addition of 19.7 mL of IF-0a, 4 mL sterile water and 0.024 mL 0.5 mM menadione. For some species, the concentrations of potassium ferricyanide and menadione were adjusted to achieve the optimal redox balance or to test multiple redox conditions. Potassium ferricyanide was tested at a final concentration of 0.38, 0.12, 0.038 and 0.06 mM. Menadione was tested at a final concentration of 0.5, 0.16 and 0.05 µM. In total, this yields 9 redox conditions for testing. Reduction of the tetrazolium dye that forms the basis for the endpoint measurement was sensitive to the redox state of each bacterial culture, and thus to the ratio of menadione to potassium ferricyanide. It was therefore important to test various ratios for each bacterial isolate and was also important in some cases to test a species at multiple menadione/potassium ferricyanide ratios in order to detect all conditions in which a possible nutrient utilization was detectable. Some species were tested beyond the 20 hr time point to detect all conditions resulting in a positive result. In these cases plates were read at 20, 44 or 96 hr.

Figure 4:
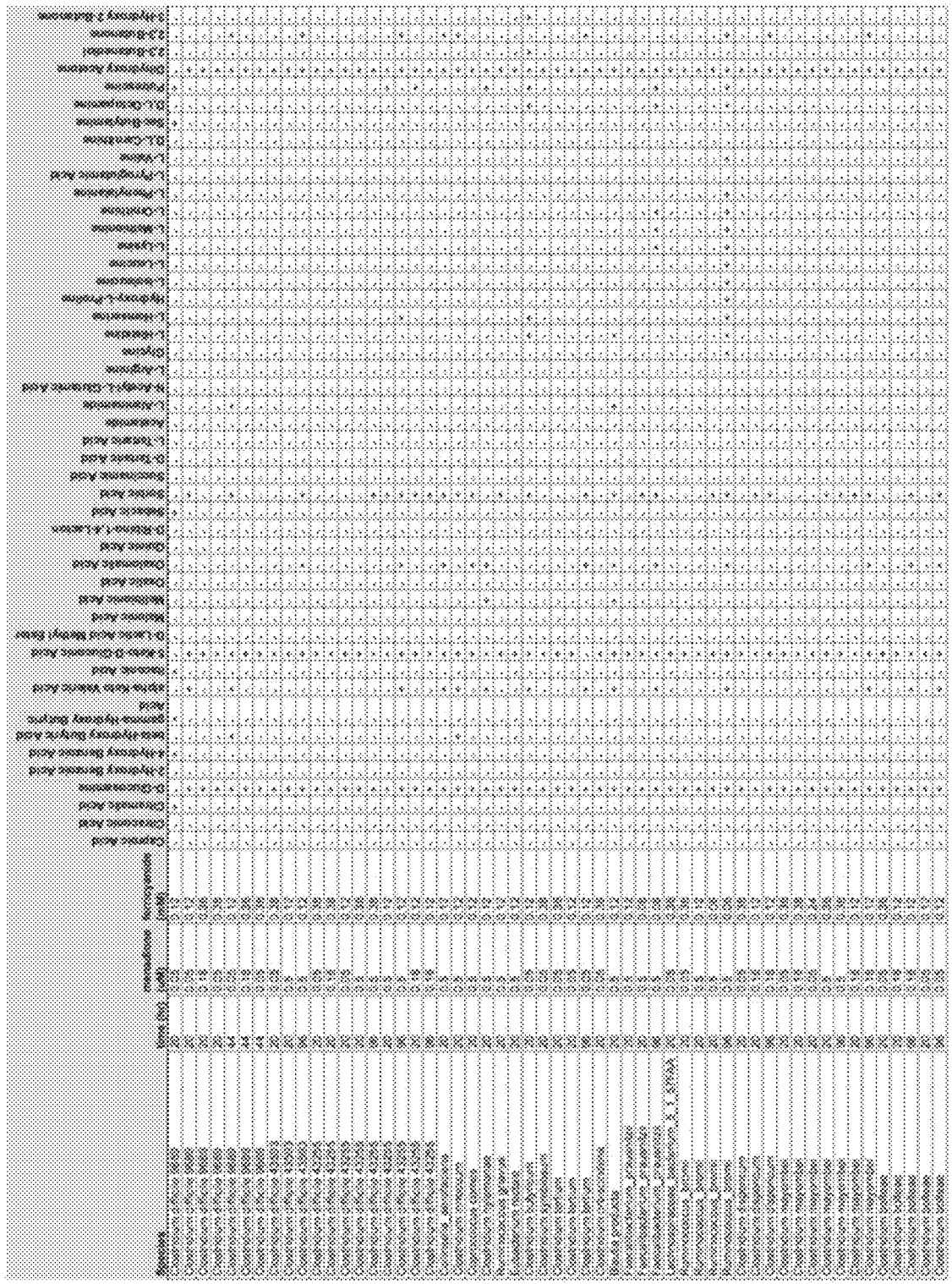
FIG. 4 illustrates the results of a nutrient utilization assay with *Clostridium difficile* and potential competitors of the pathogen. A plus sign (+) indicates that it is a nutrient for the isolate tested. A minus sign (−) indicates that it is not a nutrient for the isolate tested.

Using a sterile, 1 µL microbiological loop, a loopful of biomass was scraped from the BBA plate and resuspended in the base media by vortexing. The OD was adjusted to 0.1 at 600 nm using a SpectraMax M5 plate reader. The bacterial suspension was then aliquoted into each well of the PM1 and PM2 plates (100 µL per well). The plates were incubated at 37° C. for 20 hr in a rectangular anaerobic jar (Mitsubishi) with 3 anaerobic, hydrogen-free gas packs (Mitsubishi AnaeroPack). After 20 hr, OD at 550 nm was read using a SpectraMax M5 plate reader. Wells were scored as a weak hit if the value was 1.5× above the negative control well, and a strong hit if the value was 2× above the negative control well. The results are shown in the Table in FIG. 4.

The following list of nutrient sources were tested: L-Arabinose, N-Acetyl-D-Glucosamine, D-Saccharic Acid, SuccinicAcid, D-Galactose, L-AsparticAcid, L-Proline, D-Alanine, D-Trehalose, D-Mannose, Dulcitol, D-Serine, D-Sorbitol, Glycerol, L-Fucose, D-Glucuronic Acid, D-Gluconic Acid, D, L-alpha-Glycerol-Phosphate, D-Xylose, L-Lactic Acid, Formic Acid, D-Mannitol, L-Glutamic Acid, D-Glucose-6-Phosphate, D-Galactonic Acid-gamma-Lactone, D,L-Malic Acid, D-Ribose, Tween 20, L-Rhamnose, D-Fructose, Acetic Acid, alpha-D-Glucose, Maltose, D-Mellibiose, Thymidine, L-Asparagine, L-Aspartic Acid, D-Glucosaminic Acid, 1,2-Propanediol, Tween 40, alpha-Keto-Glutaric Acid, alpha-Keto-ButyricAcid, alpha-Methyl-D-Galactoside, alpha-D-Lactose, Lactulose, Sucrose, Uridine, L-Glutamine, M-Tartaric Acid, D-Glucose-1-Phosphate, D-Fructose-6-Phosphate, Tween 80, alpha-Hydroxy-Glutaric-gamma-lactone, alpha-Hydroxy Butyric Acid, beta-Methyl-D-Glucoside, Adonitol, Maltotriose, 2-Deoxy Adenosine, Adenosine, Glycyl-L-Aspartic Acid, Citric Acid, M-Inositol, D-Threonine, Fumaric Acid, Bromo Succinic Acid, Propionic Acid, Mucic Acid, Glycolic Acid, Glyoxylic Acid, D-Cellobiose, Inosine, Glycyl-L-Glutamic Acid, Tricarballylic Acid, L-Serine, L-Threonine, L-Alanine, L-Alanyl-Glycine, Acetoacetic Acid, N-Acetyl-beta-D-Mannosamine, Mono Methyl Succinate, Methyl Pyruvate, D-Malic Acid, L-Malic Acid, Glycyl-L-Proline, p-Hydroxy Phenyl Acetic Acid, m-Hydroxy Phenyl Acetic Acid, Tyramine, D-Psicose, L-Lyxose, Glucuronamide, Pyruvic Acid, L-Galactonic Acid-gamma-Lactone,D-Galacturonic Acid,Pheylethyl-amine,2-aminoethanol, Chondroitin Sulfate C, alpha-Cyclodextrin, beta-Cyclodextrin, gamma-Cyclodextrin, Dextrin, Gelatin, Glycogen, Inulin, Laminarin, Mannan, Pectin, N-Acetyl-D-Galactosamine, N-Acetyl-Neuramic Acid, beta-D-Allose, Amygdalin, D-Arabinose, D-Arabitol, L-Arabitol, Arbutin, 2-Deoxy-D-Ribose, I-Erythritol, D-Fucose, 3-0-beta-D-Galacto-pyranosyl-D-Arabinose, Gentibiose, L-Glucose, Lactitol, D-Melezitose, Maltitol, alpha-Methyl-D-Glucoside, beta-Methyl-D-Galactoside, 3-Methyl Glucose, beta-Methyl-D-GlucoronicAcid, alpha-Methyl-D-Mannoside, beta-Metyl-D-Xyloside, Palatinose, D-Raffinose, Salicin, Sedoheptulosan, L-Sorbose, Stachyose, D-Tagatose, Turanose, Xylitol, N-Acetyl-D-Glucosaminitol, gamma-Amino Butyric Acid, delta-Amino Valeric Acid, Butyric Acid, Capric Acid, Caproic Acid, Citraconic Acid, Citramalic Acid, D-Glucosamine, 2-Hydroxy Benzoic Acid, 4-Hydroxy Benzoic Acid, beta-Hydroxy Butyric Acid, gamma-Hydroxy Butyric Acid, alpha-Keto Valeric Acid, Itaconic Acid, 5-Keto-D-Gluconic Acid, D-Lactic Acid Methyl Ester, Malonic Acid, Melibionic Acid, Oxalic Acid, Oxalomalic Acid, Quinic Acid, D-Ribino-1,4-Lacton, Sebacic Acid, Sorbic Acid, Succinamic Acid, D-Tartaric Acid, L-Tartaric Acid, Acetamide, L-Alaninamide, N-Acetyl-L-Glutamic Acid, L-Arginine, Glycine, L-Histidine, L-Homserine, Hydroxy-L-Proline, L-Isoleucine, L-Leucine, L-Lysine, L-Methionine, L-Ornithine, L-Phenylalanine, L-Pyroglutamic Acid, L-Valine, D,L-Carnithine, Sec-Butylamine, D,L-Octopamine, Putrescine, Dihydroxy Acetone, 2,3-Butanediol, 2,3-Butanone, 3-Hydroxy 2-Butanone.

Additionally, one of skill in the art could design nutrient utilization assays for a broader set of nutrients using the methods described above including complex polysaccharides or prebiotics.

A similar screen can be performed to test the utilization of vitamins, amino acids, or cofactors. In these instances, Biolog MicroPlates for screening of vitamins, amino acids or cofactors that are of interest would be used in place of the PM1 and PM2 plates, for example PMS. Table 2 contains a list of representative vitamins, minerals, and cofactors. For each strain tested, a universal carbon source such as glucose will be used as a positive control to demonstrate reduction of the tetrazolium dye under the specific conditions of the assay.

Example 17. In Vitro Screening of Microbes for 7-Alphadehydroxylase Activity

Cultures of individual microbes are grown overnight and frozen for later use as described according to Example 9. The sodium salts of CA, CDCA, GCA, GCDCA, TCA, and TCDCA (Sigma) are obtained and prepared as aqueous stock solutions. For initial screening to define organisms capable of 7-alphadehydroxylation reactions, growth media are prepared containing 0.4 mM of each bile salt. Cultures are inoculated from a 1:100 dilution of the frozen stock into the media and grown in an anaerobic chamber for 24-48 hours, or until the culture is turbid. Two mL of culture is acidified by the addition of 1 mL of 2N HCl and 100 ug of 23-nor-deoxycholic acid (Steraloids) as an internal reference standard. The acidified mixture is extracted twice with 6 mL of diethyl ether. The organic extracts are combined and then evaporated and derivatized to methyl esters with diazomethane. Gas chromatography is performed on a 7 ft (ca. 2 m) 3% OV-1 column at 260° C. and a 3% OV-17 column at 250° C. after trimethylsilylation of the methylated bile acids with Tri-Sil (Pierce, Rockford, Ill.). The retention times of the silylated bile acids are compared with those of reference products representing CA, CDCA, DCA and LCA.

For strains showing 7-alphadehydroxylase activity, a kinetic assessment is performed by harvesting a growing culture of each organisms of interest, washing and resuspending in fresh media at a concentration of between 108 to 1010 cfu/mL. The sodium salts of CA, CDCA, GCA, GCDCA, TCA, and TCDCA are then added at 0.5 to 5 mM and the resulting culture is sampled at 1, 2, 4 and 8 hours. The sample is analyzed as described above to find organisms with maximal activity. Highly active strains are selected for further incorporation into microbial compositions that exhibit maximal 7-alphadehydroxylase activity.

Example 18. In Vitro Screening of Microbes for Bile Salt Hydrolase Activity

Cultures of individual microbes are grown overnight and frozen for later use as described according to Example 9. The sodium salts of GCA, GCDCA, TCA, and TCDCA (Sigma) are obtained and prepared as aqueous stock solutions. Overnight, actively growing cultures are combined with 0.5 to 5 mM of conjugated bile acid and allowed to incubate for 24-48 hours. To analyze cultures, 0.5 mL of culture is first centrifuged at 3,000×g for 10 min to remove the bacteria, and is then acidified with 5 uL of 6 N HCl. This acidified supernatant is combined with an equal volume of methanol containing 4 mM of 23-nordeoxycholic as an internal standard. The samples are vortexed for at least 2 min and clarified by centrifugation at 1000×g for 15 min. Samples are filtered through a 0.2 um filter prior to HPLC analysis according to the method described by Jones et al 2003 J Med Sci 23: 277-80. Briefly, the isocratic method is performed on a reversed-phase C-18 column (LiChrosorb RP-18, 5 m, 250×4.6 mm from HiChrom, Novato, Calif., USA). Acetate buffer is prepared daily with 0.5 M sodium acetate, adjusted to pH 4.3 with o-phosphoric acid, and filtered through a 0.22 m filter. The flow is 1.0 mL/min and the detection is performed at 205 nm. The injection loop is set to 20 uL.

For strains showing bile salt hydrolase activity, a kinetic assessment is performed by harvesting a growing culture of each organisms of interest, washing and resuspending in fresh media at a concentration of between 108 to 1010 cfu/mL. The sodium salts of GCA, GCDCA, TCA, and TCDCA are then added at 0.5 to 5 mM and the resulting culture is sampled at 1, 2, 4 and 8 hours. The sample is analyzed by HPLC as described above to find organisms with maximal activity. Highly active strains are selected for further incorporation into microbial compositions that exhibit maximal bile salt hydrolase activity.

Example 19. In vitro Screening of Microbial Communities for 7-alpha-dehydroxylase Activity Measurement of the conversion of 7-alpha-hydroxyl bile salts (primary bile salts) to 7-dehydroxy-bile salts (secondary bile salts) by single bacterial strains or bacterial communities is determined in an in vitro assay, and can be used to screen a library of organisms, whole communities or subsets of communities using limiting dilutions to identify simpler compositions. Communities to be studies include cecal or fecal communities from animals with altered gastrointestinal microbiota due to antibiotics, diet, genetics, enterohepatic metabolism, or other experimental perturbations that cause GI alterations, or from human fecal samples from healthy individuals or those with altered gastrointestinal microbiomes due to antibiotics, diet, enterohepatic metabolism, metabolic dysfunction, or gastrointestinal infection. Dilutions or subsets of these communities (such as could be generated by selective culturing for of the whole community to enrich for aerobes, anaerobes, Gram positives, Gram negatives, spore formers or using other microbiological selections known to one skilled in the art) can be utilized to identify a group of organisms required for a particular multi-step conversion.

To assay 7-alpha-dehydroxylation activity in vitro, an enzymatic assay is established to quantify the amount of 7-alphahydroxy bile acid in a sample. Recombinant 7-alpha-hydroxysteroid dehydrogenase (7-alpha-HSDH) from $E.$ $coli$ (MyBiosource.com) is an enzyme that oxidizes the 7-hydroxy group to a ketone and simultaneously reduces NAD+ to NADH+H+. The production of NADH is monitored at 340 nm using the extinction co-efficient of $6.2 \times 10^3$ M-1 cm-1.

A community of microbes is prepared according to Example 9 or, alternatively a preparation of cecal or fecal bacteria from mice or from human feces or a dilution thereof, or an enriched community thereof, can be tested after being washed 5 times to remove bile acids from the matrix. To the initial sample, a mixture of one or more primary bile acids including but not limited to CA, CDCA or any of their taurine or glycine conjugates is added to a final total concentration of 0.5-5 mM. An initial 100 uL aliquot is removed and heated at 55° C. for 15 min to quench further enzymatic activity. The bacterial composition is then incubated under anaerobic conditions at 37° C., and aliquots are removed sequentially after 30 min, 1 hour, 2 hours, 4 and 8 hours and heated as per above. An assay mix is prepared by combining 0.9 mL glycine-NaOH buffer pH 9.5, 50 uL of 53 mM NAD+ (Sigma), and 20 uL of freshly prepared 7-alpha-HSDH (4 mg/mL in distilled water). 80 uL of assay mix is combined with 20 uL of each aliquot in a 96-well microtiter plate and incubated at 37° C. on a SpectraMax m5 plate reader, monitoring A340. The incubation is allowed to proceed until the A340 value achieves its maximum. Total 7-alpha-hydroxyl bile acid is determined using the extinction coefficient for NADH. Changes due to dehydroxylation by the bacterial composition are calculated by subtracting the final value at any timepoint from the initial value.

Microbial communities of interest can be further fractionated using methods described in Example 9.

Example 20. In Vitro Evaluation of Mixed Microbial Cultures for Bile Acid Metabolism Candidates strains identified in Examples 17, 18 and 19 above are tested using the methods defined for bile salt hydrolase activity and 7-alphadehydroxylase activity are combined in communities to evaluate synergies among strains and define ecologies for further testing in animal models. Synergies include: i) the potential for more rapid conversion from conjugated primary bile salts to unconjugated, dehydryoxylated bile acids; ii) the potential for a broader range of products than determined by the additive combination of activities; iii) equivalent activity at a lower concentration (cfu) of the individual strains. Combinations exhibiting such synergies are particularly favored for subsequent in vivo testing. Another important function of a community is to remove endproducts of a microbial conversion so as to avoid inhibition of growth through product accumulation. For bile acid conversion, communities can optionally include organisms capable of degrading taurine, using it both as a carbon and nitrogen source and using the sulfonic acid group as an electron acceptor in fermentation.

Example 21. Combinations of Bacterial Compositions For SCFA Production Under Variable Conditions Combinations of synergistic bacterial compositions may be selected such that the composition is capable of producing SCFA under a wide range of in vitro conditions when the entire mixture is tested together. That is, a combination of bacterial compositions comprises multiple pairs of organisms that, together with a complex carbon source, are capable of synthesizing SCFA. Combinations may be constructed that are capable of producing a given set of SCFAs, for example butyrate and proprionate, but not acetate, or that produce butyrate, proprionate and acetate, but that the acetate is then used by another organism as a carbon source. A number of specific combinations of final SCFAs may be generated by communities designed by one skilled in the art. Construction of bacterial combinations follows the protocol described in Example 9.

Example 22. De Novo Design of Network Ecologies with Specific Functional Properties The role of the microbiome in mediating and influencing human metabolic function is well established. Microbes produce secondary bile acids (as example, Louis P, Flint H J. 2009. Diversity, metabolism and microbial ecology of butyrate-producing bacteria from the human large intestine. FEMS Microbiol Lett 294: 1-8.), short chain fatty acids (for example, Smith P M et al. 2013 Science. The microbial metabolites, short-chain fatty acid regulate colonic Treg cell homeostasis 341: 569-73) as well as numerous other functional metabolites that influence immunity and metabolic health of the human host.

Figure 12:
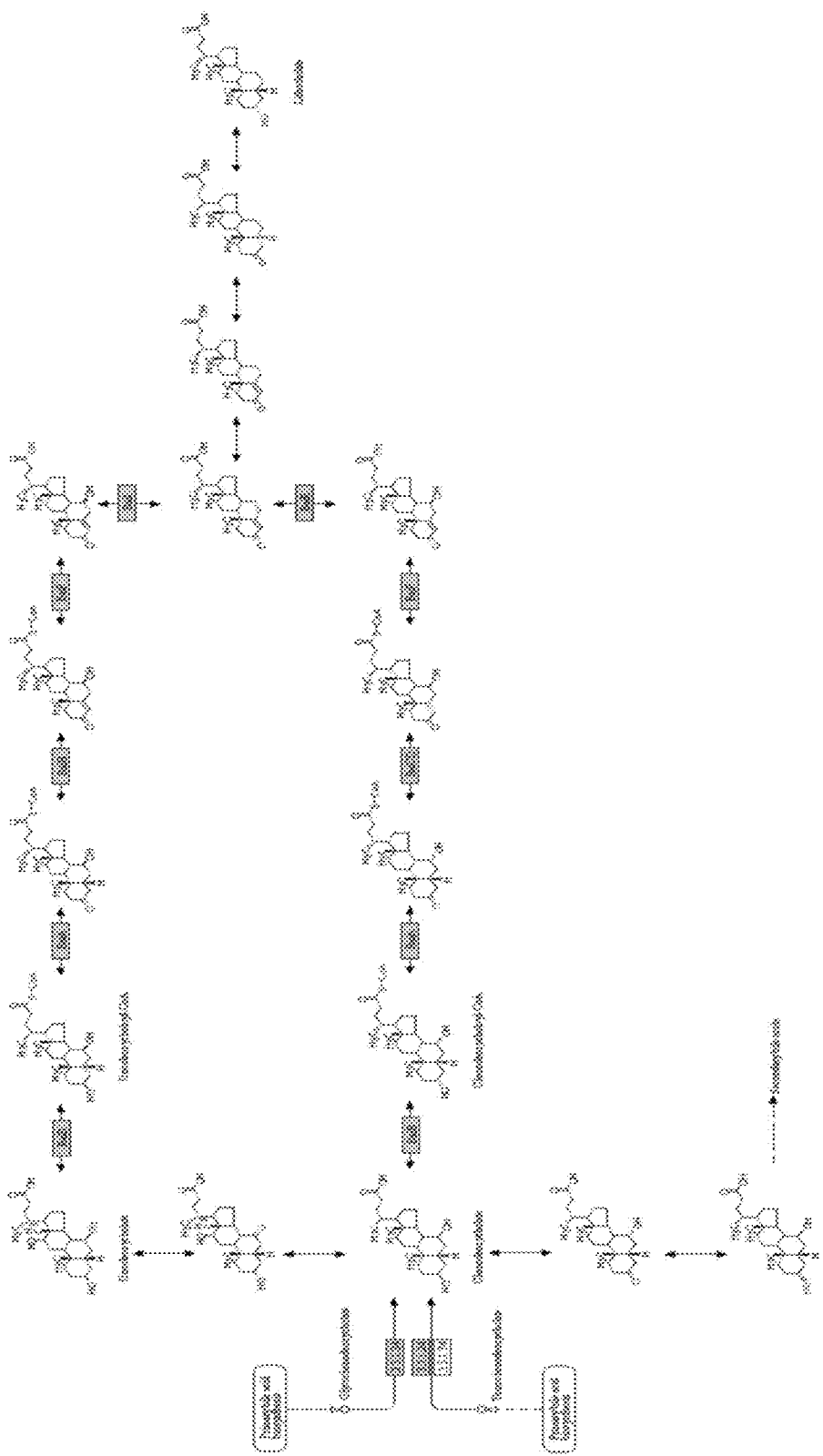
FIG. 12 shows secondary bile acid metabolism KEGG Orthology Pathway and associated enzymatic gene products defined by EC numbers.
Figure 13:
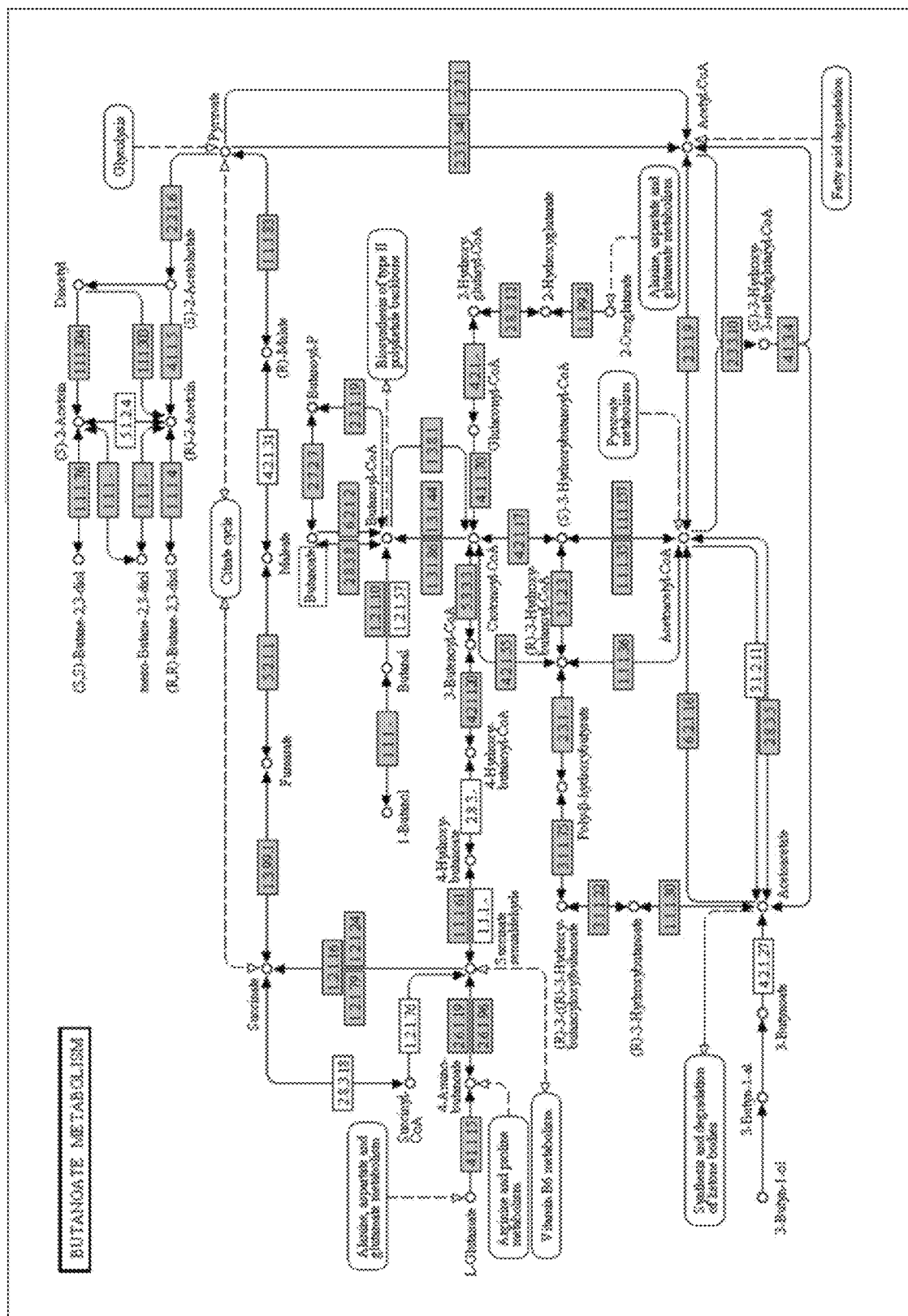
FIG. 13 shows Butyrate (a.k.a butanoate) production KEGG Orthology Pathway and associated enzymatic gene products defined by EC numbers.
Figure 14:
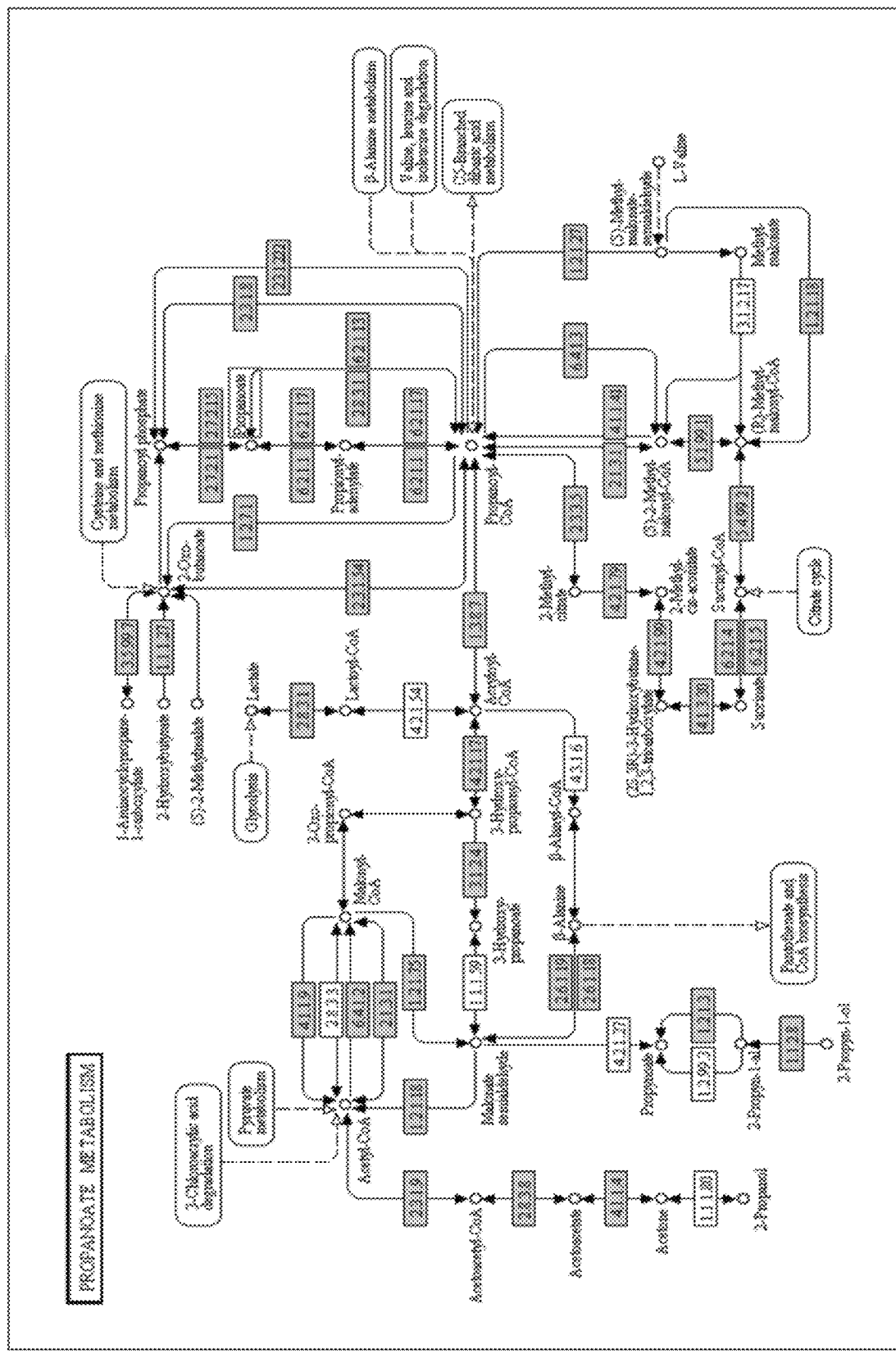
FIG. 14 shows Propionate (a.k.a. propanoate) production KEGG Orthology Pathway and associated enzymatic gene products defined by EC numbers.
Figure 15:
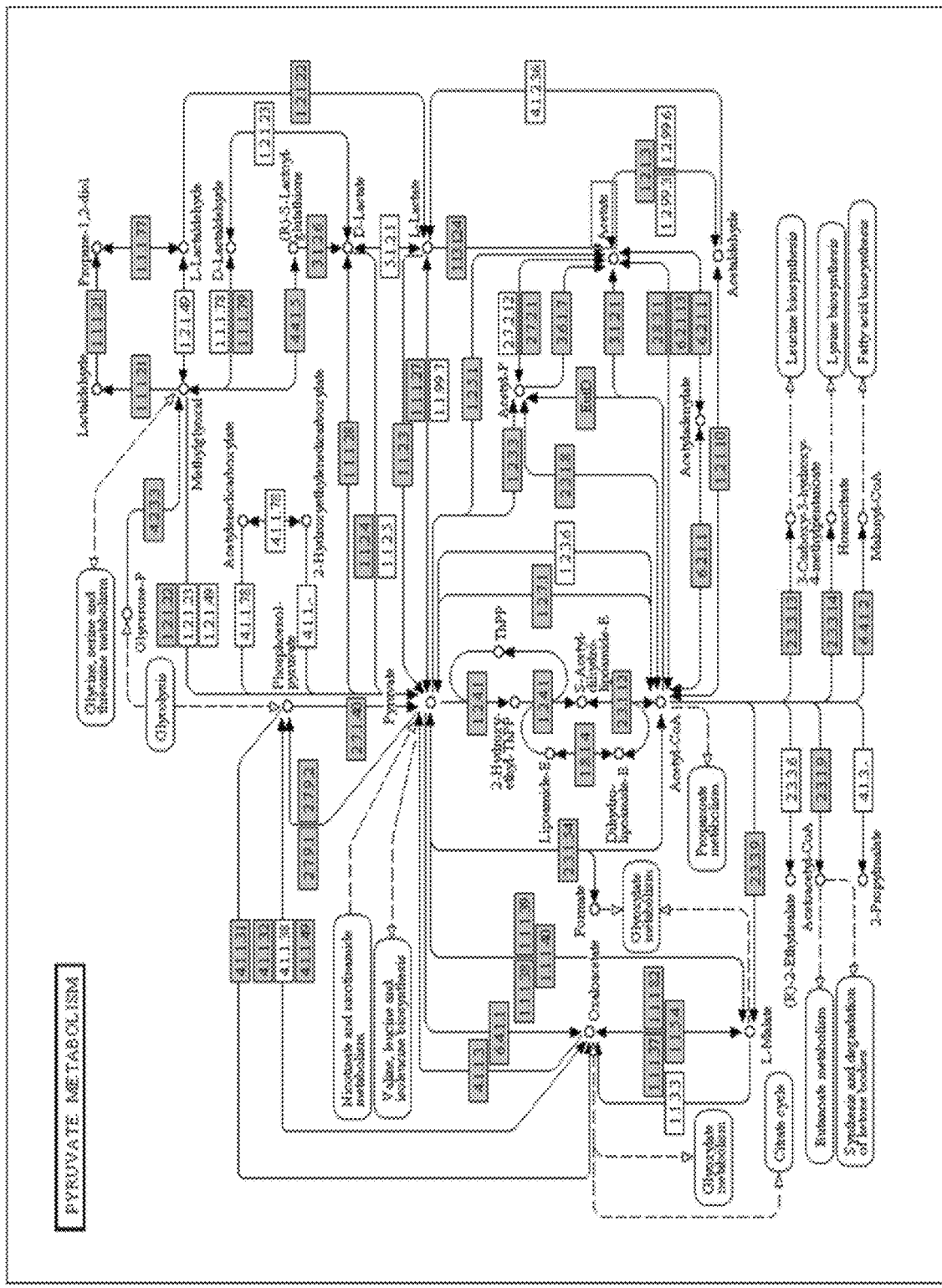
FIG. 15 shows Acetate production KEGG Orthology Pathway and associated enzymatic gene products defined by EC numbers.

To identify consortia of microbes suitable for the use as therapeutics, to influence host metabolic functions, and to treat microbial dysbiosis one can computationally derive in silico network ecologies that possess specific metabolic functions such as, but not limited to, a single or multiple metabolic nodes in the functional pathways involved in secondary bile acid biosynthesis (FIG. 12), butyrate metabolism (FIG. 13), propionate metabolism (FIG. 14), or pyruvate metabolism (FIG. 15). As additional examples, network ecologies can be in silico designed to target host genes involved in important host:microbe innate and adaptive immune responses through targets such as the Toll-like receptors (TLRs) and nucleotide-binding oligomerization domains (NOD) (Saleh M, Trinchieri G. 2011. Innate immune mechanisms of colitis and colitis-associated colorectal cancer. Nat Rev Immunol 11: 9-20. and Knight P, Campbell B J, Rhodes J M. 2008. Host-bacteria interaction in inflammatory bowel disease. Br Med Bull 88: 95-113.). In addition, the functional pathways to target for in silico network ecology design can be empirically defined by comparing the microbiomes of samples derived from different phenotypes such as but not limited to a state of disease and a state of health. For example, one can compare the microbiome and corresponding metabolic functional profile of individuals with and without insulin resistance. Vrieze et al. have shown that treatment with vancomycin can reduce the diversity of the microbiome and result in a small, but statistically significant change in peripheral insulin sensitivity. Similar changes are not observed following amoxicillin treatment (Vrieze, A et al., 2013, J Hepatol. Impact of oral vancomycin on gut microbiota, bile acid metabolism, and insulin sensitivity dx.doi.org/10.1016/j.jhep.2013.11.034). Decreased insulin sensitivity was associated with a decrease in the presence of secondary bile acids DCA, LCA and iso-LCA and an increase in primary bile acids CA and CDCA increased. In another example, Applicants can compare the microbiome and metabolomic profile of healthy individuals to those with CDAD disease. In yet another example, Applicants can compare the microbiome and metabolomic profile of healthy individuals to those that harbor IBD, IBS, Ulcerative Colitis, Crohn's Disease, Type-2-Diabetes, or Type-1-Diabetes.

For both CDAD and insulin resistance, Applicants can define the functional metabolic profile of the respective disease and health microbiomes using the 16S and metagenomic genomic methods outlined in Example 15. In another embodiment, Applicants can use the transcriptomic and metabolomic methods outlined in Example 15. In another embodiment we use functional metabolic information garnered from the literature and derived from functional screens such as but not limited to Biolog MicroPlates (see Example 16). From these profiles, Applicants can generate a metabolic function matrix for both the disease state and the health state. This matrix is comprised of columns of OTUs and rows of KEGG Orthology Pathways delineated as described in Example 15. A metabolic function matrix can be generated for both the disease state and the health state. From these disease and health matrices, Applicants can compute a delta-function matrix (i.e. difference matrix) that defines the OTUs, the relative abundance of the metabolic pathways they harbor, and the difference in the relative abundance between the disease and health state. In another embodiment, the relative abundances are discretized to be a binary, ternary, or quaternary factor. This delta-function matrix defines the differences in the microbiome distinguishing the disease state from the health state.

One can then design a network ecology with the desired functional characteristics described by the delta-function matrix. In one embodiment, one can use a greedy algorithm to optimize for the most parsimonious solution to the delta-function matrix. One can design towards (i.e. select) the minimal number of OTUs to capture the full breadth of KEGG Orthology Pathways that are represented in the health state. In short, the greedy algorithm repetitively samples the OTUs spanning the greatest number of health associated KEGGs until the desired breath of KEGGs is obtained to define a functional network ecology comprised of specific OTUs. In another embodiment, one can optimize the greedy algorithm to weigh OTUs that are from specific phylogenetic clades. In another embodiment, one can start with the computationally derived network ecologies derived using the methods defined in Example 5 to both seed and constrain the greedy algorithm to return functional network ecologies that embody the co-occurrence relationships that exist between OTUs. Microbial therapeutic compositions comprised of the OTUs of the computed network ecologies are constructed using the methods defined in Example 9. In one embodiment, constraints around network ecologies are defined by networks found in specific individuals. In another embodiment, strains of each OTU that are used for construction preferentially are selected from strains isolated from the same individual since these strains are evolutionary co-evolved and have an increased likelihood of functional synergy.

In another embodiment, Applicants computationally defined in silico a network ecology with the explicit capacity to produce butyrate. In this embodiment, Applicants defined the health state in terms of the metabolic pathways and associated gene products required for the metabolism of non-digestable carbohydrates via fermentation by colonic bacteria and by the gene products leading from mono- and di-saccharides and simple substrates such as acetate and lactate to butyrate (FIGS. 12-15). We then used the IMG functional database (http://img.jgi.doe.gov) of OTU KEGG Orthology Pathways (i.e. ko_id) to generate a metabolic function matrix comprised of columns of OTUs and rows of KEGG Orthology Pathways delineated as described in Example 15. This matrix was restricted to OTUs known to reside in the gastrointestinal tract. From this metabolic function matrix we used the greedy algorithm described above to design network ecologies capable of butyrate production.

Example 23. Identification of Organisms Harboring butyryl-CoA: Acetate CoA Transferase Genes A panel of putative butyrate forming bacteria can be screened for the presence of butyryl-CoA: acetate CoA transferase genes to define candidates for SCFA production. Bacteria are scraped from isolated colonies on agar plates or from liquid culture (media selected from Example 9) and subjected to DNA isolation in 96-well plates. 1 μl of microbial culture or an amount of a bacterial colony approximately 1 μL in volume is added to 9 μl of Lysis Buffer (25 mM NaOH, 0.2 mM EDTA) in each well of a 96 well, thin walled PCR plate, sealed with an adhesive seal, and the mixture is incubated at 95° C. for 30 minutes. Subsequently, the samples are cooled to 4° C. and neutralized by the addition of 10 μl of Neutralization Buffer (40 mM Tris-HCl) and then diluted 10-fold in Elution Buffer (10 mM Tris-HCl), at which point the genomic DNA is suitable for use in downstream amplifications such as PCR amplification. Alternatively, genomic DNA is extracted from pure microbial cultures using commercially available kits such as the Mo Bio Ultraclean® Microbial DNA Isolation Kit (Mo Bio Laboratories, Carlsbad, Calif.) or by standard methods known to those skilled in the art.

Degenerate primers are designed to selectively amplify the gene for butyryl-CoA:acetate CoA transferase based on published genomic sequences. Examples of primers are BCoATforward: 5' GCIGAICATTTCACITG-GAAYWSITGGCAYATG (SEQ ID NO: 2047); and BCoA-Treverse: 5' CCTGCCTTTGCAATRTCIACRAANGC (SEQ ID NO: 2048), where I=inosine; N=any base; W=A or T; Y=T or C; S=C or G. Amplification is as follows: 1 cycle of 95° C. for 3 min; 40 cycles of 95° C., 53° C., and 72° C. for 30 s each with data acquisition at 72° C.; 1 cycle each of 95° C. and 55° C. for 1 min; and a stepwise increase of the temperature from 55 to 95° C. (at 10 s/0.5° C.) to obtain melting curve data and evaluate product complexity. The target amplicon is about 530 nt in length.

Example 24. Identification of Organisms Harboring Butyrate-Kinase Genes

Butyrate may be produced by substrate level phosphorylation of butyrylCoA by butyrate-kinase and subsequent phosphorylation of ADP to generate ATP and butyrate. DNA isolation and PCR amplification was performed as in Example 23 with the exception that the following primers were used: BUKfor: 5' GTATAGATTACTIR-YIA-THAAYCCNGG (SEQ. ID NO: 2049); and BUKrev: 5' CAAGCTCRTCIACIACIACNGGRTCNAC (SEQ ID NO: 2050), where I=inosine; N=any base; R=A or G.

Example 25. Identification of Organisms with butyryl-CoA: Acetate CoA Transferase Enzymatic Activity Bacterial strains are grown overnight in an anaerobic chamber at 37° C. in pre-reduced media selected from those described in Example 9. 10 mL of the bacterial culture is harvested by centrifugation at 10,000 rpm for 10 min, cooled to 4° C. on ice, and disrupted by sonication as described (Duncan, S. et al., 2002 Appl Environ Microbiol Acetate utilization and butyryl coenzyme A (CoA):acetate-CoA transferase in butyrate producing bacteria from the human large intestine 68: 5186-90). ButyrylCoA: acetate CoA transferase activities are determined by the method of Barker, scaled for application to a microtiter plate (Barker H A, et al., 1955 Methods Enzymol 1: 599-600).

Example 26. Identification of Organisms with Butyrate-Kinase, Propionate-Kinase and Acetate-Kinase Enzymatic Activity Bacterial strains are grown overnight in an anaerobic chamber at 37° C. in pre-reduced media selected from those described in Example 9. 10 mL of the bacterial culture is harvested by centrifugation at 10,000 rpm for 10 min, cooled to 4° C. on ice, and disrupted by sonication as described (Duncan, S. et al., 2002 Appl Environ Microbiol Acetate utilization and butyryl coenzyme A (CoA):acetate-CoA transferase in butyrate producing bacteria from the human large intestine 68: 5186-90). Butyrate-, propionate-, and acetate-kinase activities were determined by colorimetric the method of Rose (Rose I A, 1955 Methods Enzymol Acetate kinase of bacteria 1: 591-5).

Example 27. Characterization of Propionate or Butyrate Production from a Variety of Carbon Sources Strains identified as having either genes for butyrate or propionate fermentation or having the corresponding enzymatic activities are assayed in vitro using a variety of simple carbon sources for the production of propionate and butyrate. Bacteria are grown overnight in complex media selected from Example 9 in an anaerobic chamber at 37° C. When cultures are visibly turbid, the bacteria are pelleted at 10,000×g for 10 min, the spent media is removed, and they are resuspended in pre-reduced minimal media containing essential vitamins and cofactors (pyridoxamine, p-aminobenzoic acid, biotin, nicotinic acid, folic acid, nicotinamide, choline, pantothenate, riboflavin or vitamin), divalent mineral salts (including the chloride salts of Mg2+, Ca2+ and Mn2+), and organic nitrogenous nutrients (especially glycine, glutamate or asparagine) but lacking carbohydrate as a carbon source. Alternatively, strains may be resuspended in a dilution of the original rich media, for instance a 1:10 or 1:100 dilution, such that essential factors are available but a required carbon source is limiting.

Various carbon sources are added to individual cell suspensions. These include acetate and D and L isomers of lactate, simple sugars including glucose, galactose, mannose, arabinose, xylose or any other naturally sugar, amino sugars such as N-acetyl glucosamine, galactosamine, sialic acid or glucosamine, sugar alcohols such as glycerol, erythritol, threitol, mannitol, inositol or sorbitol. In addition, the cell suspensions are individually incubated with complex carbon sources including di-, tri-, oligo- and polysaccharide carbon sources including fructans, starches, cellulose, galactomannans, xylans, arabinoxylans, pectins, inulin, and fructooligosaccharides. Tested carbon sources also include glycopeptides and glycoproteins, such as mucin. The cell suspension is incubated overnight in a sealed 96-well plate in order prevent the escape of volatile products.

At the end of the incubation period, the production of propionate, butyrate and other SCFAs is determined according to the following protocol:

Reagents
Internal Standard: 2-ethylbutyric acid, 2-EBA (100 mM)
SCFA Mixed Standard: formic acid 10 mM, acetic acid 30 mM, propionic acid 20 mM, isobutyric acid 5 mM, n-butyric acid 20 mM, n-valeric acid 5 mM, isovaleric acid 5 mM, sodium lactate 10 mM, sodium succinate 10 mM, phenylacetic acid 5 mM
MTBSTFA Derivatizing Reagent (N-Methyl-N-(tert-butyldimethylsilyl)-trifluoroacetamide), purchased from Regis Technologies
Concentrated HCl
Deionized Water
Diethyl ether (unstabilized)
Hexane Linearity Standards Preparation: Linearity Standard 1 is prepared using straight SCFA Standard. Linearity Standard 2 is prepared using 100 uL of SCFA Standard and 900 uL of water. Linearity Standard 3 is prepared using 100 uL of Linearity Standard 2 and 900 uL of water.

SCFA Extraction:
Extractions of samples (Media and Culture Supernatant), water blanks, and linearity standards were prepared in 4-mL vials using 250 uL of sample, blank, or standard, 250 uL of concentrated HCl, and 50 uL of Internal Standard (2-EBA). Once combined, the sample, standards, and blanks were vortexed and allowed to stand for about 5-10 minutes. Diethyl ether (2000 uL) was added to each of the samples, standards and blanks, and each was liquid-liquid extracted for approximately 2 minutes. The aqueous and organic phases of the extracted samples, standards and blanks were allowed to separate. Once the layers separated, 1000 uL of the ether layer was transferred to 2-mL micro-centrifuge tubes and centrifuged at 14 k for 2 minutes to remove any remaining water.

| Sample/Standard/Blank* | 250 uL |
|---|---|
| HCl | 250 uL |
| Internal Standard (2-EBA) | 50 uL |
| Ether | 2000 uL |

*substitute deionized water for blank preparations

Derivatization:
Derivatization of all samples, blanks and standards was conducted in HPLC vials using 175 uL of the upper ether layer of samples or standards and 25 uL of MTBSTFA derivatizing reagent. The reaction mixture was vortexed and allowed to sit at RT for 24 hours. After 24 hours, the ether was removed using a gentle stream of nitrogen, and the residual material was dissolved in 50 uL of hexane. (Note: solvent was removed until no further change in volume was apparent, ~5-10 min). The derivatized solutions were transferred to small-volume inserts for GC-MS analysis.

An aliquot of the resulting derivatized material is injected into a gas chromatograph (Hewlett Packard 6890) coupled to a mass spectrometer detector (Agilent Technologies 5973). Analyses are completed using DB-5MS (60 m, 0.25 mm i.d., 0.25 mm film coating; P. J. Cobert, St. Louis, Mo.) and electronic impact (70 eV) for ionization. A linear temperature gradient is used. The initial temperature of 80° C. is held for 1 min, then increased to 280° C. (15° C./min) and maintained at 280° C. for 5 min. The source temperature and emission current are 200° C. and 300 mA, respectively. The injector and transfer line temperatures are 250° C. Quantitation is completed in selected ion monitoring acquisition mode by comparison to labeled internal standards [formate was also compared to acetate-13C1,d2]. The m/z ratios of monitored ions for formic acid, acetic acid, propionic acid, butyric acid, acetate, proprionate and butyrate are as follows: 103 (formic acid), 117 (acetic acid), 131 (propionic acid), 145 (butyric acid), 121 ([2H2]- and [1-13C]acetate), 136 ([2H5]propionate), and 149 ([13C4]butyrate).

At the completion of the experiment, a database is generated for each tested organism defining what carbon sources yield which SCFAs. In each case where a microbe is capable of making propionate or butyrate from acetate, lactate, a simple sugar including a disaccharide, an amino sugar or sugar alcohol it is scored as positive for SCFA production. Also noted is whether organisms are capable of utilizing complex carbon sources such as polysaccharides to produce SCFA and which SCFAs are produced.

Example 28. Identification of Organisms Capable of Metabolizing Complex Carbon Sources Including Polysaccharides and Steroids Individual strains are screened for their ability to metabolize complex carbon sources including polysaccharides and steroids (such as bile salts) according to Example 16 to determine bacterial strain nutrient utilization. For a more complete characterization, specialized plates are constructed utilizing polysaccharide carbon sources including fructans, starches, cellulose, galactomannans, xylans, arabinoxylans, pectins, inulin, and fructooligosaccharides as well as carbon sources including glycopeptides and glycoproteins (such as mucin). These can be made to order by Biolog.

At the end of the experiment, a catalogue of is generated for each tested organism defining what carbon sources it can utilize.

Example 29. Construction of Cross Feeding Compositions

Data from Examples 27 and 28 are analyzed to determine combinations where one organism can make SCFAs from at least one simple carbon source but not from at least one complex carbon source (a polysaccharide or a glycoprotein), and another organism cannot make SCFAs from a simple carbon source but can utilize at least one complex carbon source as a metabolic substrate.

In these cases, a bacterial mixture is made combining a washed overnight culture of the SCFA producer and a washed overnight culture of the SCFA non-producer in a minimal media as described in Example 27 with the addition of the at least one complex carbon source. The bacterial mixture is incubated anaerobically overnight at 37° C. in minimal media or a 1:10 or 1:100 dilution of rich media, and the next day is worked up according to Example 27 in order to detect whether SCFA has been produced. Control cultures include each microbe cultured individually, and the bacterial mixture cultured overnight without the complex carbon source.

Bacterial mixtures in which control cultures do not yield SCFA but the complete mixture does define synergistic bacterial compositions. Synergistic bacterial compositions may be tested for further effects in a variety of in vitro or in vivo models, with and without the complex carbon source, which may be considered a component of one embodiment of the synergistic bacterial composition.

Example 30. In Vivo Validation of Bacterial Composition Efficacy in for Amelioration of Leaky Gut A murine model for "leaky gut syndrome" is constructed by intraperitoneal injection of pregnant C57BL/6N mice (Charles River, Wilmington, Mass.) with 20 mg/kg poly(I:C) in 200 uL of saline on embryonic day 12.5. Control pregnant mice are injected with 200 uL of saline only (Hsiao E Y et al., 2013 Cell Microbiota modulate behavioral and physiological abnormalities associated with neurodevelopmental disorders 155: 1451-63).

Pups are randomly selected for treatment with a single bacterial composition or a combination of bacterial compositions at the time of weaning (Day 20-22) and received oral gavage every other day for 6 days. In addition, groups of animals receive mouse chow supplemented with the complex carbohydrate relevant to the bacterial composition(s) that is (are) dosed. Control groups (saline injections) receive comparable combinations of bacterial compositions, with and without the complex carbohydrate.

Animals are tested at adolescence (3 weeks post-weaning) and adulthood (8 weeks post weaning) for leaky gut. Mice are fasted for 4 hr before gavage with 0.6 g/kg 4 kDa FITC-dextran (Sigma Aldrich). Four hours later, serum samples are read for fluorescence intensity at 521 nm using an xFluor4 spectrometer (Tecan). Increased fluorescence is taken as evidence of leaky gut, while decreased fluorescence is evidence for amelioration of leaky gut induced by poly (I:C) treatment. Preferred bacterial compositions decrease leak gut in mice.

Example 31. In Vivo Validation of Bacterial Composition Efficacy in Germ Free Mice Conventionalized with Human Obese Microbiota Ridaura et al. (2013) showed that germ-free (GF) mice conventionalized with microbiota from female twins discordant for obesity showed taxonomic and phenotypic features of the human donor's microbiota. Mice receiving obese twin microbiota (Ob mice) showed significantly greater body mass and adiposity than recipients of lean twin microbiota (Ln mice). Furthermore, they observed that cohousing Ob mice and Ln mice prevented development of the obese phenotype in the Ob mice and showed that the rescue correlated with invasion of members of the microbiota from the Ln mice into the Ob mice.

Ob and Ln mice prepared as described by Ridaura et al. (2013) can be used to test the therapeutic potential of a bacterial composition for obesity. Ob and Ln mice are generated by introducing via oral gavage fecal samples from twins discordant for obesity into 8-9 week old adult male germ-free C57BL/6J mice. One gnotobiotic isolator is used per microbiota sample and each recipient mouse is individually caged within the isolator. The obese twin must have BMI>30 kg/m2 and the pair must have a sustained multi-year BMI difference of at least 5.5 kg/m2. Recipient mice are fed a low fat (4% by weight) high in plant polysaccharide (LF-HPP), autoclaved mouse chow (B&K Universal, East Yorkshire, U.K. diet 7378000).

To prepare the fecal samples for gavage into the GF mice, fecal samples provided by donors are frozen immediately after production, stored at −80° C. Samples are homogenized by mortar and pestle while submerged in liquid nitrogen and a 500 mg aliquot of the pulverized material is diluted in 5 mL of reduced PBS (PBS supplemented with 0.1% Resazurin (w/v), 0.05% L-cysteine-HCl) in an anaerobic Coy chamber (atmosphere, 75% N2, 20% CO2, 5% H2) and then vortexed for 5 min at room temperature. The suspension is settled by gravity for 5 min, and then the clarified supernatant transferred to an anaerobic crimped tube that is transported to a gnotobiotic mouse facility. Prior to transfer of the tube into the gnotobiotic isolator, the outer surface of the tube is sterilized by exposure for 20 min to chlorine dioxide in the transfer sleeve attached to the isolator. 200 μL aliquot of the suspension is provided into the stomachs of each recipient animal by gavage.

At day 15 post-colonization, the bacterial composition containing at least 108 CFU/ml per strain is administered daily by oral gavage for 4 weeks to half of the Ob mice and half of the Ln mice. The remaining Ob mice and Ln mice are administered PBS by the same regimen. Optionally, mice can receive 0-3 days of antibiotic pre-treatment prior to administration of the bacterial composition. Alternative dosing schedules and routes of administration (e.g. rectal) may be employed, including multiple doses of test article, and 103 to 1010 CFU/ml per strain of a bacterial composition may be delivered. The bacterial composition may optionally be administered together or co-formulated with prebiotic(s).

Feces are collected from the cages for analysis of bacterial carriage. Total body weight, fat mass and lean body mass are measured at baseline before colonization, at days 8 and 15 post-colonization, and days 22, 29, 35, and 42 post-colonization (7, 14, 21, and 28 days after administration of the bacterial composition) using quantitative magnetic resonance analysis of body composition (EchoMRI-3in1 instrument). At time of sacrifice, epididymal fat pads are also collected and weighed. Optionally, luminal contents of the stomach, small intestine, cecum, and colon contents as well as the liver, spleen, and mesenteric lymph nodes can be collected for subsequent analysis. Alternative or additional time points may also be collected.

By the end of the treatment period with the bacterial composition, the Ob mice receiving the bacterial composition is expected to show significant differences in body composition (change in % fat mass; fat pad weight/total body weight) as compared to the Ob group receiving PBS and the Ln groups.

Optionally, at the end of the treatment period, the body composition is determined for all mice. Bacterial compositions that produce significant changes in body composition in the Ob mice (decrease in % fat mass; decrease in fat pad weight; or decrease in total body weight) as compared to control Ob mice receiving PBS are identified as therapeutic candidates.

Example 32. In Vivo Validation of Bacterial Composition Efficacy in Germ Free Mice Conventionalized With Bacterial Composition and Lean/Obese Microbiota Controls To test the potential of a bacterial composition's ability to treat obesity, 8-9 week old GF C57BL/6J mice can be conventionalized by introducing by oral gavage a) the bacterial composition, b) fecal samples from an obese female twin discordant for obesity (obese control), or c) fecal samples from the paired lean female twin (lean control). One gnotobiotic isolator is used per microbiota sample and each recipient mouse is individually caged within the isolator. The obese twin donors must have BMI>30 kg/m2 and the donating pair must have a sustained multi-year BMI difference of at least 5.5 kg/m2. Recipient mice are fed a low fat (4% by weight) high in plant polysaccharide (LF-HPP), autoclaved mouse chow (B&K Universal, East Yorkshire, U.K. diet 7378000).

To prepare the fecal samples for gavage into the GF mice, fecal samples provided by donors are frozen immediately after production, stored at −80° C. Samples are homogenized by mortar and pestle while submerged in liquid nitrogen and a 500 mg aliquot of the pulverized material is diluted in 5 mL of reduced PBS (PBS supplemented with 0.1% Resazurin (w/v), 0.05% L-cysteine-HCl) in an anaerobic Coy chamber (atmosphere, 75% N2, 20% CO2, 5% H2) and then vortexed for 5 min at room temperature. The suspension is settled by gravity for 5 min, and then the clarified supernatant transferred to an anaerobic crimped tube that is transported to a gnotobiotic mouse facility.

To prepare the bacterial composition for gavage into the GF mice, see Example 9. Prior to transfer of tubes into the gnotobiotic isolator, the outer surface of the tube is sterilized by exposure for 20 min to chlorine dioxide in the transfer sleeve attached to the isolator. 200 μL aliquots of the fecal suspensions are provided into the stomachs of the recipient animals by gavage.

Feces are collected from the cages for analysis of bacterial carriage. Total body weight, fat mass and lean body mass are measured at baseline before colonization, at days 8, 15, 22, 29, and 35. At time of sacrifice, epididymal fat pads are also collected and weighed. Optionally, luminal contents of the stomach, small intestine, cecum, and colon contents as well as the liver, spleen, and mesenteric lymph nodes can be collected for subsequent analysis. Alternative or additional timepoints may also be collected.

By the end of the treatment period with the bacterial composition, the mice receiving the bacterial composition is expected to show body composition (change in % fat mass; fat pad weight/total body weight) and microbial composition that is similar to the lean control and that is statistically different from the obese control.

Example 33. In Vivo Validation of Bacterial Composition Efficacy in Dietary Induced Obesity Mouse Model Male C57BL/6 mice fed a high fat diet can be used to test bacterial compositions' ability to treat obesity in a diet-induced obesity (DIO mouse) prevention model. To do so, eight groups of mice (n=8) are used, with all combinations of +/− antibiotic pretreatment, bacterial composition vs. vehicle, and high fat vs. standard diet.

4 week old male C57BL/6 mice are group housed (2-5 mice per cage) in filter top cages with autoclaved bedding, and free access to autoclaved irradiated food (LabDiet 5053, LabDiet, St. Louis, Mo. 63144) and autoclaved water. For groups receiving antibiotic pretreatment, drinking water is replaced by an antibiotic cocktail consisting of 10% glucose, kanamycin (0.5 mg/mL), gentamicin (0.044 mg/mL), colistin (1062.5 U/mL), metronidazole (0.269 mg/mL), ciprofloxacin (0.156 mg/mL), ampicillin (0.1 mg/mL) and vancomycin (0.056 mg/mL) (all constituents from Sigma-Aldrich, St. Louis Mo.) for 1 week, after which autoclaved water is returned to all cages. The mice are dosed daily with a volume of 0.2 ml containing at least 1×108 cfu/ml per strain daily or an equal volume of sterile PBS. Optionally, the dose may range from 5×106 to 5×1010 cfu/ml per strain and or dosing may occur three times a week. After one week of dosing, a group (n=10) of mice dosed with vehicle and one with the bacterial composition are switched to a high fat diet (Research Diet D12492) and dosing is continued for all groups. Treatment is continued for 15 weeks following the diet shift. Alternative dosing schedules and routes of administration (e.g. rectal) may be employed, including multiple doses of test article, and 103 to 1010 CFU/ml per strain of a bacterial composition may be delivered. The bacterial composition may be optionally be administered together or co-formulated with prebiotic(s).

Body weight will be measured three times per week throughout the study. Blood will be drawn by submandibular bleed every three weeks, from which serum cholesterol and triglycerides will be measured. Fasting blood glucose will be measured in weeks 12 and 15 following the diet shift. At sacrifice, total body, gastrocnemius, liver, epididymal fat pad, and cecum weights are measured, and the contents of the cecum as well as one lobe of the liver are stored at −80° C. By the end of the experiment, successful treatments will have statistically significant differences in total body weight, epididymal fat pad mass, or cholesterol.

Example 34. In Vivo Validation of Bacterial Composition Efficacy in Nonobese Diabetic Mouse Model of Type-1-Diabetes To demonstrate the efficacy of the microbial composition for improving the incidence of type 1 diabetes, a type 1 diabetes mouse model described previously is utilized (e.g. see Markle et al 2013. Sex differences in the gut microbiome drive hormone dependent regulation of autoimmunity. Science 339: 1084). Briefly, nonobese diabetic (NOD)/Jsd (NOD) Specific Pathogen Free (SPF) female mice are housed in sterilized static caging. The animals receive a standard mouse diet (LabDiet #5015, PMI Nutrition International) and autoclaved water. All staff uses autoclaved gowns, caps, masks, shoe covers, and sterile gloves. Animal handling and cage changes are done under HEPA filtered air. The pathogen status is determined by weekly exposure of CD-1 sentinel mice to soiled bedding from the cages in the room. Quarterly serological testing of sentinels confirmed the NOD mice are negative for: Mouse Hepatitis Virus, Minute Virus of Mice, Mouse Parvovirus, Murine Norovirus, Sendai Virus, Theiler's Murine Encephalomyelitis, Retrovirus and for endo- and ectoparasites. In addition, live animals are subjected to additional, annual comprehensive testing, including necropsy, histopathology, bacteriology and parasitology testing.

To test the microbial composition for prophylactic ability to reduce, delay or prevent disease appearance, weanling NOD females (aged 22-26 days) are gavaged with 250 uL the microbial bacterial composition using a 24G round tip gavage needle. Recipients are rested for 24 hours, and this procedure is repeated once. Optionally, mice can receive 0-3 days of antibiotic pre-treatment prior to administration with the bacterial composition. Alternative dosing schedules and routes of administration (e.g. rectal) may be employed, including multiple doses of test article, and 103 to 1010 CFU/ml per strain of a bacterial composition may be delivered. The bacterial composition may be optionally be administered together or co-formulated with prebiotic(s).

As a negative control, a group of female weanling NOD mice are gavaged with cecal contents from a female NOD mouse, and as a positive control a third group of female NOD mice are given cecal contents from a male NOD diluted 50× (v/v) and delivered in 250 ul. Spontaneous development of T1D assessment is assessed biweekly by measuring glucose levels in blood and urine. Animals are checked daily and are classified as diabetic when blood glucose exceeds 16 mmol/L or urine glucose exceeds 250 mg/dL. Additionally, serum insulin autoantibody (IAA) is measured by a micro-IAA assay (mIAA). Briefly, 125-I labeled human insulin (Perkin Elmer) is incubated with NOD serum with and without cold (unlabeled) human insulin and the immune complex is isolated by binding to protein A and G Sepharose. The assay is performed on a 96-well filtration plate to retain Sepharose beads and radioactivity is counted on a Topcount 96-well plate beta counter or similar instrument. An index is calculated by taking the difference of cpm between wells without and with cold insulin. A positive is defined by any conventional cut-off measure including a value greater than the 99th percentile of control values, or a value 3 standard deviations beyond the mean of the control values. Furthermore Insulitis is assessed. Briefly, pancreata are dissected and immediately immersed in OCT media (Tissue-Tek, Torrance, Calif.), frozen in −20° C. 2-methylbutane, and stored at −70° C. Preparation of frozen sections is performed with a Leica C M 3050 Cryostat (Leica Canada). To maximize analysis of independent islet infiltrates, three 5-μm sections are cut at least 400 μm apart. Pancreatic sections are stained with Mayer's hematoxylin and eosin Y (H+E, Sigma) to visualize leukocyte infiltration. Assessment of insulitis severity in pancreatic sections is performed by one skilled in the art. Briefly, islets are graded according to the following criteria: 0, no visible infiltrates; 1, peri-insulitis as indicated by peri-vascular and peri-islet infiltrates; 2, <25% of the islet interior 9 occluded by leukocytes displaying invasive infiltrates; 3, >25% but <50% of the islet interior invaded by leukocytes; or 4, invasive insulitis involving 50%-100% of the islet field.

To evaluate the microbial composition for treatment of disease, the procedure above is repeated whereby NOD nonobese diabetic (NOD)/Jsd (NOD) Specific Pathogen Free (SPF) female mice are housed and evaluated for development of diabetes by the criteria described above. Once a mouse develops diabetes it is gavaged with the microbial composition, and blood glucose, urine glucose, and insulin serum levels are evaluated by ELISA weekly to determine disease progression. 7 weeks later animals are sacrificed and insulitis is evaluated by methods described above. Optionally, mice can receive 0-3 days of antibiotic pre-treatment prior to administration with the bacterial composition. Alternative dosing schedules and routes of administration (e.g. rectal) may be employed, including multiple doses of test article, and 103 to 1010 CFU/ml per strain of a bacterial composition may be delivered.

Example 35. In Vivo Validation of Bacterial Composition Efficacy in Nile Rat Model of Type-2-Diabetes To test the efficacy of a microbial composition for delaying, treating or preventing the symptoms of type 2 diabetes, a Nile grass rat (*Arvicanthis niloticus*) model described previously is utilized (e.g. see Noda, K., et al. (2010). An animal model of spontaneous metabolic syndrome: Nile grass rat. The FASEB Journal 24, 2443-2453. or Chaabo, F., et al. (2010). Nutritional correlates and dynamics of diabetes in the Nile rat (*Arvicanthis niloticus*): a novel model for diet-induced type 2 diabetes and the metabolic syndrome. Nutrition & Metabolism 7, 29.). Nile rats, which spontaneously develop symptoms of type 2 diabetes and metabolic syndrome, are individually housed and have free access to autoclaved water and autoclaved standard laboratory chow (Lab Diet 5021; PMI Nutrition, St. Louis, Mo., USA). At 5 weeks of age, thrice-weekly dosing of the Nile rats with about $5\times10^8$ cfu/ml per strain of the microbial composition or an equal volume of sterile PBS by oral gavage while under light sedation with 50%/50% O2/CO2 is initiated. Optionally, the dose may range from $5\times10^6$ to $5\times10^{10}$ cfu/ml per strain and/or dosing may occur once weekly. Dosing will continue for 20 weeks post initiation, optionally lasting 15, 30, 40, or 50 weeks. The model could be modified to address prediabetes by shortening the duration to about 3 to 10 weeks post initiation of dosing.

Body weight will be measured three times per week throughout the study. Blood glucose, cholesterol, triglycerides, and hemoglobin A1C will be measured after obtaining blood by tail bleed while under light sedation with 50%/50% O2/CO2 every three weeks following initiation of dosing. At sacrifice, total body, liver, kidney, epididymal fat pad, and cecum weights are measured. Terminal plasma samples are used for measurement of insulin, blood glucose, cholesterol, triglycerides, and hemoglobin A1C. Following perfusion with PBS under deep anesthesia, the liver and kidneys are excised and fixed in 4% paraformaldehyde. Subsequently, 15 μm sections are stained with Oil-Red-O and counterstained with Mayer's hematoxylin to facilitate the identification of stores of hydrophobic lipids. The contents of the cecum are flash frozen in liquid nitrogen and stored at −80° C.

Animals treated with successful compositions will have statistically significant differences in terminal body weight, blood glucose, hemoglobin A1C, liver or kidney accumulation of lipid, and/or insulin from control animals.

Example 36. In Vivo Validation of Bacterial Composition for Prophylactic Use and Treatment in a Mouse Model of Vancomycin Resistant *Enterococcus* (VRE) Colonization The emergence and spread of highly antibiotic-resistant bacteria represent a major clinical challenge (Snitkin et al Science Translational Medicine, 2012). In recent years, the numbers of infections caused by organisms such as methicillin-resistant *Staphylococcus aureus*, carbapenem-resistant Enterobacteriaceae, vancomycin-resistant *Enterococcus* (VRE), and *Clostridium difficile* have increased markedly, and many of these strains are acquiring resistance to the few remaining active antibiotics. Most infections produced by highly antibiotic-resistant bacteria are acquired during hospitalizations, and preventing patient-to-patient transmission of these pathogens is one of the major challenges confronting hospitals and clinics. Most highly antibiotic-resistant bacterial strains belong to genera that colonize mucosal surfaces, usually at low densities. The highly complex microbiota that normally colonizes mucosal surfaces inhibits expansion of and domination by bacteria such as Enterobacteriaceae and Enterococcaceae. Destruction of the normal flora by antibiotic administration, however, leads to disinhibition antibiotic-resistant members of these bacterial families, enabling to their expansion to very high densities (Ubeda et al Journal of Clinical Investigation 2010). High-density colonization by these organisms can be calamitous for the susceptible patient, resulting in bacteremia and sepsis (Taur et al, Clinical Infectious Disease, 2012).

To test prophylactic use and treatment of a bacterial composition, a VRE infection mouse model is used as previously described (Ubeda et al, Infectious Immunity 2013, Ubeda et al, Journal of Clinical Investigation, 2010). Briefly, experiments are done with 7-week-old C57BL/6J female mice purchased from Jackson Laboratory, housed with irradiated food, and provided with acidified water. Mice are individually housed to avoid exchange of microbiota between mice due to coprophagia. For experimental infections with VRE, mice are treated with ampicillin (0.5 g/liter) in their drinking water, which is changed every 3 days.

In the treatment model, on day 1, mice are infected by means of oral gavage with 108 CFU of the vancomycin-resistant *Enterococcus faecium* strain purchased from ATCC (ATCC 700221). One day after infection (day 1), antibiotic treatment is stopped and VRE levels are determined at different time points by plating serial dilutions of fecal pellets on Enterococcosel agar plates (Difco) with vancomycin (8 ug/ml; Sigma). VRE colonies are identified by appearance and confirmed by Gram staining or other methods previously described (e.g. see Examples 1,2,3, and 4). In addition, as previously described (Ubeda et al, Journal of Clinical Investigation 2010), PCR of the vanA gene, which confers resistance to vancomycin, confirms the presence of VRE in infected mice. The bacterial composition test article such as but not limited to an ethanol treated, gradient purified spore preparation (as described herein), fecal suspension, or a Network Ecology is delivered in PBS on days 1-3 while the negative control contains only PBS and is also delivered on days 1-3 by oral gavage. Fresh fecal stool pellets are obtained daily for the duration of the experiment from days −7 to day 10. The samples are immediately frozen and stored at −80° C. DNA is extracted using standard techniques and analyzed with 16S or comparable methods (e.g. see Examples 1 and 2).

In the colonization model, ampicillin is administered as described above for day −7 to day 1, treatment with the bacterial composition or vehicle control is administered on day 0-2 and the VRE resistant bacteria at 108 CFU are administered on day 14. Fecal samples are taken throughout the experiment daily from −7 to day 21 and submitted for 16S sequencing as previously described (e.g. see Examples 1 and 2).

In both models, titers of VRE in feces are used to evaluate the success of the bacterial composition versus the negative control. A preferred bacterial composition either prevents or reduces colonization by VRE compared to the negative control, or it accelerates the decrease in colonization after cessation of antibiotics. Furthermore, each bacterial composition is assessed for the ability of the bacterial composition test article to induce a healthy microbiome, as measured by engraftment, augmentation and increase in microbiota diversity.

Example 37. In Vivo Validation of a Bacterial Composition for Prophylactic Use and Treatment of a Mouse Model of Carbapenem Resistant *Klebsiella* (CRKp) Colonization The emergence of *Klebsiella pneumoniae* strains with decreased susceptibility to carbapenems is a significant threat to hospitalized patients. Resistance to carbapenems in these organisms is most frequently mediated by *K. pneumoniae* carbapenemase (KPC), a class A beta-lactamase that also confers resistance to broad-spectrum cephalosporins and commercially available beta-lactam/beta-lactamase inhibitor combinations (Queenan et al, Clinical Microbiology Review, 2007). KPC-producing *K. pneumoniae* (KPC-Kp) strains often harbor resistance determinants against several other classes of antimicrobials, including aminoglycosides and fluoroquinolones, resulting in truly multidrug-resistant (MDR) organisms (Hirsch et al, Journal of Antimicrobial Chemotherapy, 2009). Considering the limited antimicrobial options, infections caused by KPC-Kp pose a tremendous therapeutic challenge and are associated with poor clinical outcomes.

A treatment protocol in a mouse model previously described in mice sensitive to KCP-Kp (e.g. Perez et al, Antimicrobial Agents Chemotherapy, 2011) is used to evaluate the bacterial composition (test article) for treating carbapenem resistant *Klebsiella* and reducing carriage in the GI tract. Female CF1 mice (Harlan Sprague-Dawley, Indianapolis, Ind.) are used and are individually housed and weighed between 25 and 30 g. The bacterial composition includes without limitation an ethanol treated, gradient purified spore preparation (as described herein), fecal suspension, or a Network Ecology.

The thoroughly characterized strain of *K. pneumoniae*, VA-367 (8, 9, 25) is used. This clinical isolate is genetically related to the KPC-Kp strain circulating in the Eastern United States. Characterization of the resistance mechanisms in *K. pneumoniae* VA-367 with PCR and DNA sequence analysis revealed the presence of blaKPC-3, blaTEM-1, blaSHV-11, and blaSHV-12 as well as qnrB19 and aac(6′)-lb. Additionally, PCR and DNA sequencing revealed disruptions in the coding sequences of the following outer membrane protein genes: ompK35, ompK36, and ompK37. Antibiotic susceptibility testing (AST) was performed with the agar dilution method and interpreted according to current recommendations from the Clinical and Laboratory Standards Institute (CLSI). A modified Hodge test were performed, according to a method described previously (e.g. see Anderson et al, Journal of Clinical Microbiology, 2007) with ertapenem, meropenem, and imipenem. Tigecycline and polymyxin E were evaluated by Etest susceptibility assays (AB bioMerieux, Solna, Sweden). Results for tigecycline were interpreted as suggested by the U.S. Food and Drug Administration (FDA) and according to CLSI recommendations (criteria for *Pseudomonas*) for polymyxin E.

In a prophylactic design, mice (10 per group) are assigned to receive either a bacterial composition (test article; e.g. see Example 9 or 10), or control group receiving only the vehicle. After 3 days of subcutaneous clindamycin treatment (Day −6, −5, −4) to sensitize them to KPC-Kp, mice are administered the test article or vehicle daily from day −10 to day 0, On day 0, 103 CFU of KPC-Kp VA-367 diluted in 0.5 ml phosphate-buffered saline (PBS) is administered by oral gavage. Fecal samples are collected 1, 4, 6, and 11 days after the administration of KPC-Kp to measure the concentration of carbapenem-resistant *K. pneumoniae*. Fecal samples (100 mg diluted in 800 ml of PBS) are plated onto MacConkey agar with 0.5 ug/ml of imipenem, and the number of CFU per gram of stool is determined. Efficacy of test articles is apparent as a reduction in KPC-Kp burden.

Alternatively other methods may be used to measure the levels of carbapenem-resistant *K. pneumoniae* e.g. PCR, antigen testing, as one who is skilled in the art could perform.

In a treatment design, mice are treated with subcutaneous clindamycin to reduce the normal intestinal flora 1 day before receiving 104 CFU of KPC-Kp VA-367 by oral gavage. For 7 days after oral gavage with KPC-Kp, mice receive oral gavage of normal saline (control group), or the bacterial composition. Fecal samples are collected at baseline and at 3, 6, 8, 11, 16, and 21 days after KPC-Kp VA-367 was given by gavage. The level of CRKp in feces is determined by plating serial dilutions of fecal suspensions to MacConkey agar with 0.5 ug/ml of imipenem, and the number of CFU per gram of stool is determined. Alternatively other methods may be used to measure the levels of carbapenem-resistant *K. pneumoniae* e.g. PCR, antigen testing, as one who's skilled in the art could perform. Efficacy of test articles is apparent as a reduction in KPC-Kp burden.

Example 38. In Vivo Validation of Bacterial Composition for Efficacy in for the Prophylactic Use or Treatment of Pathogenic Fungus in Mice Models The bacterial compositions of the invention can be utilized for prophylaxis or treatment of pathogenic fungus in a mouse colonized with one of several *Candida* species. Adult male CD-1 (ICR) mice are intragastrically inoculated with *C. albicans, C. tropicalis* or *C. parapsilosis* as previously described (Mellado et al., Diagnostic Microbiology and Infectious Disease 2000). Tetracycline-HCl at 1 g/L and 5% glucose are included in the drinking water starting on Day −2, 2 days before *Candida* dosing on Day 0, and throughout the experiment, to enhance colonization. $5 \times 10^7$ *Candida* are dosed in 0.1 mL on Day 0. By Day 4 all mice are colonized as detected by fecal cfu assay described below. Test articles are used in both prophylactic and treatment regimens. Prophylactic dosing with a bacterial composition including without limitation an ethanol treated, gradient purified spore preparation (as described herein), fecal suspension, or a Network Ecology occurs on Day −1 with a dose between $10^4$ and $10^{10}$ bacteria, while treatment dosing occurs on Days 1, 2 and 3 with a similar dose. Negative control groups in both regimes are dosed with PBS administered in a similar manner. All test article dosing is by oral gavage. Treated and untreated mice are kept separate in independently ventilated cages for all of the experiments. Sterilized food, bedding and bottles are used throughout the experiment. Sterilized tap water with or without supplements are also used to avoid contamination. Starting at day −1 postinfection (p.i.), mice are weighed daily and stool samples are collected from each animal and scored for consistency (0, normal feces; 1, mixed stool samples containing both solid and pasty feces; 2, pasty feces; 3, semiliquid feces; 4, liquid feces).

Feces are cultured for yeasts. Dilutions of fecal samples are titrated on Sabouraud Dextrose Chloramphenicol agar (Neogen cat #(7306) agar plates which are selective for fungi. After 24-48 h of incubation at 37° C., quantification of the cultures is achieved by counting the plates visually or by scanning the plates on a Colony Image Analysis Scanner (Spiral Biotech) and processed by the computer software CASBA 4 (Spiral Biotech). The results are noted as colony forming units (CFU) per gram of feces. Effect of bacterial composition on *Candida* colonization and quality of feces of infected mice is thus analyzed by comparing to placebo, and representative colonies are submitted for 16S/18S/ITS microbial identification before and after infection as previously described (e.g. See Example 1 and 2).

Using this model, the ability of test articles to prevent fungal dissemination and death is also tested. Starting on Day 4 in the above regimen, animals colonized with fungi are treated with immunosuppressive agents to induce deep neutropenia [defined as >500 polymorphonuclear cell per ml. Total white cells counts are performed using a hemacytometer Neubauer improved (Brand, Werthheim/Main, Germany)]. The immunosuppressive agents (150 mg/kg of cyclophosphamide (Sigma) and 65 mg/kg of 6-methylprednisolone (Sigma) are both administered intraperitoneally (i.p.) every 72-96 h until deep neutropenia is obtained and continue for 10 days. Test articles are delivered either on Day 4, 5 and 6, in parallel with the start of immunosuppression or for 3 consecutive days after deep neurtopenia is confirmed. Control animals are treated with PBS in each mode of treatment (Day 4-6, or 3 days post neutropenia. Mortality, dissemination and histology are monitored. When animals are severely ill, they are humanely euthanized with pentobarbital (Nembutal) or similar acceptable methods. Dissemination is quantified in kidneys, liver and spleen is quantified by suspending tissue separately in 2 mL of cooled PBS, and homogenizing using a lab-blender (Stomacher 80, Madrid, Spain). Aliquots of the homogenates are cultured for yeasts and bacterial flora. Results are expressed as CFU per gram of tissues. *Candida* dissemination is defined as positive cultures of at least two cultured organs. Positive culture is defined as plates yielding a value of >1.5 log 10 CFU/g of tissues. Histologic studies are also performed on five cut sections of liver, kidneys and spleen to detect yeasts.

Example 39. In Vivo Validation of Bacterial Composition for Efficacy for Prophylaxis or Treatment in a Mouse Model of Methicillin Resistant *Staphylococcus Aureus* (MRSA)

Methicillin resistant *Staphylococcus aureus* (MRSA) is a Gram positive pathogen that is a major cause of nosocomial infections including sepsis, pneumonia and surgical site infections. Both nasal and gastrointestinal carriage of MRSA are implicated as sources of organisms associated with nosocomial infections. Rectal carriage of MRSA is common in patients in intensive care units and patients with both rectal and nasal colonization had significantly higher rates of MRSA infection than did patients with nasal colonization alone (Squier et al *Staphylococcus aureus* rectal carriage and its association with infections in patients in a surgical intensive care unit and a liver transplant unit. Infect Control Hosp Epidemiol 2002; 23:495-501.)

MRSA is also associated with gastrointestinal disease, including antibiotic associated diarrhea (Boyce and Havill, Nosocomial antibiotic-associated diarrhea associated with enterotoxin-producing strains of methicillin-resistant *Staphylococcus aureus*. Am J Gastroenterol. 2005 August; 100(8):1828-34; Lo and Bourchardt, Antibiotic-associated diarrhea due to methicillin-resistant *Staphylococcus aureus*, Diagnostic Microbiology & Infectious Disease 63:388-389, 2009).

A mouse model of MRSA colonization is used to test the efficacy of bacterial compositions in treating MRSA colonization of the gut. CF1 mice are treated with streptomycin (1 mg/ml), delivered in drinking water, for 5 days, after which they are orally inoculated with 1e7 cfu MRSA daily from Day 0 to Day 5 via their drinking water (Gries et al, Growth in Cecal Mucus Facilitates Colonization of the Mouse Intestinal Tract by Methicillin-Resistant *Staphylococcus aureus*, JID 2005; 192:1621-7). Drinking water is prepared fresh each day. Colonization by MRSA is monitored by determining cfu/ml in feces each day starting on the day prior to the first day of MRSA inoculation. Feces are homogenized in sterile PBS and serial dilutions are plated to Mannitol salt agar and incubated aerobically for 48 h at 37° C. Presumptive MRSA colonies are confirmed by 16S rDNA PCR and sequencing as in (Examples 1 and 2). Bacterial compositions, control PBS or vancomycin are delivered by oral gavage starting on Day 6 for 3 days. Efficacy is observed as a reduction in MRSA cfu/g in feces, and/or faster time to a reduction of MRSA cfu/g, in the animals treated with bacterial compositions but not in control animals. Efficacy is compared to that of the positive control vancomycin, which clears the colonization.

The efficacy of bacterial compositions in preventing MRSA colonization is tested in a mouse model of prophylaxis in which CF1 mice are treated with streptomycin, delivered in drinking water, for 5 days. After 2 days without streptomycin, the mice are treated with bacterial compositions or control PBS by oral gavage for 3 days, and then inoculated with 1e7 cfu MRSA by oral gavage. Colonization by MRSA is monitored by determining cfu/ml in feces each day starting on the day prior to the first day of MRSA inoculation. Feces are homogenized in sterile PBS and serial dilutions are plated to Mannitol salt agar and incubated aerobically for 48 h at 37° C. Presumptive MRSA colonies are confirmed by 16S rDNA PCR and sequencing as in Examples 1 and 2 for 16S sequencing. Efficacy is observed as a reduction in MRSA cfu/g in feces, and/or faster reduction of MRSA cfu/g, in the animals treated with bacterial compositions compared to control animals.

Example 40. Clinical Validation of Bacterial Composition for Efficacy in Obesity To demonstrate a bacterial composition's ability to treat obesity, a group of 400 obese human subjects can be prospectively recruited. Inclusion criteria include BMI 30-45 kg/m$^2$. Exclusion criteria include Type 1 or Type 2 diabetes, treatment with any kind of anti-diabetic, anti-hyperglycemic or anti-obesity medication or surgical procedure (e.g. bariatric surgery), significant co-morbidities, participation in a formal weight loss program, either systolic blood pressure >160 mm Hg or diastolic blood pressure >100 mmHg, subjects whose body weight is not stable, as judged by the Investigator (e.g. >5% change within 3 months prior to screening).

During a double blind treatment period of 12 weeks, the experimental treatment group (n=200) receives a daily oral dose of about 1×109 CFUs of viable bacteria either in the form of vegetative organisms or spores or both, whereas the control group (n=200) is administered a placebo at an identical frequency. The composition can be formulated in a delayed release enteric coated capsule or co-administered with bicarbonate buffer to aid passage of viable organisms through the stomach. The bacterial composition may be optionally be administered together or co-formulated with prebiotic(s).

Patients can be optionally treated with a broad spectrum antibiotic 0-10 days prior to first administration of the bacterial composition. Alternative dosing schedules and routes of administration (e.g. rectal) may be employed, including multiple daily doses of test article, and a range of 103 to 1010 CFU of a given composition may be delivered.

At baseline and 6, 12, and 24 weeks after the beginning of the treatment period, change in body weight, waist and hip circumference, and waist/hip ratio will be measured. By the end of the 24 week treatment challenge period, the experimental group is expected to show significant differences from the control group in weight loss and/or waist and hip circumference, optionally 5% or greater weight loss.

Optionally, in the event an effect is detected at the end of the 24 week treatment period, the durability of the effect may be tested. All subjects will be taken off the experimental treatment and change in weight measured after 2 weeks, 4 weeks, 8 weeks, 16 weeks, and 52 weeks.

Example 41. Clinical Validation of Bacterial Composition for Efficacy in Weight Loss To demonstrate a bacterial composition's ability to cause weight loss, a group of 400 human subjects with BMI>25 kg/m$^2$ is prospectively recruited. Inclusion criteria include BMI>25 kg/m$^2$. Exclusion criteria include Type 1 or Type 2 diabetes, treatment with any kind of anti-diabetic, anti-hyperglycemic or anti-obesity medication or surgical procedure (e.g. bariatric surgery), significant co-morbidities, participation in a formal weight loss program, either systolic blood pressure >160 mm Hg or diastolic blood pressure >100 mmHg, subjects who do not show stable body weight as judged by PI (e.g. >5% change within 3 months prior to screening).

During a double blind treatment period of 24 weeks, the experimental treatment group (n=200) receives a daily oral dose of about 1×109 CFUs of viable bacteria either in the form of vegetative organisms or spores or both, whereas the control group (n=200) is administered a placebo at an identical frequency. The composition can be formulated in a delayed release enteric coated capsule or co-administered with bicarbonate buffer to aid passage of viable organisms through the stomach. The bacterial composition may be optionally be administered together or co-formulated with prebiotic(s).

Patients may be optionally treated with a broad spectrum antibiotic 0-10 days prior to first administration of the bacterial composition. Alternative dosing schedules and routes of administration (e.g. rectal) may be employed, including multiple daily doses of test article, and a range of 103 to 1010 CFU of a given composition may be delivered.

At baseline and 6, 12, and 24 weeks after the beginning of the treatment period, change in body weight will be measured. By the end of the 24 week treatment challenge period, the experimental group are expected to show significant differences from the control group in weight loss.

Optionally, in the event an effect is detected at the end of the 24 week treatment period, the durability of the effect may be tested. All subjects will be taken off the experimental treatment and change in weight measured after 2 weeks, 4 weeks, 8 weeks, 16 weeks, and 52 weeks.

Example 42. Clinical Validation of Bacterial Composition for Efficacy in Prediabetes To demonstrate a bacterial composition's ability to treat prediabetes by exerting beneficial effects on markers associated with the onset of diabetes, a group of 60 human subjects with metabolic syndrome/prediabetes is prospectively recruited. Inclusion criteria include either (a) fasting plasma glucose between 5.6 and 6.9 mmol/L and 2 hr post-glucose load plasma glucose <7.8 mmol/L, and/or (b) 2 hr post-glucose load plasma glucose in oral glucose tolerance test (OGTT) between 7.8 and 11.0 mmol/L. Exclusion criteria include established gestational, Type 1 or Type 2 diabetes, treatment with any kind of anti-diabetic, anti-hyperglycemic or anti-obesity medication or surgical procedure, use of systemic long-acting corticosteroids or prolonged use (greater than 10 days) of systemic corticosteroids, or any significant medical condition that would complicate the measurement of the endpoint or put the patient at risk.

Optionally, the study can be performed specifically in obese patients meeting the above inclusion criteria with the additional inclusion criteria of BMI 30-45 kg/m² as well as waist circumference >88 cm in women and >102 cm in men. Additional exclusion criteria include: 1) a history of surgical procedures for weight loss; 2) 2 repeat laboratory values at the screening visit of triglycerides >4.52 mmol; and 3) either systolic blood pressure >160 mm Hg or diastolic blood pressure >100 mmHg.

During a double blind treatment period of 12 weeks, the experimental treatment group (n=30) receives a daily oral dose of about 1×109 CFUs of viable bacteria either in the form of vegetative organisms or spores or both, whereas the control group is administered a placebo at an identical frequency (n=30). The composition can be formulated in a delayed release enteric coated capsule or co-administered with bicarbonate buffer to aid passage of viable organisms through the stomach. The bacterial composition may be optionally be administered together or co-formulated with prebiotic(s).

Patients can be optionally treated with a broad spectrum antibiotic 0-3 days prior to first administration of the bacterial composition. Alternative dosing schedules and routes of administration (e.g. rectal) may be employed, including multiple daily doses of test article, and a range of 103 to 1011 CFU of a given composition may be delivered.

At baseline and 4, 8 and 12 weeks after the beginning of the treatment period, glucose tolerance is tested by OGTT and HbA1c (glycosylated hemoglobin) levels measured. At the same timepoints, insulin secretion will be assessed by plasma insulin levels measured during the oral glucose tolerance tests. Homeostatic model assessment beta (HOMA-beta) will be used to quantify beta cell function and HOMA-IR for insulin sensitivity. In addition, subjects will perform home blood glucose testing once weekly at home.

By the end of the 12 week treatment period, the experimental group is expected to show significant differences from the control group in glucose tolerance, insulin sensitivity, and/or insulin secretion reflecting improved insulin sensitivity, decreased pre-diabetes symptoms and improvement in metabolic syndrome.

Optionally, in the event an effect is detected at the end of the 12 week treatment period, the durability of the effect may be tested. All subjects will be taken off their respective treatment and return for oral glucose tolerance tests after 2 weeks, 4 weeks, 8 weeks, 16 weeks, and 52 weeks to measure HbA1c, insulin secretion, HOMA-beta, and HOMA-IR.

Optionally, the treatment period can be extended to collect an additional endpoint of progression to type 2 diabetes at 6 months and 12 months after the beginning of the treatment period.

Example 43. Clinical Validation of Bacterial Composition for Efficacy in Type-2-Diabetes To demonstrate a bacterial composition's ability to treat type 2 diabetes, a group of 60 human subjects with type 2 diabetes is prospectively recruited. Inclusion criteria include diagnosis of type 2 diabetes with inadequate glycemic control on diet and exercise, glycosylated hemoglobin between 7.5% and 10.0% at screening, BMI≤45 kg/m2.

Exclusion criteria include gestational diabetes, type 1 diabetes, treatment with any kind of anti-diabetic medication in the 12 weeks prior to screening, use of anti-obesity medication/surgical procedure, use of systemic long-acting corticosteroids or prolonged use (greater than 10 days) of systemic corticosteroids, or any significant co-morbidities related to the underlying diabetic condition.

Optionally, the study can be done in non insulin dependent type 2 diabetics who have inadequate glycemic control who are taking oral medications such as metformin, sulfonylureas, DPP-4 inhibitors, GLP-1 agonists, and SGLT2 inhibitors. Optionally, the study can be done in newly diagnosed non insulin dependent type 2 diabetics who are completely treatment naive.

During a double-blinded treatment period of 18 weeks, the experimental treatment group (n=30) receives a daily oral dose of about 1×109 CFUs of viable bacteria either in the form of vegetative organisms or spores or both, whereas the control group (n=30) is administered a placebo at an identical frequency. The composition can be formulated in a delayed release enteric coated capsule or co-administered with bicarbonate buffer to aid passage of viable organisms through the stomach. The bacterial composition may be optionally be administered together or co-formulated with prebiotic(s).

Patients may be optionally treated with a broad spectrum antibiotic 0-10 days prior to first administration of the bacterial composition. Alternative dosing schedules and routes of administration (e.g. rectal) may be employed, including multiple daily doses of test article, and a range of 103 to 1010 CFUs of a given composition may be delivered.

At baseline and 6, 12 and 18 weeks after the beginning of the treatment period, HbA1c (glycosylated hemoglobin) levels, fasting plasma glucose, fasting insulin, HOMA-beta, and HOMA-IR, In addition, subjects will perform home blood glucose testing once weekly at home.

Optionally high sensitivity C-reactive protein, adiponectin, total cholesterol, low-density lipoprotein cholesterol, high-density lipoprotein cholesterol, triglycerides, systolic and diastolic blood pressure can also be measured at the same timepoints.

By the end of the 18 week treatment period, the experimental group are expected to show significant differences from the control group in change in HbA1c, fasting plasma glucose, insulin sensitivity, and/or insulin secretion from baseline.

Optionally, in the event an effect is detected at the end of the 18 week treatment period, the durability of the effect may be tested. All subjects will be taken off the experimental treatment and return for measurement of HbA1c, fasting plasma glucose, fasting insulin, HOMA-beta, and HOMA-IR after 2 weeks, 4 weeks, 8 weeks, 16 weeks, and 52 weeks.

Example 44. Clinical Validation of Bacterial Composition for Efficacy in Recent Onset Type-1-Diabetes To demonstrate a bacterial composition's ability to slow progression of recent onset type 1 diabetes, a group of 60 human subjects with recent onset type 1 diabetes is prospectively assembled.

Inclusion criteria include diagnosis of type 1 diabetes within 40 days prior to screening, positive test for at least one diabetes-related autoantibody such as GAD, IA-2, ZnT8, and/or anti-insulin (obtained within 10 days of onset of insulin therapy), peak stimulated C-peptide level ≥0.2 pmol/mL following mixed meal tolerance test (MMTT), and evidence of some fraction of residual (normal) pancreatic function. Exclusion criteria include any form of diabetes other than type 1 (e.g. type 2 diabetes), prior or current treatment with corticosteroids, significant co-morbidities.

During a double-blind treatment period of 18 weeks, the experimental treatment group (n=30) receives a daily oral dose of about 1×109 CFUs of viable bacteria either in the form of vegetative organisms or spores or both, whereas the control group (n=30) is administered a placebo at an identical frequency. The composition can be formulated in a delayed release enteric coated capsule or co-administered with bicarbonate buffer to aid passage of viable organisms through the stomach. The bacterial composition may be optionally be administered together or co-formulated with prebiotic(s).

Patients can be optionally treated with a broad spectrum antibiotic 0-10 days prior to first administration of the bacterial composition. Alternative dosing schedules and routes of administration (e.g. rectal) may be employed, including multiple daily doses of test article, and a range of 103 to 1010 CFUs of a given composition are delivered.

At baseline and 6, 12 and 18 weeks after the beginning of the treatment period, stimulated C-peptide released in 2 hours during a standard mixed meal tolerance test (MMTT) and HbA1c levels will be measured. In addition, subjects will record total daily dose of insulin in a diary.

By the end of the 18 week treatment period, the experimental group is expected to show significant differences from the control group in change in stimulated C-peptide, HbA1c, and/or insulin dosage from baseline.

Optionally, in the event an effect is detected at the end of the 18 week treatment period, the durability of the effect may be tested. All subjects will be taken off the experimental treatment and return for measurement of stimulated C-peptide in response to MMTT and HbA1c levels after 2 weeks, 4 weeks, 8 weeks, 16 weeks, and 52 weeks.

Example 45. Clinical Validation of Bacterial Composition for Efficacy in Reduction of Opportunistic Pathogenic Fungus in Humans The dimorphic yeast, *Candida albicans*, is the leading fungal pathogen in normal hosts and in patients with damaged immune systems. In immunocompromised hosts such as cancer patients, transplant patients, post-operative surgical patients, premature newborns, or HIV-infected people, *C. albicans* ranks as the leading fungal pathogen. Invasion leading to systemic infection may also develop in neutropenic patients whose T cell function is comprised. (Hostetter M K, Clinical Microbiology Reviews, January 1994, pp. 29-42.) In this population, disease ranges from aggressive local infections such as periodontitis, oral ulceration, or esophagitis in HIV-infected patients, to complex and potentially lethal infections of the bloodstream with subsequent dissemination to brain, eye, heart, liver, spleen, kidneys, or bone. Recently, the incidence of systemic candidiasis, which is caused by *Candida* spp., predominantly *Candida albicans*, has increased. This increase over the last two decades has caused a rise in the use of antifungal drugs, including azoles, such as fluconazole or ketoconazol, leading to emergence of resistant organisms and thus increasing the need for alternative therapies (Looi et al., FEMS Microbiol Lett 2005).

In a prophylactic, randomized, double-blind study, healthy volunteers who have been prescreened as colonized with *Candida albicans* at >104 cfu/g by fecal culturing are randomized to receive either a placebo or a bacterial composition daily. Study volunteers are asked to avoid taking probiotics in any form in the week prior to dosing. The dosing of bacterial composition may, optionally, be modified to daily, every-other-day, weekly or any other frequency, and doses may range from 105 to 1010 CFU/mL. The subjects provide faecal and vaginal fluid samples pretreatment and on Days 7, 14 and 28 post-treatment that are cultivated on agar plates within 3 hours after delivery to the laboratory. Complementary genomic and microbiological methods are used to characterize the composition of the microbiota from each of the samples. *C. albicans* is detected by microbiological methods, for example by serial dilution and plating to fungal selective media CHROMagar *Candida* (BD cat#254093) which selects for fungal organisms, and against bacterial growth, or another fungal selective media, and also by using Taqman PCR based assay using similar methods as described previously (Maaroufi et al., J Clin Microbiol. 2003). A reduction in *C. albicans* levels in feces indicates efficacy in reducing colonization.

SUMMARY

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a tangible computer readable storage medium or any type of media suitable for storing electronic instructions, and coupled to a computer system bus. Furthermore, any computing systems referred to in the specification may include a single processor or may be architectures employing multiple processor designs for increased computing capability.

Embodiments of the invention may also relate to a computer data signal embodied in a carrier wave, where the computer data signal includes any embodiment of a computer program product or other data combination described herein. The computer data signal is a product that is presented in a tangible medium or carrier wave and modulated or otherwise encoded in the carrier wave, which is tangible, and transmitted according to any suitable transmission method.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

Tables

Lengthy table referenced here

US10881696-20210105-T00001

Please refer to the end of the specification for access instructions.

Lengthy table referenced here

US10881696-20210105-T00002

Please refer to the end of the specification for access instructions.

Lengthy table referenced here

US10881696-20210105-T00003

Please refer to the end of the specification for access instructions.

Lengthy table referenced here

US10881696-20210105-T00004

Please refer to the end of the specification for access instructions.

Lengthy table referenced here

US10881696-20210105-T00005

Please refer to the end of the specification for access instructions.

Lengthy table referenced here

US10881696-20210105-T00006

Please refer to the end of the specification for access instructions.

Lengthy table referenced here

US10881696-20210105-T00007

Please refer to the end of the specification for access instructions.

Lengthy table referenced here

US10881696-20210105-T00008

Please refer to the end of the specification for access instructions.

Lengthy table referenced here

US10881696-20210105-T00009

Please refer to the end of the specification for access instructions.

Lengthy table referenced here

US10881696-20210105-T00010

Please refer to the end of the specification for access instructions.

Lengthy table referenced here

US10881696-20210105-T00011

Please refer to the end of the specification for access instructions.

Lengthy table referenced here

US10881696-20210105-T00012

Please refer to the end of the specification for access instructions.

Lengthy table referenced here

US10881696-20210105-T00013

Please refer to the end of the specification for access instructions.

Lengthy table referenced here
US10881696-20210105-T00014

Please refer to the end of the specification for access instructions.

Lengthy table referenced here
US10881696-20210105-T00015

Please refer to the end of the specification for access instructions.

Lengthy table referenced here
US10881696-20210105-T00016

Please refer to the end of the specification for access instructions.

Lengthy table referenced here
US10881696-20210105-T00017

Please refer to the end of the specification for access instructions.

Lengthy table referenced here
US10881696-20210105-T00018

Please refer to the end of the specification for access instructions.

Lengthy table referenced here
US10881696-20210105-T00019

Please refer to the end of the specification for access instructions.

Lengthy table referenced here
US10881696-20210105-T00020

Please refer to the end of the specification for access instructions.

Lengthy table referenced here
US10881696-20210105-T00021

Please refer to the end of the specification for access instructions.

Lengthy table referenced here
US10881696-20210105-T00022

Please refer to the end of the specification for access instructions.

Lengthy table referenced here
US10881696-20210105-T00023

Please refer to the end of the specification for access instructions.

LENGTHY TABLES

The patent contains a lengthy table section. A copy of the table is available in electronic form from the USPTO web site (https://seqdata.uspto.gov/?pageRequest=docDetail&DocID=US10881696B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10881696B2). An electronic copy of the "Sequence Listing" will also be available from the USPTO upon request and payment of the fee set forth in 37 CFR 1.19(b)(3).

What is claimed is:

1. A method of treating or reducing the severity of a disorder selected from the group consisting of *Clostridium difficile* infection and ulcerative colitis, comprising: administering to a mammalian subject in need thereof an effective amount of a therapeutic bacterial composition, the therapeutic bacterial composition comprising a plurality of isolated bacteria, wherein the plurality of isolated bacteria comprises: a first bacterial operational taxonomic units (OTU) comprising a 16S rDNA comprising a sequence at least 97% identical to SEQ ID NO: 774, a second bacterial OTU comprising a 16S rDNA comprising a sequence at least 97% identical to SEQ ID NO: 856, a third bacterial OTU comprising a 16S rDNA comprising a sequence at least 97% identical to SEQ ID NO: 880, and a fourth bacterial OTU comprising a 16S rDNA comprising a sequence at least 97% identical to SEQ ID NO: 1670.

2. The method of claim 1, wherein the first bacterial OTU comprises a 16S rDNA comprising SEQ ID NO: 774, the second bacterial OTU comprises a 16S rDNA comprising SEQ ID NO: 856, the third bacterial OTU comprises a 16S rDNA comprising SEQ ID NO: 880, and the fourth bacterial OTU comprises a 16S rDNA comprising SEQ ID NO: 1670.

3. The method of claim 1, wherein the therapeutic bacterial composition is substantially depleted of a residual habitat product of a fecal material.

4. The method of claim 1, wherein the therapeutic bacterial composition is capable of inducing the formation of IgA, RegIII-gamma, IL-10, regulatory T cells, TGF-beta, alpha-defensin, or beta-defensin in the mammalian subject.

5. The method of claim 1, wherein the therapeutic bacterial composition is provided as an oral finished pharmaceutical dosage form including at least one pharmaceutically acceptable carrier.

6. The method of claim 5, wherein the oral finished pharmaceutical dosage form comprises at least about $1\times10^4$ colony forming units of each of the first, second, third, and fourth bacterial OTUs per dose of the composition.

7. The method of claim 5, wherein the oral finished pharmaceutical dosage form is a capsule.

8. The method of claim 5, wherein the oral finished pharmaceutical dosage form is a tablet.

9. The method of claim 5, wherein the oral finished pharmaceutical dosage form is a powder.

10. The method of claim 1, wherein the therapeutic bacterial composition is prepared by ethanol treatment.

11. The method of claim 1, wherein the therapeutic bacterial composition is prepared by heat treatment.

12. The method of claim 1, wherein the therapeutic bacterial composition is provided as an oral finished pharmaceutical dosage form comprising at least $1\times10^4$ colony forming units of each of the first, second, third, and fourth bacterial OTUs per dose of the composition and including at least one pharmaceutically acceptable carrier and the therapeutic bacterial composition is prepared by ethanol treatment.

13. The method of claim 1, wherein the therapeutic bacterial composition is provided as an oral finished pharmaceutical dosage form comprising at least $1\times10^4$ colony forming units of each of the first, second, third, and fourth bacterial OTUs per dose of the composition and including at least one pharmaceutically acceptable carrier and the therapeutic bacterial composition is prepared by heat treatment.

14. The method of claim 1, wherein the therapeutic bacterial composition is provided as an oral finished pharmaceutical dosage form comprising at least $1\times10^4$ colony forming units of each of the first, second, third, and fourth bacterial OTUs per dose of the composition and including at least one pharmaceutically acceptable carrier and the therapeutic bacterial composition is prepared by ethanol treatment, and wherein the therapeutic bacterial composition is substantially depleted of a residual habitat product of a fecal material.

15. The method of claim 1, wherein the therapeutic bacterial composition is provided as an oral finished pharmaceutical dosage form comprising at least $1\times10^4$ colony forming units of each of the first, second, third, and fourth bacterial OTUs per dose of the composition and including at least one pharmaceutically acceptable carrier and the therapeutic bacterial composition is prepared by heat treatment, and wherein the therapeutic bacterial composition is substantially depleted of a residual habitat product of a fecal material.

16. The method of claim 1, wherein the therapeutic bacterial composition is provided as an oral finished pharmaceutical dosage form comprising at least $1\times10^4$ colony forming units of each of the first, second, third, and fourth bacterial OTUs per dose of the composition and including at least one pharmaceutically acceptable carrier and wherein the oral finished pharmaceutical dosage form is a capsule, a tablet, or a powder.

17. The method of claim 1, comprising administering an antibiotic to the mammalian subject prior to administering the therapeutic bacterial composition.

* * * * *